(12) United States Patent
Kelly et al.

(10) Patent No.: US 11,945,806 B2
(45) Date of Patent: Apr. 2, 2024

(54) STABILIZATION OF AMYLOIDOGENIC IMMUNOGLOBULIN LIGHT CHAINS

(71) Applicant: The Scripps Research Institute, La Jolla, CA (US)

(72) Inventors: Jeffery W. Kelly, La Jolla, CA (US); Gareth John Morgan, La Jolla, CA (US); Nicholas Lok Yan, La Jolla, CA (US); Hank Michael James Petrassi, La Jolla, CA (US)

(*) Notice: Subject to any disclaimer, the term of this patent is extended or adjusted under 35 U.S.C. 154(b) by 94 days.

(21) Appl. No.: 17/593,812

(22) PCT Filed: Mar. 29, 2020

(86) PCT No.: PCT/US2020/025607
§ 371 (c)(1),
(2) Date: Sep. 24, 2021

(87) PCT Pub. No.: WO2020/205683
PCT Pub. Date: Oct. 8, 2020

(65) Prior Publication Data
US 2022/0204485 A1 Jun. 30, 2022

Related U.S. Application Data

(60) Provisional application No. 62/826,476, filed on Mar. 29, 2019.

(51) Int. Cl.
| | |
|---|---|
| *C07D 471/10* | (2006.01) |
| *C07C 255/30* | (2006.01) |
| *C07C 311/39* | (2006.01) |
| *C07C 317/24* | (2006.01) |
| *C07D 207/06* | (2006.01) |
| *C07D 207/48* | (2006.01) |
| *C07D 215/227* | (2006.01) |
| *C07D 233/72* | (2006.01) |
| *C07D 235/02* | (2006.01) |
| *C07D 239/47* | (2006.01) |
| *C07D 311/18* | (2006.01) |
| *C07D 319/06* | (2006.01) |
| *C07D 405/04* | (2006.01) |
| *C07D 405/06* | (2006.01) |
| *C07D 405/12* | (2006.01) |
| *C07D 407/12* | (2006.01) |
| *C07D 487/10* | (2006.01) |

(52) U.S. Cl.
CPC .......... *C07D 405/12* (2013.01); *C07C 255/30* (2013.01); *C07C 311/39* (2013.01); *C07C 317/24* (2013.01); *C07D 207/06* (2013.01); *C07D 207/48* (2013.01); *C07D 215/227* (2013.01); *C07D 233/72* (2013.01); *C07D 235/02* (2013.01); *C07D 239/47* (2013.01); *C07D 311/18* (2013.01); *C07D 319/06* (2013.01); *C07D 405/04* (2013.01); *C07D 405/06* (2013.01); *C07D 407/12* (2013.01); *C07D 471/10* (2013.01); *C07D 487/10* (2013.01)

(58) Field of Classification Search
None
See application file for complete search history.

(56) References Cited

FOREIGN PATENT DOCUMENTS

| | | |
|---|---|---|
| CN | 102558049 A | 7/2012 |
| WO | 0040562 A1 | 7/2000 |
| WO | 2010/056914 A1 | 5/2010 |
| WO | 2014/153533 A1 | 9/2014 |
| WO | 2016/183578 A1 | 11/2016 |
| WO | 2016/203402 A1 | 12/2016 |

OTHER PUBLICATIONS

Abid-Jarraya Nihel, et al., "Solid-state fluorescence properties of small iminocourmarin derivatives and their analogues in the coumarin series." Dyes and Pigments; Apr. 25, 2016; pp. 177-184; vol. 132; Elsevier Applied Science Publishers; Barking, GB.

Arendt, B.K., et al., "Biologic and genetic characterization of the novel amyloidogenic lambda light chain-secreting human cell lines, ALMC-1 and ALMC-2." Blood; 2008; 112(5):1931-1941.

Barik, A., et al., "Evidence for the TICT mediated nonradiative deexcitation process for the excited coumarin-1 dye in high polarity protic solvents." Chemical Physics; 2005; 315(3):277-285.

Berk, J.L., et al., "Repurposing diflunisal for familial amyloid polyneuropathy: a randomized clinical trial." JAMA ; 2013; 310(24):2658-2667.

Blancas-Mejia, L.M., et al., "Thermodynamic and fibril formation studies of full length immunoglobulin light chain AL-09 and its germline protein using scan rate dependent thermal unfolding." Biophys Chem; 2015; 207:13-20.

Bodi, K., et al., "AL-Base: a visual platform analysis tool for the study of amyloidogenic immunoglobulin light chain sequences." Amyloid; 2009; 16(1):1-8.

Brumshtein, B., et al., "Inhibition by small-molecule ligands of formation of amyloid fibrils of an immunoglobulin light chain variable domain." ELIFE; 2015; 4:e10935.

Bulawa, C.E., et al., "Tafamidis, a potent and selective transthyretin kinetic stabilizer that inhibits the amyloid cascade." Proceedings of the National Academy of Sciences; May 29, 2012; pp. 9629-9634; vol. 109(24).

(Continued)

*Primary Examiner* — Samantha L Shterengarts
(74) *Attorney, Agent, or Firm* — Rimon, P.C.; Dale L. Rieger

(57) ABSTRACT

In immunoglobulin light chain amyloidosis (AL), the unique antibody light chain (LC) protein that is secreted by monoclonal plasma cells in each patient misfolds and/or aggregates, a process leading to organ degeneration. For treating AL patients, such as those with substantial cardiac involvement who have difficulty tolerating existing chemotherapy regimens, provided herein are small molecule compounds of Formula Ia, Formula Ib, and Formula II that are kinetic stabilizers of the native dimeric structure of full-length LCs, which compounds can slow or stop the amyloidogenicity cascade at its origin.

3 Claims, 18 Drawing Sheets

(56) References Cited

OTHER PUBLICATIONS

Coelho, T., et al., "Tafamidis for transthyretin familial amyloid polyneuropathy: a randomized, controlled trial." Neurology; 2012; 79(8):785-792.

Coelho, T., et al., "Long-term effects of tafamidis for the treatment of transthyretin familial amyloid polyneuropathy." Journal of neurology; 2013; 260(11):2802-2814.

Edmundson, A.B., et al., "Binding of 2,4-dinitrophenyl compounds and other small molecules to a crystalline lambda-type Bence-Jones dimer." Biochemistry; 1974; 13(18):3816-3827.

Garazd, M.M., et al., "Modified coumarins. 27. Synthesis and antioxidant activity of 3-substituted 5,7-dihydroxy-4-methylcoumarins." Chemistry of Natural Compounds; Jan. 1, 2007; pp. 19-23; vol. 43(1).

Glenner, G.G., et al., "An amyloid protein: the amino-terminal variable fragment of an immunoglobulin light chain." Biochem Biophys Res Commun; 1970; 41(5):1287-1289.

Glenner, G.G., et al., "Creation of "amyloid" fibrils from Bence Jones proteins in vitro." Science; 1971; 174(4010):712-714.

Hammarstrom, P., et al., "Prevention of transthyretin amyloid disease by changing protein misfolding energetics." Science; 2003; 299(5607):713-716.

Hong, M., et al., "Antibody recognition of the pandemic H1N1 Influenza virus hemagglutinin receptor binding site." J Virol; 2013; 87(22):12471-12480.

Huang, D.B., et al., "Pitfalls of molecular replacement: the structure determination of an immunoglobulin light-chain dimer." Acta crystallographica. Section D, Biological crystallography; 1996; 52(Pt 6):1058-1066.

Hurle, M.R., et al., "A role for destabilizing amino acid replacements in light-chain amyloidosis." Proc Natl Acad Sci USA; 1994; 91(12):5446-5450.

Kawaguchi, M., et al., "Development and cellular application of visible-light-controllable HNA releasers based on caged Piloty's acid." Chem. Comm.; 2018; 54; 10371-10374.

Kitamura, K., et al., "Visible light-induced nitric oxide release from a novel nitrobenzene derivative cross-conjugated with a coumarin fluorophore." Bioorg. Med. Chem. Lett.; 2014; 24(24); 5660-5662.

Kloiber, K., et al., "Longitudinal exchange: an alternative strategy towards quanitifcation of dynamics parameters in ZZ exhcnage spectroscopy." J Biomol NMR; 2011; 51(1-2): 123-129.

Kourelis, T.V., et al., "Clarifying immunoglobulin gene usage in systemic and localized immunoglobulin light-chain amyloidosis by mass spectrometry." Blood;2017; 129(3):299-306.

Lavatelli, F., et al., "Amyloidogenic and associated proteins in systemic amyloidosis proteome of adipose tissue." Mol Cell Proteomics; 2008; 7(8):1570-1583.

Liao, R., et al., "Infusion of light chains from patients with cardiac amyloidosis causes diastolic dysfunction in isolated mouse hearts." Circulation; 2001; 104(14):1594-1597.

Makley, L.N., et al., " Pharmacological chaperone for alpha-crystallin partially restores transparency in cataract models." Science; 2015; 350(6261):674-677.

Matos, M.J., et al., "Focusing on New Monoamine Oxidase Inhibitors: Differently Substituted Coumarins As An Interesting Scaffold." Current Topics in Medicinal Chemistry; Jan. 1, 2012; pp. 2210-2239; vol. 12(20); Bentham Science Publishers Ltd.; Hilversum, NL.

Maurer, M.S., et al., "Tafamidis Treatment for Patients with Transthyretin Amyloid Cardiomyopathy." N Engl J Med; 2018; 379(11):1007-1016.

McGovern, S.L., et al., "A common mechanism underlying promiscuous inhibitors from virtual and high-throughput screening." J Med Chem; 2002; 45(8):1712-1722.

Merlini, G., et al., "Systemic immunoglobulin light chain amyloidosis." Nat Rev Dis Primers; 2018; 4(1):38.

Milani, P., et al., "Novel Therapies in Light Chain Amyloidosis." Kidney Int Rep; 2018; 3(3):530-541.

Morgan, G.J., et al, "The Kinetic Stability of a Full-Length Antibody Light Chain Dimer Determines whether Endoproteolysis Can Release Amyloidogenic Variable Domains." J Mol Biol; 2016; 428(21):4280-4297.

Morgan, G.J., et al., "Incomplete Refolding of Antibody Light Chains to Non-Native, Protease-Sensitive Conformations Leads to Aggregation: A Mechanism of Amyloidogenesis in Patients?" Biochemistry; 2017; 56(50):6597-6614.

Morgan, Gareth, "Small molecule stabilizers of amyloidogenic antibody light chains." Oral presentation (#OP28) made at the XVI International Symposium on Amyloidosis; Mar. 27, 2018.

Morgan, G.J., et al., "Stabilization of amyloidogenic immunoglobulin light chains by small molecules." Proceedings of the National Academy of Sciences; Apr. 23, 2019; pp. 8360-8369; vol. 116(17).

Oberti, L., et al., "Concurrent structural and biophysical traits link with immunoglobulin light chains amyloid propensity." Sci Rep; 2017; 7(1):16809.

Olsen, K.E., et al., "Fragments of the constant region of immunoglobulin light chains are constituents of AL-amyloid proteins." Biochem Biophys Res Commun; 1998; 251(2):642-647.

Palladini, G., et al., "New criteria for response to treatment in immunoglobulin light chain amyloidosis based on free light chain measurement and cardiac biomarkers: impact on survival outcomes." J Clin Oncol; 2012; 30(36):4541-4549.

Palladini, G., et al., "Presentation and outcome with second-line treatment in AL amyloidosis previously sensitive to hontransplant therapies." Blood; 2018; 131(5):525-532.

Pan, S., et al., "A reaction-based ratiometric fluorescent sensor for the detection of Hg(II) ions in both cells and bacteria." Chem. Comm.; 2018; 39(54); 4955-4958.

Pantoliano, M.W., et al., "High-density miniaturized thermal shift assays as a general strategy for drug discovery." J Biomol Screen; 2001; 6(6):429-440.

Perfetti, V., et al., "Evidence that amyloidogenic light chains undergo antigen-driven selection." Blood; 1998; 91(8):2948-2954.

Pokkuluri, P.R., et al., Tertiary structure of human lambda 6 light chains. Amyloid : the international journal of experimental and clinical investigation : the official journal of the International Society of Amyloidosis; 1999; 6(3):165-171.

Ramirez-Alvarado, M. "Amyloid formation in light chain amyloidosis." Curr Top Med Chem; 2012; 12(22); 2523-2533.

Renella, E., et al., "The role of domain interactions in the aggregation of full-length immunoglobulin light chains." Proc. Natl. Acad. Sci. USA; 2018; 116; 854-863.

Rosenblum, H., et al., "TTR (Transthyretin) Stabilizers Are Associated with Improved Survival in Patients with TTR Cardiac Amyloidosis." Circ Heart Fail; 2018; 11(4); e004769; 1-9.

Schiffer, M., et al. "Structure of a λ-type Bence-Jones protein at 3.5-Å resolution." Biochemistry; 1973; 12(23):4620-4631.

Sekijima, et al., Orally administered diflunisal stabilizes transthyretin against dissociation required for amyloidogenesis. Amyloid; 2006 13(4):236-249.

Sellam, et al., "Potentiation of fluindione or warfarin by dexamethasone in multiple myeloma and AL amyloidosis." Joint Bone Spine; Oct. 1, 2007; pp. 446-452; vol. 74(5); Elsevier; Amsterdam, NL.

Sikkink, L.A., et al.,"Salts enhance both protein stability and amyloid formation of an immunoglobulin light chain." Biophys Chem; 2008;135(1-3): 25-31.

Sipe, J.D., et al., "Amyloid fibril proteins and amyloidosis: chemical identification and clinical classification International Society of Amyloidosis 2016 Nomenclature Guidelines." Amyloid : the international journal of experimental and clinical Investigation : the official journal of the International Society of Amyloidosis; 2016; 23(4):209-213.

Traven, V.F. et al., "Photoinduced formation of the laser dye coumarin 6 from its dihydro derivatives." Dyes and Pigments; Jul. 3, 2017; pp. 159-168; vol. 146(3); Elsevier Applied Science Publishers; Barking, GB.

Wall, J., et al. "Thermodynamic instability of human l 6 light chains: correlation with fibrillogenicity." Biochemistry; 1999; 38(42):14101-14108.

Wolwertz, M.L., et al. "Probing the role of lambda6 immunoglobulin light chain dimerization in amyloid formation." Biochim Biophys Acta; 2016; 1864(4):409-418.

(56) References Cited

OTHER PUBLICATIONS

Yuwen, T., et al. "Dramatic Decrease in CEST Measurement Times Using Multi-Site Excitation." Chemphyschem; 2018; 19(14):1707-1710.
Zhang, J.H., et al., "A Simple Statistical Parameter for Use in Evaluation and Validation of High Throughput Screening Assays." J Biomol Screen; 1999; 4(2):67-73.
Zhou, J., et al., "A ratiometric fluorescent probe for fast and sensitive detection of peroxynitrite: a boronate ester as the receptor to initiate a cascade reaction" RSC Adv.; 2014; 93(4); pp. 51589-51592.
Reddy et al. Antimicrobial Agents and Chemotherapy, 2014, v. 58, pp. 3312-3326.
Kaur et al. J. Biomol. Structure and Dynamics, 2016, pp. 3043-3060.
"STN Search Report 1", from the product catalog provided by Aurora Fine Chemicals, etc., "Database Registry (online)", CAS registration No. 1327686-08-7, etc. (2011).

STABILIZATION OF AMYLOIDOGENIC IMMUNOGLOBULIN LIGHT CHAINS

RELATED APPLICATIONS

The present application claims the benefit of priority to U.S. Provisional Patent Application No. 62/826,476, filed on Mar. 29, 2019, and which application is incorporated by reference as if fully set forth herein.

STATEMENT OF GOVERNMENT SUPPORT

The present application is a 371 of PCT/US2020/025607, filed Mar. 29, 2020, which claims the benefit of priority to U.S. Provisional Patent Application No. 62/826,476, filed on Mar. 29, 2019, and which is applications are incorporated by reference as if fully set forth herein.

BACKGROUND

Light chain (LC) amyloidosis is a progressive and often fatal degenerative disease caused by conformational changes within immunoglobulin light chains after secretion by clonal plasma cells that result in organ toxicity, e.g. cardiomyopathy, nephrotic syndrome and end-stage renal failure. The light chain conformational changes also often lead to light chain aggregation, which may also drive proteotoxicity in some post-mitotic tissues. The pathologic mechanisms of disease leading to organ toxicity include both toxicity of amyloidogenic LC and mass effects of deposits, both modulated by misfolded LC concentration. Light chain amyloidosis patients are treated today by targeting the cancer component of this disease (proliferating clonal plasma cells) employing chemotherapy cocktails typically involving proteasome inhibitors (and when possible, stem cell transplants), which ideally eliminate the clonal plasma cells secreting full-length light chains. However, complete clonal plasma cell eradication is achieved in only 30-40% of the patients and most eventually relapse. Organ response, as a measure of improvement in organ function, is often limited (<50%). Organ damage remains the major source of mortality and morbidity. Moreover, light chain amyloidosis patients exhibiting cardiac involvement are often too sick to tolerate chemotherapy and die within a year of diagnosis.

SUMMARY

Light chain amyloidosis is caused by conformational changes within immunoglobulin light chains that generally lead to aggregation. Current chemotherapy treatments aim to eliminate the clonal plasma cells that secrete full-length light chains; however, complete eradication is achieved in only 30-40% of the patients. The kinetic stabilizer strategy introduced herein does not require an understanding of the non-native light chain structure-proteotoxicity relationships driving organ degeneration in light chain amyloidosis (AL) to be successful at stopping disease progression because it stops light chain conformational excursions at the beginning of the aggregation cascade. The small molecule kinetic stabilizers identified herein bind to conserved residues at the variable domain-variable domain interface in the native dimer, stabilizing this putative non-toxic structure. Without being bound by any theory, we hypothesize that small molecule kinetic stabilizers of immunoglobulin light chains will be successful at stopping disease progression because they stop light chain conformational excursions at the beginning of the aggregation cascade. These function strictly analogously to tafamidis, which has proven to be efficacious for the transthyretin amyloidoses. The small molecule kinetic stabilizers disclosed herein bind to conserved residues at the variable domain-variable domain interface in the native light chain dimer, stabilizing this putative non-toxic structure against the conformational changes and aggregation that cause light chain amyloidosis.

The present disclosure provides in various embodiments an LC kinetic stabilizer, i.e., a compound of Formula Ia, Formula Ib, Formula II or a pharmaceutically acceptable salt thereof as defined herein:

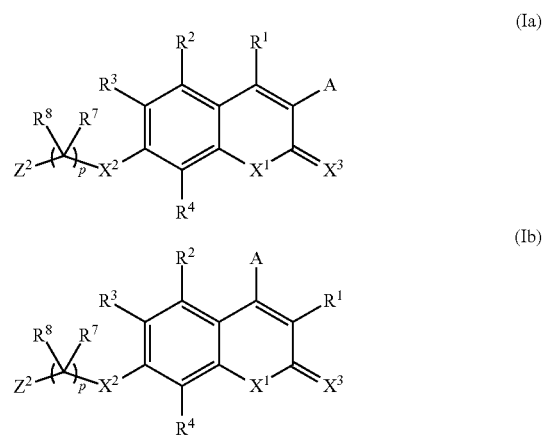

wherein
A is H or

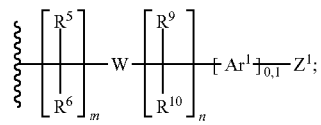

$X^1$ is O or $NR^0$;
$X^2$ is selected from the group consisting of a bond, $NR^{12}$, O, C(O), C(O)$NR^{11}$, and $CR^{12}R^{11}$;
$X^3$ is O or $NR^{13}$;
W is selected from the group consisting of a bond, OC(O), C(O)O, C(O)$NR^{14}$, $NR^{14}$C(O)O, OC(O)$NR^{14}$, $NR^{14}$C(O), $NR^{14}$C(O)$NR^{15}$, $NR^{14}$,

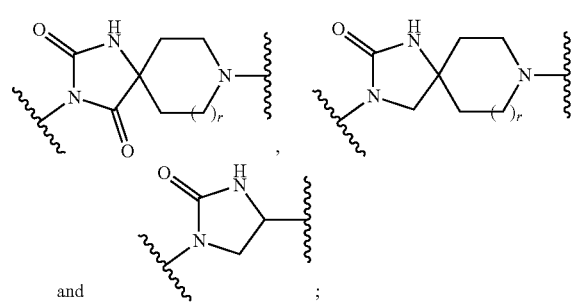

m is an integer selected from 1, 2, 3, 4, 5, and 6;
n is an integer selected from 0, 1, 2, 3, 4, 5, and 6;
p is an integer selected from 0, 1, 2, 3, 4, 5, and 6;
r is an integer selected from 0, 1, 2, and 3;

$Z^1$ is selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S), halogen, $NR^{16}R^{17}$, $COOR^{18}$; $OR^{18}$, $NR^{16}SO_2R^{18}$, $NR^{16}COR^{18}$, $X^4(CR^{21}R^{22})_aCONR^{16}R^{17}$, $X^4(CR^{21}R^{22})_aCOOR^{18}$, $X^4(CR^{21}R^{22})_aCOR^{18}$, $X^4(CR^{21}R^{22})_aNR^{16}R^{17}$, $X^4(CR^{21}R^{22})_aOR^{18}$, $SO2NR^{16}R^{17}$, $X^4(CR^{21}R^{22})_aNR^{16}COR^{18}$, $C(N{=}R^{23})NR^{24}OH$, and

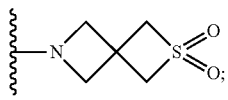

wherein
$X^4$ is a bond, 0, or $NR^0$; and
a is an integer selected from 0, 1, 2, 3, 4, 5, and 6;
$Z^2$ is selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_2$-$C_6$-alkynyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S), CN, $OR^{18}$ and $NR^{19}R^{20}$;
$Ar^1$ is a divalent moiety selected from $C_6$-$C_{10}$-arylene and 5- to 10-membered heteroarylene wherein 1-4 heteroaryl members are independently selected from N, O, and S;
$R^1$ is selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S), OH, $(CR^{21}R^{22})_bOR^{18}$ (b is an integer selected from 0, 1, 2, 3, 4, 5, and 6), halogen, and $(C_1$-$C_6)$haloalkyl;
$R^2$, $R^3$, and $R^4$ are independently selected from the group consisting of H, $C_1$-$C_6$-alkyl, —($C_1$-$C_6$-alkyl)($C_6$-$C_{10}$-aryl), OH, $(CR^{21}R^{22})_bOR^{18}$, halogen, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S);
$R^0$ and $R^5$-$R^{22}$ are independently selected from the group consisting of H, $C_1$-$C_6$-alkyl, $C_1$-$C_6$-haloalkyl, $C_3$-$C_8$-cycloalkyl, 3- to 6-membered heterocycloalkyl (wherein 1-4 ring members are independently selected from N, O, and S), $C_2$-$C_6$-alkenyl, $C_2$-$C_6$-alkynyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S);
$R^{16}$ and $R^{17}$ are independently selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S), $C(O)OR$'s, $C(O)R^{18}$, and $SO_2R^{18}$;
$R^{14}$ and $R^9$, together with the atoms to which they are bound, optionally are a 3- to 8-membered ring;
$R^{15}$ and $R^9$, together with the atoms to which they are bound, optionally are a 3- to 8-membered ring;
$R^{16}$ and $R^9$, together with the atoms to which they are bound, optionally are a 3- to 8-membered ring;
$R^{16}$ and $R^{14}$, together with the atoms to which they are bound, optionally are a 3- to 8-membered ring;
$R^{16}$ and $R^{15}$, together with the atoms to which they are bound, optionally are a 3- to 8-membered ring;
$R^{16}$ and $R^{17}$, together with the atoms to which they are bound, optionally are a 3- to 8-membered ring wherein ring members are selected from C, O and N;
$R^{19}$ and $R^{20}$, together with the atoms to which they are bound, optionally are a 3- to 8-membered ring;
$R^{21}$ and $R^{22}$, together with the atoms to which they are bound, optionally are a 3- to 8-membered ring;
OR
a compound according to Formula II, or a pharmaceutically acceptable salt thereof:

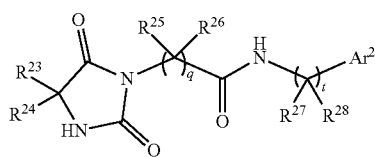

(II)

wherein
$R^{23}$-$R^{28}$ are independently selected from the group consisting of H, halo, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S); $Ar^2$ is $C_6$-$C_{10}$-aryl or 5- to 10-membered heteroaryl (wherein 1-4 heteroaryl members are independently selected from N, O, and S;

q is an integer selected from 0, 1, 2, 3, and 4;

t is an integer selected from 0, 1, 2, 3, and 4;

wherein any alkyl, cycloalkyl, heterocycloalkyl, alkenyl, cycloalkenyl, heterocycloalkenyl, aryl, heteroaryl, and ring moiety in Formula Ia, Formula Ib, or Formula II is optionally substituted with one to six substituents selected from the group consisting of hydroxy, halo, $C_1$-$C_6$-haloalkyl, —$NR'_2$ (wherein each R' is independently selected from the group consisting of H, $C_1$-$C_6$-alkyl, $C_2$-$C_6$-alkenyl, $C_2$-$C_6$-alkynyl, and $C_6$-$C_{10}$-aryl), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl ($C_1$-$C_6$-alkoxy), —C(O)$NH_2$, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_6$-$C_{10}$-aryl), 3- to 14-membered heterocycloalkyl and —($C_1$-$C_6$-alkyl)-(3- to 14-membered heterocycle) (wherein 1-4 heterocycle members are independently selected from N, O, and S), and —O($C_6$-$C_{14}$-aryl).

In some embodiments, the compound of Formula Ia, Formula Ib, and Formula II does not include any of the following compounds:

1

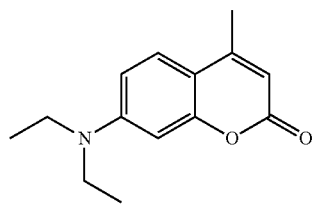

2

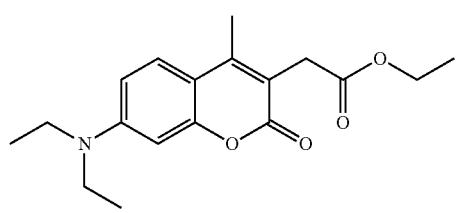

3

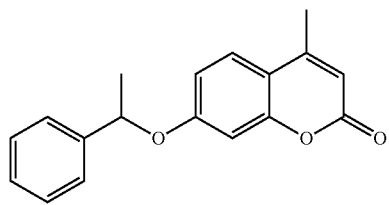

4

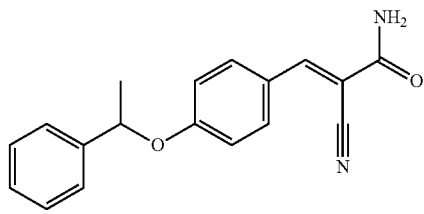

8

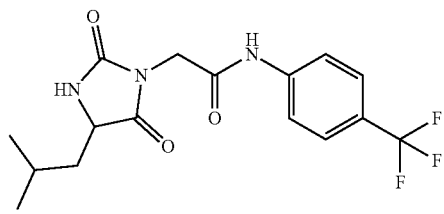

9

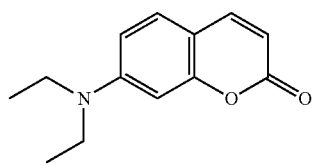

10

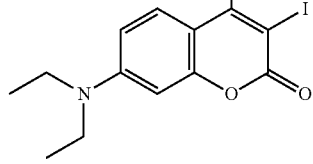

11

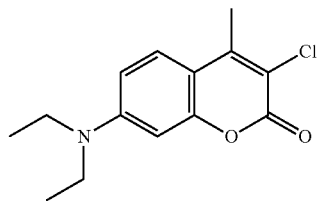

12

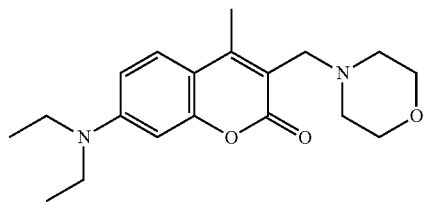

13

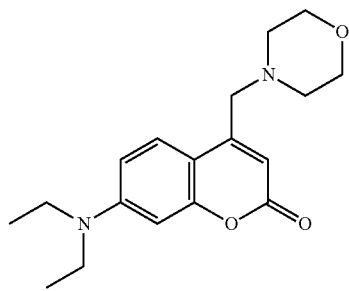

14
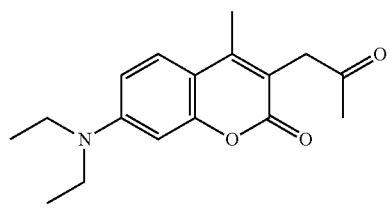
15
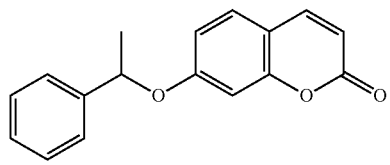
19
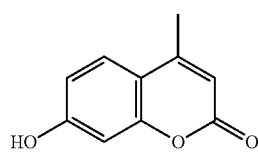
20
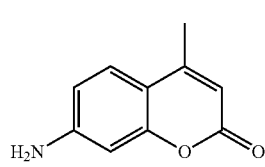
21
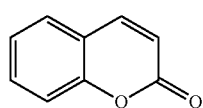
24
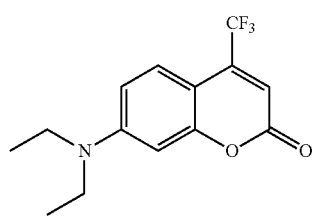
25
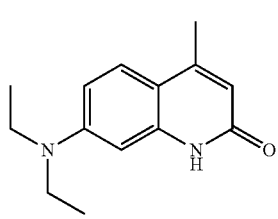
26
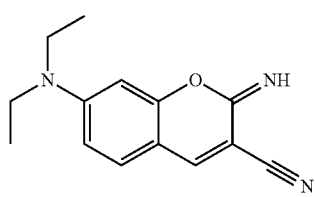
28
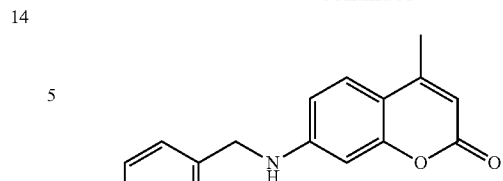
33
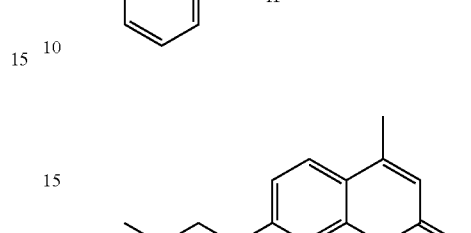
35
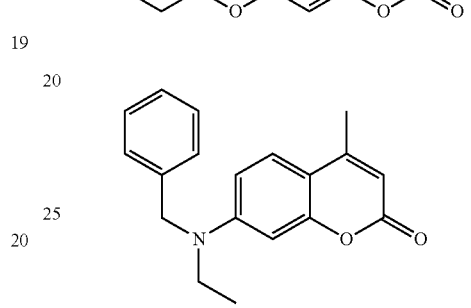
36
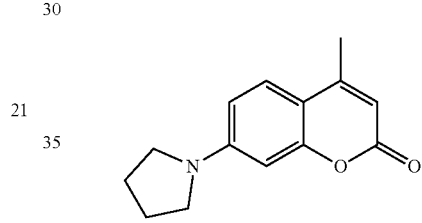
38
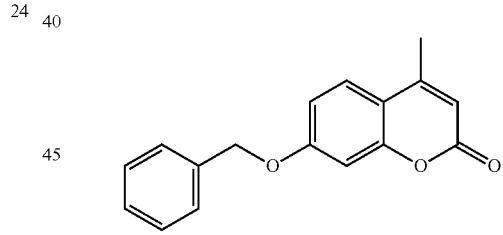
50
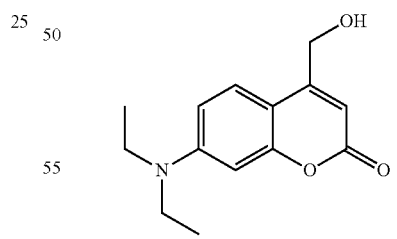
54
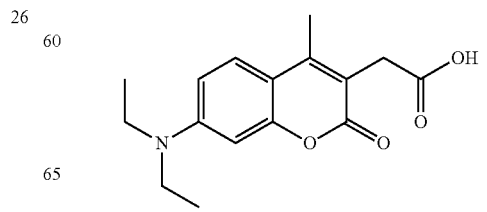

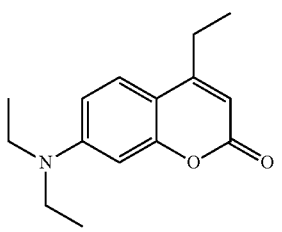

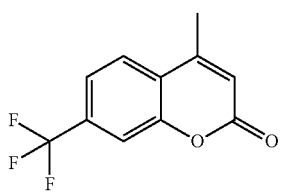

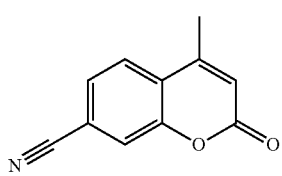

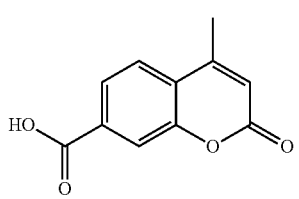

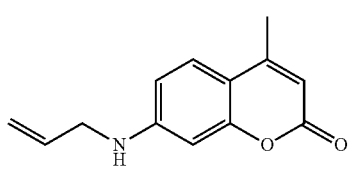

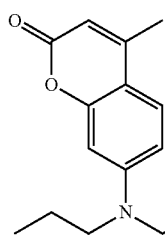

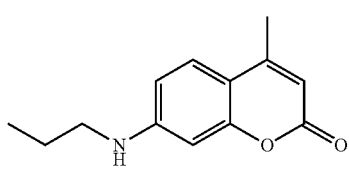

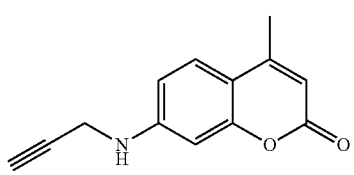

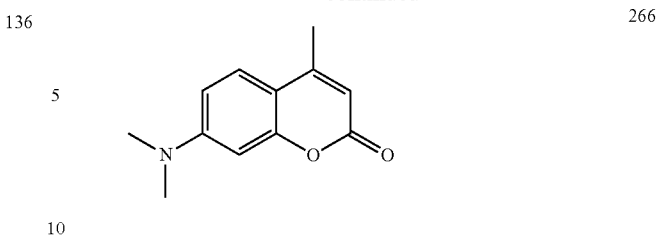

In various embodiments, provided is a method of stabilizing an immunoglobulin light chain dimer in a native conformation thereof, comprising contacting the dimer and an effective amount of any compound described herein, including all enumerated compounds, such as any one of the formulae 1-21 (see Table 1, below).

Further, in various embodiments, provided is a method of treatment of light chain amyloidosis in a patient, comprising administering to the patient an effective amount of any compound described herein, including all enumerated compounds, such as any one of the formulae 1-21 (see Table 1, below).

The present disclosure also provides in an embodiment a pharmaceutical composition comprising a compound of Formula Ia, Formula Ib, Formula II, or any enumerated compound described herein, in combination with a pharmaceutically acceptable carrier.

Figure 1A:
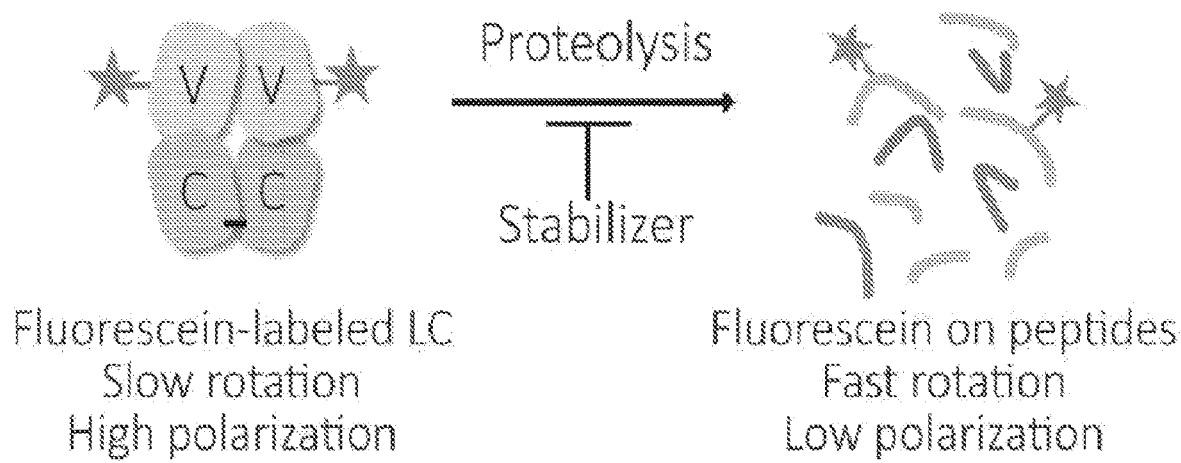
FIG. 1: High-throughput screen for LC kinetic stabilizers. a) LCs consist of variable (V, yellow) and constant (C, grey) immunoglobulin domains, which form homodimers linked by a disulfide bond between C214 residues (black line). Cleavage of dye-labeled protein by protease leads to a decrease in FP in the resulting peptides. The rate of proteolysis depends on a LC's kinetic stability, which can be enhanced by the binding of a stabilizing small molecule. b) Proteolysis of fluorescein-labeled and unlabeled LCs, co-incubated with 100 nM PK and visualized by SDS-PAGE. Symbols show normalized band intensities and lines show fits to a single exponential decay model, n=3. Black, Coomassie stained total LC (10 µM); green, fluorescence of labeled LC (20 nM). c) Kinetics of fluorescein-labeled LC proteolysis measured by FP at 37° C. in a fluorimeter cuvette. Lines show fits to a single exponential decay model. d) Kinetics of proteolysis measured by FP in a 384-well plate at 22° C. Points show data for individual wells and lines show the mean, n=16. e) The extent of proteolysis after 24 h at 22° C. depends on the concentration of the LC-stabilizing kosmotrope $Na_2SO_4$, but not on the concentration of protease. f) Post-proteolysis compound addition to LCs identifies false-positive screen hits. Each point represents the mean measurement (n=3) for a single compound. Green shaded areas indicate compounds considered to be hits. g) Compounds that provide protection from both serine protease PK and metalloprotease thermolysin (green area) are likely to be stabilizers of LCs, rather than protease inhibitors.

μM). c) Titrations of LC constructs into 1 (1 μM), n=3. Lines indicate fits to a one-site binding model. d) Affinities of 1 for recombinant LC variants, n=3, measured as for (c). e) SV-AUC of WIL-FL C214S (20 μM) and WIL-V (20 μM) in the absence (red) or presence (blue) of 1 (100 μM). Data for dimeric WIL-FL (20 μM) are shown in grey. f) Titration of κ I O18/O8-FL (blue) and AL12-FL (red) into 1 (1 μM). Data for WIL-FL (grey) are shown for comparison. Inset: fluorescence spectra of 1 (1 μM) in PBS (dashed grey line) or the presence of 20 μM κ I O18/O8-FL (blue) or AL12-FL (red). g) Competition of 1 (1 μM) for the WIL-FL binding site indicates that the presence of other hit molecules (10 μM) reduces binding of 1 (1 μM). The unrelated molecule diflunisal (Dif) does not compete with 1 for LC binding. h) Binding of 1 to human serum albumin (HSA) in the presence or absence of diflunisal determined by fluorescence of 1, measured as for (c). i) Fluorescence of 1 in the presence of the LC homodimer (black) or LC:HC heterodimer (Fab, red) of the human IgG antibody 5J8.

FIG. 3: Kinetic stabilizer binding to the V-domain-V-domain dimer interface. Crystal structures of JTO-FL with bound 1 (in orange) (LC blue, cyan) and without 1 (LC grey). a) Overview of structures aligned by one chain of the dimer. b) Kinetic stabilizer 1 binds in a pocket formed by the side chains of residues 44, 87 and 98 from one protomer and 36', 44', and 46' from the other protomer. Residues are numbered according to the Kabat system. c) Surface representation of the binding site region. 1 binds in a pocket that is not present in the unliganded LC. d) Conservation of binding site residues in human germline LC genes mapped onto the JTO-FL•1 structure. Red, highly conserved residues; blue, weakly conserved residues.

FIG. 4: Kinetic stabilizer 1 binds to LCs in solution. a) Superposition of selected region of $^1H$-$^{15}N$ HSQC NMR spectra of WIL-FL (0.05 mM monomeric concentration) in the absence (blue contours) or presence of 1 at LC:1 ratios (LC monomer:ligand) of 1:0.8 (red) and 1:2.2 (green). b) Residues with combined chemical shift changes $\Delta\overline{\omega}_{HN}$ larger than 0.1 ppm upon binding of 1 are mapped as red spheres onto the structure of the JTO-FL•1 complex; the ligand is shown as yellow or green sticks in the two possible but mutually exclusive binding sites. c) Intensity of peaks associated with free LC dimer ($LC_2$, blue) and complex ($LC_2$•1, green) as a function of 1 binding to WIL-FL. d) HSQC spectral region highlighting correlations for residue Q38 of JTO-V. Colors are as for (a). Note the presence of exchange peaks connecting free and ligand bound correlations when approximately equal amounts of $LC_2$ and 1 are added. e) $^{15}N$ transverse relaxation rates ($R_2$) for WIL-V (averaged over 29 residues) and JTO-V (32 residues) with (green) or without (blue) addition of 1. f) Spectra of WIL-V residue Q38, in the absence (blue) or presence of 1, at LC:1 ratios of 1:0.9 (red) and 1:2.2 (green). Note that the cross peaks from the bound form at LC:1 of 1:0.9 are broadened.

FIG. 5: Small molecule kinetic stabilizer binding stabilizes LCs against proteolysis, unfolding and aggregation. a) Proteolysis of recombinant WIL-FL C214S (10 μM) in the presence of vehicle (red) or 1 (100 μM; blue). Symbols show LC band quantitation and lines show fits to a single exponential decay model. b) Unfolding rates of WIL-FL (5 μM) in the presence of 5 (Table 1; 50 μM; orange) or vehicle (red) as a function of urea concentration. Symbols represent rates calculated for individual kinetic transients and lines are fits to a 2-state unfolding model. c) Equilibrium urea titrations of WIL-FL (5 μM) in the presence of 1 (100 μM; blue symbols), 5 (Table 1; 50 μM; orange symbols) or vehicle (red symbols). d) NMR hydrogen-deuterium exchange measurements of JTO-V (100 μM, left panel) and WIL-V (200 μM right panel) in the presence (blue) or absence (red) of 1 (400 μM). Exchange rates were converted to free energies. Symbols show residues for which rates could be measured. Dashed lines indicate the average stability for each V-domain. e) Proteolysis of the plasma cell-secreted LC, ALMC2 (5 μM), in the presence of vehicle (red) or 1 (100 μM; blue). The line represents a fit to a single exponential decay model. f) Residual soluble WIL-FL C214S dimer (10 uM) measured by SEC at pH 5, 37° C. in the presence (blue) or absence (red) of 1 (200 μM), as a function of time to assess aggregation kinetics by starting material disappearance. Individual reactions are shown by dashed lines; curves represent fits of all samples in a category (±1) to a single exponential decay model.

DETAILED DESCRIPTION

In AL, the current treatments aim to eradicate the clonal plasma cells that secrete FL LCs (2, 46). However, complete suppression of the production of amyloidogenic light chain (a complete hematologic response) is achieved in only 30-40% of the patients and most eventually relapse. Kinetic stabilization of LCs is unlikely to contribute to plasma cell death but could reduce organ proteotoxicity and the progression of AL. Patients with prominent cardiac involvement currently have few available options for treatment and represent an urgent unmet medical need, as they are often too sick to tolerate chemotherapy. Kinetic stabilizer pretreatment is useful by allowing these patients to tolerate chemotherapy. In this context, FL LC stabilization also is useful in a method for maintenance therapy upon recurrence of AL after treatment. Because reemergence of the clonal plasma cells is generally slow, organ toxicity caused by conformationally unstable circulating LC can be minimized by kinetic stabilizer treatment (47).

An advantage of the small molecule LC kinetic stabilizers disclosed herein is their ability to bind to and stabilize the FL LCs of most patients because conserved residues comprise the kinetic stabilizer binding site. Thus, in accordance with an embodiment, the present disclosure provides a method for identifying patients whose LCs are amenable to kinetic stabilization by measuring susceptibility of their LC in plasma to PK endoproteolysis in the presence and absence of the kinetic stabilizer, determining the relative difference in susceptibilities, and identifying the patients most likely to benefit from kinetic stabilization of LCs.

Definitions

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(C H$_3$)$_2$, and the like. Thus, alkyl groups include primary alkyl groups, secondary alkyl groups, and tertiary alkyl groups. An alkyl group can be unsubstituted or optionally substituted at 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F or fluoro, —Cl or chloro, —Br or bromo, or —I or iodo.

The term "alkenyl" refers to straight or branched chain hydrocarbyl groups including from 2 to about 20 carbon atoms having 1-3, 1-2, or at least one carbon to carbon double bond. An alkenyl group can be unsubstituted or optionally substituted with one or more substituents at 1 or more, e.g., 1, 2, 3, 4, 5, or even 6 positions, which substituents are attached at any available atom to produce a stable compound, with substitution as described herein. "Optionally substituted alkenyl" refers to alkenyl or substituted alkenyl.

"Alkyne or "alkynyl" refers to a straight or branched chain unsaturated hydrocarbon having the indicated number of carbon atoms, such as 2 to 6, and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents at 1 or more, e.g., 1, 2, 3, 4, 5, or even 6 positions, which substituents are attached at any available atom to produce a stable compound, with substitution as described herein. "Optionally substituted alkynyl" refers to alkynyl or substituted alkynyl.

The term "cycloalkyl" refers to a saturated monocyclic, bicyclic, tricyclic, or polycyclic, 3- to 14-membered ring system, such as a $C_3$-$C_8$-cycloalkyl. The cycloalkyl may be attached via any atom. Representative examples of car cycloalkyl bocyclyl include, but are not limited to cyclopropyl, cyclobutyl, cyclopentyl, and cyclohexyl. A cycloalkyl group can be unsubstituted or optionally substituted with one or more substituents at 1 or more, e.g., 1, 2, 3, 4, 5, or even 6 positions, which substituents are attached at any available atom to produce a stable compound, with substitution as described herein.

"Aryl" when used alone or as part of another term means a carbocyclic aromatic group whether or not fused having the number of carbon atoms designated or if no number is designated, up to 14 carbon atoms, such as a $C_6$-$C_{14}$-aryl. Particular aryl groups are phenyl, naphthyl, biphenyl, phenanthrenyl, naphthacenyl, and the like (see e.g. *Lang's Handbook of Chemistry* (Dean, J. A., ed) 13th ed. Table 7-2 [1985]). A particular aryl is phenyl. "Aryl" can be optionally fused with a carbocyclyl ring, as herein defined. An aryl group can be unsubstituted or optionally substituted with one or more substituents attached at any available atom to produce a stable compound, wherein the substituents are as described herein. "Optionally substituted aryl" refers to aryl or substituted aryl.

The term "heteroatom" refers to N, O, and S. Compounds of the present disclosure that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, 1-pyrazolopyrimidinyl, imidazopyrazinyl, triazolopyrazinyl, and indolyl. A heteroaryl group can be unsubstituted or optionally substituted with one or more substituents, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" means a saturated or partially unsaturated non-aromatic monocyclic, bicyclic, tricyclic or polycyclic ring system that has from 3 to 14, such as 3 to 6, atoms in which from 1 to 3 carbon atoms in the ring are replaced by heteroatoms of O, S or N. A heterocycloalkyl is optionally fused with aryl or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A heterocycloalkyl group can be unsubstituted or optionally substituted with one or more substituents, such as 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

The term "oxo" refers to a =O atom bound to an atom that is part of a saturated or unsaturated moiety. Thus, the =O atom can be bound to a carbon, sulfur, or nitrogen atom that is part of a cyclic or acyclic moiety.

A "hydroxyl" or "hydroxy" refers to an —OH group.

The substituent —$CO_2H$ may be replaced with bioisosteric replacements such as:

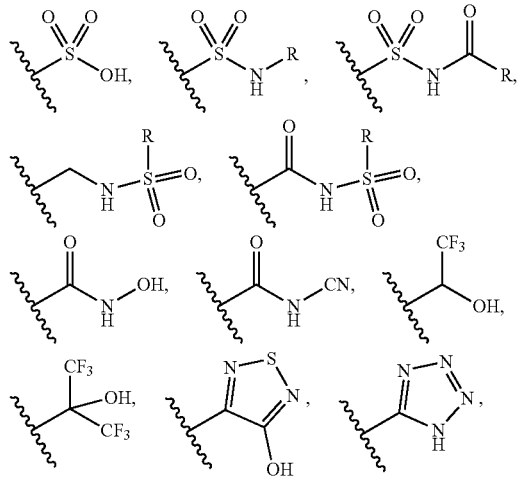

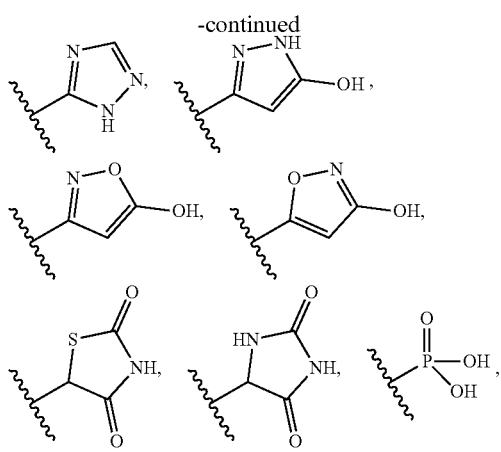

and the like, wherein R has the same definition as $R^A$ as defined herein. See, e.g., THE PRACTICE OF MEDICINAL CHEMISTRY (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified to the contrary, the term "compound" is inclusive in that it encompasses a compound or a pharmaceutically acceptable salt, stereoisomer, isotopologue, and/or tautomer thereof. Thus, for instance, a compound of Formula IA or Formula IB includes a pharmaceutically acceptable salt of a tautomer of the compound.

In this disclosure, a "pharmaceutically acceptable salt" is a pharmaceutically acceptable, organic or inorganic acid or base salt of a compound described herein. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In various embodiments, the terms refer to minimizing the spread or worsening of the disease resulting from the administration of one or more prophylactic or therapeutic compounds described herein to a patient with such a disease.

The terms "prevent," "preventing," and "prevention" refer to the prevention of the onset, recurrence, or spread of the disease in a patient resulting from the administration of a compound described herein.

The term "effective amount" refers to an amount of a compound as described herein or other active ingredient sufficient to provide a therapeutic or prophylactic benefit in the treatment or prevention of a disease or to delay or minimize symptoms associated with a disease. Further, a therapeutically effective amount with respect to a compound as described herein means that amount of therapeutic agent alone, or in combination with other therapies, that provides a therapeutic benefit in the treatment or prevention of a disease. Used in connection with a compound as described herein, the term can encompass an amount that improves overall therapy, reduces or avoids symptoms or causes of disease, or enhances the therapeutic efficacy of or is synergistic with another therapeutic agent.

A "patient" or subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult. In the present disclosure, the terms "patient" and "subject" are used interchangeably.

Compounds

The present disclosure provides in various embodiments an LC kinetic stabilizer, i.e., a compound of Formula Ia or Ib, or a pharmaceutically acceptable salt thereof:

(Ia)

(Ib)

wherein

A is H or

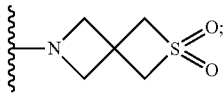 [SMILES: *N1CC2(C1)CS(=O)(=O)C2]

$X^1$ is O or $NR^0$;

$X^2$ is selected from the group consisting of a bond, $NR^{12}$, O, C(O), C(O)$NR^{11}$, and $CR^{12}R^{11}$;

$X^3$ is O or $NR^{13}$;

W is selected from the group consisting of a bond, OC(O), C(O)O, C(O)$NR^{14}$, $NR^{14}$C(O)O, OC(O)$NR^{14}$, $NR^{14}$C(O), $NR^{14}$C(O)$NR^{15}$, $NR^{14}$,

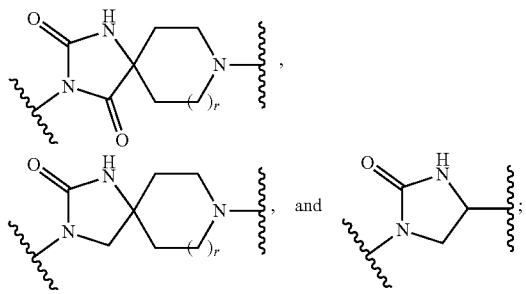

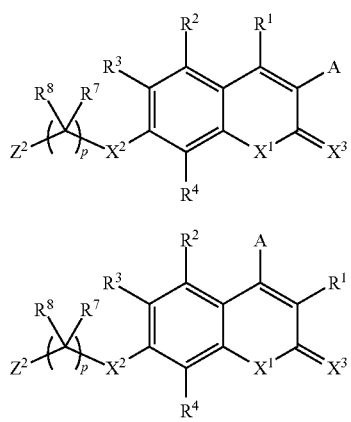

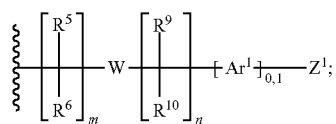

m is an integer selected from 1, 2, 3, 4, 5, and 6;
n is an integer selected from 0, 1, 2, 3, 4, 5, and 6;
p is an integer selected from 0, 1, 2, 3, 4, 5, and 6;
r is an integer selected from 0, 1, 2, and 3;
$Z^1$ is selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl) ($C_6$-$C_{10}$-aryl), —($C_1$-$C_6$-alkyl)(5- to 10-membered heteroaryl) (wherein 1-4 heteroaryl members are independently selected from N, O, and S), halogen, $NR^{16}R^{17}$, $COOR^{18}$, $OR^{18}$, $NR^{16}SO_2R^{18}$, $NR^{16}COR^{18}$, $X^4(CR^{21}R^{22})_aCONR^{16}R^{17}$, $X^4(CR^{21}R^{22})_aCOOR^{18}$, $X^4(CR^{21}R^{22})_aCOR^{18}$, $X^4(CR^{21}R^{22})_aNR^{16}R^{17}$, $X^4$ $(CR^{21}R^{22})_aOR^{18}$, $SO2NR^{16}R^{17}$, $X^4(CR^{21}R^{22})_a$ $NR^{16}COR^{18}$, $C(N=R^{23})NR^{24}OH$, and wherein $X^4$ is a bond, O, or $NR^0$; and
a is an integer selected from 0, 1, 2, 3, 4, 5, and 6;
$Z^2$ is selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_2$-$C_6$-alkynyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S), CN, $OR^{18}$ and $NR^{19}R^{20}$;
$Ar^1$ is a divalent moiety selected from $C_6$-$C_{10}$-arylene and 5- to 10-membered heteroarylene (wherein 1-4 heteroaryl members are independently selected from N, O, and S);
$R^1$ is selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S), OH, $(CR^{21}R^{22})_bOR^{18}$ (b is an integer selected from 0, 1, 2, 3, 4, 5, and 6), halogen, and ($C_1$-$C_6$)haloalkyl;

$R^2$, $R^3$, and $R^4$ are independently selected from the group consisting of H, $C_1$-$C_6$-alkyl, —($C_1$-$C_6$-alkyl)($C_6$-$C_{10}$-aryl), OH, $(CR^{21}R^{22})_bOR^{18}$, halogen, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S);

$R^0$ and $R^5$-$R^{22}$ are independently selected from the group consisting of H, $C_1$-$C_6$-alkyl, $C_1$-$C_6$-haloalkyl, $C_3$-$C_8$-cycloalkyl, 3- to 6-membered heterocycloalkyl (wherein 1-4 ring members are independently selected from N, O, and S), $C_2$-$C_6$-alkenyl, $C_2$-$C_6$-alkynyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S);

$R^{16}$ and $R^{17}$ are independently selected from the group consisting of H, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S), $C(O)OR^{18}$, $C(O)R^{18}$, and $SO_2R^{18}$;

$R^{14}$ and $R^9$, together with the atoms to which they are bound, optionally are a 3- to 8-membered ring;

$R^{15}$ and $R^9$, together with the atoms to which they are bound, optionally are a 3- to 8-membered ring;

$R^{16}$ and $R^9$, together with the atoms to which they are bound, optionally are a 3- to 8-membered ring;

$R^{16}$ and $R^{14}$, together with the atoms to which they are bound, optionally are a 3- to 8-membered ring;

$R^{16}$ and $R^{15}$, together with the atoms to which they are bound, optionally are a 3- to 8-membered ring;

$R^{16}$ and $R^{17}$, together with the atoms to which they are bound, optionally are a 3- to 8-membered ring wherein ring members are selected from C, O and N;

$R^{19}$ and $R^{20}$, together with the atoms to which they are bound, optionally are a 3- to 8-membered ring;

$R^{21}$ and $R^{22}$, together with the atoms to which they are bound, optionally are a 3- to 8-membered ring;

OR a compound according to Formula II, or a pharmaceutically acceptable salt thereof:

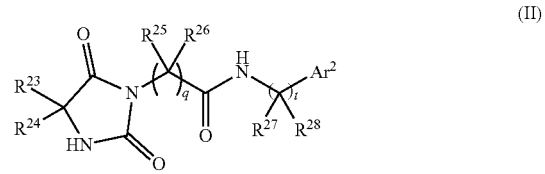

(II)

wherein $R^{23}$-$R^{28}$ are independently selected from the group consisting of H, halo, $C_1$-$C_6$-alkyl, $C_3$-$C_8$-cycloalkyl, 3- to 6-membered heterocycloalkyl (wherein 1-4 ring members are independently selected from N, O, and S), $C_2$-$C_6$-alkenyl, $C_3$-$C_8$-cycloalkenyl, 3- to 6-membered heterocycloalkenyl (wherein 1-4 ring members are independently selected from N, O, and S), $C_6$-$C_{10}$-aryl, 5- to 10-membered heteroaryl (wherein 1-4 heteroaryl members are independently selected from N, O, and S), —($C_1$-$C_6$-alkyl)($C_6$-$C_{10}$-aryl), —($C_1$-$C_6$-alkyl)(5- to 10-membered heteroaryl) (wherein 1-4 heteroaryl members are independently selected from N, O, and S);

$Ar^2$ is $C_6$-$C_{10}$-aryl or 5- to 10-membered heteroaryl (wherein 1-4 heteroaryl members are independently selected from N, O, and S;

q is an integer selected from 0, 1, 2, 3, and 4;

t is an integer selected from 0, 1, 2, 3, and 4;

wherein any alkyl, cycloalkyl, heterocycloalkyl, alkenyl, cycloalkenyl, heterocycloalkenyl, aryl, heteroaryl, and ring moiety in Formula Ia, Formula Ib, or Formula II is optionally substituted with one to six substituents selected from the group consisting of hydroxy, halo, $C_1$-$C_6$-haloalkyl, —$NR'_2$ (wherein each R' is independently selected from the group consisting of H, $C_1$-$C_6$-alkyl, $C_2$-$C_6$-alkenyl, $C_2$-$C_6$-alkynyl, and $C_1$-$C_{10}$-aryl), —NHC(O)(O$C_1$-$C_6$-alkyl), —$NO_2$, —CN, oxo, —C(O)OH, —C(O)O($C_1$-$C_6$-alkyl), —$C_1$-$C_6$-alkyl ($C_1$-$C_6$-alkoxy), —C(O)$NH_2$, —C(O)$C_1$-$C_6$-alkyl, —O$C_1$-$C_6$-alkyl, —Si($C_1$-$C_6$-alkyl)$_3$, —S(O)$_{0-2}$—($C_1$-$C_6$-alkyl), $C_6$-$C_{10}$-aryl, —($C_1$-$C_6$-alkyl)($C_1$-$C_{10}$-aryl), 3- to 14-membered heterocycloalkyl and —($C_1$-$C_6$-alkyl)-(3- to 14-membered heterocycle) (wherein 1-4 heterocycle members are independently selected from N, O, and S), and —O($C_6$-$C_{14}$-aryl).

It should be understood that, notwithstanding the definitions of Formula Ia, Formula Ib, and Formula II, in some embodiments the compound does not include any of the following compounds:

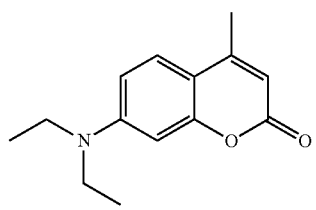

1

2
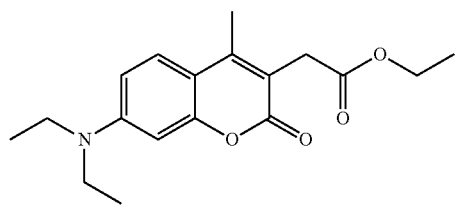
3
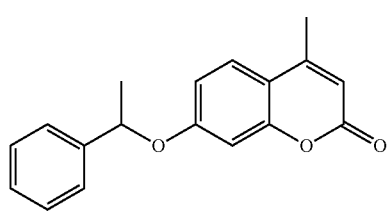
4
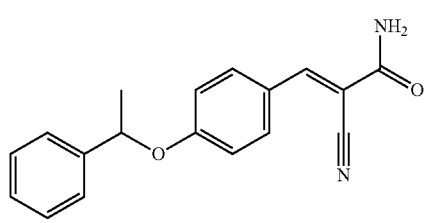
8
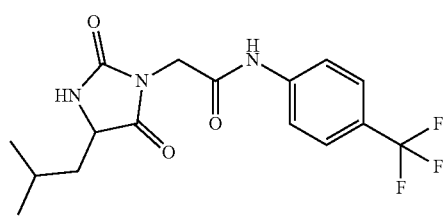
9
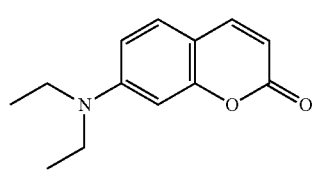
10
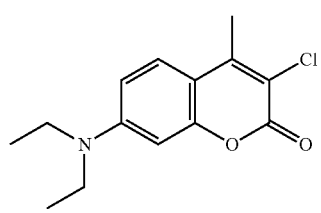
11
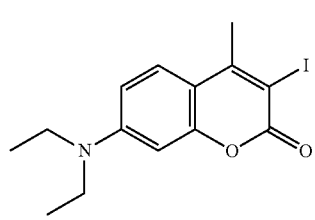
12
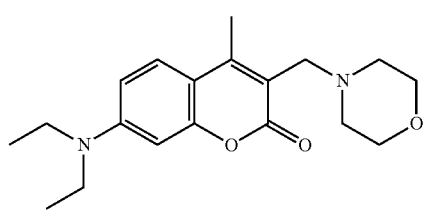
13
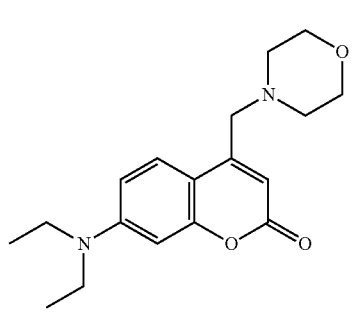
14
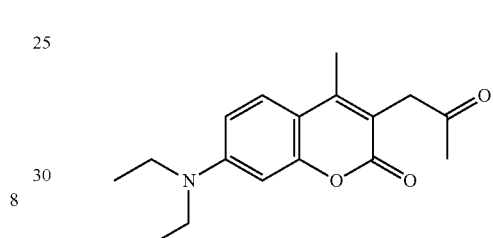
15
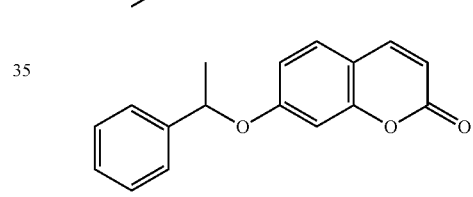
19
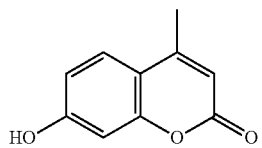
20
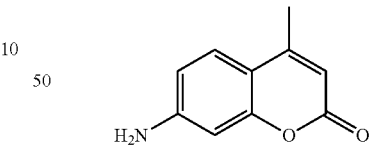
24
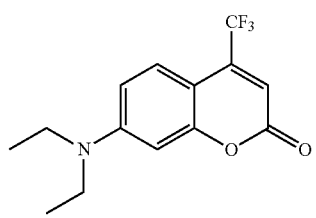

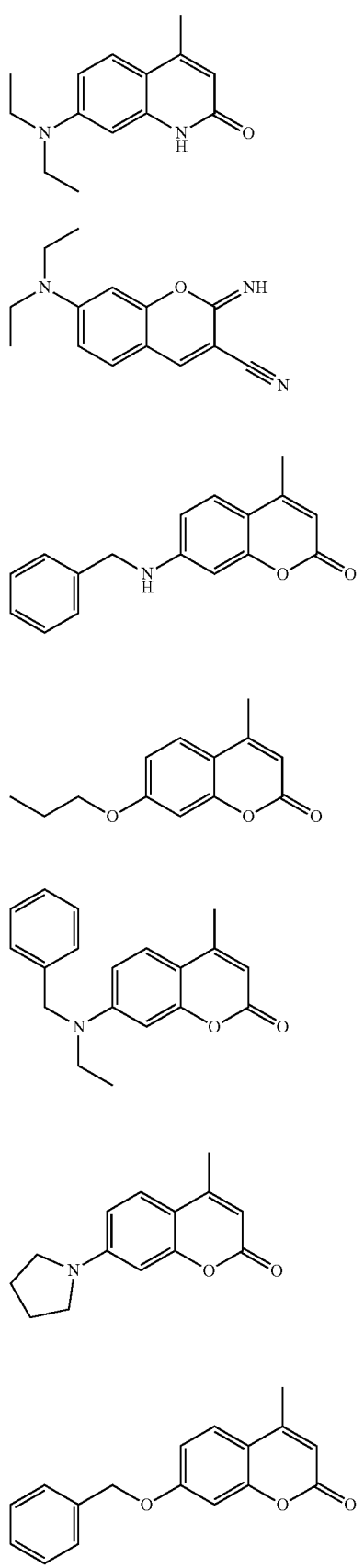
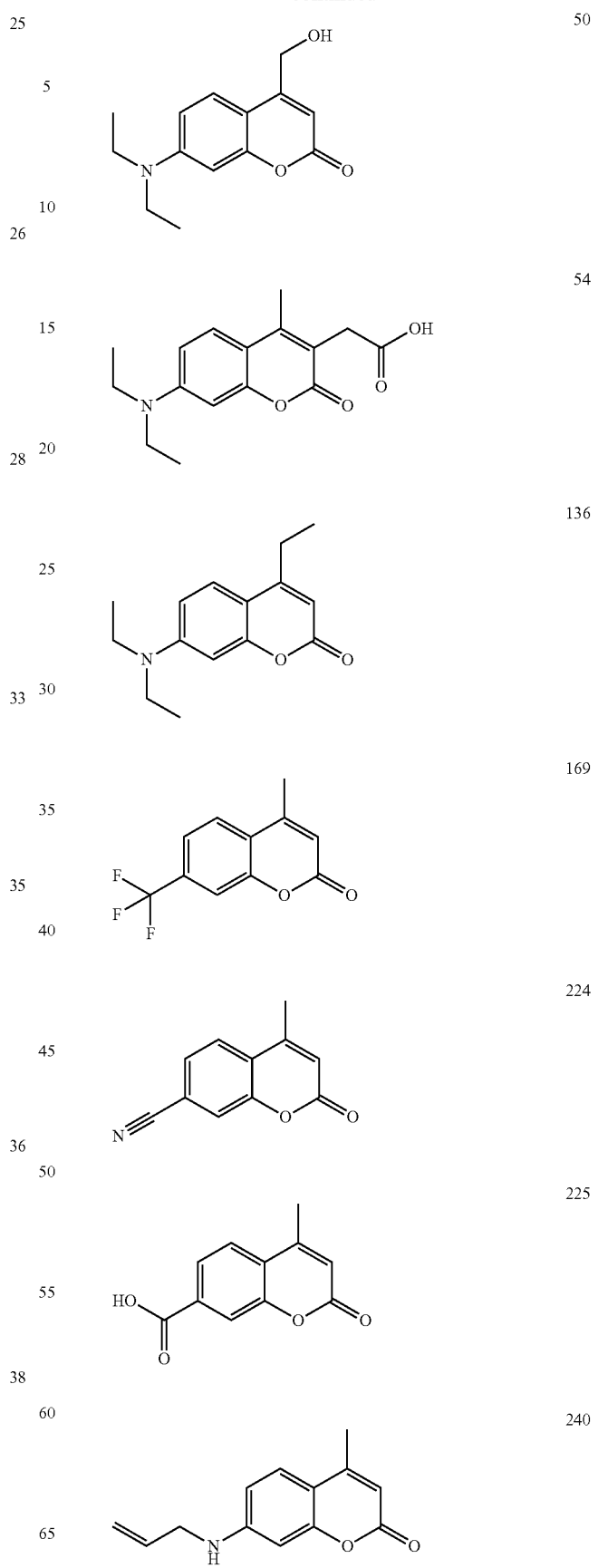

-continued

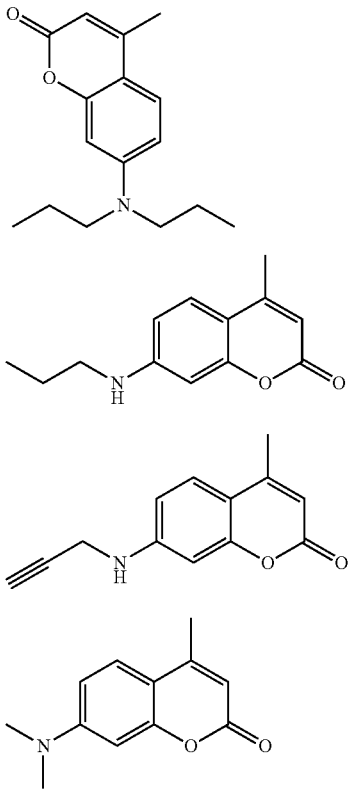

241

242

249

266

In various embodiments, the compound according to claim 1, wherein the compound is of Formula Ia. In other embodiments, the compound is of Formula Ib.

In an embodiment, each of $X^1$ and $X^3$ is O.

A further embodiment is wherein each of $R^2$, $R^3$, and $R^4$ is independently selected from H and $C_1$-$C_6$-alkyl. For example, each of $R^2$, $R^3$, and $R^4$ is H.

In an embodiment, $R^1$ is H or $C_1$-$C_6$-alkyl. For example, $R^1$ is $C_1$-$C_6$-alkyl, such as methyl.

In various embodiments, $X^2$ is $NR^{12}$ and p is 0, 1, or 2.

A further embodiment provides a compound wherein each of $Z^2$ and $R^{12}$ is independently selected from the group consisting of H, $C_1$-$C_6$-alkyl, $C_2$-$C_6$-alkenyl, $C_2$-$C_6$-alkynyl, and $C_3$-$C_8$-cycloalkyl. For example, per an embodiment, each of $Z^2$ and $R^{12}$ is $C_1$-$C_6$-alkyl. In additional embodiments, p is 0 and each of $Z^2$ and $R^{12}$ is ethyl.

In other embodiments, $X^2$ is O; $Z^2$ is $C_6$-$C_{10}$-aryl or —($C_1$-$C_6$-alkyl)($C_6$-$C_{10}$-aryl); p is 1, 2, or 3; and $R^7$ and $R^8$ are independently selected from H, $C_1$-$C_6$-alkyl. For instance, $Z^2$ is phenyl or benzyl, and $R^7$ and $R^8$ are independently selected from H, methyl, trifluoromethyl, and ethyl.

In various embodiments, A is

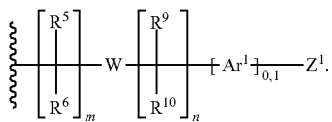

Thus, in an embodiment, A is

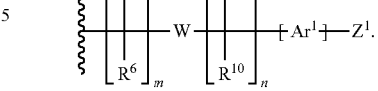

In still another embodiment, m is 2 and n is 1.

Additional embodiments provide a compound wherein W is selected from the group consisting of OC(O)$NR^{14}$; $NR^{14}$C(O)$NR^{15}$;

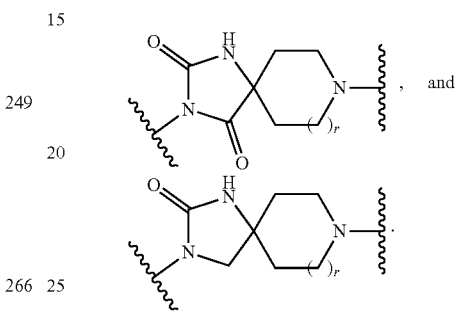

Examples of $Ar^1$, per various embodiments, include phenyl, pyrazolopyrimidinyl, imidazopyrazinyl, pyridinyl, and triazolopyrazinyl.

In some embodiments, $Z^1$ is selected from H, $C_1$-$C_6$-alkyl, and 5-membered heterocycloalkyl.

Exemplary embodiments are compounds in which the compound is of formula Ia or Ib; each of $X^1$ and $X^3$ is O; $X^2$ is $NR^{12}$, wherein $R^{12}$ is $C_1$-$C_6$-alkyl; p is 0; $Z^2$ is $C_1$-$C_6$-alkyl; A is

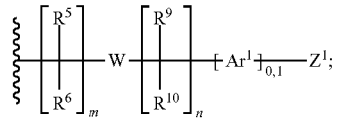

m is 2 and n is 0 or 1; W is selected from the group consisting of OC(O)$NR^{14}$, $NR^{14}$C(O)$NR^{15}$,

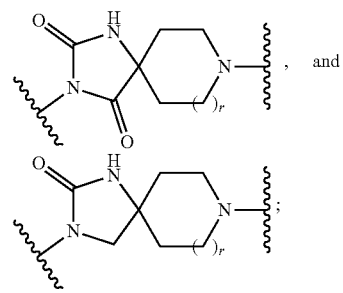

$R^5$, $R^6$, $R^9$, and $R^{10}$ are independently selected from H and $C_1$-$C_6$-alkyl; $Ar^1$ is selected from the group consisting of phenyl, pyrazolopyrimidinyl, imidazopyrazinyl, pyridinyl, and triazolopyrazinyl; and $Z^1$ is selected from the group consisting of H, $C_1$-$C_6$-alkyl, and a 5-membered heterocycloalkyl.

In exemplary embodiments, the compounds of the present disclosure, including for use in the methods described herein, include those in the table below:
| | |
|---|---|
| 1 | 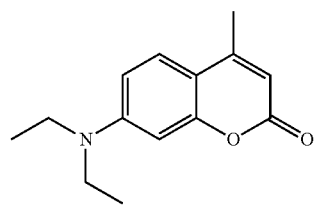 [SMILES: CCN(CC)c1ccc2c(C)cc(=O)oc2c1] |
| 2 | 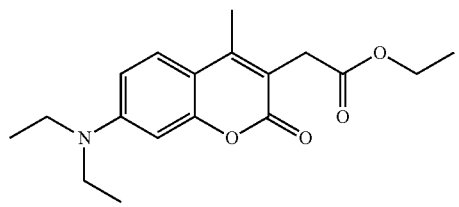 [SMILES: CCOC(=O)Cc1c(C)c2ccc(N(CC)CC)cc2oc1=O] |
| 3 | 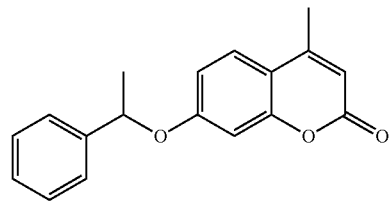 [SMILES: Cc1cc(=O)oc2cc(OC(C)c3ccccc3)ccc12] |
| 4 | 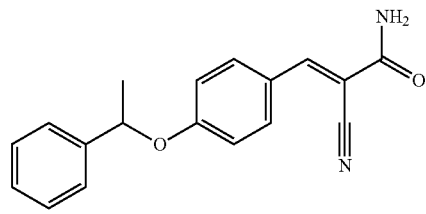 [SMILES: CC(Oc1ccc(/C=C(\C#N)C(N)=O)cc1)c1ccccc1] |
| 5 | 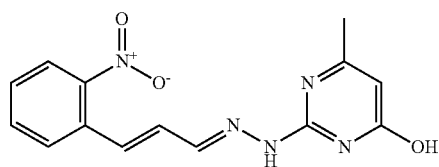 [SMILES: Cc1cc(O)nc(N/N=C/C=C/c2ccccc2[N+](=O)[O-])n1] |
| 6 | 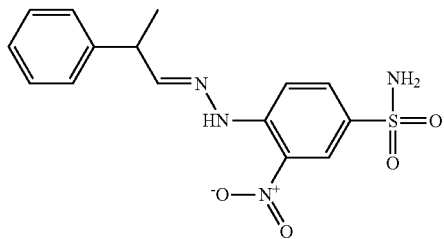 |
| 7 | 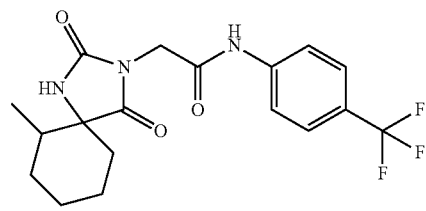 [SMILES: CC1CCCCC12NC(=O)N(CC(=O)Nc1ccc(C(F)(F)F)cc1)C2=O] |

| 8 | 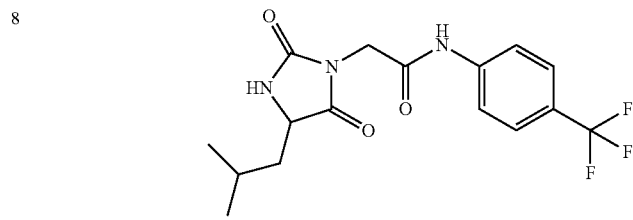 |
| --- | --- |
| 9 | 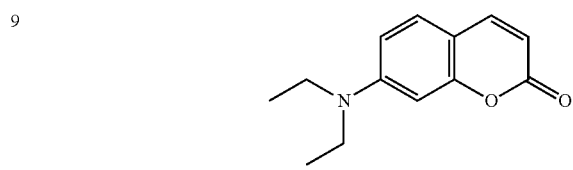 |
| 10 | 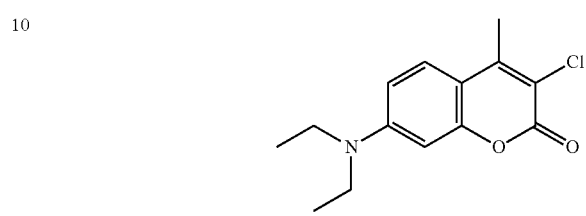 |
| 11 | 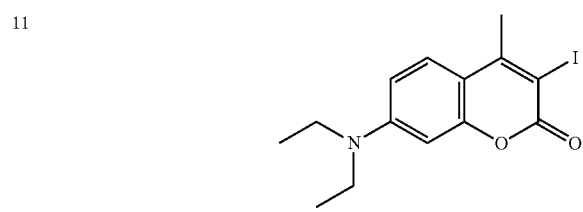 |
| 12 | 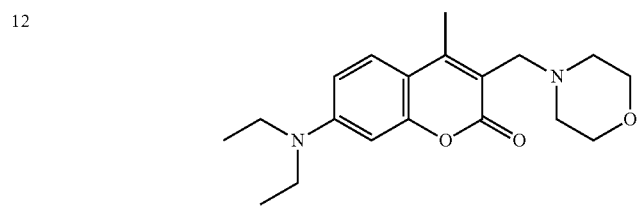 |
| 13 | 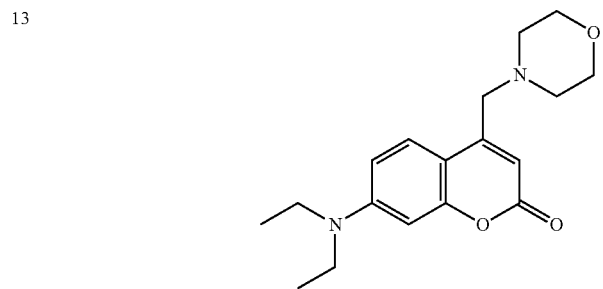 |
| 14 | 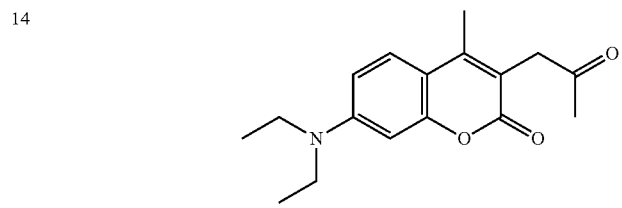 |

-continued
15 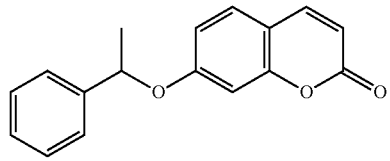 [SMILES: CC(Oc1ccc2ccc(=O)oc2c1)c1ccccc1]
16 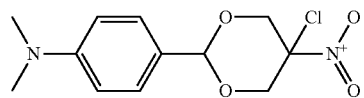
17 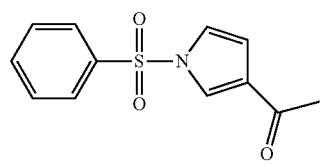 [SMILES: CC(=O)c1ccn(S(=O)(=O)c2ccccc2)c1]
18 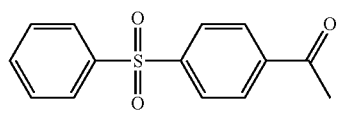
19 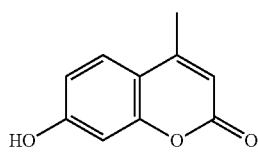
20 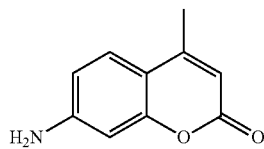
21 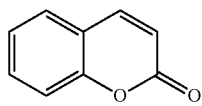 [SMILES: O=c1ccc2ccccc2o1]
22 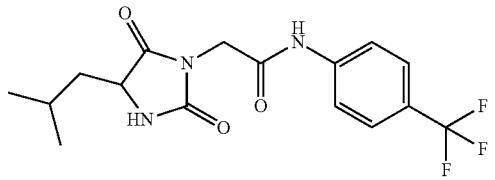 [SMILES: CC(C)CC1NC(=O)N(CC(=O)Nc2ccc(C(F)(F)F)cc2)C1=O]
Enantiomer 1
23 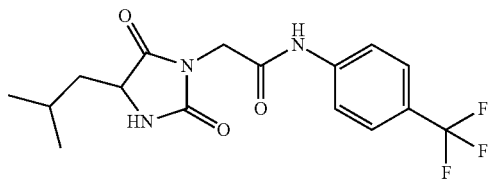 [SMILES: CC(C)CC1NC(=O)N(CC(=O)Nc2ccc(C(F)(F)F)cc2)C1=O]
Enantiomer 2

-continued
24 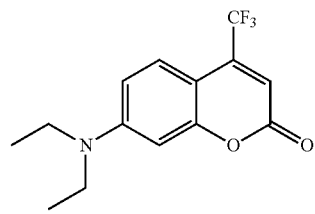 [SMILES: CCN(CC)c1ccc2c(C(F)(F)F)cc(=O)oc2c1]
25 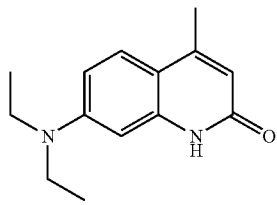
26 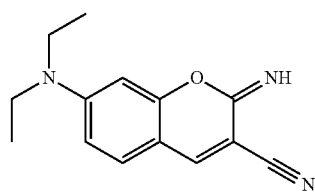 [SMILES: CCN(CC)c1ccc2cc(C#N)c(=N)oc2c1]
27 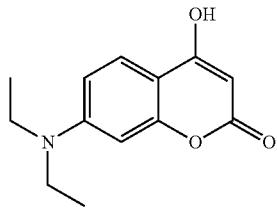 [SMILES: CCN(CC)c1ccc2c(O)cc(=O)oc2c1]
28 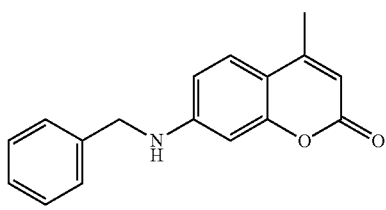 [SMILES: Cc1cc(=O)oc2cc(NCc3ccccc3)ccc12]
29 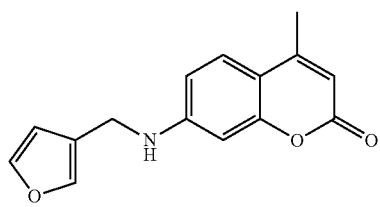 [SMILES: Cc1cc(=O)oc2cc(NCc3ccoc3)ccc12]
30 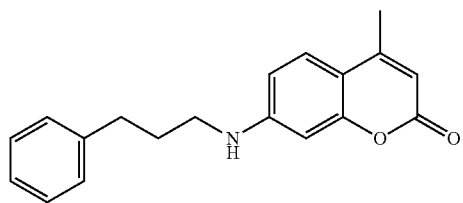 [SMILES: Cc1cc(=O)oc2cc(NCCCc3ccccc3)ccc12]

-continued
| | |
|---|---|
| 31 | 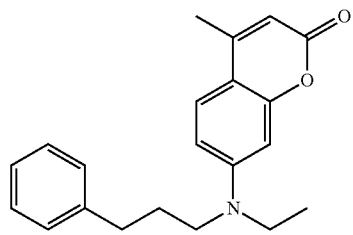 [SMILES: CCN(CCCc1ccccc1)c1ccc2c(C)cc(=O)oc2c1] |
| 32 | 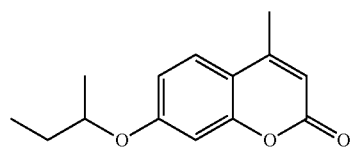 |
| 33 | 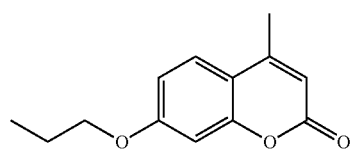 [SMILES: CCCOc1ccc2c(C)cc(=O)oc2c1] |
| 34 | 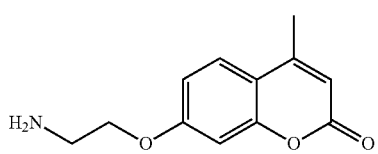 [SMILES: Cc1cc(=O)oc2cc(OCCN)ccc12] |
| 35 | 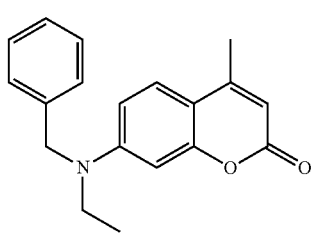 [SMILES: CCN(Cc1ccccc1)c1ccc2c(C)cc(=O)oc2c1] |
| 36 | 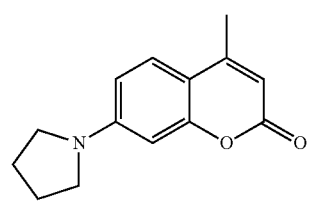 [SMILES: Cc1cc(=O)oc2cc(N3CCCC3)ccc12] |
| 37 | 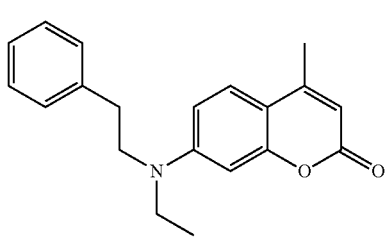 [SMILES: CCN(CCc1ccccc1)c1ccc2c(C)cc(=O)oc2c1] |
| 38 | 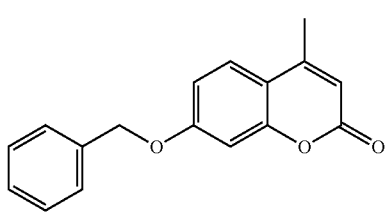 [SMILES: Cc1cc(=O)oc2cc(OCc3ccccc3)ccc12] |

-continued
| | |
|---|---|
| 39 | 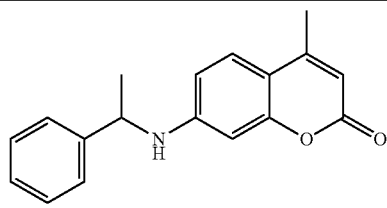 |
| 40 | 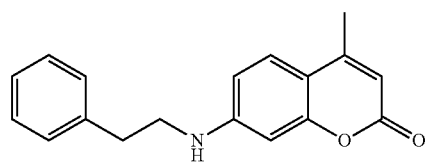 [SMILES: Cc1cc(=O)oc2cc(NCCc3ccccc3)ccc12] |
| 41 | 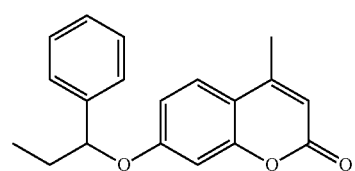 [SMILES: CCC(Oc1ccc2c(C)cc(=O)oc2c1)c1ccccc1] |
| 42 | 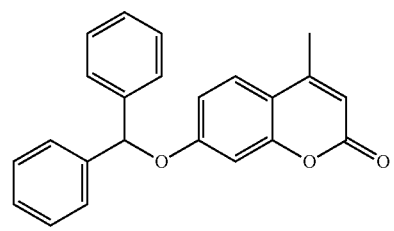 [SMILES: Cc1cc(=O)oc2cc(OC(c3ccccc3)c3ccccc3)ccc12] |
| 43 | 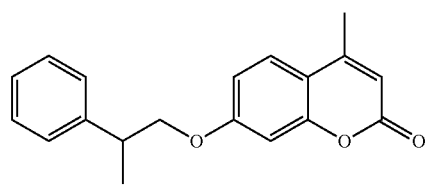 [SMILES: Cc1cc(=O)oc2cc(OCC(C)c3ccccc3)ccc12] |
| 44 | 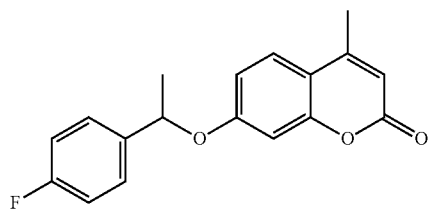 [SMILES: Cc1cc(=O)oc2cc(OC(C)c3ccc(F)cc3)ccc12] |
| 45 | 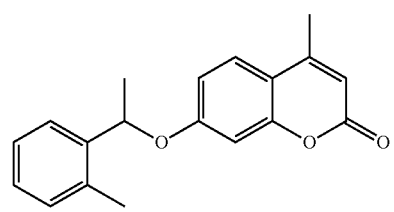 [SMILES: Cc1ccccc1C(C)Oc1ccc2c(C)cc(=O)oc2c1] |
| 46 | 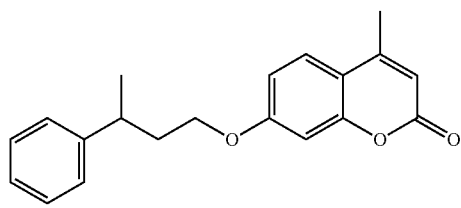 [SMILES: Cc1cc(=O)oc2cc(OCCC(C)c3ccccc3)ccc12] |

-continued
| 47 | 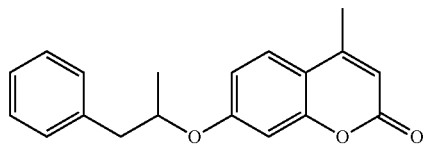 [SMILES: Cc1cc(=O)oc2cc(OC(C)Cc3ccccc3)ccc12] |
| 48 | 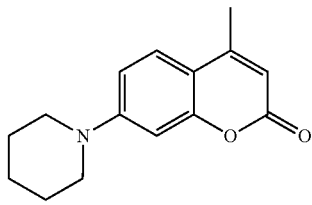 [SMILES: Cc1cc(=O)oc2cc(N3CCCCC3)ccc12] |
| 49 | 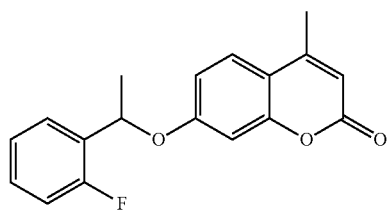 [SMILES: Cc1cc(=O)oc2cc(OC(C)c3ccccc3F)ccc12] |
| 50 | 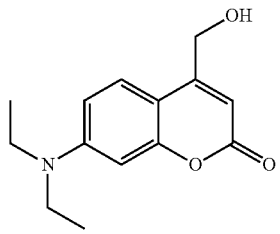 [SMILES: CCN(CC)c1ccc2c(CO)cc(=O)oc2c1] |
| 51 | 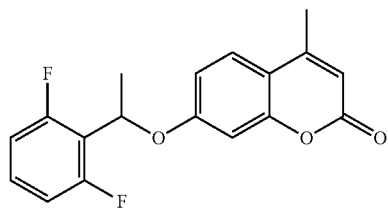 [SMILES: Cc1cc(=O)oc2cc(OC(C)c3c(F)cccc3F)ccc12] |
| 52 | 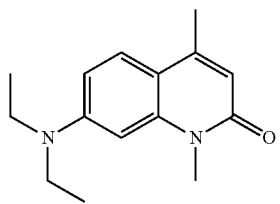 [SMILES: CCN(CC)c1ccc2c(C)cc(=O)n(C)c2c1] |
| 53 | 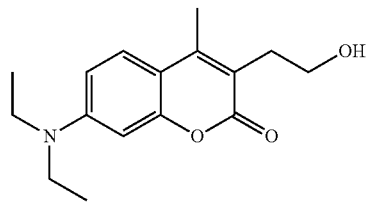 [SMILES: CCN(CC)c1ccc2c(C)c(CCO)c(=O)oc2c1] |

-continued
| | |
|---|---|
| 54 | 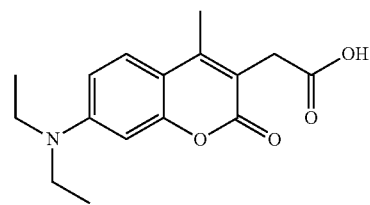 [SMILES: CCN(CC)c1ccc2c(C)c(CC(=O)O)c(=O)oc2c1] |
| 55 | 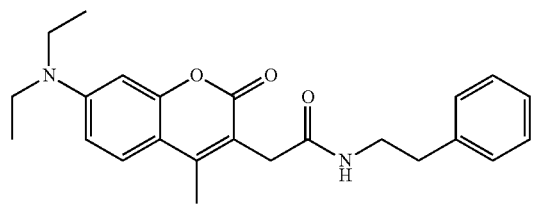 [SMILES: CCN(CC)c1ccc2c(C)c(CC(=O)NCCc3ccccc3)c(=O)oc2c1] |
| 56 | 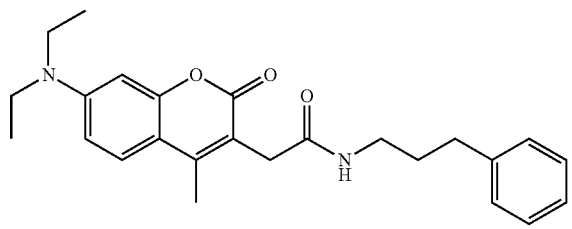 [SMILES: CCN(CC)c1ccc2c(C)c(CC(=O)NCCCc3ccccc3)c(=O)oc2c1] |
| 57 | 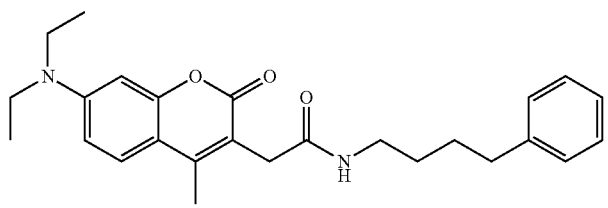 [SMILES: CCN(CC)c1ccc2c(C)c(CC(=O)NCCCCc3ccccc3)c(=O)oc2c1] |
| 58 | 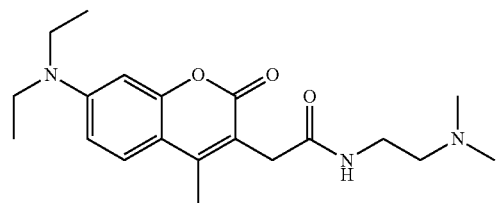 [SMILES: CCN(CC)c1ccc2c(C)c(CC(=O)NCCN(C)C)c(=O)oc2c1] |
| 59 | 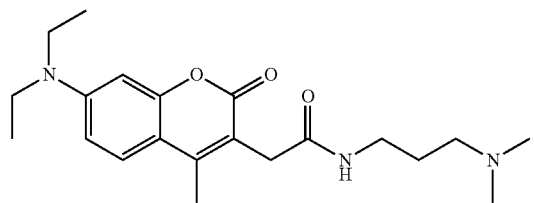 [SMILES: CCN(CC)c1ccc2c(C)c(CC(=O)NCCCN(C)C)c(=O)oc2c1] |
| 60 | 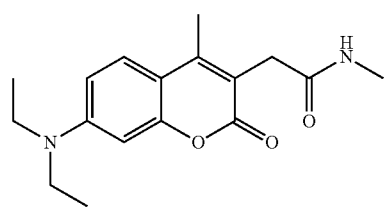 [SMILES: CCN(CC)c1ccc2c(C)c(CC(=O)NC)c(=O)oc2c1] |

-continued
61
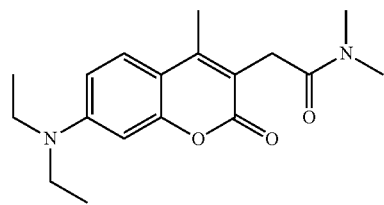 [SMILES: CCN(CC)c1ccc2c(C)c(CC(=O)N(C)C)c(=O)oc2c1]
62
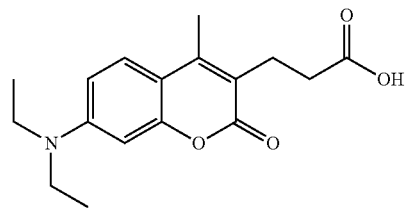 [SMILES: CCN(CC)c1ccc2c(C)c(CCC(=O)O)c(=O)oc2c1]
63
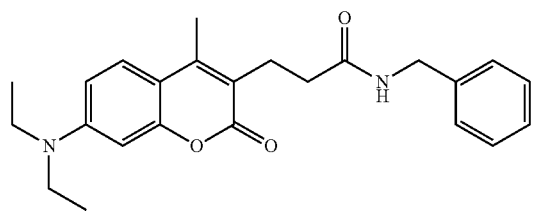 [SMILES: CCN(CC)c1ccc2c(C)c(CCC(=O)NCc3ccccc3)c(=O)oc2c1]
64
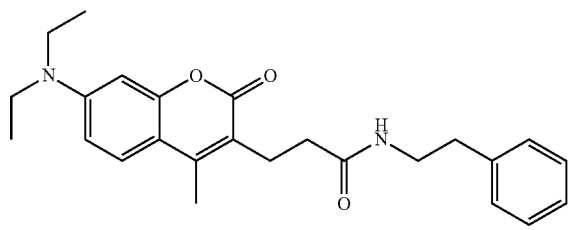 [SMILES: CCN(CC)c1ccc2c(C)c(CCC(=O)NCCc3ccccc3)c(=O)oc2c1]
65
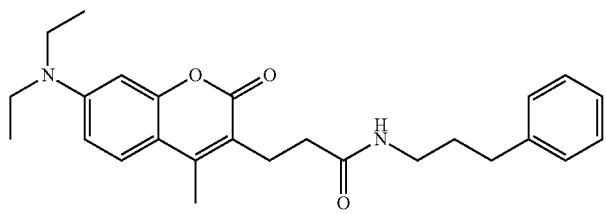 [SMILES: CCN(CC)c1ccc2c(C)c(CCC(=O)NCCCc3ccccc3)c(=O)oc2c1]
66
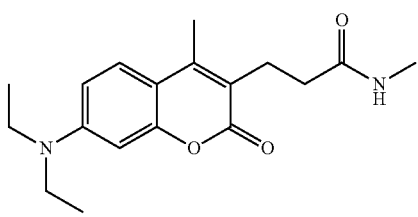 [SMILES: CCN(CC)c1ccc2c(C)c(CCC(=O)NC)c(=O)oc2c1]
67
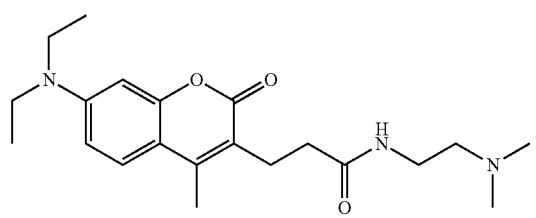 [SMILES: CCN(CC)c1ccc2c(C)c(CCC(=O)NCCN(C)C)c(=O)oc2c1]

68 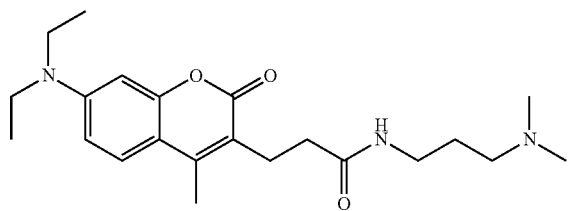 [SMILES: CCN(CC)c1ccc2c(C)c(CCC(=O)NCCCN(C)C)c(=O)oc2c1]
69 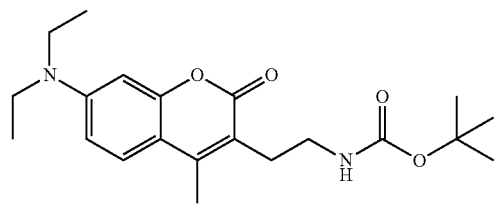 [SMILES: CCN(CC)c1ccc2c(C)c(CCNC(=O)OC(C)(C)C)c(=O)oc2c1]
70 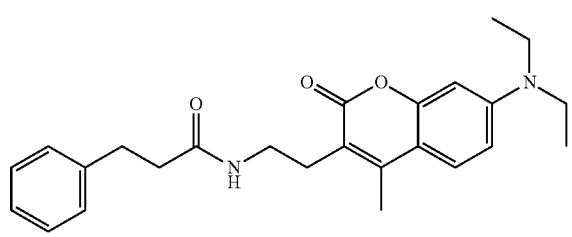 [SMILES: CCN(CC)c1ccc2c(C)c(CCNC(=O)CCc3ccccc3)c(=O)oc2c1]
71 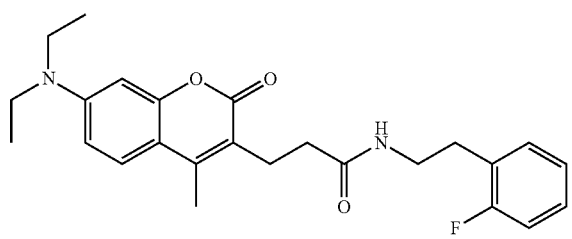 [SMILES: CCN(CC)c1ccc2c(C)c(CCC(=O)NCCc3ccccc3F)c(=O)oc2c1]
72 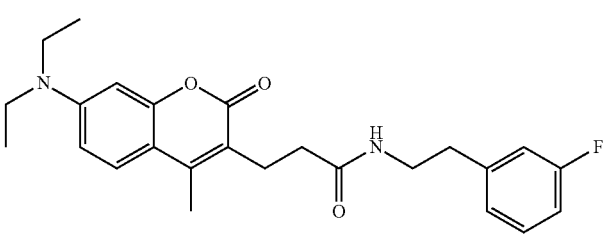 [SMILES: CCN(CC)c1ccc2c(C)c(CCC(=O)NCCc3cccc(F)c3)c(=O)oc2c1]
73 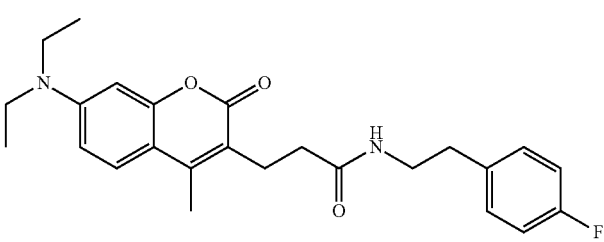 [SMILES: CCN(CC)c1ccc2c(C)c(CCC(=O)NCCc3ccc(F)cc3)c(=O)oc2c1]
74 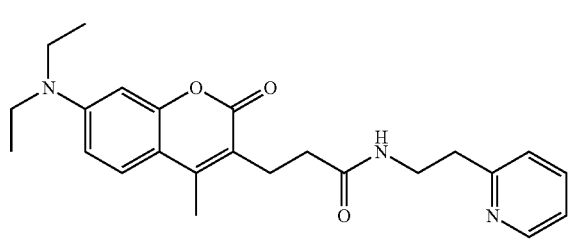 [SMILES: CCN(CC)c1ccc2c(C)c(CCC(=O)NCCc3ccccn3)c(=O)oc2c1]

75 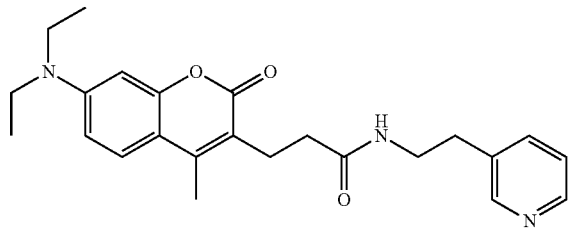 [SMILES: CCN(CC)c1ccc2c(C)c(CCC(=O)NCCc3cccnc3)c(=O)oc2c1]
76 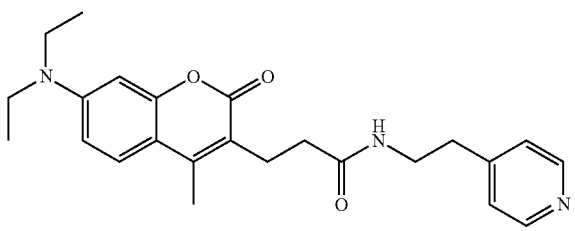 [SMILES: CCN(CC)c1ccc2c(C)c(CCC(=O)NCCc3ccncc3)c(=O)oc2c1]
77 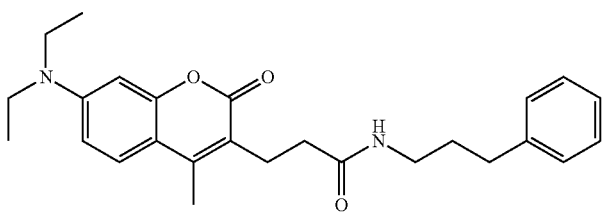 [SMILES: CCN(CC)c1ccc2c(C)c(CCC(=O)NCCCc3ccccc3)c(=O)oc2c1]
78 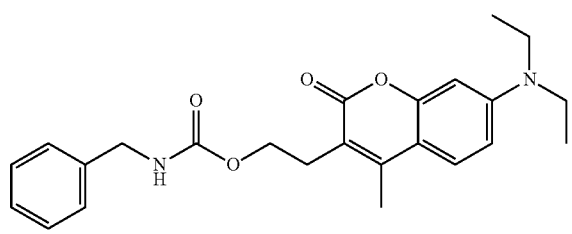 [SMILES: CCN(CC)c1ccc2c(C)c(CCOC(=O)NCc3ccccc3)c(=O)oc2c1]
79 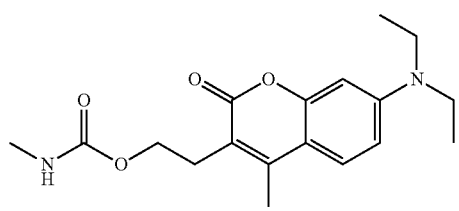 [SMILES: CCN(CC)c1ccc2c(C)c(CCOC(=O)NC)c(=O)oc2c1]
80 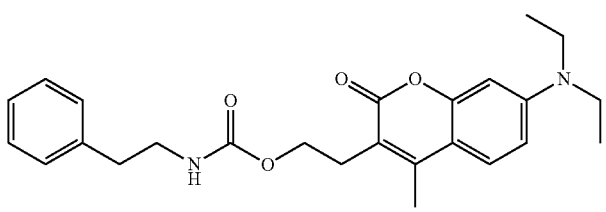 [SMILES: CCN(CC)c1ccc2c(C)c(CCOC(=O)NCCc3ccccc3)c(=O)oc2c1]
81 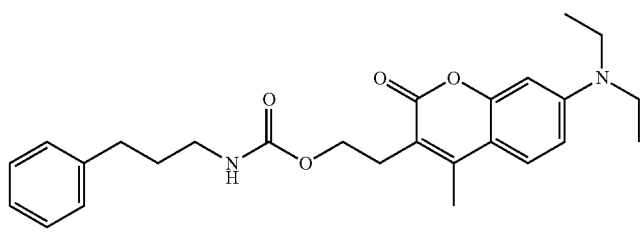 [SMILES: CCN(CC)c1ccc2c(C)c(CCOC(=O)NCCCc3ccccc3)c(=O)oc2c1]

82
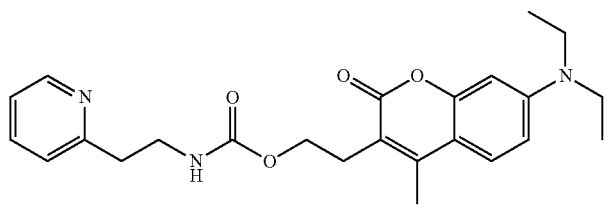 [SMILES: CCN(CC)c1ccc2c(C)c(CCOC(=O)NCCc3ccccn3)c(=O)oc2c1]
83
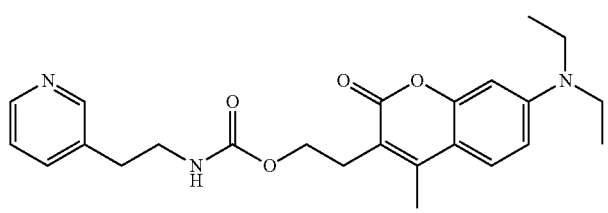 [SMILES: CCN(CC)c1ccc2c(C)c(CCOC(=O)NCCc3cccnc3)c(=O)oc2c1]
84
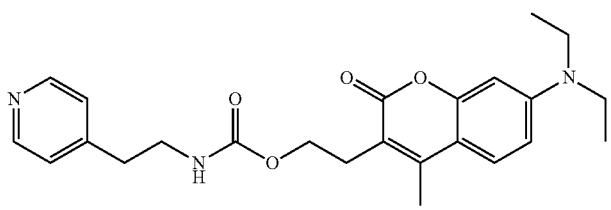 [SMILES: CCN(CC)c1ccc2c(C)c(CCOC(=O)NCCc3ccncc3)c(=O)oc2c1]
85
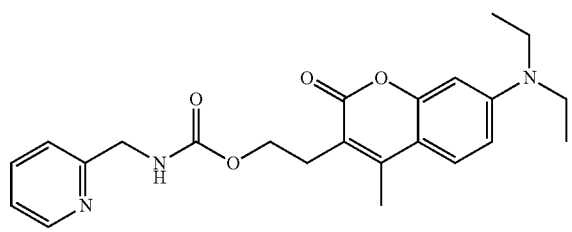 [SMILES: CCN(CC)c1ccc2c(C)c(CCOC(=O)NCc3ccccn3)c(=O)oc2c1]
86
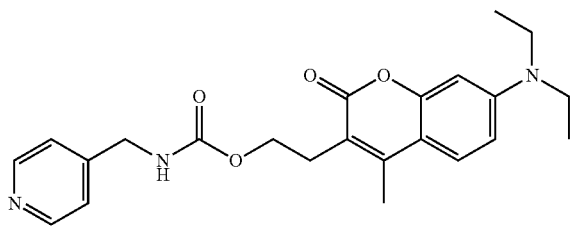 [SMILES: CCN(CC)c1ccc2c(C)c(CCOC(=O)NCc3ccncc3)c(=O)oc2c1]
87
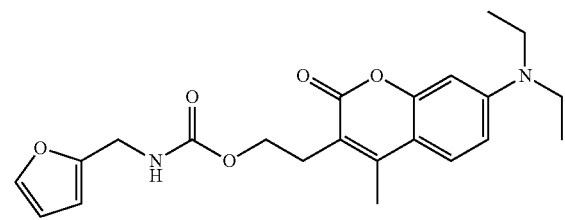 [SMILES: CCN(CC)c1ccc2c(C)c(CCOC(=O)NCc3ccco3)c(=O)oc2c1]
88
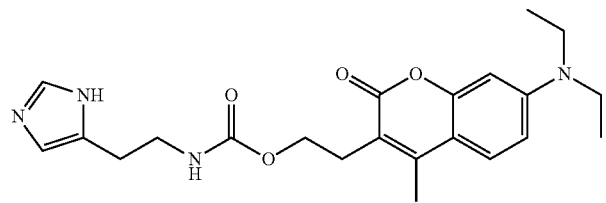 [SMILES: CCN(CC)c1ccc2c(C)c(CCOC(=O)NCCc3cnc[nH]3)c(=O)oc2c1]

| | |
|---|---|
| 89 | 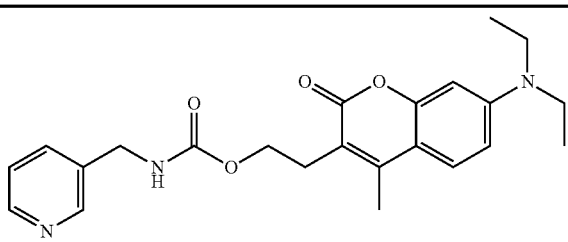 |
| 90 | 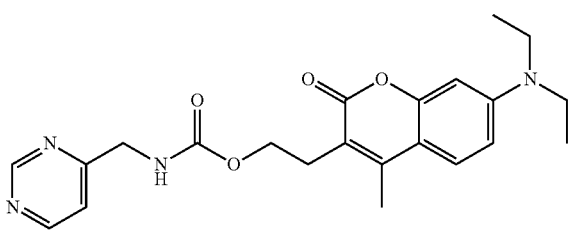 [SMILES: CCN(CC)c1ccc2c(C)c(CCOC(=O)NCc3ccncn3)c(=O)oc2c1] |
| 91 | 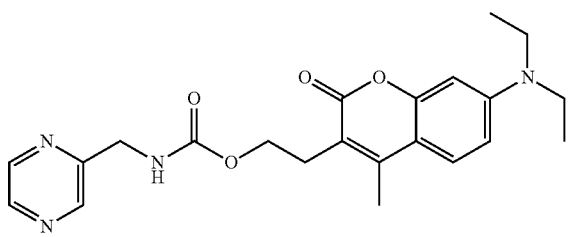 [SMILES: CCN(CC)c1ccc2c(C)c(CCOC(=O)NCc3cnccn3)c(=O)oc2c1] |
| 92 | 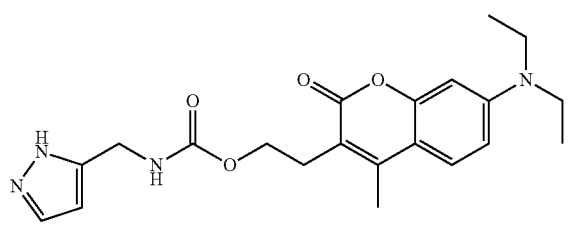 [SMILES: CCN(CC)c1ccc2c(C)c(CCOC(=O)NCc3ccn[nH]3)c(=O)oc2c1] |
| 93 | 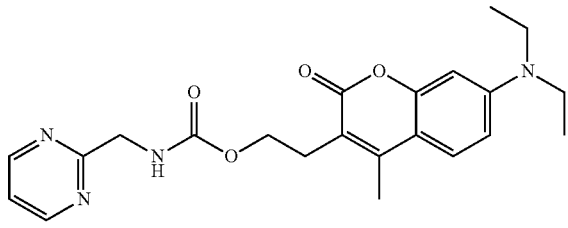 [SMILES: CCN(CC)c1ccc2c(C)c(CCOC(=O)NCc3ncccn3)c(=O)oc2c1] |
| 94 | 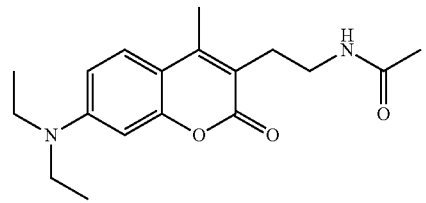 [SMILES: CCN(CC)c1ccc2c(C)c(CCNC(C)=O)c(=O)oc2c1] |
| 95 | 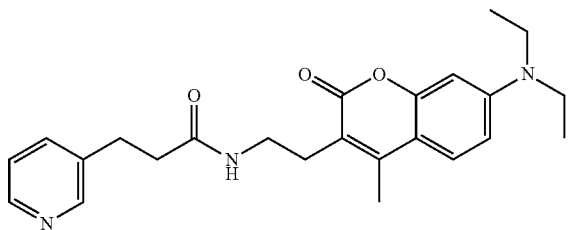 [SMILES: CCN(CC)c1ccc2c(C)c(CCNC(=O)CCc3cccnc3)c(=O)oc2c1] |

96
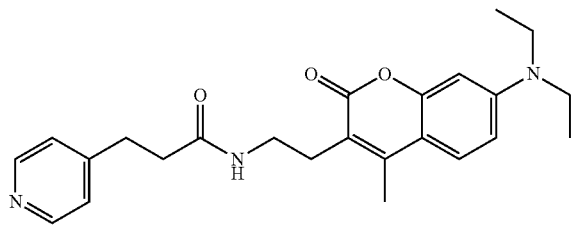 [SMILES: CCN(CC)c1ccc2c(C)c(CCNC(=O)CCc3ccncc3)c(=O)oc2c1]
97
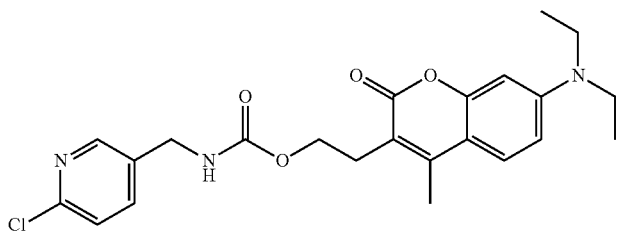 [SMILES: CCN(CC)c1ccc2c(C)c(CCOC(=O)NCc3ccc(Cl)nc3)c(=O)oc2c1]
98
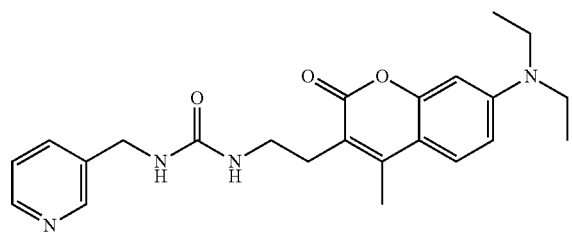
99
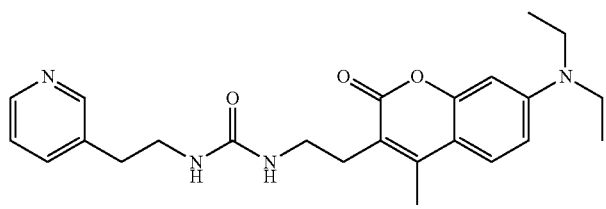 [SMILES: CCN(CC)c1ccc2c(C)c(CCNC(=O)NCCc3cccnc3)c(=O)oc2c1]
100
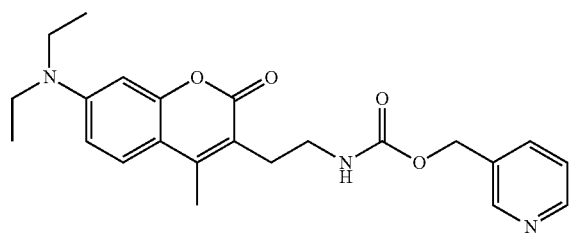 [SMILES: CCN(CC)c1ccc2c(C)c(CCNC(=O)OCc3cccnc3)c(=O)oc2c1]
101
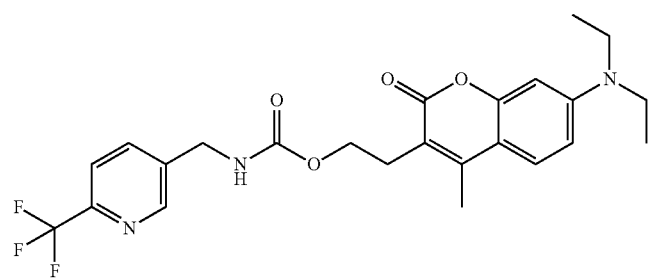 [SMILES: CCN(CC)c1ccc2c(C)c(CCOC(=O)NCc3ccc(C(F)(F)F)nc3)c(=O)oc2c1]

-continued
102
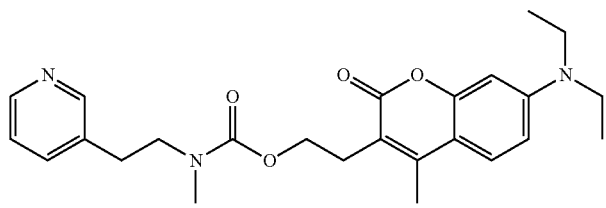 [SMILES: CCN(CC)c1ccc2c(C)c(CCOC(=O)N(C)CCc3cccnc3)c(=O)oc2c1]
103
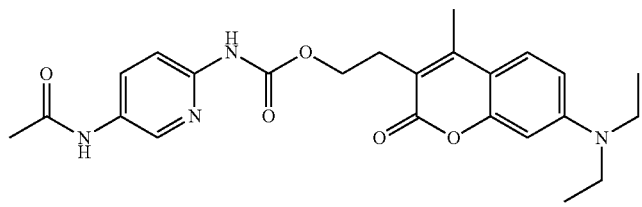 [SMILES: CCN(CC)c1ccc2c(C)c(CCOC(=O)Nc3ccc(NC(C)=O)cn3)c(=O)oc2c1]
104
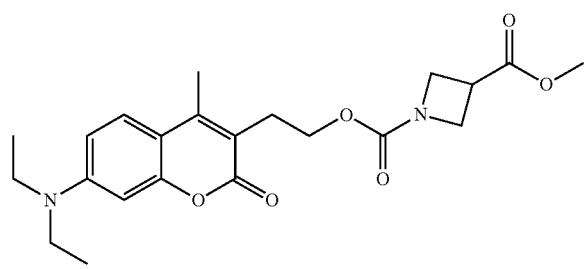 [SMILES: CCN(CC)c1ccc2c(C)c(CCOC(=O)N3CC(C(=O)OC)C3)c(=O)oc2c1]
105
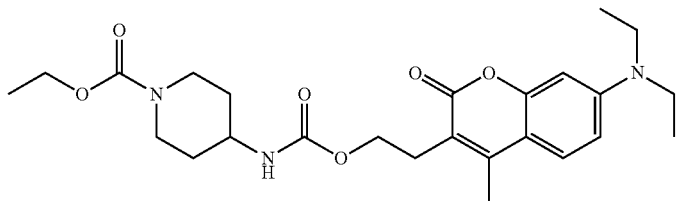 [SMILES: CCOC(=O)N1CCC(NC(=O)OCCc2c(C)c3ccc(N(CC)CC)cc3oc2=O)CC1]
106
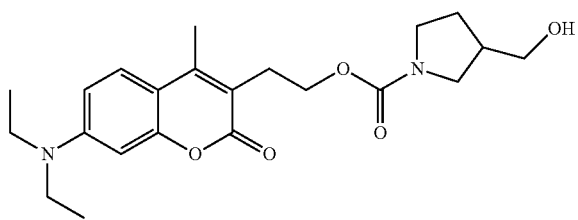 [SMILES: CCN(CC)c1ccc2c(C)c(CCOC(=O)N3CCC(CO)C3)c(=O)oc2c1]
107
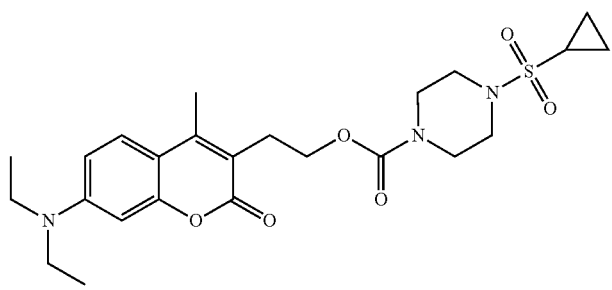 [SMILES: CCN(CC)c1ccc2c(C)c(CCOC(=O)N3CCN(S(=O)(=O)C4CC4)CC3)c(=O)oc2c1]

-continued
| | |
|---|---|
| 108 | 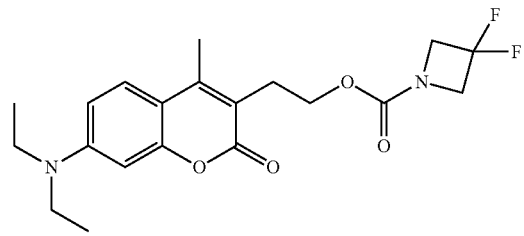 [SMILES: CCN(CC)c1ccc2c(C)c(CCOC(=O)N3CC(F)(F)C3)c(=O)oc2c1] |
| 109 | 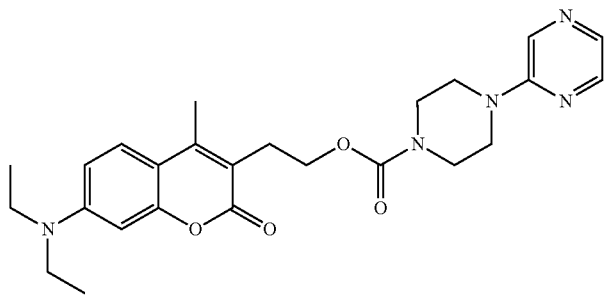 [SMILES: CCN(CC)c1ccc2c(C)c(CCOC(=O)N3CCN(c4cnccn4)CC3)c(=O)oc2c1] |
| 110 | 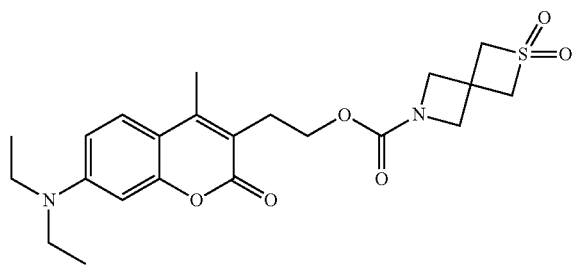 [SMILES: CCN(CC)c1ccc2c(C)c(CCOC(=O)N3CC4(C3)CS(=O)(=O)C4)c(=O)oc2c1] |
| 111 | 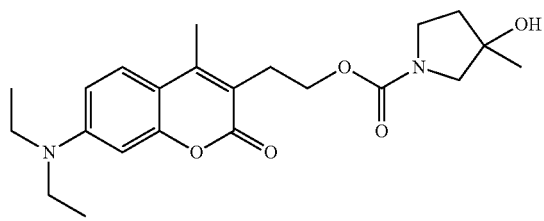 [SMILES: CCN(CC)c1ccc2c(C)c(CCOC(=O)N3CCC(C)(O)C3)c(=O)oc2c1] |
| 112 | 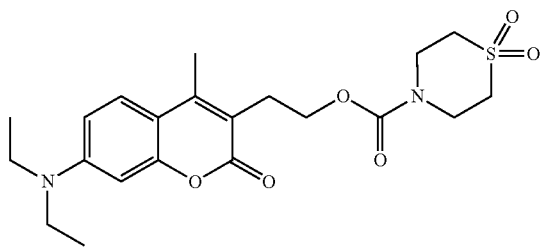 [SMILES: CCN(CC)c1ccc2c(C)c(CCOC(=O)N3CCS(=O)(=O)CC3)c(=O)oc2c1] |
| 113 | 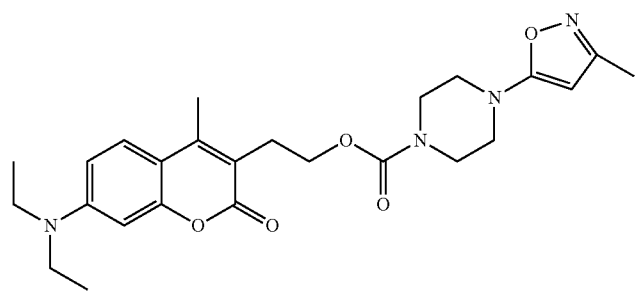 [SMILES: CCN(CC)c1ccc2c(C)c(CCOC(=O)N3CCN(c4cc(C)no4)CC3)c(=O)oc2c1] |

114
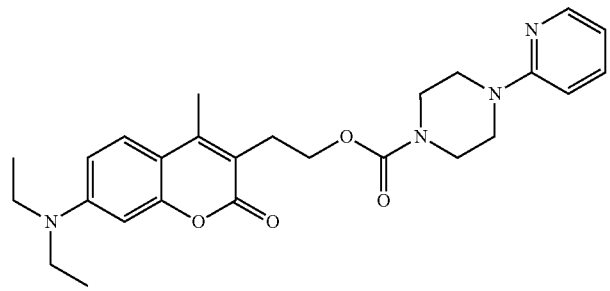 [SMILES: CCN(CC)c1ccc2c(C)c(CCOC(=O)N3CCN(c4ccccn4)CC3)c(=O)oc2c1]
115
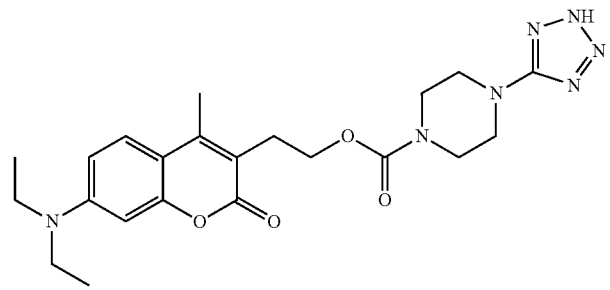 [SMILES: CCN(CC)c1ccc2c(C)c(CCOC(=O)N3CCN(c4nn[nH]n4)CC3)c(=O)oc2c1]
116
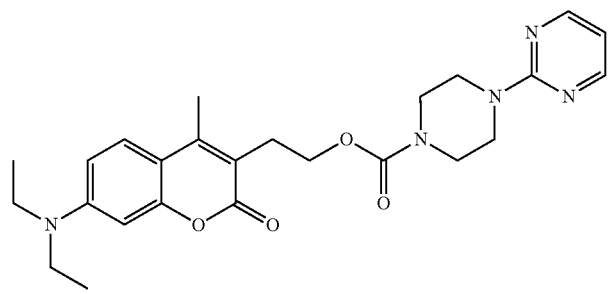 [SMILES: CCN(CC)c1ccc2c(C)c(CCOC(=O)N3CCN(c4ncccn4)CC3)c(=O)oc2c1]
117
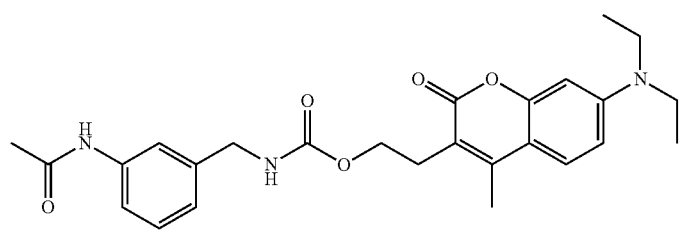 [SMILES: CCN(CC)c1ccc2c(C)c(CCOC(=O)NCc3cccc(NC(C)=O)c3)c(=O)oc2c1]
118
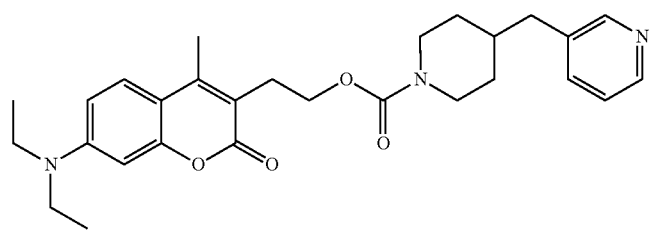 [SMILES: CCN(CC)c1ccc2c(C)c(CCOC(=O)N3CCC(Cc4cccnc4)CC3)c(=O)oc2c1]
119
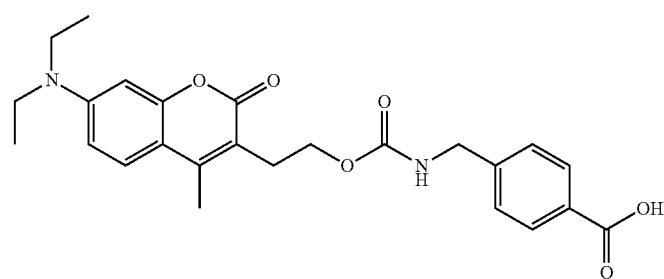 [SMILES: CCN(CC)c1ccc2c(C)c(CCOC(=O)NCc3ccc(C(=O)O)cc3)c(=O)oc2c1]

-continued
120 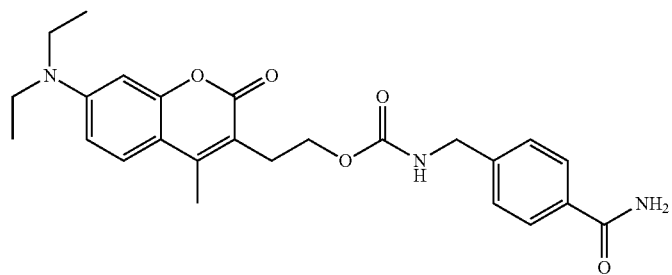 [SMILES: CCN(CC)c1ccc2c(C)c(CCOC(=O)NCc3ccc(C(N)=O)cc3)c(=O)oc2c1]
121 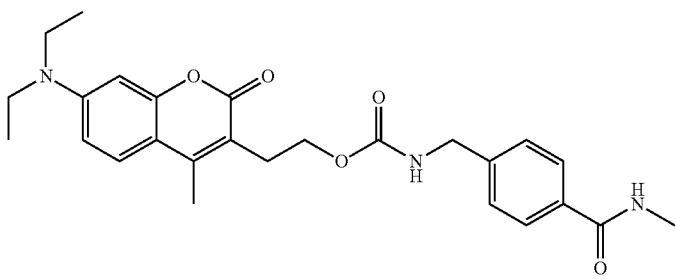 [SMILES: CCN(CC)c1ccc2c(C)c(CCOC(=O)NCc3ccc(C(=O)NC)cc3)c(=O)oc2c1]
122 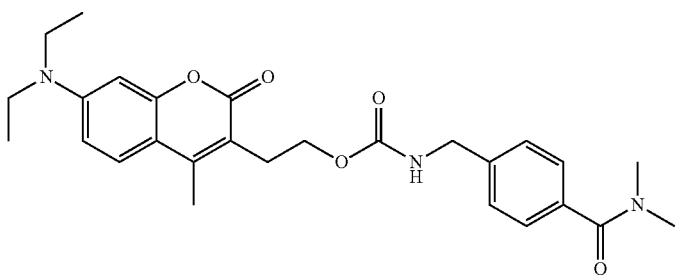 [SMILES: CCN(CC)c1ccc2c(C)c(CCOC(=O)NCc3ccc(C(=O)N(C)C)cc3)c(=O)oc2c1]
123 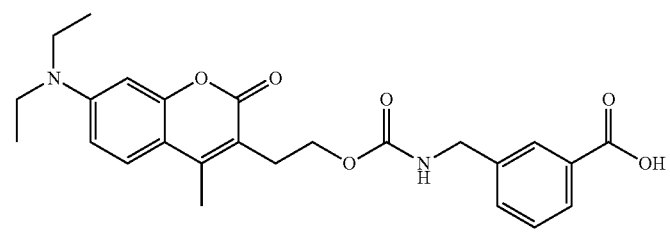 [SMILES: CCN(CC)c1ccc2c(C)c(CCOC(=O)NCc3cccc(C(=O)O)c3)c(=O)oc2c1]
124 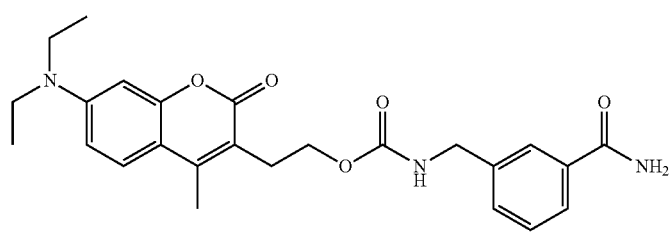 [SMILES: CCN(CC)c1ccc2c(C)c(CCOC(=O)NCc3cccc(C(N)=O)c3)c(=O)oc2c1]
125 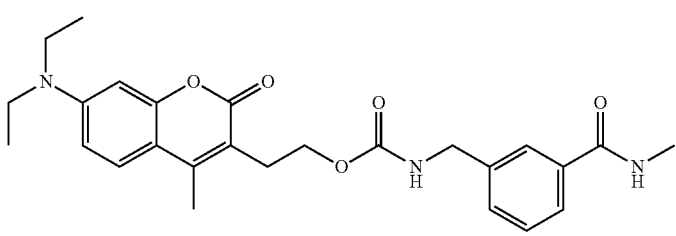 [SMILES: CCN(CC)c1ccc2c(C)c(CCOC(=O)NCc3cccc(C(=O)NC)c3)c(=O)oc2c1]

126 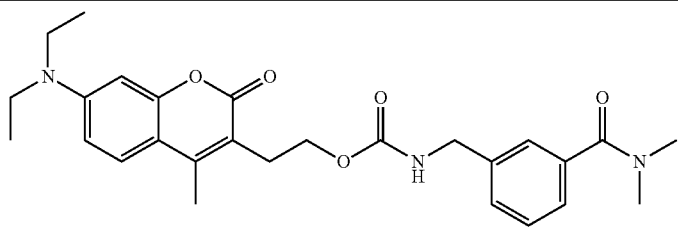
127 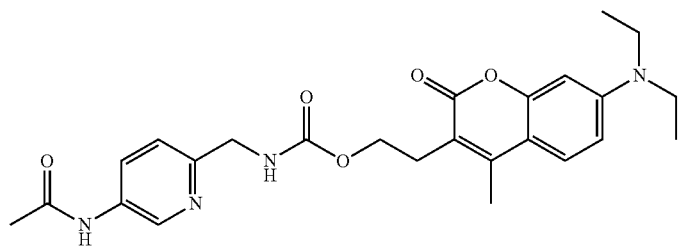 [SMILES: CCN(CC)c1ccc2c(C)c(CCOC(=O)NCc3ccc(NC(C)=O)cn3)c(=O)oc2c1]
128 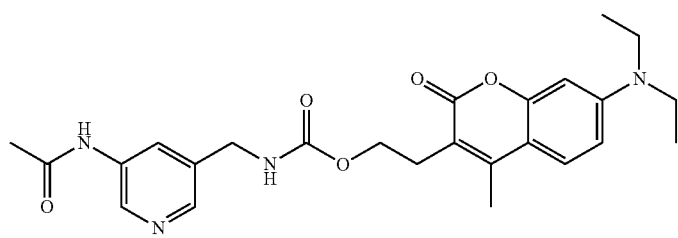 [SMILES: CCN(CC)c1ccc2c(C)c(CCOC(=O)NCc3cncc(NC(C)=O)c3)c(=O)oc2c1]
129 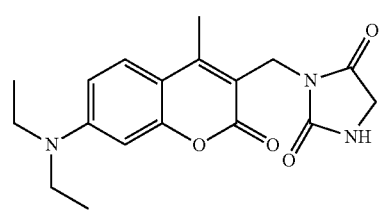 [SMILES: CCN(CC)c1ccc2c(C)c(CN3C(=O)CNC3=O)c(=O)oc2c1]
130 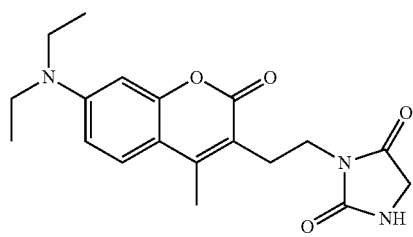 [SMILES: CCN(CC)c1ccc2c(C)c(CCN3C(=O)CNC3=O)c(=O)oc2c1]
131 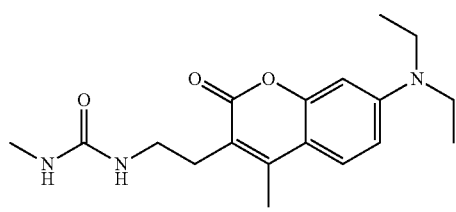 [SMILES: CCN(CC)c1ccc2c(C)c(CCNC(=O)NC)c(=O)oc2c1]
132 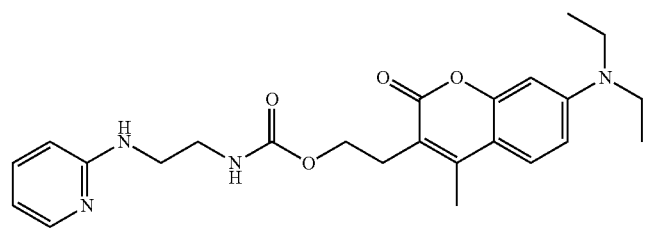 [SMILES: CCN(CC)c1ccc2c(C)c(CCOC(=O)NCCNc3ccccn3)c(=O)oc2c1]

-continued
133
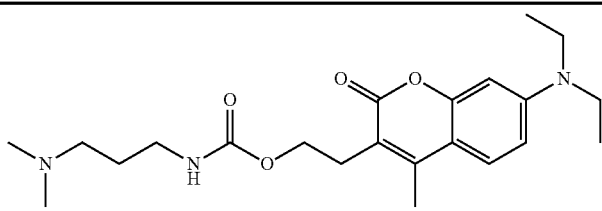
134
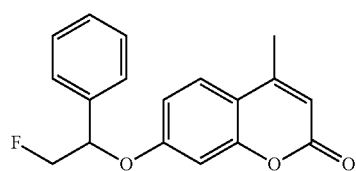 [SMILES: Cc1cc(=O)oc2cc(OC(CF)c3ccccc3)ccc12]
135
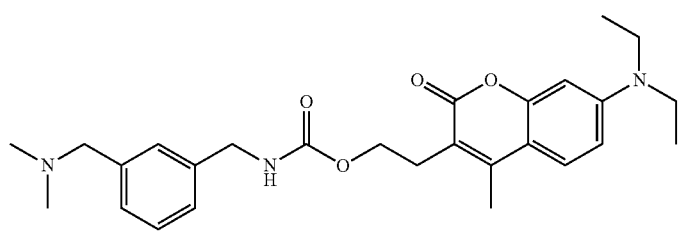 [SMILES: CCN(CC)c1ccc2c(C)c(CCOC(=O)NCc3cccc(CN(C)C)c3)c(=O)oc2c1]
136
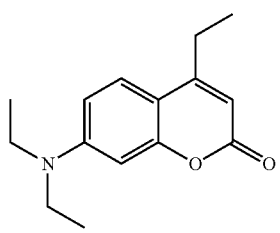 [SMILES: CCc1cc(=O)oc2cc(N(CC)CC)ccc12]
137
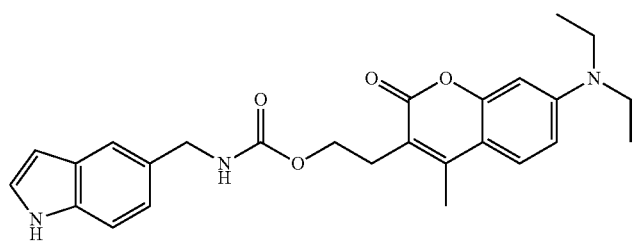 [SMILES: CCN(CC)c1ccc2c(C)c(CCOC(=O)NCc3ccc4[nH]ccc4c3)c(=O)oc2c1]
138
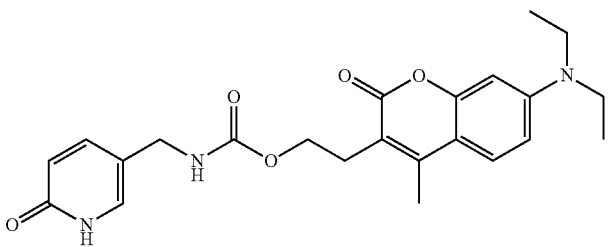 [SMILES: CCN(CC)c1ccc2c(C)c(CCOC(=O)NCc3ccc(=O)[nH]c3)c(=O)oc2c1]
139
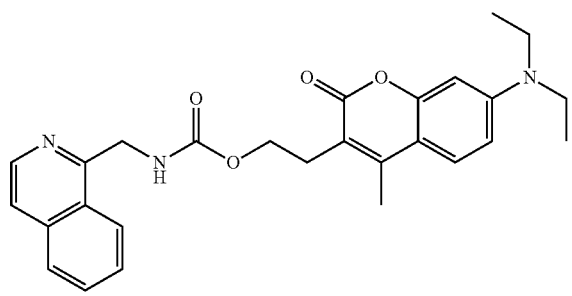 [SMILES: CCN(CC)c1ccc2c(C)c(CCOC(=O)NCc3nccc4ccccc34)c(=O)oc2c1]

140
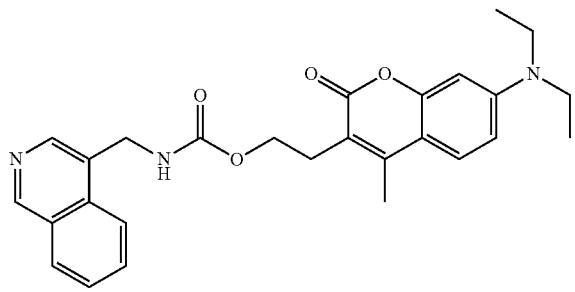 [SMILES: CCN(CC)c1ccc2c(C)c(CCOC(=O)NCc3cncc4ccccc34)c(=O)oc2c1]
141
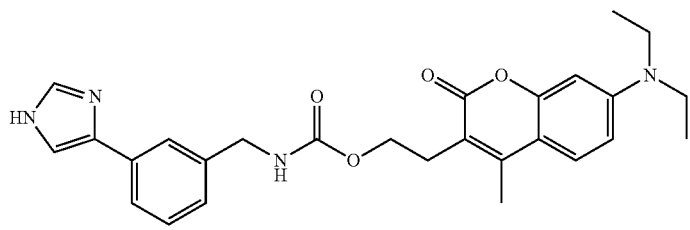 [SMILES: CCN(CC)c1ccc2c(C)c(CCOC(=O)NCc3cccc(-c4c[nH]cn4)c3)c(=O)oc2c1]
142
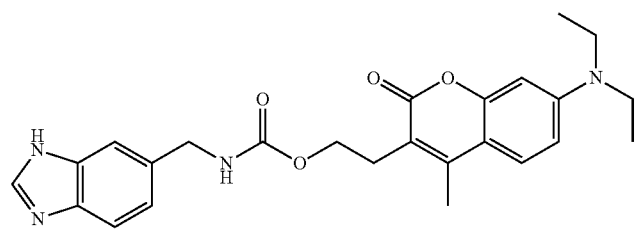 [SMILES: CCN(CC)c1ccc2c(C)c(CCOC(=O)NCc3ccc4nc[nH]c4c3)c(=O)oc2c1]
143
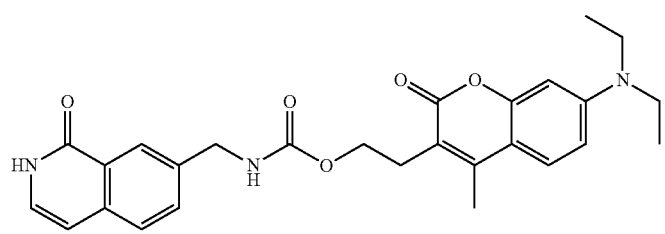 [SMILES: CCN(CC)c1ccc2c(C)c(CCOC(=O)NCc3ccc4cc[nH]c(=O)c4c3)c(=O)oc2c1]
144
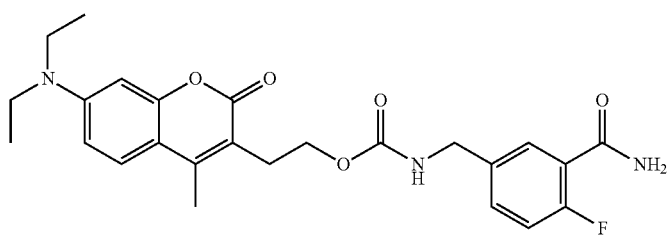 [SMILES: CCN(CC)c1ccc2c(C)c(CCOC(=O)NCc3ccc(F)c(C(N)=O)c3)c(=O)oc2c1]
145
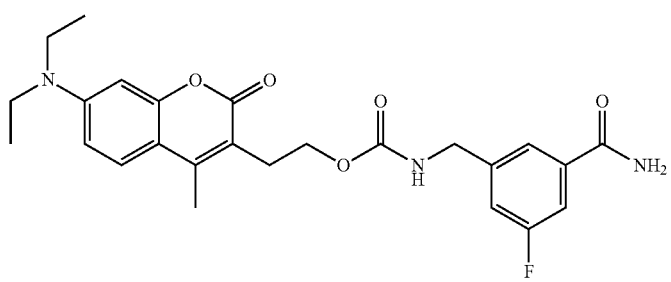 [SMILES: CCN(CC)c1ccc2c(C)c(CCOC(=O)NCc3cc(F)cc(C(N)=O)c3)c(=O)oc2c1]

146
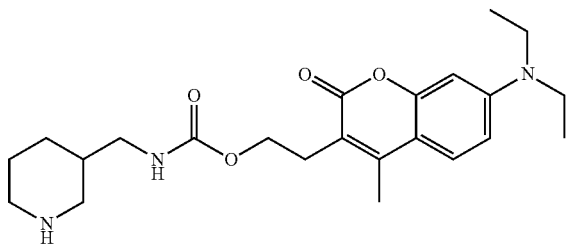 [SMILES: CCN(CC)c1ccc2c(C)c(CCOC(=O)NCC3CCCNC3)c(=O)oc2c1]
147
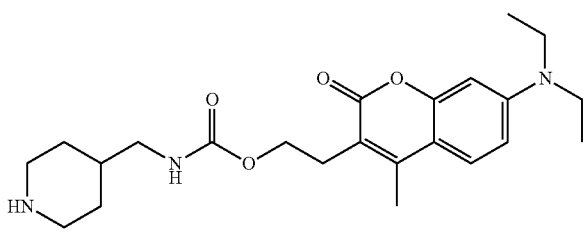 [SMILES: CCN(CC)c1ccc2c(C)c(CCOC(=O)NCC3CCNCC3)c(=O)oc2c1]
148
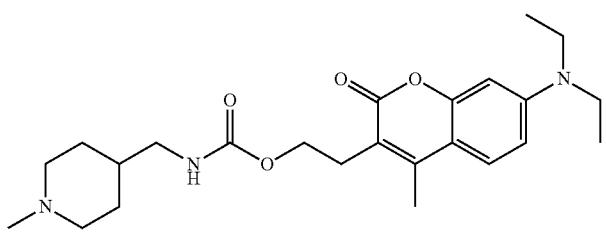 [SMILES: CCN(CC)c1ccc2c(C)c(CCOC(=O)NCC3CCN(C)CC3)c(=O)oc2c1]
149
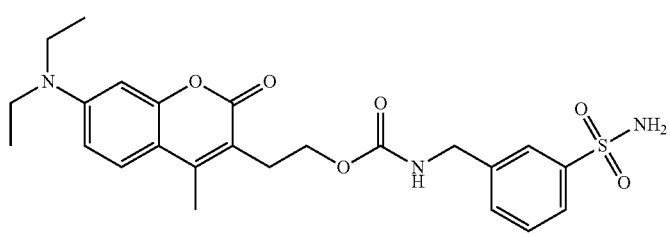 [SMILES: CCN(CC)c1ccc2c(C)c(CCOC(=O)NCc3cccc(S(N)(=O)=O)c3)c(=O)oc2c1]
150
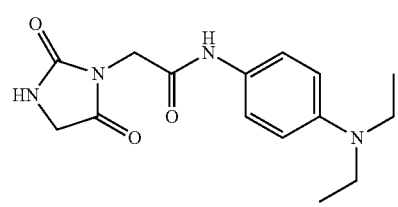 [SMILES: CCN(CC)c1ccc(NC(=O)CN2C(=O)CNC2=O)cc1]
151
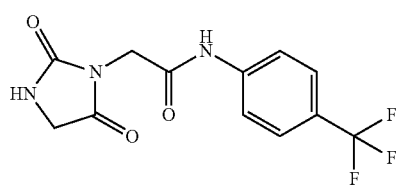 [SMILES: O=C(CN1C(=O)CNC1=O)Nc1ccc(C(F)(F)F)cc1]
152
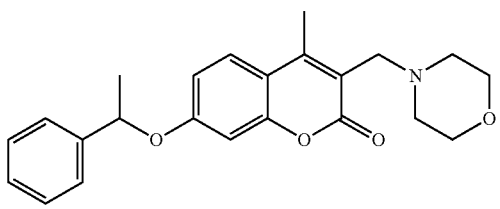 [SMILES: Cc1c(CN2CCOCC2)c(=O)oc2cc(OC(C)c3ccccc3)ccc12]

153 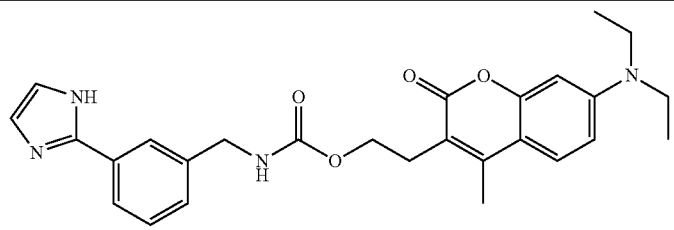
154 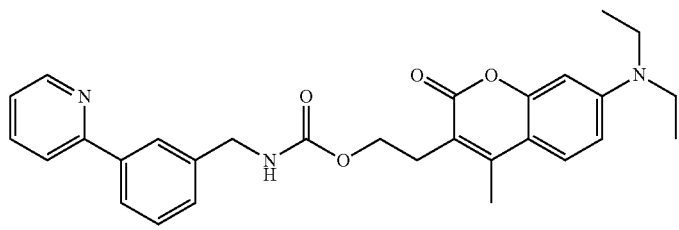
155 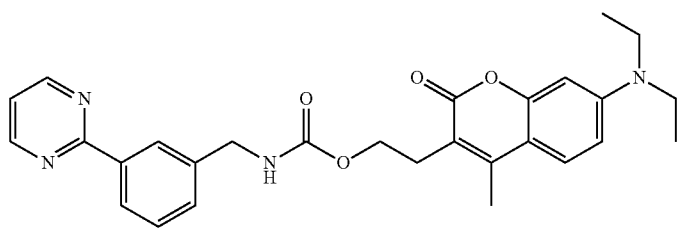 [SMILES: CCN(CC)c1ccc2c(C)c(CCOC(=O)NCc3cccc(-c4ncccn4)c3)c(=O)oc2c1]
156 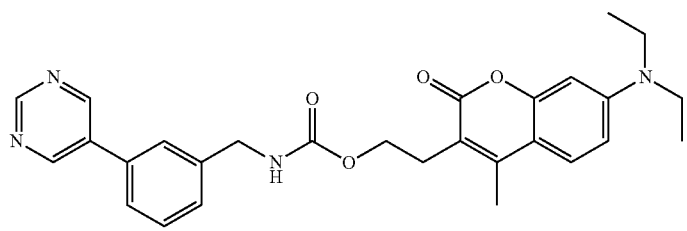 [SMILES: CCN(CC)c1ccc2c(C)c(CCOC(=O)NCc3cccc(-c4cncnc4)c3)c(=O)oc2c1]
157 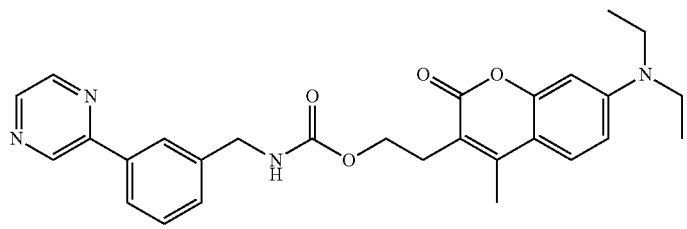 [SMILES: CCN(CC)c1ccc2c(C)c(CCOC(=O)NCc3cccc(-c4cnccn4)c3)c(=O)oc2c1]
158 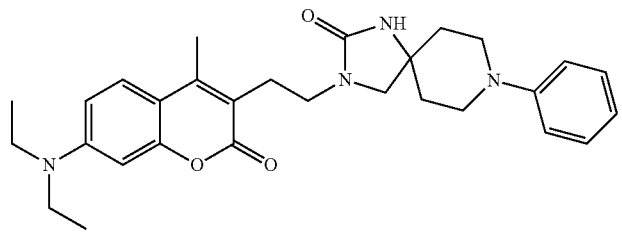 [SMILES: CCN(CC)c1ccc2c(C)c(CCN3CC4(CCN(c5ccccc5)CC4)NC3=O)c(=O)oc2c1]
159 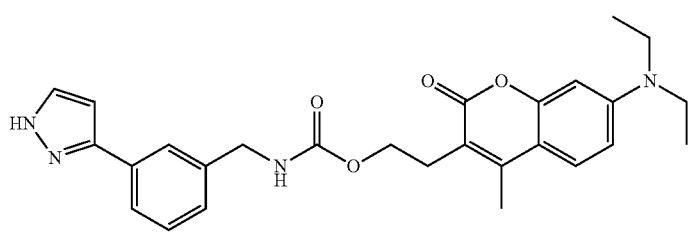 [SMILES: CCN(CC)c1ccc2c(C)c(CCOC(=O)NCc3cccc(-c4cc[nH]n4)c3)c(=O)oc2c1]

160
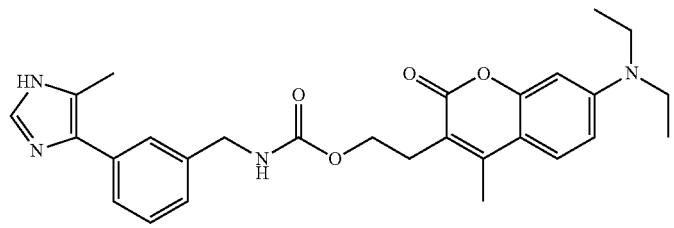 [SMILES: CCN(CC)c1ccc2c(C)c(CCOC(=O)NCc3cccc(-c4nc[nH]c4C)c3)c(=O)oc2c1]
161
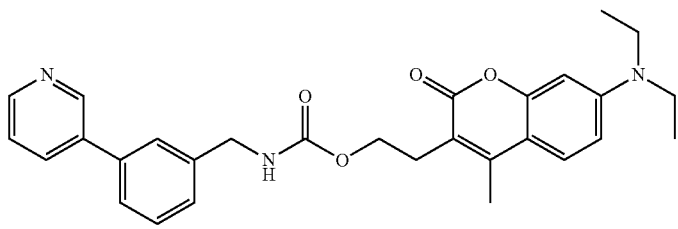 [SMILES: CCN(CC)c1ccc2c(C)c(CCOC(=O)NCc3cccc(-c4cccnc4)c3)c(=O)oc2c1]
162
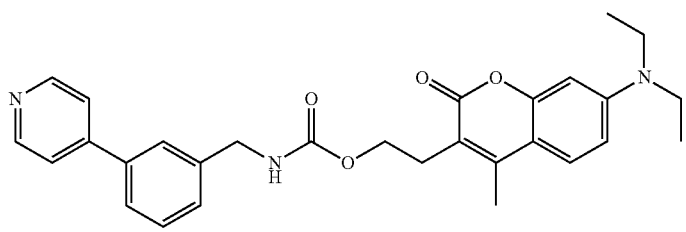 [SMILES: CCN(CC)c1ccc2c(C)c(CCOC(=O)NCc3cccc(-c4ccncc4)c3)c(=O)oc2c1]
163
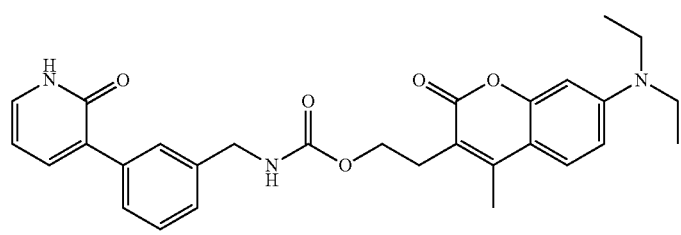 [SMILES: CCN(CC)c1ccc2c(C)c(CCOC(=O)NCc3cccc(-c4ccc[nH]c4=O)c3)c(=O)oc2c1]
164
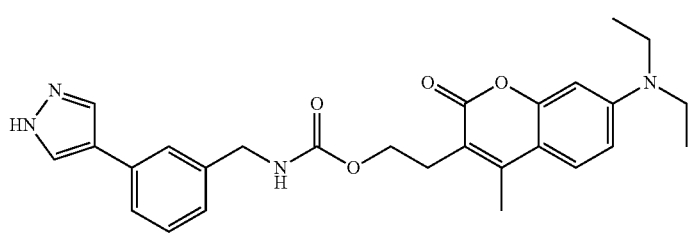 [SMILES: CCN(CC)c1ccc2c(C)c(CCOC(=O)NCc3cccc(-c4cn[nH]c4)c3)c(=O)oc2c1]
165
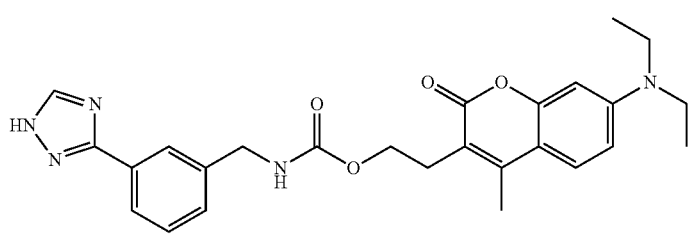 [SMILES: CCN(CC)c1ccc2c(C)c(CCOC(=O)NCc3cccc(-c4nc[nH]n4)c3)c(=O)oc2c1]

166
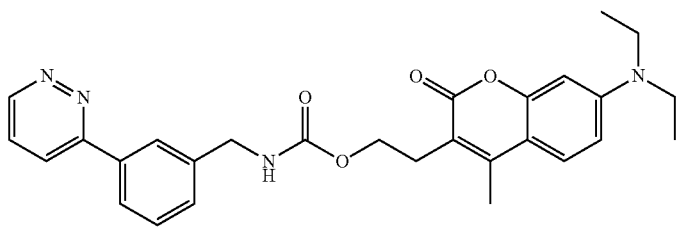 [SMILES: CCN(CC)c1ccc2c(C)c(CCOC(=O)NCc3cccc(-c4cccnn4)c3)c(=O)oc2c1]
167
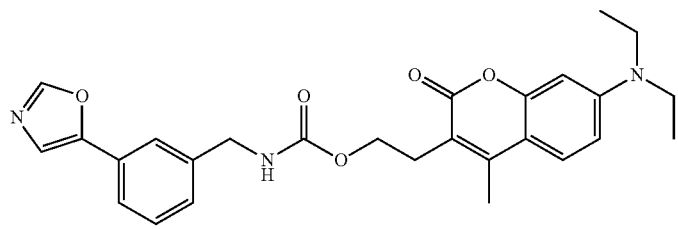 [SMILES: CCN(CC)c1ccc2c(C)c(CCOC(=O)NCc3cccc(-c4cnco4)c3)c(=O)oc2c1]
168
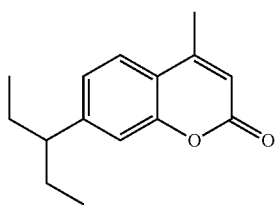 [SMILES: CCC(CC)c1ccc2c(C)cc(=O)oc2c1]
169
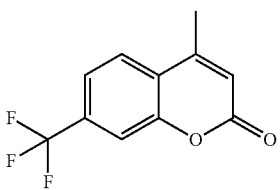 [SMILES: Cc1cc(=O)oc2cc(C(F)(F)F)ccc12]
170
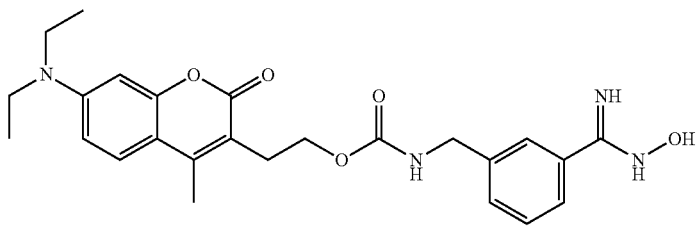 [SMILES: CCN(CC)c1ccc2c(C)c(CCOC(=O)NCc3cccc(C(=N)NO)c3)c(=O)oc2c1]
171
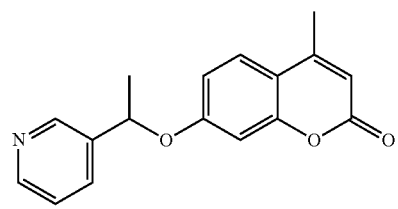 [SMILES: Cc1cc(=O)oc2cc(OC(C)c3cccnc3)ccc12]
172
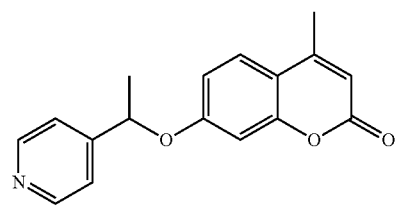

-continued
173 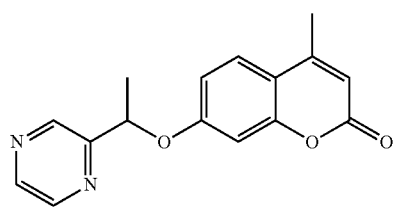 [SMILES: Cc1cc(=O)oc2cc(OC(C)c3cnccn3)ccc12]
174 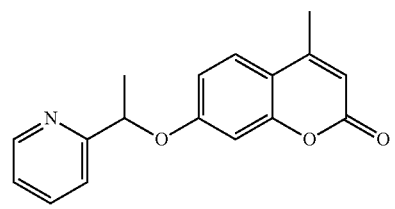 [SMILES: Cc1cc(=O)oc2cc(OC(C)c3ccccn3)ccc12]
175 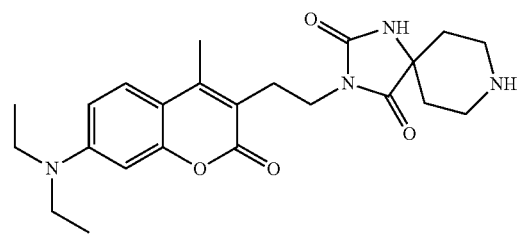 [SMILES: CCN(CC)c1ccc2c(C)c(CCN3C(=O)NC4(CCNCC4)C3=O)c(=O)oc2c1]
176 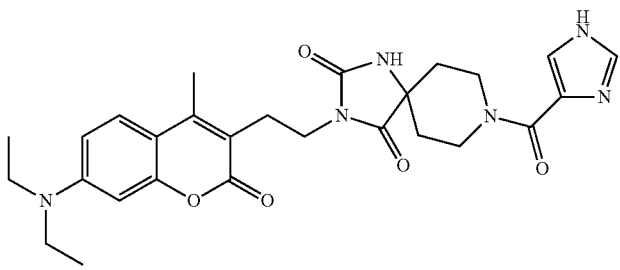 [SMILES: CCN(CC)c1ccc2c(C)c(CCN3C(=O)NC4(CCN(C(=O)c5c[nH]cn5)CC4)C3=O)c(=O)oc2c1]
177 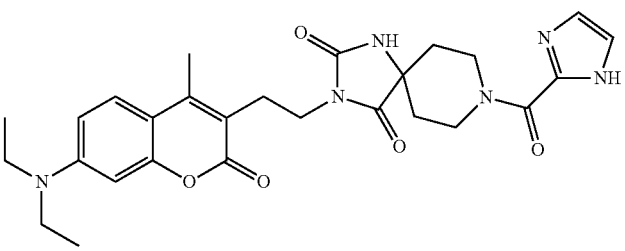 [SMILES: CCN(CC)c1ccc2c(C)c(CCN3C(=O)NC4(CCN(C(=O)c5ncc[nH]5)CC4)C3=O)c(=O)oc2c1]
178 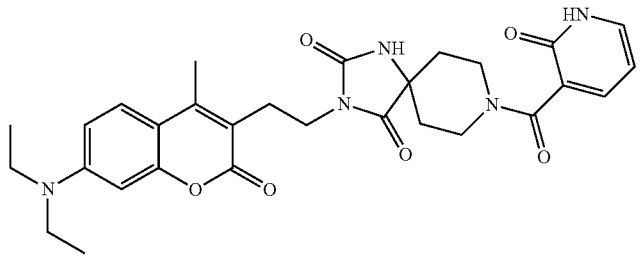 [SMILES: CCN(CC)c1ccc2c(C)c(CCN3C(=O)NC4(CCN(C(=O)c5ccc[nH]c5=O)CC4)C3=O)c(=O)oc2c1]

-continued
179
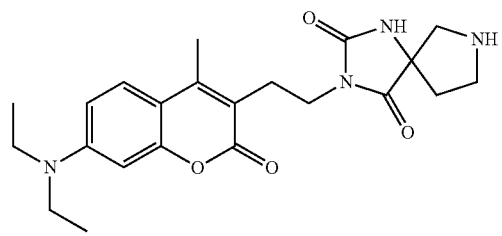 [SMILES: CCN(CC)c1ccc2c(C)c(CCN3C(=O)NC4(CCNC4)C3=O)c(=O)oc2c1]
180
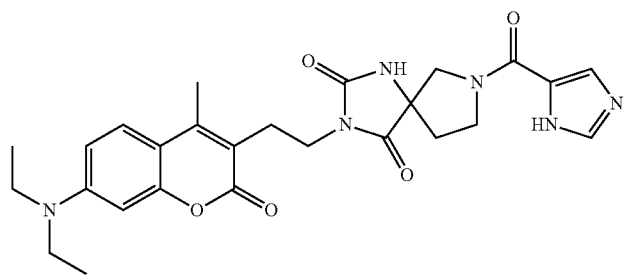 [SMILES: CCN(CC)c1ccc2c(C)c(CCN3C(=O)NC4(CCN(C(=O)c5cnc[nH]5)C4)C3=O)c(=O)oc2c1]
181
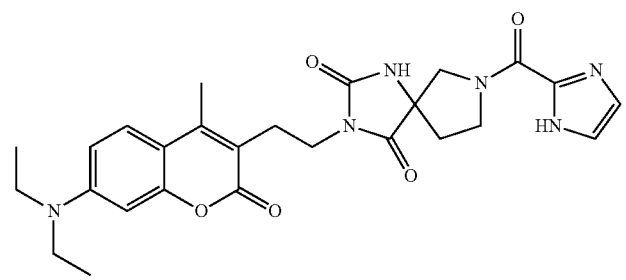 [SMILES: CCN(CC)c1ccc2c(C)c(CCN3C(=O)NC4(CCN(C(=O)c5ncc[nH]5)C4)C3=O)c(=O)oc2c1]
182
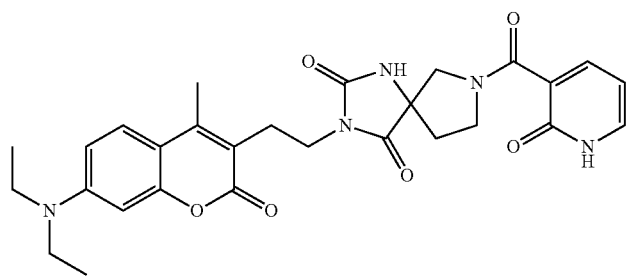 [SMILES: CCN(CC)c1ccc2c(C)c(CCN3C(=O)NC4(CCN(C(=O)c5ccc[nH]c5=O)C4)C3=O)c(=O)oc2c1]
183
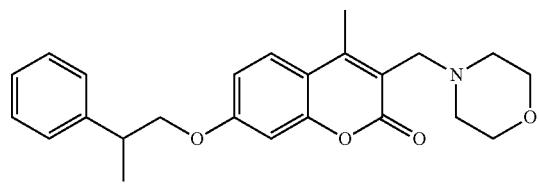 [SMILES: Cc1c(CN2CCOCC2)c(=O)oc2cc(OCC(C)c3ccccc3)ccc12]
184
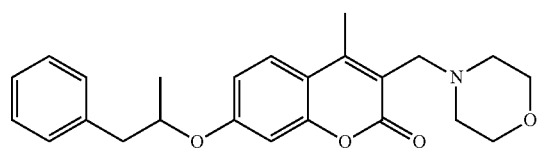 [SMILES: Cc1c(CN2CCOCC2)c(=O)oc2cc(OC(C)Cc3ccccc3)ccc12]

-continued
185
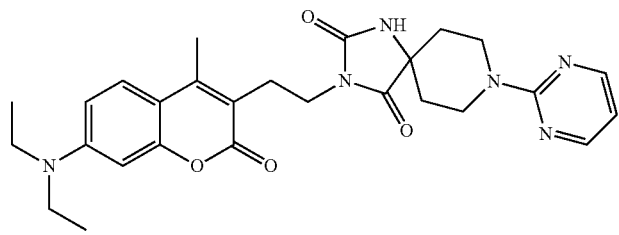 [SMILES: CCN(CC)c1ccc2c(C)c(CCN3C(=O)NC4(CCN(c5ncccn5)CC4)C3=O)c(=O)oc2c1]
186
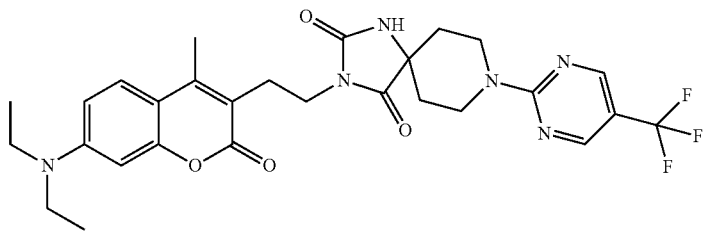 [SMILES: CCN(CC)c1ccc2c(C)c(CCN3C(=O)NC4(CCN(c5ncc(C(F)(F)F)cn5)CC4)C3=O)c(=O)oc2c1]
187
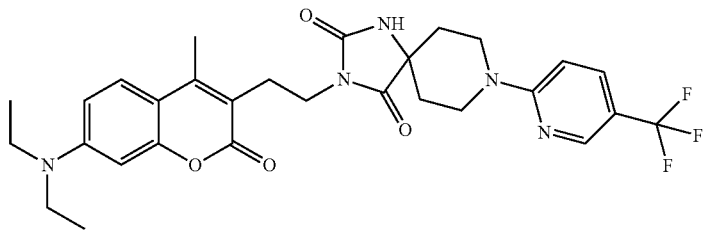 [SMILES: CCN(CC)c1ccc2c(C)c(CCN3C(=O)NC4(CCN(c5ccc(C(F)(F)F)cn5)CC4)C3=O)c(=O)oc2c1]
188
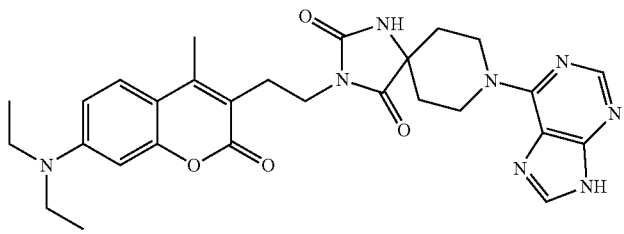 [SMILES: CCN(CC)c1ccc2c(C)c(CCN3C(=O)NC4(CCN(c5ncnc6[nH]cnc56)CC4)C3=O)c(=O)oc2c1]
189
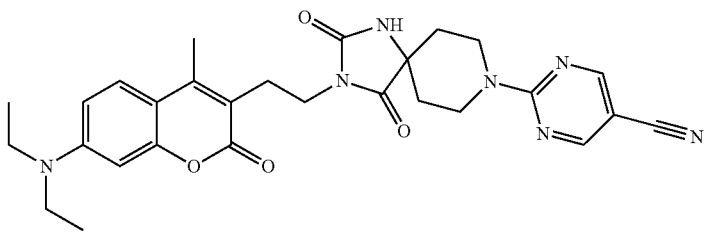
190
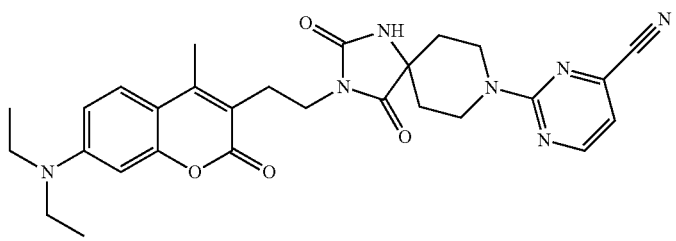 [SMILES: CCN(CC)c1ccc2c(C)c(CCN3C(=O)NC4(CCN(c5nccc(C#N)n5)CC4)C3=O)c(=O)oc2c1]

191 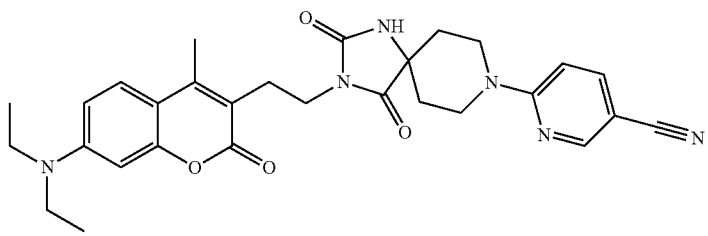 [SMILES: CCN(CC)c1ccc2c(C)c(CCN3C(=O)NC4(CCN(c5ccc(C#N)cn5)CC4)C3=O)c(=O)oc2c1]
192 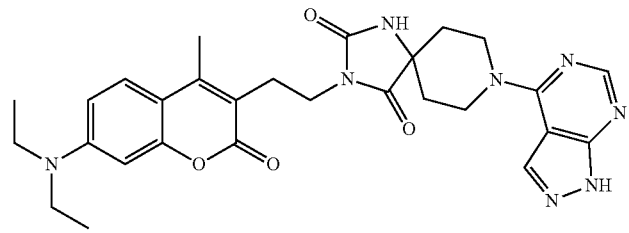 [SMILES: CCN(CC)c1ccc2c(C)c(CCN3C(=O)NC4(CCN(c5ncnc6[nH]ncc56)CC4)C3=O)c(=O)oc2c1]
193 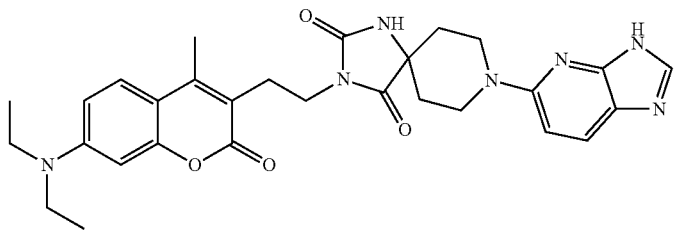 [SMILES: CCN(CC)c1ccc2c(C)c(CCN3C(=O)NC4(CCN(c5ccc6nc[nH]c6n5)CC4)C3=O)c(=O)oc2c1]
194 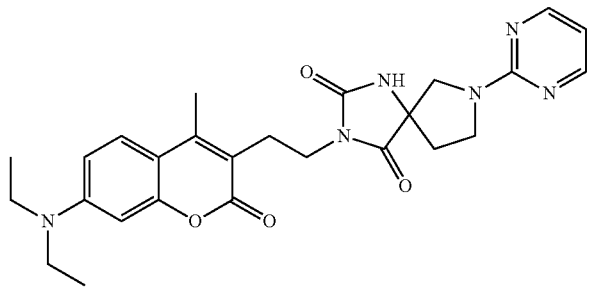 [SMILES: CCN(CC)c1ccc2c(C)c(CCN3C(=O)NC4(CCN(c5ncccn5)C4)C3=O)c(=O)oc2c1]
195 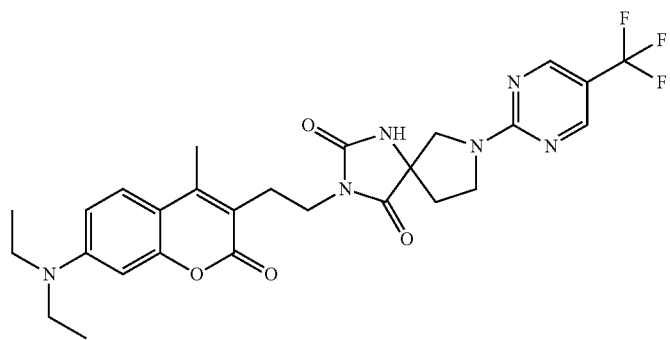 [SMILES: CCN(CC)c1ccc2c(C)c(CCN3C(=O)NC4(CCN(c5ncc(C(F)(F)F)cn5)C4)C3=O)c(=O)oc2c1]

196
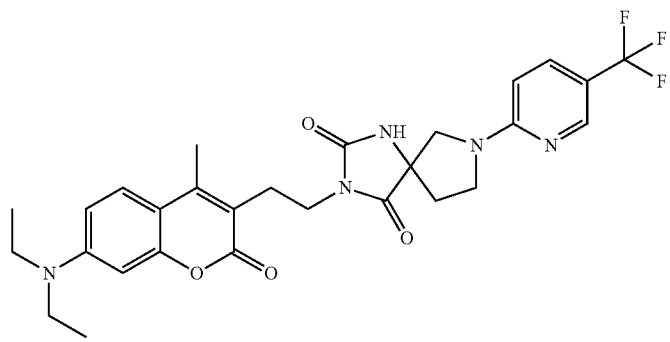 [SMILES: CCN(CC)c1ccc2c(C)c(CCN3C(=O)NC4(CCN(c5ccc(C(F)(F)F)cn5)C4)C3=O)c(=O)oc2c1]
197
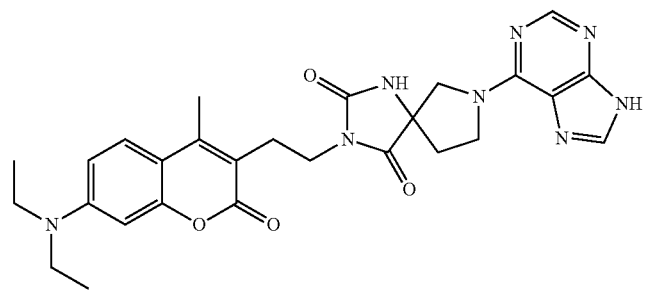 [SMILES: CCN(CC)c1ccc2c(C)c(CCN3C(=O)NC4(CCN(c5ncnc6[nH]cnc56)C4)C3=O)c(=O)oc2c1]
198
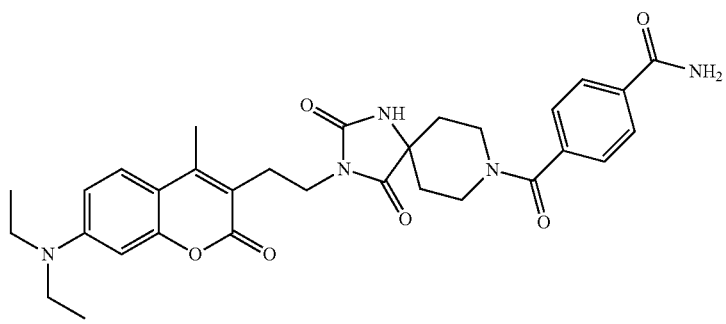 [SMILES: CCN(CC)c1ccc2c(C)c(CCN3C(=O)NC4(CCN(C(=O)c5ccc(C(N)=O)cc5)CC4)C3=O)c(=O)oc2c1]
199
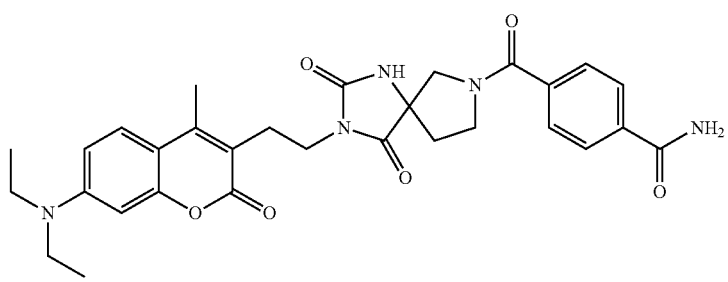 [SMILES: CCN(CC)c1ccc2c(C)c(CCN3C(=O)NC4(CCN(C(=O)c5ccc(C(N)=O)cc5)C4)C3=O)c(=O)oc2c1]
200
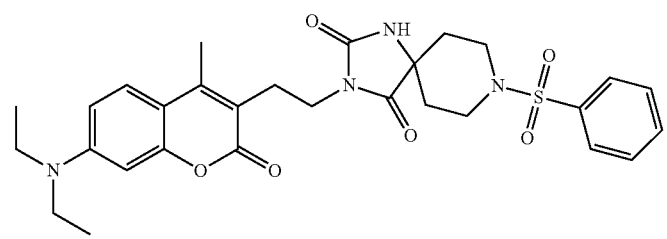 [SMILES: CCN(CC)c1ccc2c(C)c(CCN3C(=O)NC4(CCN(S(=O)(=O)c5ccccc5)CC4)C3=O)c(=O)oc2c1]

201 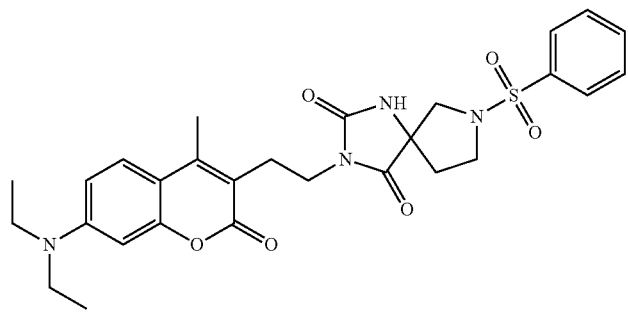 [SMILES: CCN(CC)c1ccc2c(C)c(CCN3C(=O)NC4(CCN(S(=O)(=O)c5ccccc5)C4)C3=O)c(=O)oc2c1]
202 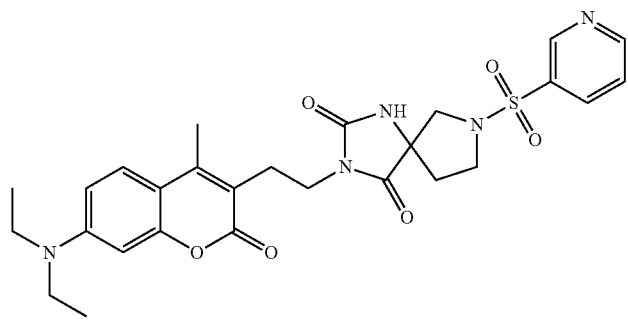 [SMILES: CCN(CC)c1ccc2c(C)c(CCN3C(=O)NC4(CCN(S(=O)(=O)c5cccnc5)C4)C3=O)c(=O)oc2c1]
203 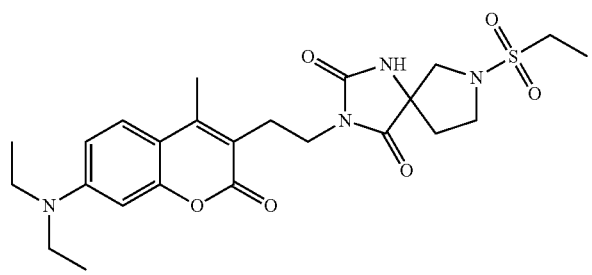 [SMILES: CCN(CC)c1ccc2c(C)c(CCN3C(=O)NC4(CCN(S(=O)(=O)CC)C4)C3=O)c(=O)oc2c1]
204 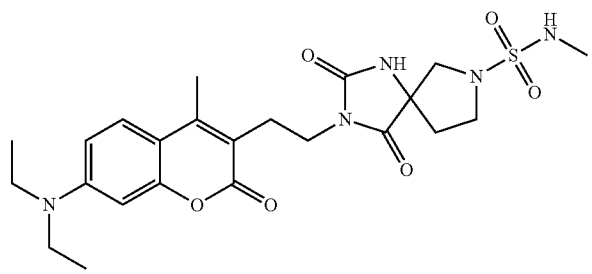
205 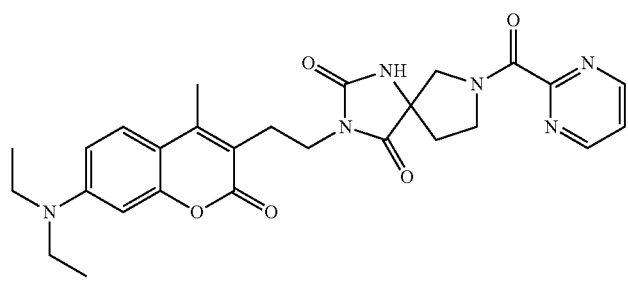 [SMILES: CCN(CC)c1ccc2c(C)c(CCN3C(=O)NC4(CCN(C(=O)c5ncccn5)C4)C3=O)c(=O)oc2c1]

-continued
206 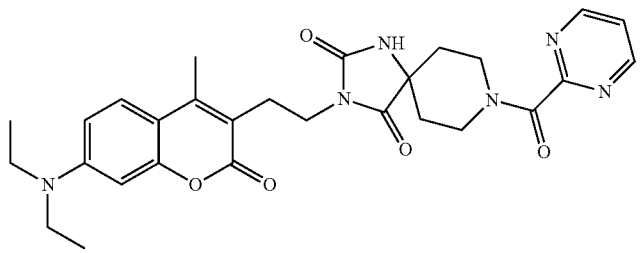 [SMILES: CCN(CC)c1ccc2c(C)c(CCN3C(=O)NC4(CCN(C(=O)c5ncccn5)CC4)C3=O)c(=O)oc2c1]
207 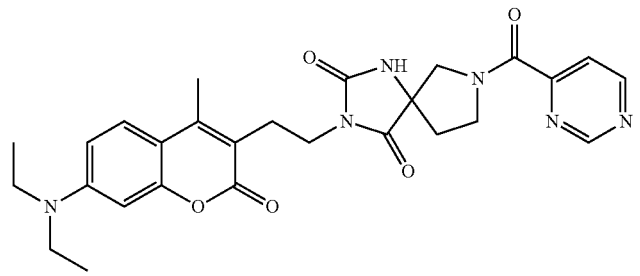 [SMILES: CCN(CC)c1ccc2c(C)c(CCN3C(=O)NC4(CCN(C(=O)c5ccncn5)C4)C3=O)c(=O)oc2c1]
208 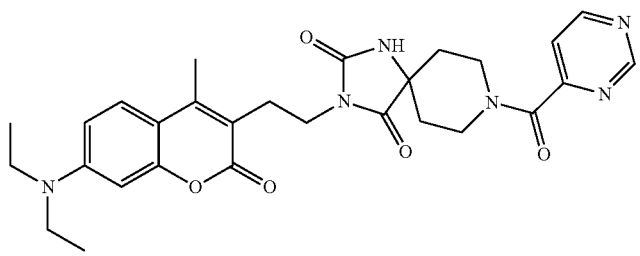 [SMILES: CCN(CC)c1ccc2c(C)c(CCN3C(=O)NC4(CCN(C(=O)c5ccncn5)CC4)C3=O)c(=O)oc2c1]
209 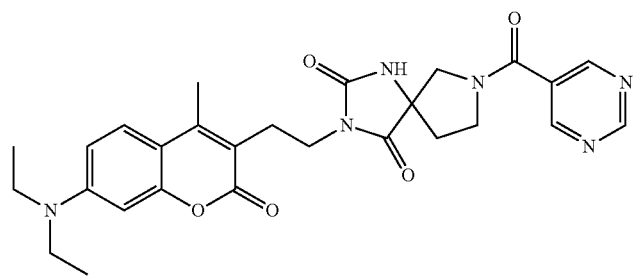 [SMILES: CCN(CC)c1ccc2c(C)c(CCN3C(=O)NC4(CCN(C(=O)c5cncnc5)C4)C3=O)c(=O)oc2c1]
210 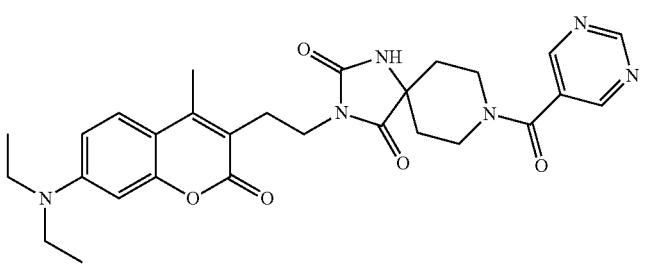 [SMILES: CCN(CC)c1ccc2c(C)c(CCN3C(=O)NC4(CCN(C(=O)c5cncnc5)CC4)C3=O)c(=O)oc2c1]
211 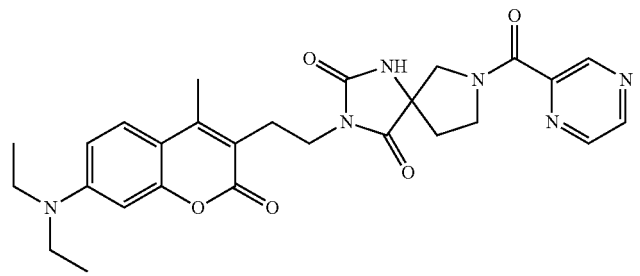 [SMILES: CCN(CC)c1ccc2c(C)c(CCN3C(=O)NC4(CCN(C(=O)c5cnccn5)C4)C3=O)c(=O)oc2c1]

-continued
| | |
|---|---|
| 212 | 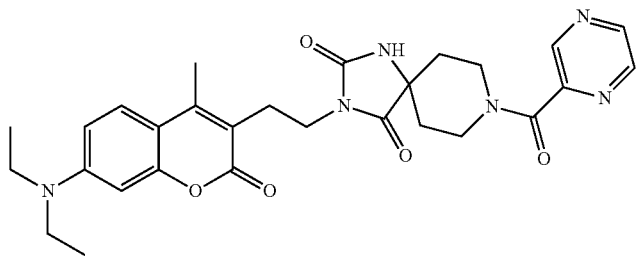 [SMILES: CCN(CC)c1ccc2c(C)c(CCN3C(=O)NC4(CCN(C(=O)c5cnccn5)CC4)C3=O)c(=O)oc2c1] |
| 213 | 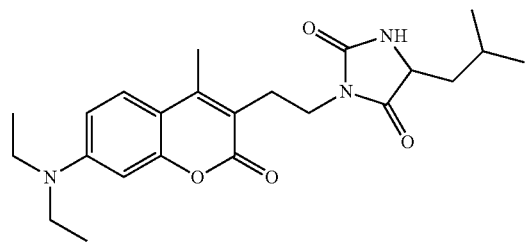 [SMILES: CCN(CC)c1ccc2c(C)c(CCN3C(=O)NC(CC(C)C)C3=O)c(=O)oc2c1] |
| 214 | 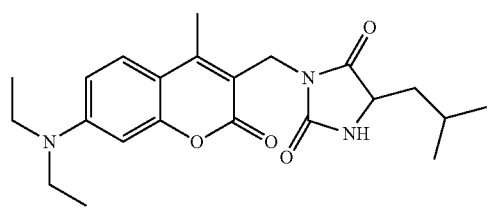 [SMILES: CCN(CC)c1ccc2c(C)c(CN3C(=O)NC(CC(C)C)C3=O)c(=O)oc2c1] |
| 215 | 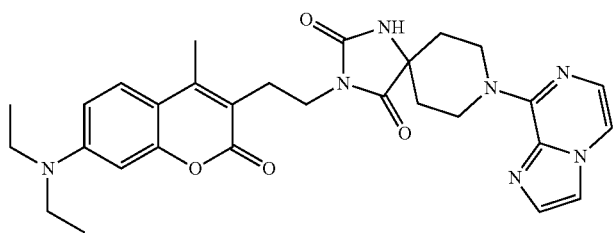 [SMILES: CCN(CC)c1ccc2c(C)c(CCN3C(=O)NC4(CCN(c5nccn6ccnc56)CC4)C3=O)c(=O)oc2c1] |
| 216 | 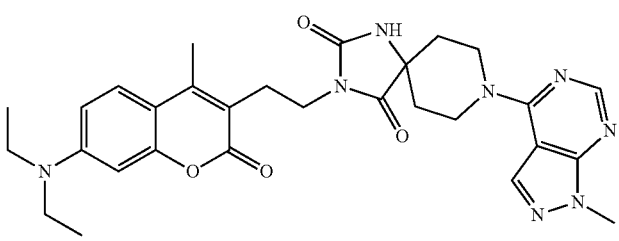 [SMILES: CCN(CC)c1ccc2c(C)c(CCN3C(=O)NC4(CCN(c5ncnc6c5cnn6C)CC4)C3=O)c(=O)oc2c1] |
| 217 | 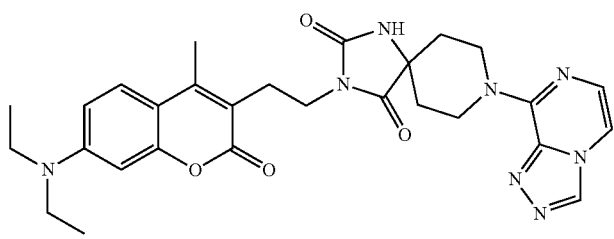 [SMILES: CCN(CC)c1ccc2c(C)c(CCN3C(=O)NC4(CCN(c5nccn6cnnc56)CC4)C3=O)c(=O)oc2c1] |

-continued
218
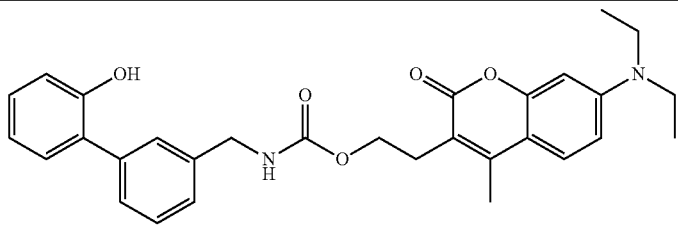
219
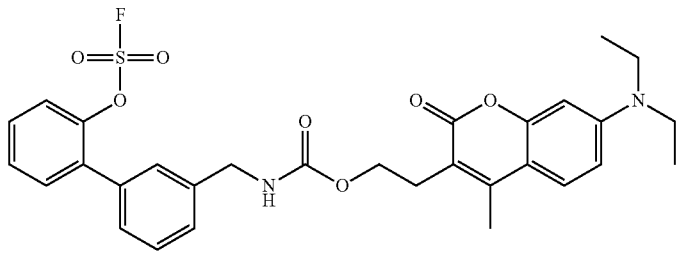 [SMILES: CCN(CC)c1ccc2c(C)c(CCOC(=O)NCc3cccc(-c4ccccc4OS(=O)(=O)F)c3)c(=O)oc2c1]
220
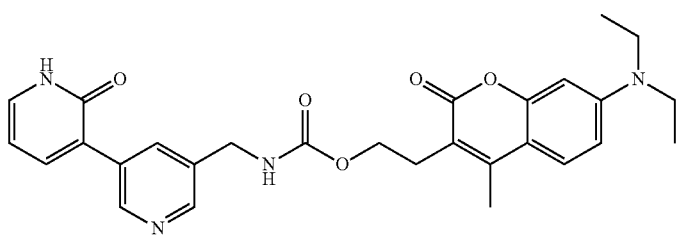 [SMILES: CCN(CC)c1ccc2c(C)c(CCOC(=O)NCc3cncc(-c4ccc[nH]c4=O)c3)c(=O)oc2c1]
221
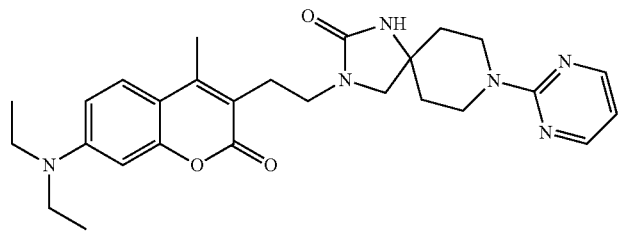 [SMILES: CCN(CC)c1ccc2c(C)c(CCN3CC4(CCN(c5ncccn5)CC4)NC3=O)c(=O)oc2c1]
222
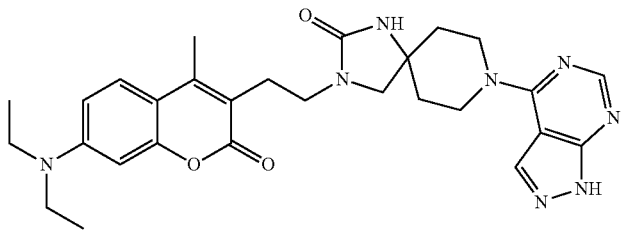 [SMILES: CCN(CC)c1ccc2c(C)c(CCN3CC4(CCN(c5ncnc6[nH]ncc56)CC4)NC3=O)c(=O)oc2c1]
223
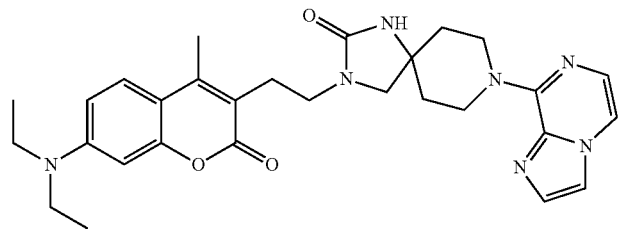 [SMILES: CCN(CC)c1ccc2c(C)c(CCN3CC4(CCN(c5nccn6ccnc56)CC4)NC3=O)c(=O)oc2c1]
224
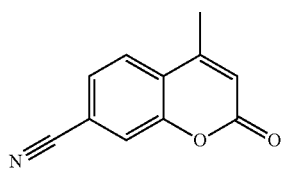

-continued
| | |
|---|---|
| 225 | 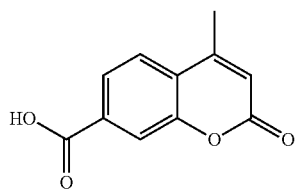 |
| 226 | 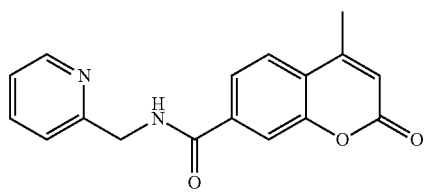 [SMILES: Cc1cc(=O)oc2cc(C(=O)NCc3ccccn3)ccc12] |
| 227 | 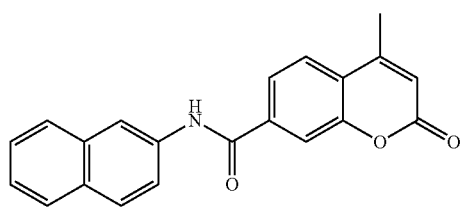 [SMILES: Cc1cc(=O)oc2cc(C(=O)Nc3ccc4ccccc4c3)ccc12] |
| 228 | 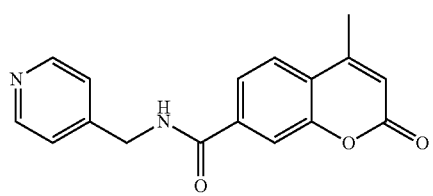 [SMILES: Cc1cc(=O)oc2cc(C(=O)NCc3ccncc3)ccc12] |
| 229 | 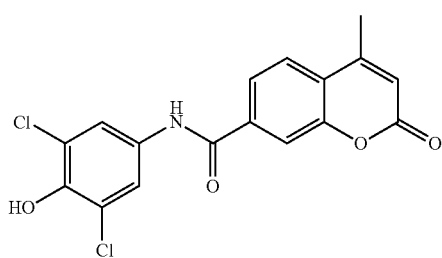 [SMILES: Cc1cc(=O)oc2cc(C(=O)Nc3cc(Cl)c(O)c(Cl)c3)ccc12] |
| 230 | 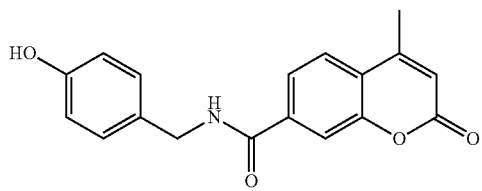 [SMILES: Cc1cc(=O)oc2cc(C(=O)NCc3ccc(O)cc3)ccc12] |
| 231 | 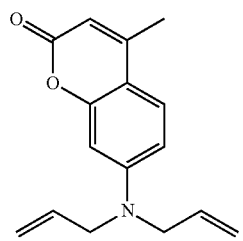 [SMILES: C=CCN(CC=C)c1ccc2c(C)cc(=O)oc2c1] |

232 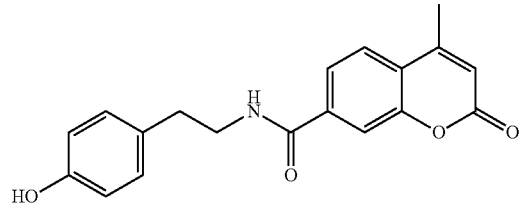 [SMILES: Cc1cc(=O)oc2cc(C(=O)NCCc3ccc(O)cc3)ccc12]
233 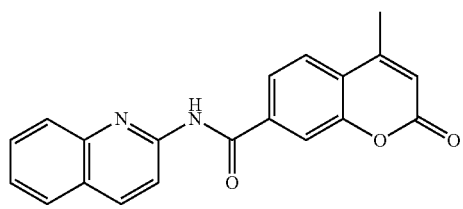 [SMILES: Cc1cc(=O)oc2cc(C(=O)Nc3ccc4ccccc4n3)ccc12]
234 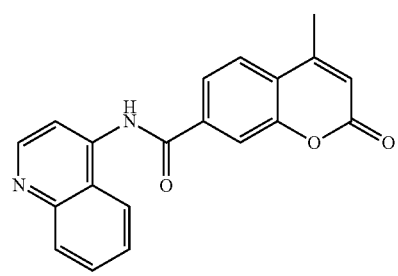 [SMILES: Cc1cc(=O)oc2cc(C(=O)Nc3ccnc4ccccc34)ccc12]
235 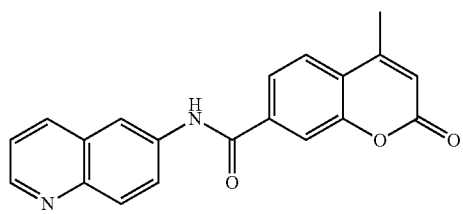 [SMILES: Cc1cc(=O)oc2cc(C(=O)Nc3ccc4ncccc4c3)ccc12]
236 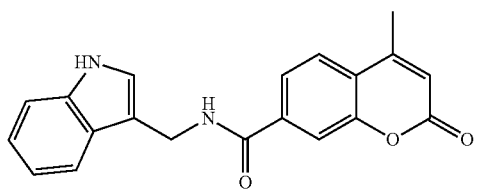 [SMILES: Cc1cc(=O)oc2cc(C(=O)NCc3c[nH]c4ccccc34)ccc12]
237 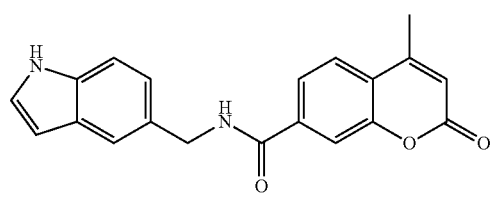 [SMILES: Cc1cc(=O)oc2cc(C(=O)NCc3ccc4[nH]ccc4c3)ccc12]
238 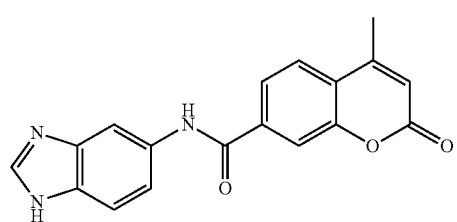 [SMILES: Cc1cc(=O)oc2cc(C(=O)Nc3ccc4[nH]cnc4c3)ccc12]

-continued
239
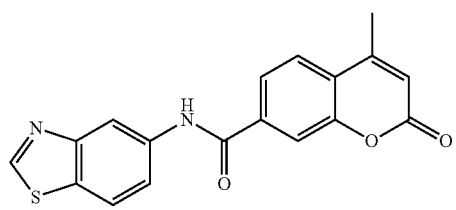 [SMILES: Cc1cc(=O)oc2cc(C(=O)Nc3ccc4scnc4c3)ccc12]
240
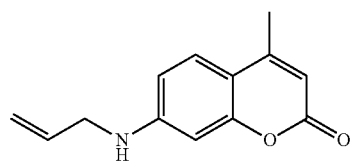 [SMILES: C=CCNc1ccc2c(C)cc(=O)oc2c1]
241
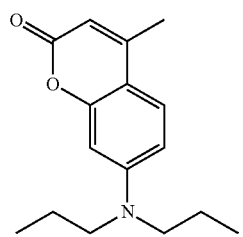 [SMILES: CCCN(CCC)c1ccc2c(C)cc(=O)oc2c1]
242
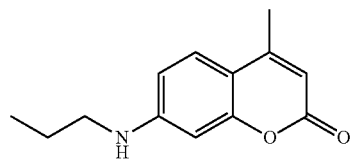 [SMILES: CCCNc1ccc2c(C)cc(=O)oc2c1]
243
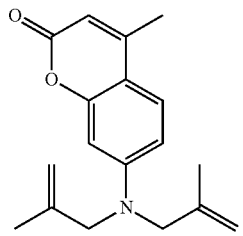 [SMILES: C=C(C)CN(CC(=C)C)c1ccc2c(C)cc(=O)oc2c1]
244
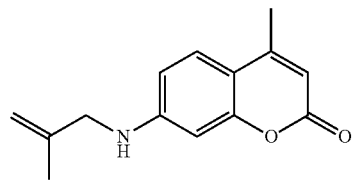 [SMILES: C=C(C)CNc1ccc2c(C)cc(=O)oc2c1]
245
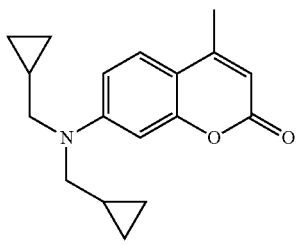 [SMILES: Cc1cc(=O)oc2cc(N(CC3CC3)CC3CC3)ccc12]

| | |
|---|---|
| 246 | 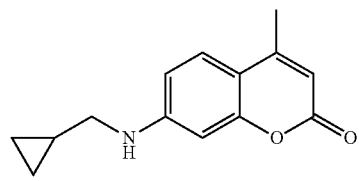 [SMILES: Cc1cc(=O)oc2cc(NCC3CC3)ccc12] |
| 247 | 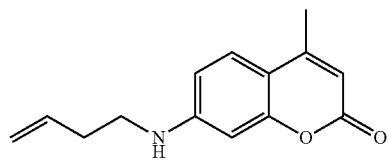 [SMILES: C=CCCNc1ccc2c(C)cc(=O)oc2c1] |
| 248 | 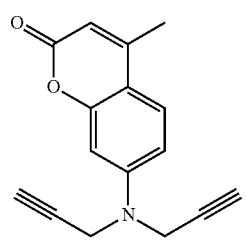 [SMILES: C#CCN(CC#C)c1ccc2c(C)cc(=O)oc2c1] |
| 249 | 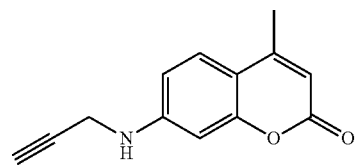 [SMILES: C#CCNc1ccc2c(C)cc(=O)oc2c1] |
| 250 | 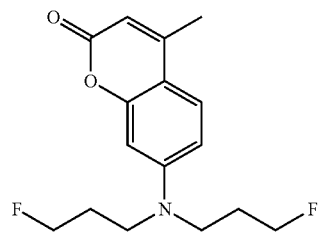 [SMILES: Cc1cc(=O)oc2cc(N(CCCF)CCCF)ccc12] |
| 251 | 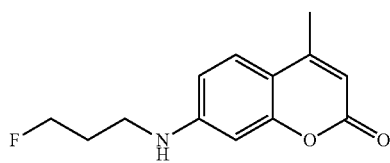 [SMILES: Cc1cc(=O)oc2cc(NCCCF)ccc12] |
| 252 | 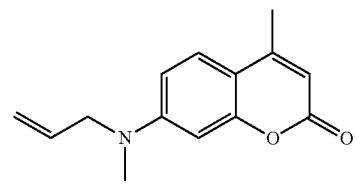 [SMILES: C=CCN(C)c1ccc2c(C)cc(=O)oc2c1] |
| 253 | 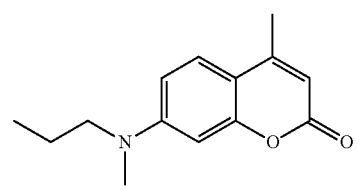 [SMILES: CCCN(C)c1ccc2c(C)cc(=O)oc2c1] |

-continued
| | |
|---|---|
| 254 | 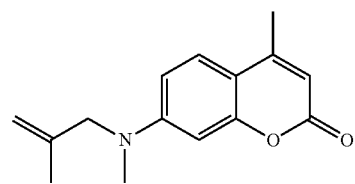 [SMILES: C=C(C)CN(C)c1ccc2c(C)cc(=O)oc2c1] |
| 255 | 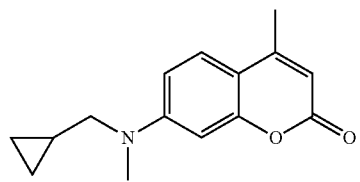 [SMILES: Cc1cc(=O)oc2cc(N(C)CC3CC3)ccc12] |
| 256 | 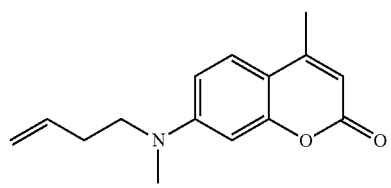 [SMILES: C=CCCN(C)c1ccc2c(C)cc(=O)oc2c1] |
| 257 | 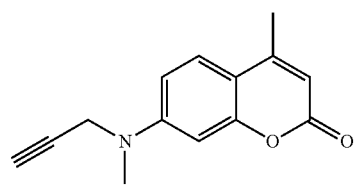 [SMILES: C#CCN(C)c1ccc2c(C)cc(=O)oc2c1] |
| 258 | 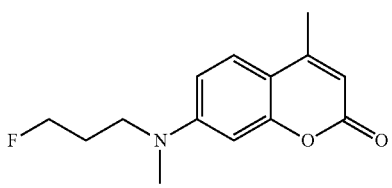 [SMILES: Cc1cc(=O)oc2cc(N(C)CCCF)ccc12] |
| 259 | 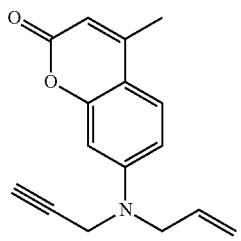 [SMILES: C#CCN(CC=C)c1ccc2c(C)cc(=O)oc2c1] |
| 260 | 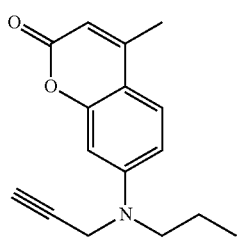 [SMILES: C#CCN(CCC)c1ccc2c(C)cc(=O)oc2c1] |

261 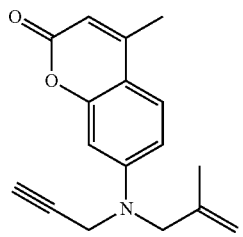 [SMILES: C#CCN(CC(=C)C)c1ccc2c(C)cc(=O)oc2c1]
262 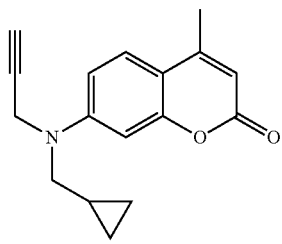 [SMILES: C#CCN(CC1CC1)c1ccc2c(C)cc(=O)oc2c1]
263 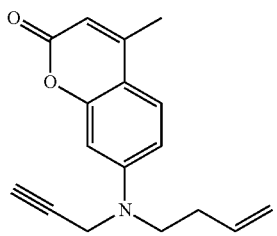 [SMILES: C#CCN(CCC=C)c1ccc2c(C)cc(=O)oc2c1]
264 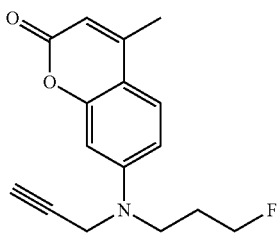 [SMILES: C#CCN(CCCF)c1ccc2c(C)cc(=O)oc2c1]
265 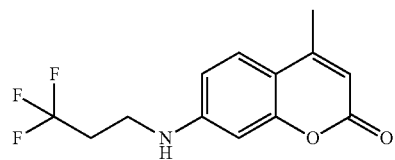 [SMILES: Cc1cc(=O)oc2cc(NCCC(F)(F)F)ccc12]
266 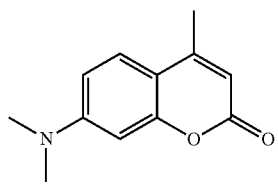
267 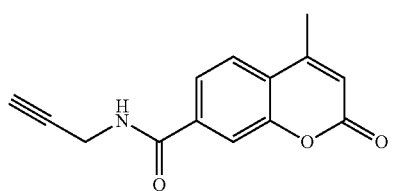 [SMILES: C#CCNC(=O)c1ccc2c(C)cc(=O)oc2c1]

-continued
| 268 | 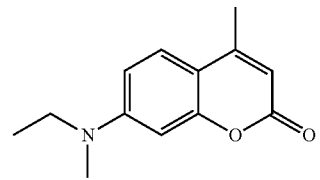 [SMILES: CCN(C)c1ccc2c(C)cc(=O)oc2c1] |
| 269 | 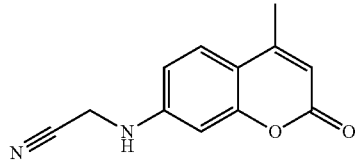 [SMILES: Cc1cc(=O)oc2cc(NCC#N)ccc12] |
| 270 | 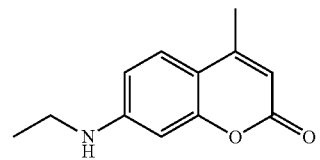 |
| 271 | 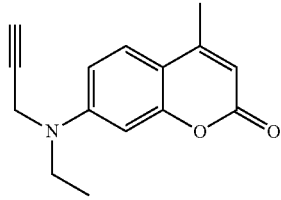 [SMILES: C#CCN(CC)c1ccc2c(C)cc(=O)oc2c1] |
| 272 | 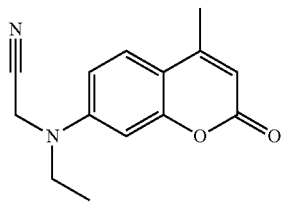 [SMILES: CCN(CC#N)c1ccc2c(C)cc(=O)oc2c1] |
| 273 | 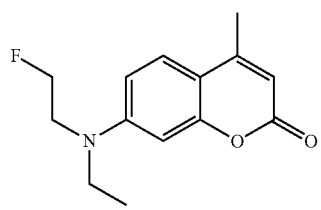 [SMILES: CCN(CCF)c1ccc2c(C)cc(=O)oc2c1] |
| 274 | 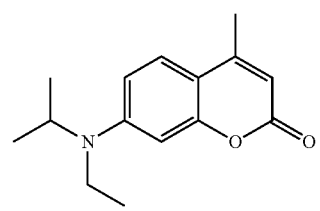 [SMILES: CCN(c1ccc2c(C)cc(=O)oc2c1)C(C)C] |
| 275 | 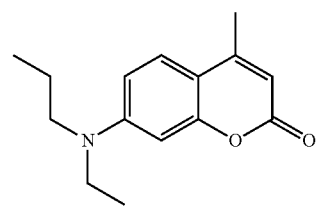 [SMILES: CCCN(CC)c1ccc2c(C)cc(=O)oc2c1] |

-continued
276
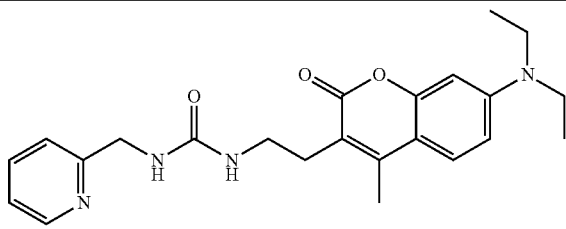
277
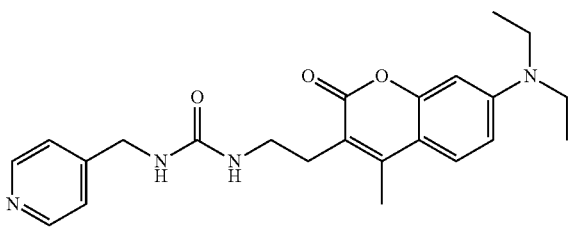 [SMILES: CCN(CC)c1ccc2c(C)c(CCNC(=O)NCc3ccncc3)c(=O)oc2c1]
278
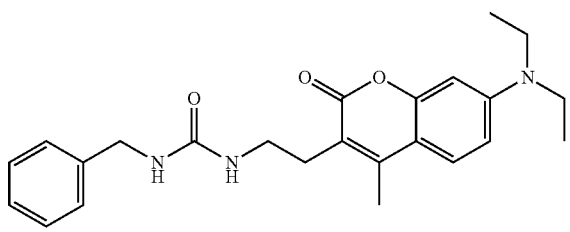 [SMILES: CCN(CC)c1ccc2c(C)c(CCNC(=O)NCc3ccccc3)c(=O)oc2c1]
279
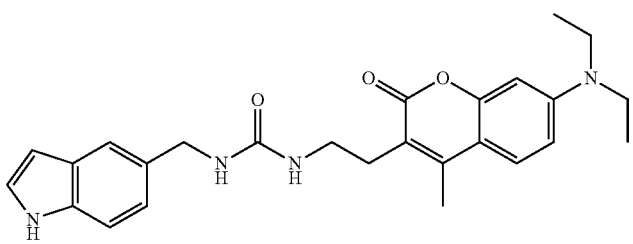
280
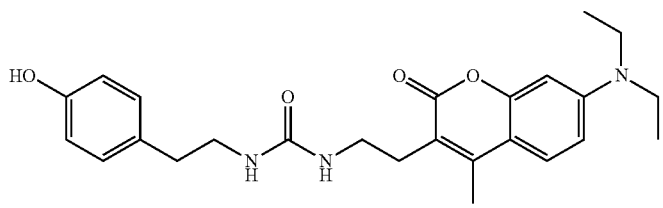 [SMILES: CCN(CC)c1ccc2c(C)c(CCNC(=O)NCCc3ccc(O)cc3)c(=O)oc2c1]
281
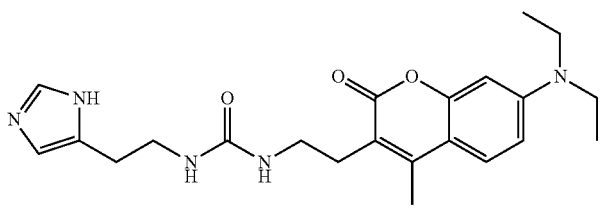 [SMILES: CCN(CC)c1ccc2c(C)c(CCNC(=O)NCCc3cnc[nH]3)c(=O)oc2c1]
282
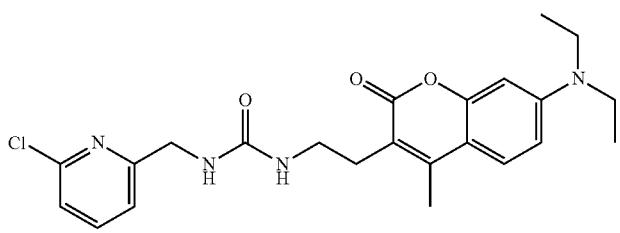 [SMILES: CCN(CC)c1ccc2c(C)c(CCNC(=O)NCc3cccc(Cl)n3)c(=O)oc2c1]

283 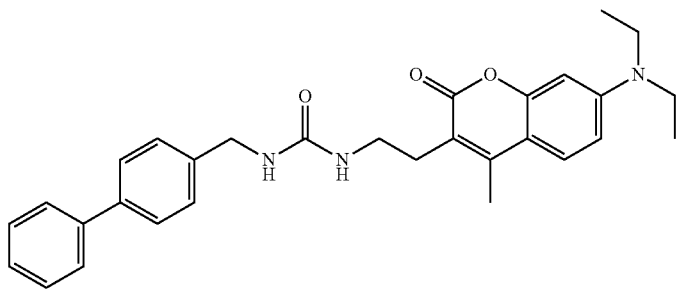 [SMILES: CCN(CC)c1ccc2c(C)c(CCNC(=O)NCc3ccc(-c4ccccc4)cc3)c(=O)oc2c1]
284 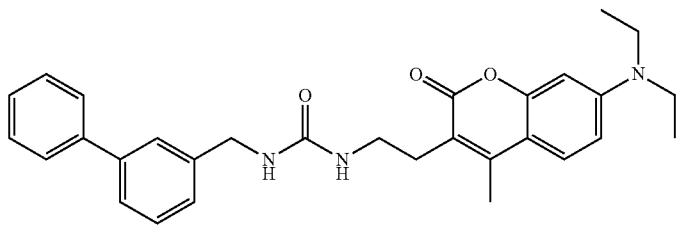 [SMILES: CCN(CC)c1ccc2c(C)c(CCNC(=O)NCc3cccc(-c4ccccc4)c3)c(=O)oc2c1]
285 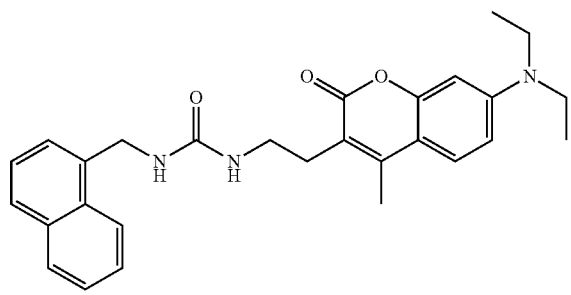
286 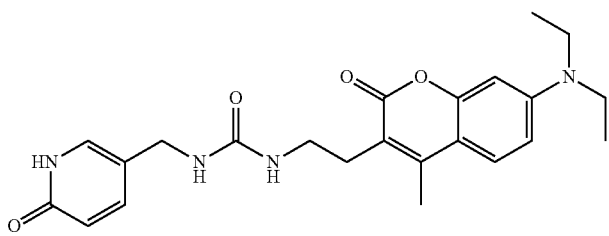 [SMILES: CCN(CC)c1ccc2c(C)c(CCNC(=O)NCc3ccc(=O)[nH]c3)c(=O)oc2c1]
287 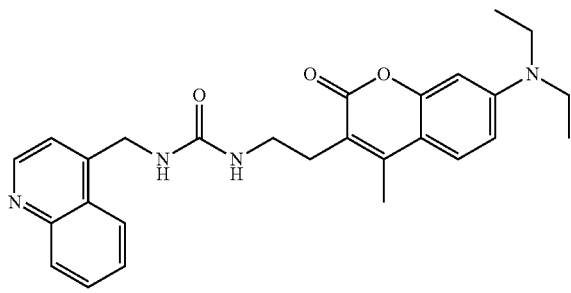 [SMILES: CCN(CC)c1ccc2c(C)c(CCNC(=O)NCc3ccnc4ccccc34)c(=O)oc2c1]
288 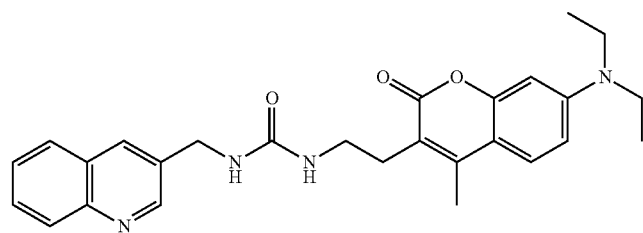 [SMILES: CCN(CC)c1ccc2c(C)c(CCNC(=O)NCc3cnc4ccccc4c3)c(=O)oc2c1]

289 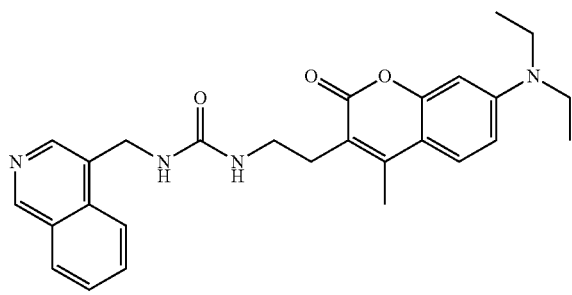 [SMILES: CCN(CC)c1ccc2c(C)c(CCNC(=O)NCc3cncc4ccccc34)c(=O)oc2c1]
290 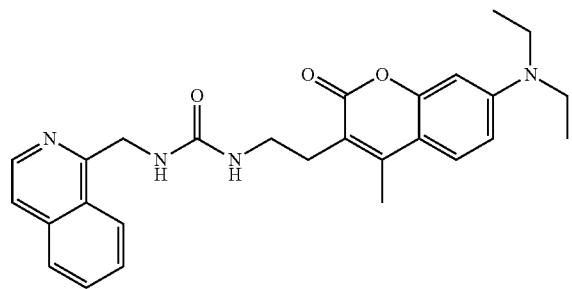 [SMILES: CCN(CC)c1ccc2c(C)c(CCNC(=O)NCc3nccc4ccccc34)c(=O)oc2c1]
291 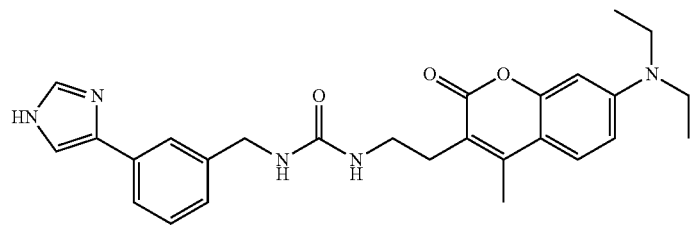 [SMILES: CCN(CC)c1ccc2c(C)c(CCNC(=O)NCc3cccc(-c4c[nH]cn4)c3)c(=O)oc2c1]
292 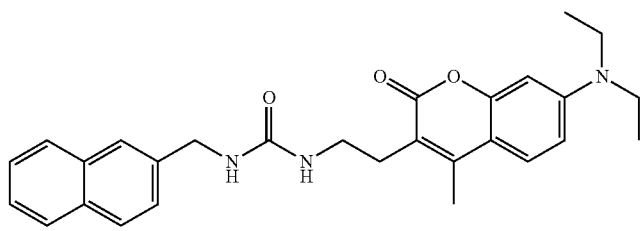 [SMILES: CCN(CC)c1ccc2c(C)c(CCNC(=O)NCc3ccc4ccccc4c3)c(=O)oc2c1]
293 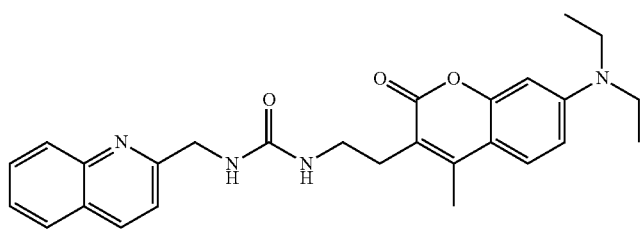 [SMILES: CCN(CC)c1ccc2c(C)c(CCNC(=O)NCc3ccc4ccccc4n3)c(=O)oc2c1]
294 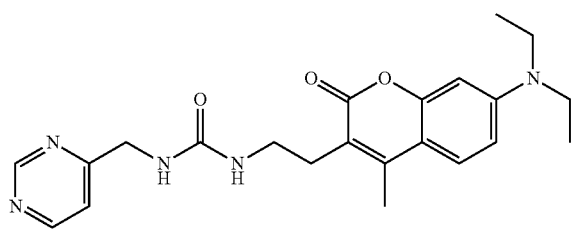 [SMILES: CCN(CC)c1ccc2c(C)c(CCNC(=O)NCc3ccncn3)c(=O)oc2c1]

295
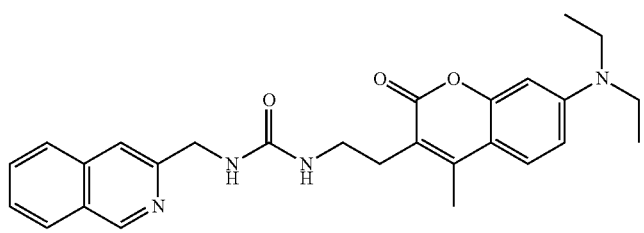 [SMILES: CCN(CC)c1ccc2c(C)c(CCNC(=O)NCc3cc4ccccc4cn3)c(=O)oc2c1]
296
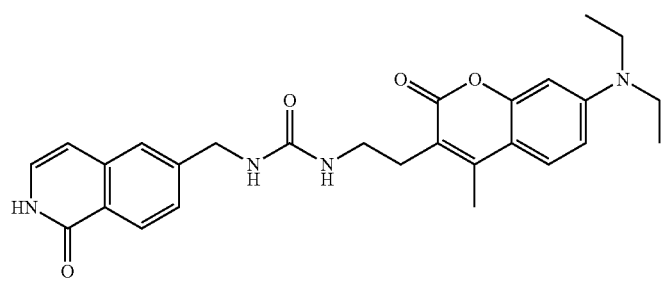 [SMILES: CCN(CC)c1ccc2c(C)c(CCNC(=O)NCc3ccc4c(=O)[nH]ccc4c3)c(=O)oc2c1]
297
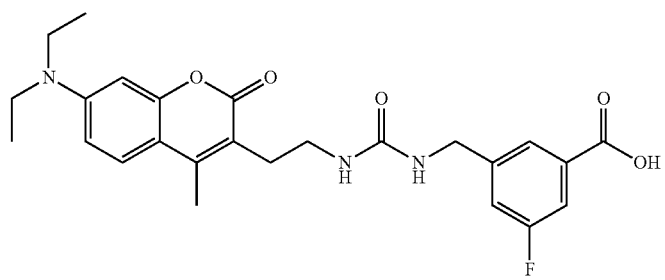 [SMILES: CCN(CC)c1ccc2c(C)c(CCNC(=O)NCc3cc(F)cc(C(=O)O)c3)c(=O)oc2c1]
298
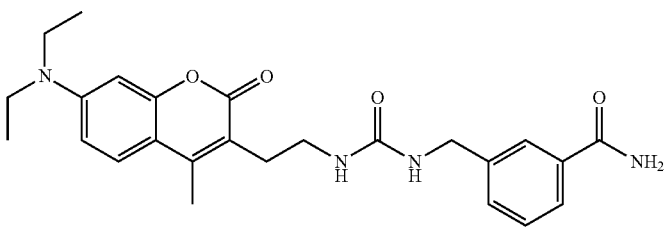
299
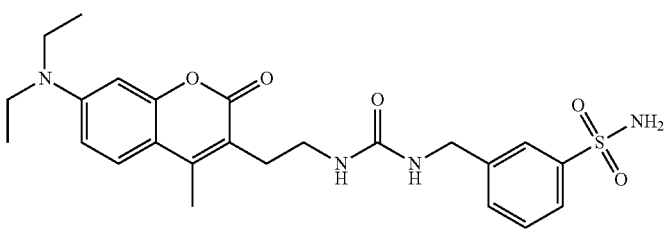
300
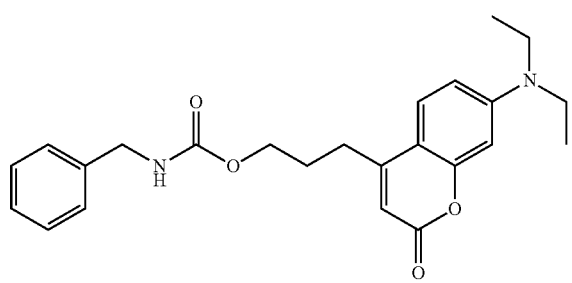 [SMILES: CCN(CC)c1ccc2c(CCCOC(=O)NCc3ccccc3)cc(=O)oc2c1]

301 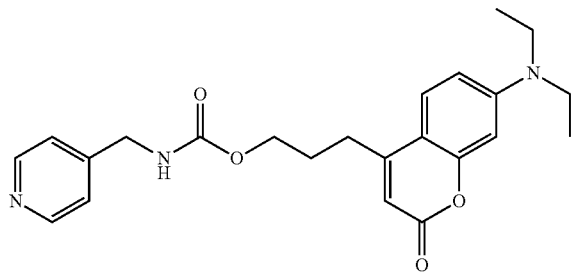 [SMILES: CCN(CC)c1ccc2c(CCCOC(=O)NCc3ccncc3)cc(=O)oc2c1]
302 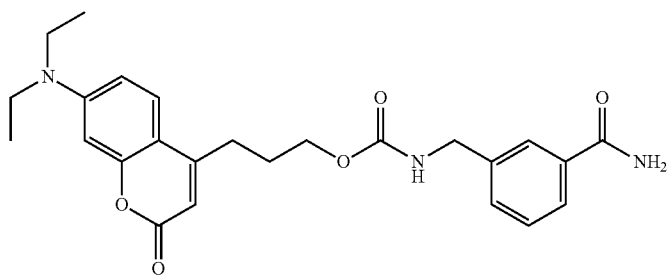 [SMILES: CCN(CC)c1ccc2c(CCCOC(=O)NCc3cccc(C(N)=O)c3)cc(=O)oc2c1]
303 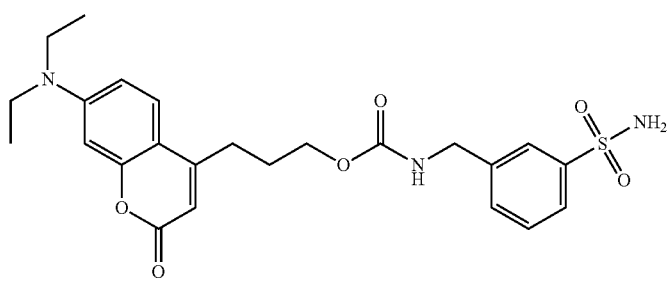 [SMILES: CCN(CC)c1ccc2c(CCCOC(=O)NCc3cccc(S(N)(=O)=O)c3)cc(=O)oc2c1]
304 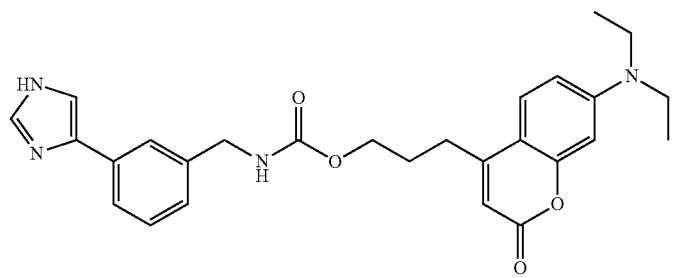 [SMILES: CCN(CC)c1ccc2c(CCCOC(=O)NCc3cccc(-c4c[nH]cn4)c3)cc(=O)oc2c1]
305 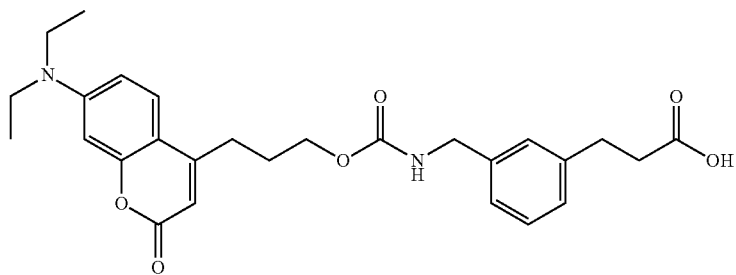 [SMILES: CCN(CC)c1ccc2c(CCCOC(=O)NCc3cccc(CCC(=O)O)c3)cc(=O)oc2c1]

306
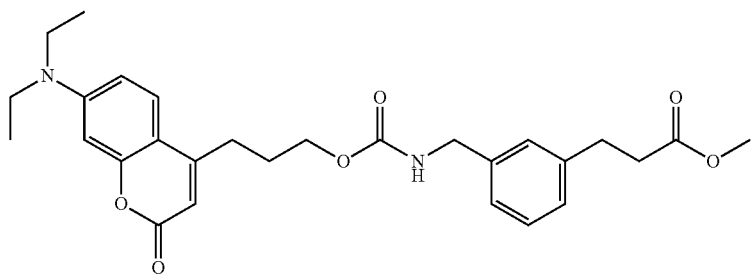 [SMILES: CCN(CC)c1ccc2c(CCCOC(=O)NCc3cccc(CCC(=O)OC)c3)cc(=O)oc2c1]
307
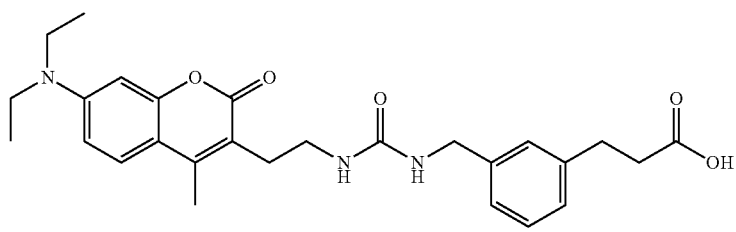
308
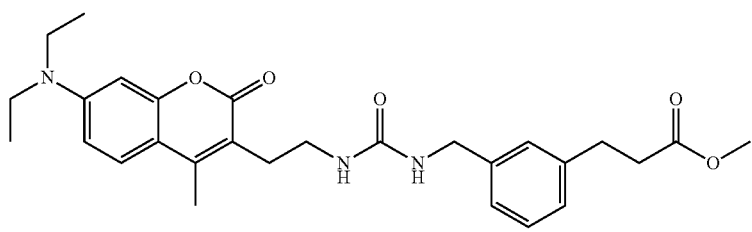 [SMILES: CCN(CC)c1ccc2c(C)c(CCNC(=O)NCc3cccc(CCC(=O)OC)c3)c(=O)oc2c1]
309
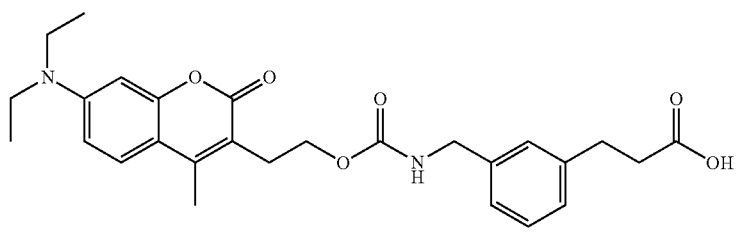 [SMILES: CCN(CC)c1ccc2c(C)c(CCOC(=O)NCc3cccc(CCC(=O)O)c3)c(=O)oc2c1]
310
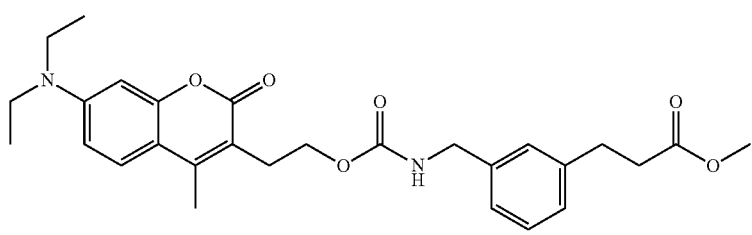 [SMILES: CCN(CC)c1ccc2c(C)c(CCOC(=O)NCc3cccc(CCC(=O)OC)c3)c(=O)oc2c1]
311
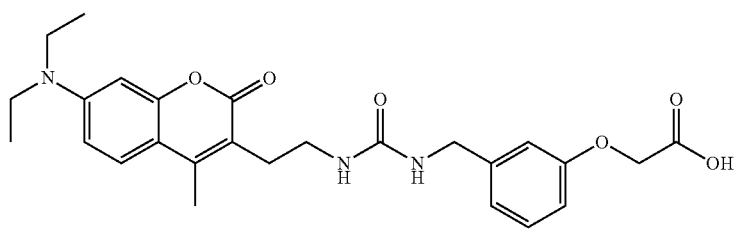 [SMILES: CCN(CC)c1ccc2c(C)c(CCNC(=O)NCc3cccc(OCC(=O)O)c3)c(=O)oc2c1]

312

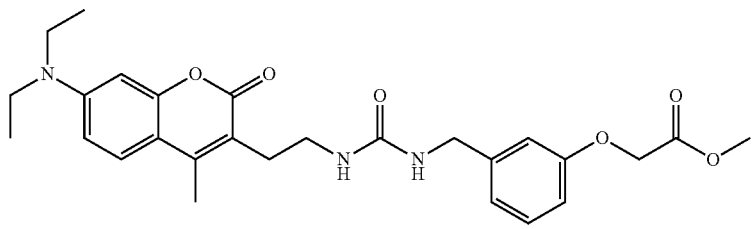

In other embodiments, the compound is of Formula II.

In Formula II compounds, per an embodiment, each of q and t is 0 or 1 and $Ar^2$ is $C_6$-$C_{10}$-aryl. For example, q is 1 and t is 0. In an embodiment, $Ar^2$ is phenyl optionally substituted with —$NR'_2$ (wherein each R' is independently selected from the group consisting of H, $C_1$-$C_6$-alkyl) and $C_1$-$C_6$-haloalkyl.

In Formula II compounds, still further embodiments provide each of $R^{25}$, $R^{26}$, $R^{27}$, and $R^{28}$ as independently H or $C_1$-$C_6$-alkyl. For example, each of $R^{25}$, $R^{26}$, $R^{27}$, and $R^{28}$ is H.

Specific examples of Formula II compounds are chosen from the following table:

7

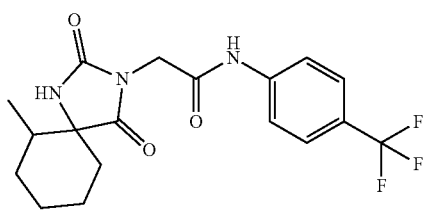 [SMILES: CC1CCCCC12NC(=O)N(CC(=O)Nc1ccc(C(F)(F)F)cc1)C2=O]

8

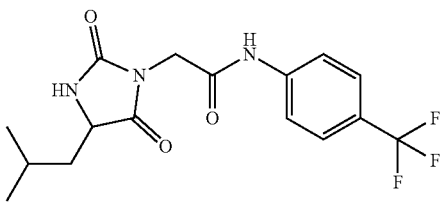 [SMILES: CC(C)CC1NC(=O)N(CC(=O)Nc2ccc(C(F)(F)F)cc2)C1=O]

22

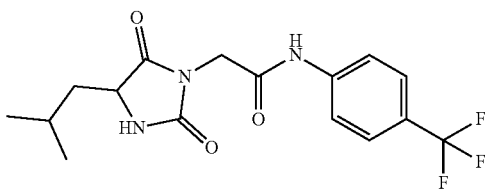

Enantiomer 1

23

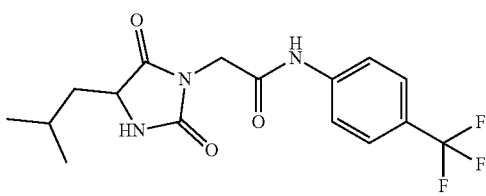

Enantiomer 2

150

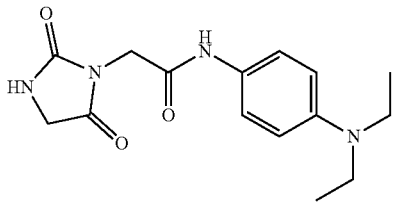 [SMILES: CCN(CC)c1ccc(NC(=O)CN2C(=O)CNC2=O)cc1]

151

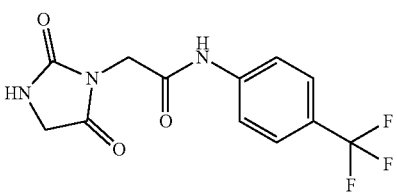 [SMILES: O=C(CN1C(=O)CNC1=O)Nc1ccc(C(F)(F)F)cc1]

Pharmaceutical Composition

The disclosure also provides a pharmaceutical composition comprising a therapeutically effective amount of one or more compounds described herein, or a pharmaceutically acceptable salt, stereoisomer, and/or tautomer thereof in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

In one embodiment, the pharmaceutical composition comprises any enumerated compound described herein or a pharmaceutically acceptable salt, stereoisomer, and/or tautomer thereof, and a pharmaceutically acceptable carrier.

The pharmaceutical composition of the present disclosure is formulated, dosed, and administered in a fashion consistent with good medical practice. Factors for consideration in this context include the particular disorder being treated, the particular subject being treated, the clinical condition of the subject, the cause of the disorder, the site of delivery of the agent, the method of administration, the scheduling of administration, and other factors known to medical practitioners.

The "therapeutically effective amount" of a compound or a pharmaceutically acceptable salt, stereoisomer, and/or tautomer thereof that is administered is governed by such considerations, and is the minimum amount necessary to exert a therapeutic effect. Such amount may be below the amount that is toxic to normal cells, or the subject as a whole. Generally, the initial therapeutically effective amount of a compound (or a pharmaceutically acceptable salt, stereoisomer, or tautomer thereof) of the present disclosure that is administered is in the range of about 0.01 to about 200 mg/kg or about 0.1 to about 20 mg/kg of patient body weight per day, with the typical initial range being about 0.3 to about 15 mg/kg/day. Oral unit dosage forms, such as tablets and capsules, may contain from about 0.1 mg to about 1000 mg of a compound (or a pharmaceutically acceptable salt, stereoisomer, or tautomer thereof) of the present disclosure. In another embodiment, such dosage forms contain from about 50 mg to about 500 mg of a compound (or a pharmaceutically acceptable salt, stereoisomer, or tautomer thereof) of the present disclosure. In yet another embodiment, such dosage forms contain from about 25 mg to about 200 mg of a compound (or a pharmaceutically acceptable salt, stereoisomer, or tautomer thereof) of the present disclosure. In still another embodiment, such dosage forms contain from about 10 mg to about 100 mg of a compound (or a pharmaceutically acceptable salt, stereoisomer, or tautomer thereof) of the present disclosure. In a further embodiment, such dosage forms contain from about 5 mg to about 50 mg of a compound (or a pharmaceutically acceptable salt, stereoisomer, or tautomer thereof) of the present disclosure. In any of the foregoing embodiments the dosage form can be administered once a day or twice per day.

The compositions of the present disclosure can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions as described herein include without limitation tablets, troches, lozenges, aqueous or oily suspensions, dispersible powders or granules, emulsion, hard or soft capsules, syrups or elixirs.

In another aspect, also encompassed are pharmaceutical compositions suitable for single unit dosages that comprise a compound of the disclosure or its pharmaceutically acceptable stereoisomer, salt, or tautomer and a pharmaceutically acceptable carrier.

The compositions of the present disclosure that are suitable for oral use may be prepared according to any method known to the art for the manufacture of pharmaceutical compositions. For instance, liquid formulations of the compounds of the present disclosure contain one or more agents selected from the group consisting of sweetening agents, flavoring agents, coloring agents and preserving agents in order to provide pharmaceutically palatable preparations of a compound of the present disclosure.

For tablet compositions, a compound of the present disclosure in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions, a compound of the present disclosure is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending a compound of the present disclosure in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide a compound of the present disclosure in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation reaction products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula IA or Formula IB may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Methods of Use

Secretion of an immunoglobulin light chain (LC) by a clonally expanded plasma cell population can lead to the disease light chain amyloidosis (AL)—both a cancer and a proteinopathy (1, 2). "Free" LCs secreted without an associated antibody heavy chain initially adopt a well-defined homodimeric structure, wherein the monomers may be covalently linked by an inter-chain disulfide bond (FIG. 1a) (3). LC monomers comprise an N-terminal variable (V) domain attached to a C-terminal constant (C) domain. Each patient's clonal plasma cells secrete a single, unique LC sequence. Most LCs are rapidly removed by the kidney.

However, since amyloidogenic full-length (FL) LCs are generally less stable than non-amyloidogenic FL LCs, they can misfold, or misfold and misassemble, into non-native species including cross-$\beta$-sheet amyloid fibrils, which are a hallmark of AL (4-8). Sequence also seems to play a role, as not all destabilized FL LCs aggregate in patients (4-8). How aggregation occurs in patients is not known, but several processes have been described in vitro, including destabilization-dependent endoproteolysis that releases amyloidogenic LC fragments (4, 9, 10). LC fragments including V-domains are observed in patient deposits alongside FL LCs (11-13).

Since the structure-proteotoxicity relationships driving AL are not well understood, a conservative strategy is to block FL LC misfolding at its origin by stabilizing the FL LC native state. Such a strategy has been effective at ameliorating the transthyretin amyloidoses (14-19). A small molecule that stabilizes FL LC dimers prevents any misfolding and/or endoproteolysis required for LC aggregation and organ toxicity. Such molecules are referred to herein as kinetic stabilizers, since they reduce the rate at which LCs transiently visit non-native, aggregation-prone and protease-sensitive conformations (20). The interfaces between the domains of the LC dimer are an important determinant of stability and aggregation propensity that have been identified as potential targets for stabilization (21, 22). Thus, it is an object herein to provide treatments that prevent newly synthesized and secreted FL LCs from misfolding and aggregating, thus reducing organ proteotoxicity, such that patients can eventually tolerate effective chemotherapy regimens.

Using a protease-coupled fluorescence polarization assay that assesses LC kinetic stability, 650,000 small molecules were screened, which identified FL LC kinetic stabilizers in four structural classes that protect recombinant and plasma cell-secreted λ6a LCs from endoproteolysis. Nuclear magnetic resonance (NMR) and x-ray crystallography revealed that these small molecules bind to the V-domain-V-domain interface in the FL LC dimer and in isolated V-domains, utilizing conserved residues found in most patient-derived LCs.

In light of these discoveries and other data disclosed herein, the present disclosure provides in various embodiments a method of stabilizing an immunoglobulin light chain dimer in a native conformation thereof. The method comprises contacting the dimer and an effective amount of any compound disclosed herein, include a compound of Formula Ia, Formula Ib, Formula II, and all enumerated compounds disclosed herein. The contacting can occur in vivo, ex vivo, and in vitro.

In another embodiment, the present disclosure provides a method of treating light chain amyloidosis in a patient. The method comprises administering to the patient an effective amount of any compound disclosed herein, include a compound of Formula Ia, Formula Ib, Formula II, and all enumerated compounds disclosed herein.

The present disclosure also provides a method of prophylactic treatment, comprising administering a therapeutically effective amount of a compound described herein to an AL patient who has undergone chemotherapy treatment, post-autologous stem cell transplantation, or has relapsed from prior chemotherapy treatment.

Any of the methods described herein are suitable for use in combination with conventional chemotherapy (e.g., alkylating agents and steroid-based regimen: melphalan, dexamethasone and cyclophosphamide). The combination therapy method can include, per one embodiment, the administration of an immunomodulatory agent such as thalidomide, lenalidomide or pomalidomide, a proteasome inhibitor such as bortezomib, or both.

In additional embodiments, any of the methods described herein are carried out in combination with anti-CD38 Ab and/or other chemotherapy treatments that target an underlying plasma cell clone.

Further combination therapies include any of the methods described herein with administration of UPR activators, such as ATF-6 activators and/or chemotherapy, or anti-amyloid therapies, such as therapeutic antibodies directly targeting amyloid deposits. All of these combinations are contemplated.

EXAMPLES

Compound Syntheses and Characterization

General Synthetic Procedures. All reagents and solvents were obtained from commercial suppliers and used without further purification. $^{1}$H, $^{13}$C, and $^{19}$F NMR spectra were recorded on either a Varian Mercury-400, a Bruker DRX-500, or a Bruker DRX-600 equipped with a DCH cryoprobe. Normal-phase chromatography was performed on a Teledyne Isco CombiFlash NextGen 300+ using Luknova Super-Sep SiO$_2$ columns. Preparative-scale reverse phase high performance liquid chromatography (RP-HPLC) was performed on an Agilent 1260 Infinity LC system using a Gemini NX-C18 column (110 Å pore size, 5 μm particle size, 150×21.2 mm dimensions, mobile phase A=0.1% TFA in H$_2$O, mobile phase B=0.1% TFA in MeCN). Final compound purities were determined by analytical RP-HPLC and were >95% in purity. Mass spectrometry data were collected at The Scripps Research Institute Center for Mass Spectrometry (ESI-MS; Agilent Technologies, LC/MSD TOF G1969A and GC-MS; Agilent Technologies, 6850 Network GC System, 5973 Mass Selective Detector).

Abbreviations

Boc=tert-butyloxycarbonyl
CataCXium® A=Di(1-adamantyl)-n-butylphosphine
CDI=carbonyldiimidazole
DCM=dichloromethane
DIAD=diisopropyl azodicarbonate
DIPEA=diisopropyl ethylamine
DMF=N,N-dimethylformamide
DMP=Dess-Martin periodinane
DMPU=N,N'-dimethylpropyleneurea
HATU=1-[Bis(dimethylamino)methylene]-1H-1,2,3-triazolo[4,5-b]pyridinium 3-oxid hexafluorophosphate
HMPT=N-[bis(dimethylamino)phosphoryl]-N-methylmethanamine
HPLC=high-performance liquid chromatography
LDA=lithium diisopropylamide
NBS=N-bromosuccinimide
NMR=nuclear magnetic resonance
MOM=methoxymethyl
RuPhos=2-Dicyclohexylphosphino-2',6'-diisopropoxybiphenyl
TBAF=tetrabutylammonium fluoride
TBS=tert-butyldimethylsilyl
TFA=trifluoroacetic acid
THF=tetrahydrofuran
THP=tetrahydropyran
Xantphos=4,5-Bis(diphenylphosphino)-9,9-dimethylxanthene Compounds (22) and (23). Compounds 22 and 23 are enantiomers of racemate 8, and they were separated on a Waters UPC2 SFC with a Daicel IA column (3 μm, 4.6×250 mm) under isocratic conditions (4 mL/min, 30% MeOH/CO2, 1600 psi backpressure) at 30° C. The enantiomers were detected by UV absorbance (265 nm) and manually fractionated. After separation, the individual enantiomers were analyzed on the same instrument and method but were detected by UV absorbance (245 nm).

7-(diethylamino)-4-methylquinolin-2(1H)-one (25). To a stirred suspension of 7-amino-4-methylquinolin-2(1H)-one (174 mg, 1 eq), acetic acid (240 mg, 4 eq), and $NaBH(OAc)_3$ (848 mg, 4 eq) in 1,2-dichloroethane (10 mL) was added acetaldehyde (154 mg, 3.5 eq) on an ice-water bath. The yellow suspension was stirred at 0° C. for 3 hr, during which the crystalline starting material gradually dissolved. The mixture was partitioned between DCM (20 mL) and water (20 mL), then extracted with DCM (3×20 mL). The combined organics were washed with brine, dried over $MgSO_4$, filtered, and concentrated under reduced pressure. The residue was purified by flash column chromatography ($SiO_2$, 100% EtOAc) to afford 25 as a light yellow solid (177 mg, 77%). ESI-MS [M+1]: 231.0. $^1$H NMR (400 MHz, Chloroform-d) δ 9.76 (s, 1H), 7.48 (d, J=9.1 Hz, 1H), 6.63 (dd, J=9.1, 2.5 Hz, 1H), 6.30 (d, J=2.5 Hz, 1H), 6.23 (s, 1H), 3.45 (q, J=7.1 Hz, 4H), 2.42 (s, 3H), 1.24 (t, J=7.1 Hz, 6H).

7-(diethylamino)-2-imino-2H-chromene-3-carbonitrile (26). The title compound was prepared according to literature procedures, see e.g.: Zhou, J., et al. RSC Adv. 2014, 93(4), 51589-51592.

7-(diethylamino)-4-hydroxy-2H-chromen-2-one (27). The title compound was prepared according to literature procedures, see e.g.: Pan, S., et al. Chem. Comm. 2018, 39(54), 4955-4958.

Scheme 1.

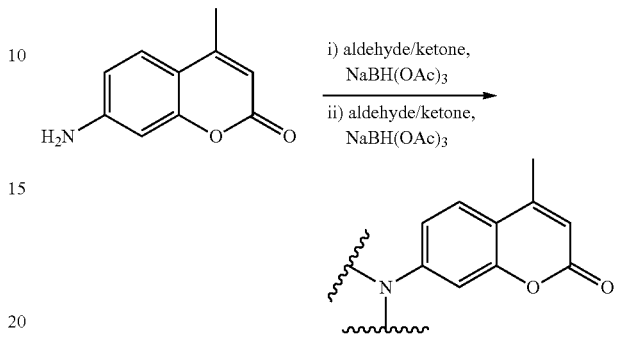

7-(benzylamino)-4-methyl-2H-chromen-2-one (28). To a stirred suspension of 7-amino-4-methyl-2H-chromen-2-one (174 mg, 1 eq) and benzaldehyde (159 mg, 1.5 eq) in MeCN (5 mL) was added $NaBH(OAc)_3$ (414 mg, 2 eq) and the yellow suspension stirred at room temperature for 16 hours. The mixture was partitioned between DCM (20 mL) and water (20 mL), then extracted with DCM (3×20 mL). The combined organics were washed with brine, dried over $MgSO_4$, filtered, and concentrated under reduced pressure. The residue was purified by flash column chromatography ($SiO_2$, EtOAc/hexanes) to afford 28 as a yellow solid (80 mg, 30%). ESI-MS [M+1]: 266.0. $^1$H NMR (500 MHz, Chloroform-d) δ 7.41-7.33 (m, 5H), 7.36-7.27 (m, 1H), 6.57 (dd, J=8.7, 2.4 Hz, 1H), 6.49 (d, J=2.3 Hz, 1H), 5.98 (q, J=1.2 Hz, 1H), 4.76 (s, 1H), 4.41 (s, 2H), 2.34 (d, J=1.2 Hz, 3H).

7-((furan-3-ylmethyl)amino)-4-methyl-2H-chromen-2-one (29). The title compound was prepared analogously to 28, using furan-3-carbaldehyde. ESI-MS [M+1]: 256.0. $^1$H NMR (500 MHz, Chloroform-d) δ 7.43 (dt, J=7.3, 1.6 Hz, 2H), 7.38 (d, J=8.6 Hz, 1H), 6.57 (dd, J=8.7, 2.3 Hz, 1H), 6.52 (d, J=2.3 Hz, 1H), 6.42 (dd, J=1.9, 0.9 Hz, 1H), 5.99 (d, J=1.3 Hz, 1H), 4.56 (t, J=5.5 Hz, 1H), 4.24 (d, J=4.5 Hz, 2H), 2.35 (d, J=1.2 Hz, 3H).

4-methyl-7-((3-phenylpropyl)amino)-2H-chromen-2-one (30). The title compound was prepared analogously to 28, using 3-phenylpropanal. ESI-MS [M+1]: 294.0. $^1$H NMR (500 MHz, Chloroform-d) δ 7.40-7.29 (m, 3H), 7.28-7.19 (m, 3H), 6.47 (dd, J=8.6, 2.4 Hz, 1H), 6.43 (d, J=2.3 Hz, 1H), 6.00 (q, J=1.2 Hz, 1H), 4.18 (s, 1H), 3.23 (t, J=7.0 Hz, 2H), 2.77 (t, J=7.5 Hz, 2H), 2.36 (d, J=1.1 Hz, 3H), 2.06-1.96 (m, 2H).

7-(ethyl(3-phenylpropyl)amino)-4-methyl-2H-chromen-2-one (31). To a stirred suspension of compound 30 (1 eq) and $NaBH(OAc)_3$ (3 eq) in MeCN (2 mL) was added acetaldehyde (5 eq) on an ice-water bath, and the yellow suspension warmed to room temperature over 16 hours. The mixture was partitioned between DCM (20 mL) and water (20 mL), then extracted with DCM (3×20 mL). The combined organics were washed with brine, dried over $MgSO_4$, filtered, and concentrated under reduced pressure. The residue was purified by flash column chromatography ($SiO_2$, EtOAc/hexanes) to afford 31 as a viscous yellow oil. ESI-MS [M+1]: 322.1. $^1$H NMR (500 MHz, Chloroform-d) δ 7.40-7.30 (m, 3H), 7.28-7.20 (m, 3H), 6.56-6.47 (m, 2H), 5.99-5.94 (m, 1H), 3.47-3.33 (m, 4H), 2.70 (t, J=7.7 Hz, 2H), 2.35 (d, J=1.2 Hz, 3H), 2.03-1.93 (m, 2H), 1.20 (t, J=7.1 Hz, 3H).

7-(sec-butoxy)-4-methyl-2H-chromen-2-one (32). A stirred mixture of 7-hydroxy-4-methylcoumarin (176 mg, 1 eq), 2-bromobutane (274 mg, 2 eq), $K_2CO_3$ (276 mg, 2 mmol), and KI (83 mg, 0.5 mmol) in DMF (5 mL) was heated at 80° C. overnight under argon. The mixture was diluted with 45 mL water, then extracted with diethyl ether (3×20 mL), dried over $MgSO_4$, filtered, and concentrated under reduced pressure. The residue was purified by flash column chromatography ($SiO_2$, 25% EtOAc in hexanes) to afford 32 as a viscous light-yellow oil. ESI-MS [M+1]: 233.0.

4-methyl-7-propoxy-2H-chromen-2-one (33). The title compound was prepared analogously to 32, using 1-bromopropane. ESI-MS [M+1]: 219.0.

7-(2-aminoethoxy)-4-methyl-2H-chromen-2-one (34). A stirred mixture of 7-hydroxy-4-methyl-2H-chromen-2-one (132 mg), tert-butyl (2-bromoethyl)carbamate (203 mg), $K_2CO_3$ (276 mg), and KI (83 mg) in DMF (5 mL) was heated at 70° C. overnight under argon. The mixture was diluted with 45 mL water, then extracted with DCM (3×20 mL), dried over $MgSO_4$, filtered, and concentrated under reduced pressure. The residue was purified by flash column chromatography. The intermediate was dissolved in 1.5 mL DCM and thereto was added 500 μL TFA, and the solution stirred for 2 hrs at room temperature. The residue was concentrated in vacuo and purified by reverse-phase preparative HPLC to afford the title compound as a viscous light-yellow oil. ESI-MS [M+1]: 220.0.

7-(benzyl(ethyl)amino)-4-methyl-2H-chromen-2-one (35). The title compound was prepared analogously to 31, using 28 as starting material. ESI-MS [M+1]: 294.0. 1H NMR (500 MHz, Chloroform-d) δ 7.42-7.31 (m, 3H), 7.31-7.24 (m, 1H), 7.24-7.19 (m, 2H), 6.63 (dd, J=8.9, 2.6 Hz, 1H), 6.57 (d, J=2.6 Hz, 1H), 5.98 (q, J=1.2 Hz, 1H), 4.62 (s, 2H), 3.58 (q, J=7.1 Hz, 2H), 2.34 (d, J=1.1 Hz, 3H), 1.34-1.25 (m, 4H).

4-methyl-7-(pyrrolidin-1-yl)-2H-chromen-2-one (36). A suspension of 7-amino-4-methyl-2H-chromen-2-one (175 mg, 1 mmol), 1,4-dibromobutane (259 mg, 1.2 eq), $K_2CO_3$ (414 mg), and KI (83 mg, 0.5 mmol) in DMF (5 mL) was heated at 80° C. for 16 hours. The mixture was partitioned between DCM (20 mL) and water (20 mL), then extracted with DCM (3×20 mL). The combined organics were washed with brine, dried over $MgSO_4$, filtered, and concentrated under reduced pressure. The residue was purified by flash column chromatography ($SiO_2$, EtOAc/hexanes) to afford 36 as a yellow solid. ESI-MS [M+1]: 230.0.

7-(ethyl(phenethyl)amino)-4-methyl-2H-chromen-2-one (37). The title compound was prepared analogously to 31, using 40 as starting material. ESI-MS [M+1]: 308.0. $^1$H NMR (500 MHz, Chloroform-d) δ 7.43 (d, J=8.9 Hz, 1H), 7.39-7.31 (m, 2H), 7.30-7.20 (m, 3H), 6.64 (dd, J=8.9, 2.6 Hz, 1H), 6.58 (d, J=2.6 Hz, 1H), 5.99 (q, J=1.2 Hz, 1H), 3.63-3.56 (m, 2H), 3.36 (q, J=7.1 Hz, 2H), 2.96-2.89 (m, 2H), 2.38 (d, J=1.2 Hz, 3H), 1.18 (t, J=7.1 Hz, 3H).

7-(benzyloxy)-4-methyl-2H-chromen-2-one (38). The title compound was prepared analogously to 34, using benzyl bromide. $^1$H NMR (500 MHz, Chloroform-d) δ 7.53 (d, J=8.8 Hz, 1H), 7.49-7.34 (m, 4H), 6.96 (dd, J=8.8, 2.5 Hz, 1H), 6.92 (d, J=2.5 Hz, 1H), 6.16 (q, J=1.2 Hz, 1H), 5.16 (s, 1H), 2.42 (d, J=1.2 Hz, 2H).

4-methyl-7-((1-phenylethyl)amino)-2H-chromen-2-one (39). The title compound was prepared analogously to 34, using (1-bromoethyl)benzene and 7-amino-4-methyl-2H-chromen-2-one as starting materials. ESI-MS [M+1]: 280.0.

4-methyl-7-(phenethylamino)-2H-chromen-2-one (40). The title compound was prepared analogously to 28, using 2-phenylacetaldehyde. ESI-MS [M+1]: 280.0.

4-methyl-7-(1-phenylpropoxy)-2H-chromen-2-one (41). The title compound was prepared analogously to 32, using (1-bromopropyl)benzene, to afford 41 as a white solid (158.4 mg, 54%). $^1$H NMR (400 MHz, Chloroform-d) δ 7.44 (d, J=8.8 Hz, 1H), 7.40-7.24 (m, 3H), 6.88 (dd, J=8.8, 2.5 Hz, 1H), 6.74 (d, J=2.5 Hz, 1H), 6.12-6.07 (m, 1H), 5.09 (dd, J=7.3, 5.6 Hz, 1H), 2.36 (d, J=1.3 Hz, 3H), 2.07 (dq, J=14.7, 7.3 Hz, 1H), 1.93 (ddd, J=13.5, 7.3, 5.7 Hz, 1H), 1.03 (t, J=7.4 Hz, 3H).

7-(benzhydryloxy)-4-methyl-2H-chromen-2-one (42). The title compound was prepared analogously to 32, using (bromomethylene)dibenzene. $^1$H NMR (500 MHz, Chloroform-d) δ 7.51-7.25 (m, 10H), 6.99 (dd, J=8.8, 2.5 Hz, 1H), 6.87 (d, J=2.5 Hz, 1H), 6.29 (s, 1H), 6.13 (q, J=1.2 Hz, 1H), 2.38 (d, J=1.2 Hz, 2H).

4-methyl-7-(2-phenylpropoxy)-2H-chromen-2-one (43). The title compound was prepared analogously to 32, using 2-phenylpropyl 4-methylbenzenesulfonate, to afford 43 as a white solid (60.3 mg, 71%). $^1$H NMR (500 MHz, Chloroform-d) δ 7.53 (d, J=8.8 Hz, 1H), 7.49-7.34 (m, 5H), 6.96 (dd, J=8.8, 2.5 Hz, 1H), 6.92 (d, J=2.5 Hz, 1H), 6.16 (q, J=1.2 Hz, 1H), 5.16 (s, 2H), 2.42 (d, J=1.2 Hz, 3H), 1.29 (s, 3H).

7-(1-(4-fluorophenyl)ethoxy)-4-methyl-2H-chromen-2-one (44) The title compound was prepared analogously to 32, using 1-(1-bromoethyl)-4-fluorobenzene. $^1$H NMR (500 MHz, Chloroform-d) δ 7.46 (d, J=8.8 Hz, 1H), 7.39-7.31 (m, 2H), 7.10-7.01 (m, 2H), 6.86 (dd, J=8.8, 2.5 Hz, 1H), 6.74 (d, J=2.5 Hz, 1H), 6.12 (q, J=1.2 Hz, 1H), 5.37 (q, J=6.4 Hz, 1H), 2.38 (d, J=1.3 Hz, 3H), 1.68 (d, J=6.4 Hz, 3H).

4-methyl-7-(1-(o-tolyl)ethoxy)-2H-chromen-2-one (45). The title compound was prepared analogously to 32, using 1-(1-bromoethyl)-2-methylbenzene, to afford 58 as a white solid (172.7 mg, 78%). $^1$H NMR (500 MHz, Chloroform-d) δ 7.45 (d, J=8.8 Hz, 1H), 7.39-7.33 (m, 1H), 7.23-7.13 (m, 3H), 6.84 (dd, J=8.8, 2.5 Hz, 1H), 6.61 (d, J=2.5 Hz, 1H), 6.10 (q, J=1.3 Hz, 1H), 5.53 (q, J=6.4 Hz, 1H), 2.46 (s, 3H), 2.39-2.35 (m, 3H), 1.67 (d, J=6.4 Hz, 3H).

4-methyl-7-(3-phenylbutoxy)-2H-chromen-2-one (46). The title compound was prepared analogously to 32, using 3-phenylbutyl 4-methylbenzenesulfonate. $^1$H NMR (500 MHz, Chloroform-d) δ 7.48 (d, J=8.8 Hz, 1H), 7.37-7.29 (m, 2H), 7.23 (dtd, J=7.2, 2.7, 1.0 Hz, 3H), 6.82 (dd, J=8.8, 2.5 Hz, 1H), 6.75 (d, J=2.5 Hz, 1H), 6.14 (q, J=1.2 Hz, 1H), 3.94 (ddd, J=9.4, 6.6, 5.6 Hz, 1H), 3.88 (ddd, J=9.4, 7.4, 6.3 Hz, 1H), 3.09-2.97 (m, 1H), 2.41 (d, J=1.2 Hz, 3H), 2.22-2.02 (m, 2H), 1.37 (d, J=7.0 Hz, 3H).

4-methyl-7-((1-phenylpropan-2-yl)oxy)-2H-chromen-2-one (47). The title compound was prepared analogously to 32, using 1-phenylpropan-2-yl 4-methylbenzenesulfonate, to afford 56 as a white solid (154.5 mg, 70%). $^1$H NMR (500 MHz, Chloroform-d) δ 7.49 (d, J=8.5 Hz, 1H), 7.38-7.21 (m, 5H), 6.88-6.81 (m, 2H), 6.14 (q, J=1.2 Hz, 1H), 4.67 (q, J=6.1 Hz, 1H), 3.13 (dd, J=13.8, 6.1 Hz, 1H), 2.89 (dd, J=13.8, 6.5 Hz, 1H), 2.41 (d, J=1.2 Hz, 3H), 1.38 (d, J=6.1 Hz, 3H).

4-methyl-7-(piperidin-1-yl)-2H-chromen-2-one (48). The title compound was prepared analogously to 36, using 1,5-dibromopropane. ESI-MS [M+1]: 244.0. $^1$H NMR (400 MHz, Chloroform-d) δ 7.42 (d, J=8.9 Hz, 1H), 6.84 (dd, J=8.9, 2.6 Hz, 1H), 6.73 (d, J=2.5 Hz, 1H), 6.03 (t, J=1.2 Hz, 1H), 3.36 (t, J=5.1 Hz, 5H), 2.38 (d, J=1.2 Hz, 4H), 1.77-1.65 (m, 3H).

7-(1-(2-fluorophenyl)ethoxy)-4-methyl-2H-chromen-2-one (49). The title compound was prepared analogously to 32, using 1-(1-bromoethyl)-2-fluorobenzene, to afford 49 as a white solid (185.6 mg, 83%). $^1$H NMR (400 MHz, Chloroform-d) δ 7.46 (d, J=8.8 Hz, 1H), 7.40 (td, J=7.6, 1.8 Hz, 1H), 7.33-7.23 (m, 1H), 7.22-7.05 (m, 2H), 6.88 (dd, J=8.8, 2.5 Hz, 1H), 6.76 (d, J=2.5 Hz, 1H), 6.12 (q, J=1.3 Hz, 1H), 5.72 (q, J=6.4 Hz, 1H), 2.38 (d, J=1.2 Hz, 3H), 1.71 (d, J=6.4 Hz, 3H).

(1 mL) and stirred for 16 hr at room temperature. The reaction was quenched with 1 mL saturated aqueous $NH_4Cl$. The mixture was diluted with 20 mL $H_2O$ and extracted with EtOAc (3×20 mL). The combined organics were washed once with brine, dried over $MgSO_4$, filtered, and concentrated in vacuo. The residue was purified by flash column chromatography to afford the title compound as a tan solid. ESI-MS [M+1]: 245.0. $^1$H NMR (400 MHz, Chloroform-d) δ 7.51 (d, J=9.0 Hz, 1H), 6.64 (dd, J=9.0, 2.4 Hz, 1H), 6.42 (d, J=2.4 Hz, 1H), 6.30 (s, 1H), 3.67 (s, 3H), 3.48 (q, J=7.1 Hz, 4H), 2.39 (s, 3H), 1.26 (t, J=7.1 Hz, 6H).

Scheme 2.

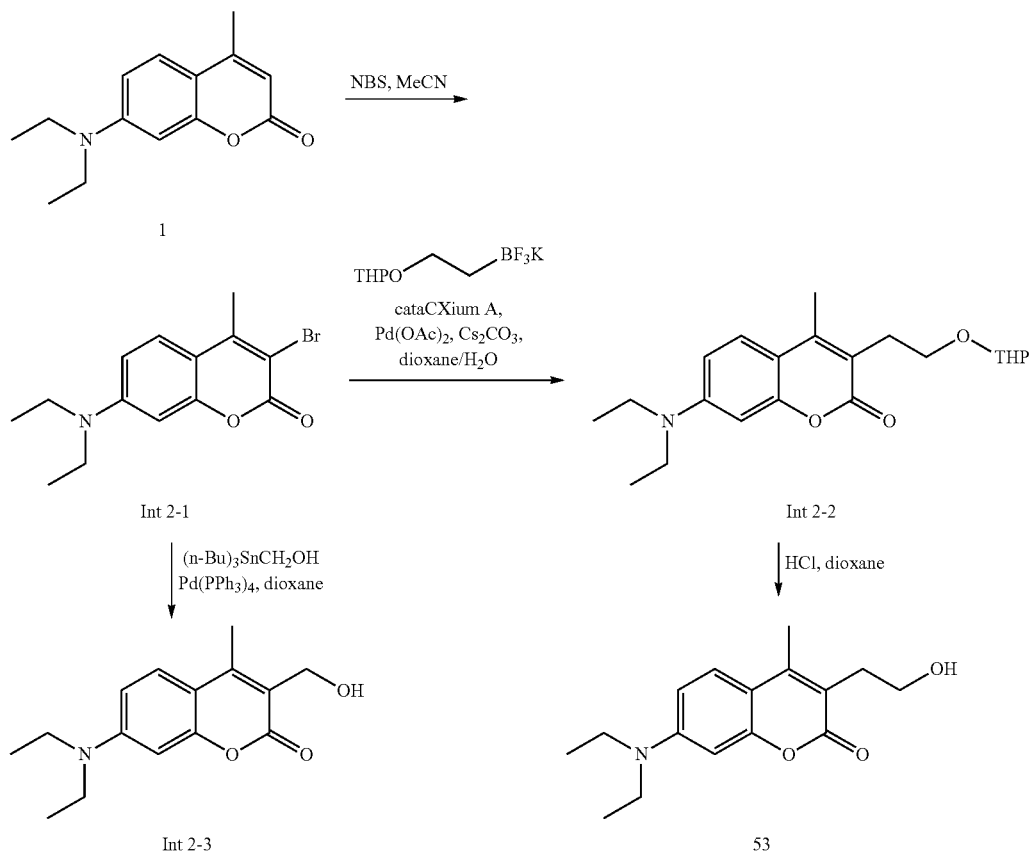

7-(diethylamino)-4-(hydroxymethyl)-2H-chromen-2-one (50). The title compound was prepared using literature procedures, see e.g.: Kawaguchi, M., et al. Chem. Comm. 2018, 73(54), 10371-10374.

7-(1-(2,6-difluorophenyl)ethoxy)-4-methyl-2H-chromen-2-one (51). The title compound was prepared analogously to 36, using 2-(1-bromoethyl)-1,3-difluorobenzene. $^1$H NMR (400 MHz, Chloroform-d) δ 7.47 (d, J=8.8 Hz, 1H), 7.25 (tt, J=8.4, 6.3 Hz, 1H), 6.95-6.85 (m, 3H), 6.83 (d, J=2.5 Hz, 1H), 6.12 (q, J=1.2 Hz, 1H), 5.81 (q, J=6.6 Hz, 1H), 2.38 (d, J=1.2 Hz, 3H), 1.84 (d, J=6.6 Hz, 3H).

7-(diethylamino)-1,4-dimethylquinolin-2(1H)-one (52). Under argon, a solution of 25 (40 mg, 1 eq) in DMF (1 mL) was added to NaH (8.2 mg, 60% in mineral oil, 1.2 eq) on ice, and the suspension stirred for 10 min on ice. Thereto was added a solution of methyl iodide (30 mg, 1.2 eq) in DMF 3-bromo-7-(diethylamino)-4-methyl-2H-chromen-2-one (Int 2-1). The title intermediate was prepared by literature procedures, see e.g.: Kitamura, K., et al. Bioorg. Med. Chem. Lett. 2014, 24(24), 5660-5662.

7-(diethylamino)-4-methyl-3-(2-((tetrahydro-2H-pyran-2-yl)oxy)ethyl)-2H-chromen-2-one (Int 2-2). A mixture of Int 2-1 (1.3 g, 4.19 mmol, 1 eq), potassium trifluoro(2-((tetrahydro-2H-pyran-2-yl)oxy)ethyl)borate (1.09 g, 4.61 mmol, 1.1 eq), bis(1-adamantyl)-butyl-phosphane (300 mg, 838 μmol, 0.2 eq), Pd(OAc)$_2$ (282 mg, 1.26 mmol, 0.3 eq) and Cs$_2$CO$_3$ (4.10 g, 12.5 mmol, 3 eq) in dioxane (30 mL) and H$_2$O (13 mL) was degassed and purged with N$_2$ for 3 times, and then the mixture was stirred at 100° C. for 12 hours under N$_2$ atmosphere. The reaction mixture was quenched by addition of H$_2$O (300 mL), and then extracted with EtOAc (100 mL×3). The combined organic layers were dried over Na₂SO₄, filtered and concentrated under reduced pressure to give a residue. The residue was purified by reverse-phase preparative HPLC to give Int 2-2 (1.2 g, 3.34 mmol, 79% yield) as a yellow solid. ¹H NMR (400 MHz, chloroform-d) δ=7.44-7.39 (m, 1H), 6.64-6.58 (m, 1H), 6.51 (d, J=2.8 Hz, 1H), 4.59 (t, J=4.0 Hz, 1H), 3.94-3.77 (m, 2H), 3.59 (td, J=6.9, 9.6 Hz, 1H), 3.53-3.45 (m, 1H), 3.41 (q, J=6.8 Hz, 4H), 2.98-2.89 (m, 2H), 2.42-2.36 (m, 3H), 1.81-1.72 (m, 1H), 1.72-1.62 (m, 1H), 1.59-1.43 (m, 4H), 1.20 (t, J=6.8 Hz, 6H).

7-(diethylamino)-3-(hydroxymethyl)-4-methyl-2H-chromen-2-one (Int 2-3). A mixture of Int 2-1 (3 g, 9.67 mmol, 1 eq), tributylstannylmethanol (4.04 g, 12.6 mmol, 1.3 eq) and Pd(PPh₃)₄ (559 mg, 484 μmol, 0.05 eq) in dioxane (30 mL) was bubbled with nitrogen and vial was sealed. The mixture was stirred at 100° C. for 16 hours and then 120° C. for 6 hours. The mixture was purified by column chromatography over silica gel (petroleum ether/ethyl acetate 10/1 to 1/1). The desired fractions were collected and concentrated under vacuum to give Int 2-3 (924 mg, 3.39 mmol, 35% yield, 96% purity) as a yellow solid. LC-MS [ESI, M+1]: 262. ¹H NMR (400 MHz, CDCl₃) δ=7.45 (d, J=9.2 Hz, 1H), 6.62 (dd, J=2.8, 9.2 Hz, 1H) 6.50 (d, J=2.8, 1H), 4.67 (d, J=6.8, 1H), 3.42 (q, J=7.2, 4H), 2.97 (t, J=6.8, 1H), 2.42 (s, 1H), 1.22 (q, J=7.2, 4H).

7-(diethylamino)-3-(2-hydroxyethyl)-4-methyl-2H-chromen-2-one (53). A solution of Int 2-2 (1.9 g, 5.29 mmol, 1 eq) in HCl/dioxane (4 M, 50 mL) was stirred at 20° C. for 30 min. The mixture was concentrated under reduced pressure. The residue was purified by reverse-phase preparative HPLC. The desired fractions were collected and lyophilized to give 53 (734 mg, 45%) as a brown gum. ¹H NMR (400 MHz, DMSO-d6) δ=7.58-7.48 (m, 1H), 6.75-6.63 (m, 11H), 6.52-6.42 (m, 1H), 4.61-4.53 (m, 1H), 3.75-3.59 (m, 2H), 3.46-3.37 (m, 6H), 2.84-2.73 (m, 2H), 2.37-2.27 (m, 3H), 1.73-1.52 (m, 2H), 1.49-1.34 (m, 4H), 1.16-1.07 (m, 6H). LC-MS [ESI, M+1]: 276.1.

Scheme 3.

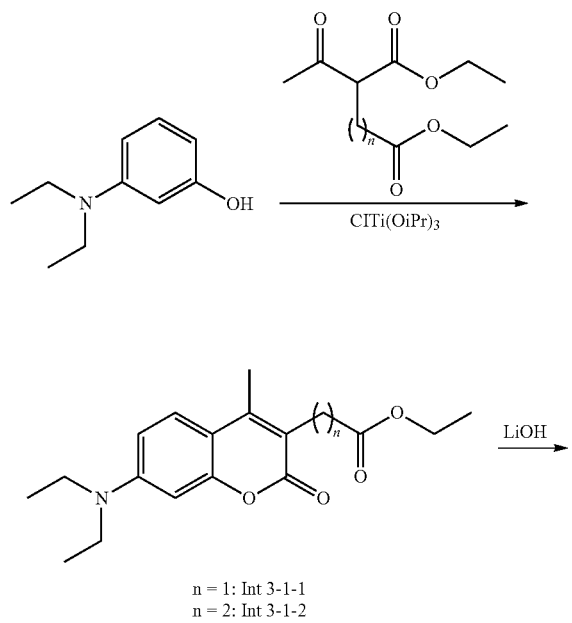

n = 1: Int 3-1-1
n = 2: Int 3-1-2

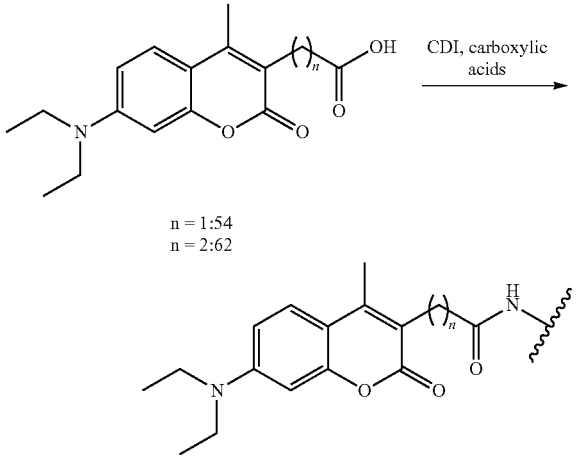

n = 1:54
n = 2:62

Ethyl 2-(7-(diethylamino 4-methyl-2-oxo-2H-chromen-3-yl)acetate (Int 3-1-1). To a stirred solution of 3-diethylaminophenol (412.5 mg, 1 eq) and diethyl 2-acetylsuccinate (703 mg, 1.3 eq) in toluene (5 mL) was added ClTi(OiPr)₃ (717 mg) and the dark brown suspension refluxed overnight. Thereto was added sat. aqueous Rochelle's salt (10 mL) and the emulsion was filtered through Celite. The filtrate was extracted with EtOAc (3×20 mL). The combined organics were washed once with brine, dried over MgSO₄, filtered, and concentrated in vacuo. The residue was purified by flash column chromatography to afford a mixture of the title intermediate and the isopropyl ether as a brown oil.

2-(7-(diethylamino)-4-methyl-2-oxo-2H-chromen-3-yl) acetic acid (54). To a solution of Int 3-1-1 in H₂O (2 mL), MeOH (2 mL), and THF (2 mL) was added lithium hydroxide monohydrate (3 eq) and the light brown suspension stirred at room temperature for 16 hours. The mixture was acidified by addition of 1 M HCl and extracted with EtOAc (3×20 mL). The combined organics were washed once with brine, dried over MgSO₄, filtered, and concentrated in vacuo, to afford a brown solid. A sample was purified by reverse-phase preparative HPLC to afford the title compound as a yellow solid. LC-MS [ESI, M+1]: 290.0. ¹H NMR (400 MHz, Chloroform-d) δ 7.59 (d, J=9.0 Hz, 1H), 6.95 (dd, J=8.9, 2.5 Hz, 1H), 6.80 (d, J=2.5 Hz, 1H), 3.78 (s, 2H), 3.51 (q, J=7.1 Hz, 3H), 2.44 (s, 2H), 1.23 (t, J=7.1 Hz, 6H).

ethyl 3-(7-(diethylamino)-4-methyl-2-oxo-2H-chromen-3-yl)propanoate (Int 3-1-2). The title intermediate was prepared analogously to Int 3-1-1, using diethyl 2-acetylpentanedioate.

2-(7-(diethylamino)-4-methyl-2-oxo-2H-chromen-3-yl)-N-phenethylacetamide (55). To a stirred solution of 54 (40 mg, 1 eq) in DMF (1 mL) was added CDI (33 mg, 1.5 eq) and stirred at room temperature for 1 hrs, during which the color changed from orange-red to yellow. Thereto was added 2-phenylethan-1-amine (49 mg, 3 eq) and stirred for an additional hour at room temperature. The mixture was diluted with 19 mL H₂O and extracted with EtOAc (3×20 mL). The combined organics were washed once with brine, dried over MgSO₄, filtered, and concentrated in vacuo. The residue was purified by flash column chromatography (SiO₂, 0 to 45% EtOAc in hexanes) to afford the title compound as a light yellow solid. In other examples, purification was achieved using reverse-phase preparative HPLC. ESI-MS [M+1]: 393.2. ¹H NMR (500 MHz, Chloroform-d) δ 7.45 (d, J=9.1 Hz, 1H), 7.25-7.16 (m, 2H), 7.16-7.09 (m, 3H), 6.65

(dd, J=9.1, 2.6 Hz, 1H), 6.53 (d, J=2.6 Hz, 1H), 6.46 (s, 1H), 3.53-3.40 (m, 8H), 2.78 (t, J=7.1 Hz, 2H), 2.46 (s, 3H), 1.24 (t, J=7.1 Hz, 6H).

2-(7-(diethylamino)-4-methyl-2-oxo-2H-chromen-3-yl)-N-(3-phenylpropyl)acetamide (56). The title compound was prepared analogously to 55, using 3-phenylpropan-1-amine. ESI-MS [M+1]: 407.2. $^1$H NMR (500 MHz, Chloroform-d) δ 7.46 (d, J=9.1 Hz, 1H), 7.30-7.22 (m, 2H), 7.25-7.13 (m, 3H), 6.64 (dd, J=9.1, 2.6 Hz, 1H), 6.57-6.49 (m, 2H), 3.54 (s, 2H), 3.44 (q, J=7.1 Hz, 4H), 3.24 (td, J=7.1, 5.9 Hz, 2H), 2.66-2.58 (m, 2H), 2.52 (s, 3H), 1.89-1.76 (m, 2H), 1.23 (t, J=7.1 Hz, 6H).

2-(7-(diethylamino)-4-methyl-2-oxo-2H-chromen-3-yl)-N-(4-phenylbutyl)acetamide (57). The title compound was prepared analogously to 55, using 4-phenylbutan-1-amine. ESI-MS [M+1]: 421.2. $^1$H NMR (500 MHz, Chloroform-d) δ 7.45 (d, J=9.1 Hz, 1H), 7.25-7.16 (m, 2H), 7.13 (d, J=7.0 Hz, 3H), 6.65 (dd, J=9.1, 2.6 Hz, 1H), 6.53 (d, J=2.6 Hz, 1H), 6.46 (s, 1H), 3.53-3.40 (m, 9H), 2.78 (t, J=7.1 Hz, 2H), 2.46 (s, 3H), 1.24 (t, J=7.1 Hz, 6H).

2-(7-(diethylamino)-4-methyl-2-oxo-2H-chromen-3-yl)-N-(2-(dimethylamino)ethyl)acetamide (58). The title compound was prepared analogously to 55, using $N^1,N^1$-dimethylethane-1,2-diamine. ESI-MS [M+1]: 360.2. $^1$H NMR (400 MHz, Chloroform-d) δ 7.45 (d, J=9.0 Hz, 1H), 6.72 (s, 1H), 6.62 (dd, J=9.1, 2.6 Hz, 1H), 6.51 (d, J=2.6 Hz, 1H), 3.55 (s, 2H), 3.43 (q, J=7.1 Hz, 4H), 3.30 (q, J=6.1 Hz, 2H), 2.50 (s, 3H), 2.41 (q, J=6.0 Hz, 2H), 2.24 (s, 6H), 1.22 (t, J=7.1 Hz, 6H).

2-(7-(diethylamino)-4-methyl-2-oxo-2H-chromen-3-yl)-N-(3-(dimethylamino)propyl)acetamide (59). The title compound was prepared analogously to 55, using $N^1,N^1$-dimethylpropane-1,3-diamine. ESI-MS [M+1]: 374.2. $^1$H NMR (400 MHz, Chloroform-d) δ 7.44 (d, J=9.0 Hz, 1H), 6.62 (dd, J=9.0, 2.6 Hz, 1H), 6.50 (d, J=2.6 Hz, 1H), 3.55 (s, 3H), 3.43 (q, J=7.1 Hz, 4H), 3.28 (dt, J=10.0, 5.0 Hz, 3H), 2.45 (s, 4H), 2.32 (t, J=6.6 Hz, 3H), 2.09 (s, 6H), 1.22 (t, J=7.1 Hz, 6H).

2-(7-(diethylamino)-4-methyl-2-oxo-2H-chromen-3-yl)-N-methylacetamide (60). The title compound was prepared analogously to 55, using methylamine. ESI-MS [M+1]: 303.1. $^1$H NMR (400 MHz, Chloroform-d) δ 7.45 (d, J=9.1 Hz, 1H), 6.62 (dd, J=9.1, 2.6 Hz, 1H), 6.53-6.43 (m, 2H), 3.54 (s, 2H), 3.43 (q, J=7.1 Hz, 4H), 2.76 (d, J=4.9 Hz, 3H), 2.50 (s, 3H), 1.22 (t, J=7.1 Hz, 6H).

2-(7-(diethylamino)-4-methyl-2-oxo-2H-chromen-3-yl)-N,N-dimethylacetamide (61). The title compound was prepared analogously to 55, using dimethylamine. ESI-MS [M+1]: 317.1 $^1$H NMR (400 MHz, Chloroform-d) δ 7.43 (d, J=9.0 Hz, 11H), 6.60 (dd, J=9.0, 2.6 Hz, 1H), 6.51 (d, J=2.6 Hz, 11H), 3.70 (s, 2H), 3.42 (q, J=7.1 Hz, 4H), 2.98 (s, 3H), 2.39 (s, 3H), 1.21 (t, J=7.0 Hz, 6H).

3-(7-(diethylamino)-4-methyl-2-oxo-2H-chromen-3-yl)propanoic acid (62). The title compound was prepared analogously to 54, using Int 3-1-2. ESI-MS [M+1]: 304.0

N-benzyl-3-(7-(diethylamino)-4-methyl-2-oxo-2H-chromen-3-yl)propenamide (63). The title compound was prepared analogously to 55, using 62 and benzylamine. ESI-MS [M+1]: 393.2. $^1$H NMR (500 MHz, Chloroform-d) δ 7.41 (d, J=9.0 Hz, 1H), 7.35-7.14 (m, 6H), 6.62 (dd, J=9.0, 2.6 Hz, 1H), 6.47 (d, J=2.6 Hz, 11H), 5.24 (s, 11H), 4.38 (t, J=6.0 Hz, 3H), 3.42 (q, J=7.1 Hz, 4H), 2.95 (t, J=7.5 Hz, 2H), 2.51 (t, J=7.5 Hz, 2H), 2.37 (s, 3H), 1.22 (t, J=7.1 Hz, 6H).

3-(7-(diethylamino)-4-methyl-2-oxo-2H-chromen-3-yl)-N-phenethylpropanamide (64). The title compound was prepared analogously to 55, using 62 and 2-phenylethan-1-amine. ESI-MS [M+1]: 407.2. $^1$H NMR (400 MHz, Chloroform-d) δ 7.43 (d, J=9.0 Hz, 1H), 7.33-7.10 (m, 6H), 6.62 (dd, J=9.1, 2.6 Hz, 1H), 6.51 (d, J=2.6 Hz, 1H), 5.84 (s, 1H), 3.47 (dq, J=29.3, 7.1 Hz, 7H), 2.94 (t, J=7.5 Hz, 2H), 2.78 (t, J=7.1 Hz, 2H), 2.44 (t, J=7.5 Hz, 2H), 1.22 (t, J=7.1 Hz, 6H).

3-(7-(diethylamino)-4-methyl-2-oxo-2H-chromen-3-yl)-N-(3-phenylpropyl)propenamide (65). The title compound was prepared analogously to 55, using 62 and 3-phenylpropan-1-amine. ESI-MS [M+1]: 421.2. $^1$H NMR (400 MHz, Chloroform-d) δ 7.41 (d, J=9.0 Hz, 1H), 7.33-7.21 (m, 4H), 7.25-7.08 (m, 6H), 6.60 (dd, J=9.0, 2.6 Hz, 1H), 6.49 (d, J=2.6 Hz, 1H), 3.42 (q, J=7.1 Hz, 3H), 3.27 (q, J=6.7 Hz, 1H), 2.95 (t, J=7.4 Hz, 1H), 2.61 (dt, J=16.8, 7.7 Hz, 4H), 2.48 (t, J=7.4 Hz, 1H), 2.40 (s, 2H), 1.80 (h, J=7.3 Hz, 4H), 1.22 (t, J=7.1 Hz, 6H).

3-(7-(diethylamino)-4-methyl-2-oxo-2H-chromen-3-yl)-N-methylpropanamide (66). The title compound was prepared analogously to 55, using 62 and methylamine. ESI-MS [M+1]: 317.1. $^1$H NMR (500 MHz, Chloroform-d) δ 7.42 (d, J=9.0 Hz, 1H), 6.61 (dd, J=9.0, 2.6 Hz, 1H), 6.48 (d, J=2.6 Hz, 1H), 6.00 (s, 1H), 3.41 (q, J=7.1 Hz, 4H), 2.95 (q, J=7.7 Hz, 2H), 2.78 (d, J=4.9 Hz, 3H), 2.46 (t, J=7.5 Hz, 2H), 2.40 (s, 3H), 1.21 (t, J=7.1 Hz, 6H).

3-(7-(diethylamino)-4-methyl-2-oxo-2H-chromen-3-yl)-N-(2-(dimethylamino)ethyl)propenamide (67). The title compound was prepared analogously to 55, using 62 and $N^1,N^1$-dimethylethane-1,2-diamine. ESI-MS [M+1]: 317.1. $^1$H NMR (500 MHz, Chloroform-d) δ 7.41 (d, J=9.1 Hz, 1H), 6.60 (dd, J=9.0, 2.6 Hz, 1H), 6.52 (s, 1H), 6.49 (d, J=2.6 Hz, 1H), 3.63 (s, 1H), 3.41 (q, J=7.1 Hz, 4H), 3.35 (q, J=5.7 Hz, 2H), 2.94 (dd, J=8.4, 6.8 Hz, 2H), 2.54-2.39 (m, 4H), 2.40 (s, 3H), 2.28 (s, 5H), 1.21 (t, J=7.1 Hz, 6H).

3-(7-(diethylamino)-4-methyl-2-oxo-2H-chromen-3-yl)-N-(3-(dimethylamino)propyl)propenamide (68). The title compound was prepared analogously to 55, using 62 and $N^1,N^1$-dimethylpropane-1,3-diamine. ESI-MS [M+1]: 388.1. $^1$H NMR (500 MHz, Chloroform-d) δ 7.42 (d, J=9.1 Hz, 1H), 6.93 (d, J=6.0 Hz, 1H), 6.60 (dd, J=9.0, 2.6 Hz, 1H), 6.49 (d, J=2.6 Hz, 1H), 3.41 (q, J=7.1 Hz, 5H), 3.30 (td, J=6.5, 5.4 Hz, 2H), 2.94 (dd, J=8.4, 6.8 Hz, 2H), 2.43 (dd, J=8.3, 6.9 Hz, 2H), 2.33 (t, J=6.6 Hz, 2H), 2.20 (s, 6H), 1.62 (p, J=6.6 Hz, 2H), 1.21 (t, J=7.1 Hz, 6H).

Scheme 4.

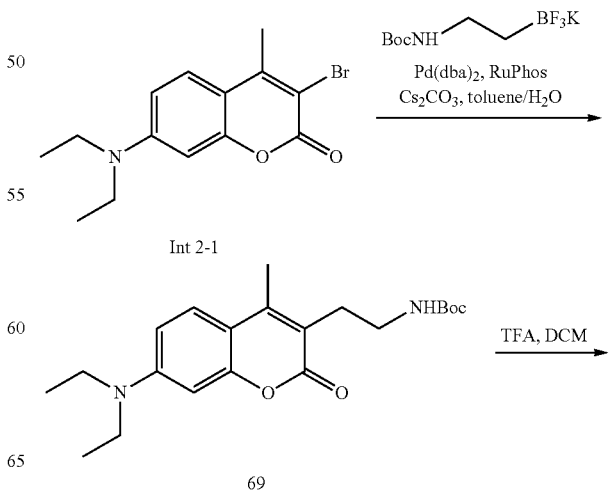

69

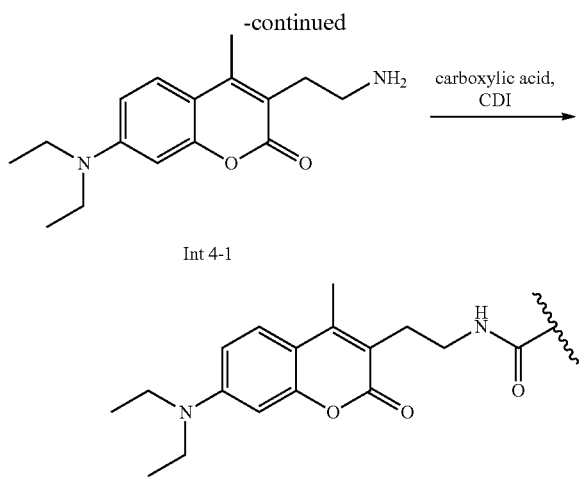

Tert-butyl (2-(7-(diethylamino)-4-methyl-2-oxo-2H-chromen-3-yl)ethyl)carbamate (69). A mixture of Int 2-1 (310 mg, 1 eq), potassium 2-(Boc-aminoethyl)trifluoroborate (301 mg, 1.2 eq), RuPhos (93 mg, 0.2 eq) and $Cs_2CO_3$ (977 mg, 3 eq) in toluene (4.5 mL) and $H_2O$ (1.5 mL) in a microwave tube was sparged with argon for 5 minutes while stirring. Thereto was added $Pd(dba)_2$ (58 mg, 0.1 eq) and further sparged for an additional minute. The vial was sealed and heated at 90° C. for 16 hr. The initially red biphasic mixture turned dark orange, and a black precipitate appeared. The reaction was then diluted with water (15 mL) and extracted with EtOAc (3×20 mL). The combined organics were washed once with brine, dried over $MgSO_4$, filtered, and concentrated under reduced pressure. The residue was purified by flash column chromatography ($SiO_2$, 0 to 25% EtOAc in hexanes) to afford 69 as a yellow solid (249.3 mg, 67%). ESI-MS [M+1]: 375.2. $^1$H NMR (400 MHz, $CDCl_3$) δ=7.42 (br d, J=9.2 Hz, 1H), 6.60 (dd, J=2.4, 9.2 Hz, 1H), 6.50 (d, J=2.4 Hz, 1H), 4.95-4.77 (m, 1H), 3.41 (q, J=7.2 Hz, 4H), 3.31 (q, J=6.4 Hz, 2H), 2.84 (br t, J=6.7 Hz, 2H), 2.39 (s, 3H), 1.43 (s, 9H), 1.21 (t, J=7.2 Hz, 6H).

3-(2-aminoethyl)-7-(diethylamino)-4-methyl-2H-chromen-2-one (Int 4-1). To a stirred solution of 69 (450 mg) in DCM (4 mL) was added neat TFA (1 mL) and stirred at room temperature for 16 hours. The mixture was concentrated in vacuo and then treated with saturated $NaHCO_3$. The yellow precipitate that appeared was filtered and washed with $H_2O$ to afford the title intermediate as a yellow solid (321 mg, 98%). ESI-MS [M+1]: 275.2 $^1$H NMR (600 MHz, DMSO-$d_6$) δ 7.80 (s, 3H), 7.56 (d, J=9.1 Hz, 1H), 6.72 (dd, J=9.1, 2.6 Hz, 1H), 6.50 (d, J=2.6 Hz, 1H), 3.43 (q, J=7.0 Hz, 3H), 3.40 (s, 1H), 2.96-2.87 (m, 2H), 2.82 (dd, J=8.6, 6.6 Hz, 2H), 2.37 (s, 3H), 1.12 (t, J=7.0 Hz, 6H).

N-(2-(7-(diethylamino)-4-methyl-2-oxo-2H-chromen-3-yl)ethyl)-3-phenylpropanamide (70). The title compound was prepared analogously to 55, using 3-phenylpropanoic acid and Int 4-1. ESI-MS [M+1]: 407.2. $^1$H NMR (400 MHz, Chloroform-d) δ 7.43 (d, J=9.0 Hz, 1H), 7.31-7.17 (m, 4H), 7.23-7.09 (m, 2H), 6.63 (dd, J=9.0, 2.6 Hz, 1H), 6.50 (d, J=2.6 Hz, 1H), 6.18 (t, J=5.0 Hz, 1H), 3.49-3.34 (m, 6H), 2.95 (dd, J=8.9, 6.9 Hz, 2H), 2.83 (t, J=6.8 Hz, 2H), 2.47 (dd, J=8.9, 6.9 Hz, 2H), 1.23 (t, J=7.1 Hz, 6H).

3-(7-(diethylamino)-4-methyl-2-oxo-2H-chromen-3-yl)-N-(2-fluorophenethyl)propenamide (71). The title compound was prepared analogously to 55, using 62 and 2-(2-fluorophenyl)ethan-1-amine. ESI-MS [M+1]: 425.2. $^1$H NMR (400 MHz, Chloroform-d) δ 7.42 (d, J=9.1 Hz, 1H), 7.28-6.93 (m, 6H), 6.61 (dd, J=9.0, 2.6 Hz, 1H), 6.49 (d, J=2.6 Hz, 1H), 5.95 (t, J=5.5 Hz, 1H), 3.57-3.33 (m, 7H), 2.97-2.78 (m, 6H), 2.43 (t, J=7.5 Hz, 2H), 1.21 (t, J=7.1 Hz, 6H).

3-(7-(diethylamino)-4-methyl-2-oxo-2H-chromen-3-yl)-N-(3-fluorophenethyl)propenamide (72). The title compound was prepared analogously to 55, using 62 and 2-(3-fluorophenyl)ethan-1-amine. ESI-MS [M+1]: 425.2. $^1$H NMR (400 MHz, Chloroform-d) δ 7.43 (d, J=9.0 Hz, 1H), 7.30-7.16 (m, 1H), 7.02-6.82 (m, 3H), 6.62 (dd, J=9.0, 2.6 Hz, 1H), 6.51 (d, J=2.6 Hz, 1H), 5.91 (s, 1H), 3.55-3.34 (m, 6H), 2.93 (t, J=7.5 Hz, 2H), 2.80 (dt, J=14.1, 7.0 Hz, 2H), 2.51-2.38 (m, 4H), 1.35-1.15 (m, 6H).

3-(7-(diethylamino)-4-methyl-2-oxo-2H-chromen-3-yl)-N-(4-fluorophenethyl)propenamide (73). The title compound was prepared analogously to 55, using 62 and 2-(4-fluorophenyl)ethan-1-amine. ESI-MS [M+1]: 425.2. $^1$H NMR (400 MHz, Chloroform-d) δ 7.43 (d, J=9.0 Hz, 1H), 6.62 (dd, J=9.0, 2.6 Hz, 1H), 6.50 (d, J=2.6 Hz, 1H), 4.40 (t, J=5.9 Hz, 3H), 2.91 (t, J=7.4 Hz, 2H), 2.83-2.70 (m, 9H), 1.22 (t, J=7.1 Hz, 6H).

3-(7-(diethylamino)-4-methyl-2-oxo-2H-chromen-3-yl)-N-(2-(pyridin-2-yl)ethyl)propenamide (74). The title compound was prepared analogously to 55, using 62 and 2-(pyridin-2-yl)ethan-1-amine. ESI-MS [M+1]: 408.2.

3-(7-(diethylamino)-4-methyl-2-oxo-2H-chromen-3-yl)-N-(2-(pyridin-3-yl)ethyl)propenamide (75). The title compound was prepared analogously to 55, using 62 and 2-(pyridin-3-yl)ethan-1-amine. ESI-MS [M+1]: 408.2.

3-(7-(diethylamino)-4-methyl-2-oxo-2H-chromen-3-yl)-N-(2-(pyridin-4-yl)ethyl)propenamide (76). The title compound was prepared analogously to 55, using 62 and 2-(pyridin-4-yl)ethan-1-amine. ESI-MS [M+1]: 408.2.

3-(7-(diethylamino)-4-methyl-2-oxo-2H-chromen-3-yl)-N-(3-phenylpropyl)propenamide (77). The title compound was prepared analogously to 55, using 62 and 3-phenylpropan-1-amine. ESI-MS [M+1]: 421.2. $^1$H NMR (500 MHz, Chloroform-d) δ 7.43 (d, J=9.1 Hz, 1H), 7.26 (d, J=7.7 Hz, 1H), 7.24-7.11 (m, 4H), 6.62 (dd, J=9.0, 2.6 Hz, 1H), 6.49 (d, J=2.6 Hz, 1H), 6.13 (s, 1H), 3.50-3.37 (m, 7H), 2.88 (t, J=6.8 Hz, 2H), 2.63 (t, J=7.6 Hz, 2H), 2.22-2.14 (m, 2H), 2.02-1.90 (m, 2H), 1.22 (t, J=7.1 Hz, 6H).

Scheme 5.

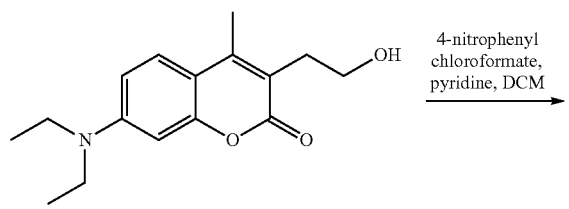

53

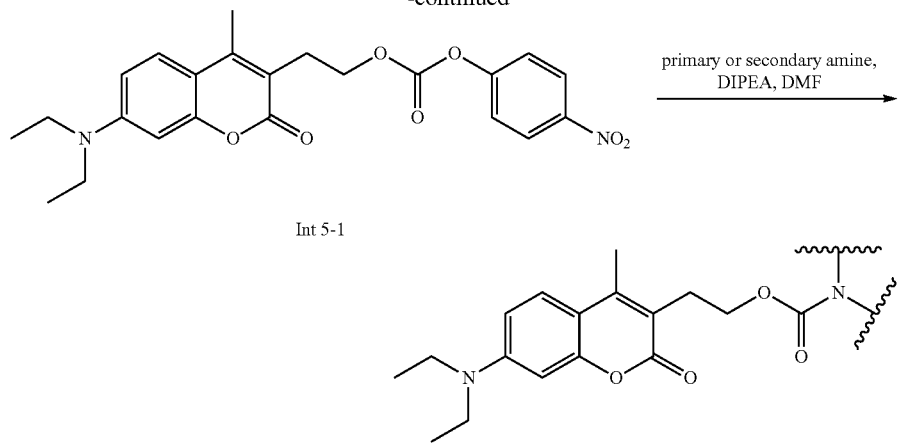

Int 5-1

2-(7-(diethylamino)-4-methyl-2-oxo-2H-chromen-3-yl) ethyl (4-nitrophenyl) carbonate (Int 5-1). To a stirred solution of 53 (500 mg, 1.82 mmol, 1 eq) and pyridine (440 µL, 5.46 mmol, 3 eq) in DCM (2 mL) under argon was added a solution of 4-nitrophenyl chloroformate (440 mg, 2.18 mmol, 1.2 eq) in DCM (2 mL), dropwise, at room temperature. The reaction was stirred for 3 hours at room temperature, during which the solution turned orange and a crystalline precipitate appeared. The mixture was partitioned between DCM (20 mL) and 0.1 M aqueous HCl (20 mL), then extracted with DCM (3×20 mL). The combined organics were washed with brine, dried over MgSO$_4$, filtered, and concentrated under reduced pressure. The residue was purified by flash column chromatography (SiO$_2$, 0 to 25% EtOAc in hexanes) to afford Int 5-1 as a yellow-orange solid (621.1 mg, 78%), which was stored at −20° C. LC-MS [ESI, M+1]: 441.2. $^1$H NMR (400 MHz, CDCl$_3$) δ=8.27-8.23 (m, 2H), 7.43 (d, J=8.8 Hz, 1H), 7.36-7.31 (m, 2H), 6.61-6.56 (m, 1H), 6.51 (d, J=2.8 Hz, 1H), 4.48 (t, J=6.8 Hz, 2H), 3.42 (q, J=7.2 Hz, 4H), 3.11 (t, J=6.8 Hz, 2H), 2.41 (s, 3H), 1.22 (t, J=7.2 Hz, 6H).

2-(7-(diethylamino)-4-methyl-2-oxo-2H-chromen-3-yl) ethyl benzylcarbamate (78). To a stirred solution of Int 5-1 (37 mg, 1 eq) and DIPEA (2 eq) in DMF (1 mL) was added benzylamine (26 mg, 3 eq). The solution immediately turned a bright yellow upon addition of amine. The reaction was stirred at room temperature for 2 hours, then diluted with 20 mL H$_2$O and basified with addition of solid Na$_2$CO$_3$. The suspension was extracted with EtOAc (3×10 mL). The combined organics were washed once with brine, dried over MgSO$_4$, filtered, and concentrated under reduced pressure. The residue was purified by flash column chromatography (SiO$_2$, EtOAc/hexanes) to afford the title compound as a yellow solid (26.1 mg, 80%). ESI-MS [M+1]: 409.2. $^1$H NMR (400 MHz, Chloroform-d) δ 7.41 (d, J=9.0 Hz, 1H), 7.37-7.27 (m, 3H), 6.61 (dd, J=9.0, 2.6 Hz, 1H), 6.51 (d, J=2.6 Hz, 1H), 4.97 (s, 1H), 4.39 (d, J=6.0 Hz, 2H), 4.28 (t, J=7.0 Hz, 2H), 3.43 (q, J=7.1 Hz, 5H), 3.01 (t, J=7.0 Hz, 2H), 2.39 (s, 3H), 1.23 (t, J=7.1 Hz, 6H).

2-(7-(diethylamino)-4-methyl-2-oxo-2H-chromen-3-yl) ethyl methylcarbamate (79). The title compound was prepared analogously to 78, using methylamine. ESI-MS [M+1]: 333.1. $^1$H NMR (400 MHz, Chloroform-d) δ 7.42 (d, J=9.0 Hz, 1H), 6.61 (dd, J=9.0, 2.6 Hz, 1H), 6.50 (d, J=2.6 Hz, 1H), 4.61 (s, 1H), 4.23 (t, J=7.1 Hz, 2H), 3.42 (q, J=7.1 Hz, 4H), 2.98 (t, J=7.1 Hz, 2H), 2.80 (d, J=4.8 Hz, 3H), 2.40 (s, 3H), 1.22 (t, J=7.1 Hz, 6H).

2-(7-(diethylamino)-4-methyl-2-oxo-2H-chromen-3-yl) ethyl phenethylcarbamate (80). The title compound was prepared analogously to 78, using 2-phenylethan-1-amine. ESI-MS [M+1]: 423.2. $^1$H NMR (400 MHz, Chloroform-d) δ 7.41 (d, J=9.0 Hz, 1H), 7.38-7.20 (m, 4H), 7.20 (d, J=7.3 Hz, 2H), 6.61 (dd, J=9.0, 2.6 Hz, 1H), 6.51 (d, J=2.5 Hz, 1H), 4.69 (d, J=6.8 Hz, 1H), 4.23 (t, J=7.1 Hz, 2H), 3.43 (q, J=7.1 Hz, 6H), 2.97 (t, J=7.1 Hz, 2H), 2.82 (t, J=7.1 Hz, 2H), 2.37 (s, 3H), 1.22 (t, J=7.1 Hz, 6H).

2-(7-(diethylamino)-4-methyl-2-oxo-2H-chromen-3-yl) ethyl (3-phenylpropyl)carbamate (81). The title compound was prepared analogously to 78, using 3-phenylpropan-1-amine. ESI-MS [M+1]: 437.2. H NMR (400 MHz, Chloroform-d) δ 7.42 (d, J=9.0 Hz, 1H), 7.36-7.26 (m, 3H), 7.26-7.15 (m, 3H), 6.60 (dd, J=9.0, 2.6 Hz, 1H), 6.51 (d, J=2.6 Hz, 1H), 4.68 (s, 1H), 4.23 (t, J=7.0 Hz, 2H), 3.43 (q, J=7.1 Hz, 4H), 3.22 (q, J=6.7 Hz, 2H), 2.99 (t, J=7.0 Hz, 2H), 2.67 (q, J=7.4 Hz, 2H), 2.40 (s, 3H), 1.85 (h, J=6.8 Hz, 2H), 1.22 (t, J=7.1 Hz, 6H).

2-(7-(diethylamino)-4-methyl-2-oxo-2H-chromen-3-yl) ethyl (2-(pyridin-2-yl)ethyl)carbamate (82). The title compound was prepared analogously to 78, using 2-(pyridin-2-yl)ethan-1-amine. ESI-MS [M+1]: 424.1. $^1$H NMR (500 MHz, Chloroform-d) δ 8.57-8.50 (m, 1H), 7.62 (td, J=7.6, 1.8 Hz, 1H), 7.39 (s, 1H), 7.20-7.11 (m, 2H), 6.60 (dd, J=9.0, 2.6 Hz, 1H), 6.50 (d, J=2.6 Hz, 1H), 5.37 (d, J=6.0 Hz, 1H), 4.22 (t, J=7.0 Hz, 2H), 3.61 (q, J=6.3 Hz, 2H), 3.42 (q, J=7.1 Hz, 4H), 2.98 (dt, J=14.9, 6.7 Hz, 4H), 2.37 (s, 3H), 1.21 (t, J=7.1 Hz, 6H).

2-(7-(diethylamino)-4-methyl-2-oxo-2H-chromen-3-yl) ethyl (2-(pyridin-3-yl)ethyl)carbamate (83). The title compound was prepared analogously to 78, using 2-(pyridin-3-yl)ethan-1-amine, to afford 83 as a tan solid (20.7 mg, 78%). ESI-MS [M+1]: 424.1.

2-(7-(diethylamino)-4-methyl-2-oxo-2H-chromen-3-yl) ethyl (2-(pyridin-4-yl)ethyl)carbamate (84). The title compound was prepared analogously to 78, using 2-(pyridin-4-yl)ethan-1-amine. ESI-MS [M+1]: 424.1. $^1$H NMR (400 MHz, Chloroform-d) δ 8.53-8.43 (m, 2H), 7.53 (d, J=7.9 Hz, 1H), 7.24 (dd, J=7.8, 4.8 Hz, 1H), 6.60 (dd, J=9.0, 2.6 Hz, 1H), 6.50 (d, J=2.6 Hz, 1H), 4.84 (s, 1H), 4.23 (t, J=7.0 Hz, 2H), 3.42 (q, J=7.1 Hz, 6H), 2.97 (dd, J=8.3, 5.7 Hz, 2H), 2.83 (t, J=7.2 Hz, 2H), 2.37 (s, 3H), 1.21 (t, J=7.1 Hz, 6H).

2-(7-(diethylamino)-4-methyl-2-oxo-2H-chromen-3-yl) ethyl (pyridin-2-ylmethyl)carbamate (85). The title compound was prepared analogously to 78, using pyridin-2-ylmethanamine. ESI-MS [M+1]: 410.2. $^1$H NMR (400 MHz, Chloroform-d) δ 8.54 (d, J=4.9 Hz, 1H), 7.65 (t, J=7.7 Hz, 1H), 7.40 (d, J=9.0 Hz, 1H), 7.28 (d, J=5.8 Hz, 1H), 7.19 (dd, J=7.5, 5.0 Hz, 1H), 6.60 (dd, J=9.1, 2.6 Hz, 1H), 6.50 (d, J=2.6 Hz, 1H), 5.76 (t, J=5.5 Hz, 1H), 4.49 (d, J=5.5 Hz, 2H), 4.28 (t, J=7.0 Hz, 2H), 3.42 (q, J=7.1 Hz, 4H), 3.00 (t, J=6.9 Hz, 2H), 2.38 (s, 3H), 1.21 (t, J=7.0 Hz, 6H).

2-(7-(diethylamino)-4-methyl-2-oxo-2H-chromen-3-yl) ethyl (pyridin-4-ylmethyl)carbamate (86). The title compound was prepared analogously to 78, using pyridin-4-ylmethanamine. ESI-MS [M+1]: 410.2. $^1$H NMR (400 MHz, Chloroform-d) δ 8.54 (d, J=5.1 Hz, 2H), 7.41 (d, J=9.0 Hz, 1H), 7.20 (d, J=5.0 Hz, 2H), 6.61 (dd, J=9.1, 2.6 Hz, 1H), 6.50 (d, J=2.5 Hz, 1H), 5.26 (d, J=6.5 Hz, 1H), 4.39 (d, J=6.3 Hz, 2H), 4.29 (t, J=7.0 Hz, 2H), 3.42 (q, J=7.1 Hz, 4H), 3.00 (t, J=7.0 Hz, 2H), 2.38 (s, 3H), 1.22 (t, J=7.0 Hz, 6H).

2-(7-(diethylamino)-4-methyl-2-oxo-2H-chromen-3-yl) ethyl (furan-2-ylmethyl)carbamate (87). The title compound was prepared analogously to 78, using furan-2-ylmethanamine. ESI-MS [M+1]: 399.2. $^1$H NMR (400 MHz, Chloroform-d) δ 7.41 (d, J=9.0 Hz, 1H), 6.61 (dd, J=9.0, 2.6 Hz, 1H), 6.50 (d, J=2.6 Hz, 1H), 6.32 (s, 1H), 6.27-6.19 (m, 1H), 5.00 (s, 1H), 4.36 (d, J=5.9 Hz, 2H), 4.26 (t, J=7.0 Hz, 2H), 3.43 (q, J=7.1 Hz, 4H), 2.99 (t, J=7.0 Hz, 2H), 2.37 (s, 3H), 1.22 (t, J=7.1 Hz, 6H).

2-(7-(diethylamino)-4-methyl-2-oxo-2H-chromen-3-yl) ethyl (2-(1H-imidazol-4-yl)ethyl)carbamate (88). The title compound was prepared analogously to 78, using 2-(1H-imidazol-4-yl)ethan-1-amine. ESI-MS [M+1]: 413.2. $^1$H NMR (400 MHz, Chloroform-d) δ 7.67 (s, 1H), 7.43 (s, 1H), 6.85 (s, 11H), 6.61 (dd, J=9.0, 2.6 Hz, 1H), 6.48 (d, J=2.5 Hz, 1H), 5.30 (t, J=6.2 Hz, 1H), 4.22 (t, J=6.8 Hz, 2H), 3.42 (q, J=7.1 Hz, 6H), 2.96 (t, J=6.8 Hz, 2H), 2.82 (d, J=6.6 Hz, 2H), 2.38 (s, 3H), 1.21 (t, J=7.1 Hz, 6H).

2-(7-(diethylamino)-4-methyl-2-oxo-2H-chromen-3-yl) ethyl (pyridin-3-ylmethyl)carbamate (89). The title compound was prepared analogously to 78, using pyridin-3-ylmethanamine, to afford 89 as a tan solid (18.7 mg, 71%). ESI-MS [M+1]: 410.2. $^1$H NMR (400 MHz, Chloroform-d) δ 8.53 (dd, J=9.1, 3.6 Hz, 2H), 7.65 (d, J=7.9 Hz, 1H), 7.40 (d, J=9.0 Hz, 1H), 7.25 (dd, J=7.8, 5.0 Hz, 1H), 6.60 (dd, J=9.0, 2.6 Hz, 1H), 6.49 (d, J=2.6 Hz, 1H), 5.25 (s, 11H), 4.38 (d, J=6.2 Hz, 2H), 3.42 (q, J=7.1 Hz, 4H), 2.98 (t, J=7.0 Hz, 2H), 2.36 (s, 3H), 1.21 (t, J=7.1 Hz, 6H).

2-(7-(diethylamino)-4-methyl-2-oxo-2H-chromen-3-yl) ethyl (pyrimidin-4-ylmethyl)carbamate (90). The title compound was prepared analogously to 78, using pyrimidin-4-ylmethanamine. ESI-MS [M+1]: 411.2. $^1$H NMR (400 MHz, Chloroform-d) δ 8.72 (d, J=4.9 Hz, 2H), 7.42 (d, J=9.0 Hz, 1H), 7.21 (d, J=9.9 Hz, 1H), 6.60 (dd, J=9.0, 2.6 Hz, 1H), 6.50 (d, J=2.6 Hz, 1H), 5.85 (s, 1H), 4.66 (d, J=5.1 Hz, 2H), 4.29 (t, J=7.1 Hz, 2H), 3.42 (q, J=7.1 Hz, 4H), 3.07-2.94 (m, 2H), 2.41 (s, 3H), 1.22 (t, J=7.1 Hz, 6H).

2-(7-(diethylamino)-4-methyl-2-oxo-2H-chromen-3-yl) ethyl (pyrazin-2-ylmethyl)carbamate (91). The title compound was prepared analogously to 78, using pyrazin-2-ylmethanamine. ESI-MS [M+1]: 411.2. $^1$H NMR (400 MHz, Chloroform-d) δ 8.63 (s, 1H), 8.59-8.47 (m, 2H), 7.40 (d, J=9.0 Hz, 1H), 6.60 (dd, J=9.0, 2.6 Hz, 1H), 6.50 (d, J=2.6 Hz, 1H), 5.63 (s, 1H), 4.55 (d, J=5.7 Hz, 2H), 4.28 (t, J=7.0 Hz, 2H), 3.42 (q, J=7.1 Hz, 4H), 3.00 (t, J=7.0 Hz, 2H), 2.38 (s, 3H), 1.22 (t, J=7.1 Hz, 6H).

2-(7-(diethylamino)-4-methyl-2-oxo-2H-chromen-3-yl) ethyl ((1H-pyrazol-5-yl)methyl)carbamate (92). The title compound was prepared analogously to 78, using (1H-pyrazol-5-yl)methanamine. ESI-MS [M+1]: 399.2. $^1$H NMR (400 MHz, Chloroform-d) δ 7.51 (d, J=2.1 Hz, 1H), 7.40 (d, J=9.0 Hz, 1H), 6.60 (dd, J=9.1, 2.6 Hz, 1H), 6.49 (d, J=2.6 Hz, 1H), 6.26-6.18 (M, 1H), 5.55 (s, 1H), 4.41 (d, J=5.8 Hz, 2H), 4.26 (t, J=6.9 Hz, 2H), 3.42 (q, J=7.1 Hz, 4H), 2.98 (q, J=5.5, 4.4 Hz, 3H), 2.36 (s, 3H), 1.21 (t, J=7.1 Hz, 6H).

2-(7-(diethylamino)-4-methyl-2-oxo-2H-chromen-3-yl) ethyl (pyrimidin-2-ylmethyl)carbamate (93). The title compound was prepared analogously to 78, using pyrimidin-2-ylmethanamine. ESI-MS [M+1]: 411.2. $^1$H NMR (500 MHz, Chloroform-d) δ 8.71 (d, J=4.9 Hz, 2H), 7.41 (s, 1H), 7.21 (t, J=5.0 Hz, 1H), 6.60 (dd, J=9.0, 2.6 Hz, 1H), 6.50 (d, J=2.6 Hz, 1H), 5.85 (t, J=5.3 Hz, 1H), 4.66 (d, J=5.1 Hz, 2H), 4.29 (t, J=7.0 Hz, 2H), 3.42 (q, J=7.1 Hz, 4H), 3.02 (t, J=7.0 Hz, 2H), 2.41 (s, 3H), 1.21 (t, J=7.1 Hz, 6H).

N-(2-(7-(diethylamino)-4-methyl-2-oxo-2H-chromen-3-yl)ethyl)acetamide (94). The title compound was prepared analogously to 55, using acetic acid and Int 4-1. ESI-MS [M+1]: 317.1. $^1$H NMR (500 MHz, Chloroform-d) δ 7.42 (d, J=9.0 Hz, 1H), 6.61 (dd, J=9.1, 2.6 Hz, 1H), 6.49 (d, J=2.6 Hz, 1H), 6.26 (d, J=5.1 Hz, 1H), 3.48-3.37 (m, 6H), 2.87 (t, J=6.8 Hz, 2H), 2.40 (s, 3H), 1.95 (s, 3H), 1.21 (t, J=7.1 Hz, 6H).

N-(2-(7-(diethylamino)-4-methyl-2-oxo-2H-chromen-3-yl)ethyl)-3-(pyridin-3-yl)propenamide (95). The title compound was prepared analogously to 55, using 3-(pyridin-3-yl)propanoic acid and Int 4-1. ESI-MS [M+1]: 408.1. $^1$H NMR (500 MHz, Chloroform-d) δ 8.46 (d, J=2.2 Hz, 1H), 8.38 (dd, J=4.8, 1.6 Hz, 1H), 7.52 (dt, J=7.9, 2.0 Hz, 1H), 7.41 (d, J=9.0 Hz, 1H), 7.16 (ddd, J=7.8, 4.8, 0.8 Hz, 1H), 6.61 (dd, J=9.1, 2.6 Hz, 1H), 6.46 (d, J=6.1, 3.5 Hz, 2H), 3.42 (q, J=7.0 Hz, 6H), 2.95 (dd, J=8.5, 6.9 Hz, 2H), 2.82 (t, J=6.8 Hz, 2H), 2.47 (dd, J=8.5, 7.0 Hz, 2H), 2.37 (s, 3H), 1.21 (t, J=7.1 Hz, 6H).

N-(2-(7-(diethylamino)-4-methyl-2-oxo-2H-chromen-3-yl)ethyl)-3-(pyridin-4-yl)propanamide (96). The title compound was prepared analogously to 55, using 3-(pyridin-4-yl)propanoic acid and Int 4-1. ESI-MS [M+1]: 408.1. $^1$H NMR (500 MHz, Chloroform-d) δ 8.49-8.42 (m, 2H), 7.42 (d, J=9.0 Hz, 1H), 7.16-7.09 (m, 2H), 6.62 (dd, J=9.1, 2.6 Hz, 1H), 6.48 (d, J=2.6 Hz, 1H), 6.43 (t, J=5.1 Hz, 1H), 3.42 (qd, J=6.8, 2.9 Hz, 6H), 2.95 (dd, J=8.6, 6.9 Hz, 2H), 2.84 (t, J=6.7 Hz, 2H), 2.48 (dd, J=8.6, 7.0 Hz, 2H), 2.37 (s, 3H), 1.21 (t, J=7.1 Hz, 6H).

2-(7-(diethylamino)-4-methyl-2-oxo-2H-chromen-3-yl) ethyl ((6-chloropyridin-3-yl)methyl)carbamate (97). The title compound was prepared analogously to 78, using (6-chloropyridin-3-yl)methanamine. ESI-MS [M+1]: 444.6. $^1$H NMR (500 MHz, Chloroform-d) δ 8.31 (d, J=2.4 Hz, 1H), 7.66-7.58 (m, 1H), 7.39 (s, 1H), 7.26 (d, J=8.3 Hz, 1H), 6.60 (dd, J=9.0, 2.6 Hz, 1H), 6.49 (d, J=2.6 Hz, 1H), 4.35 (d, J=6.2 Hz, 2H), 4.32 (s, 1H), 4.27 (t, J=6.9 Hz, 2H), 3.42 (q, J=7.1 Hz, 4H), 2.98 (t, J=6.9 Hz, 2H), 2.36 (s, 3H), 1.22 (t, J=7.1 Hz, 6H).

1-(2-(7-(diethylamino)-4-methyl-2-oxo-2H-chromen-3-yl)ethyl)-3-(pyridin-3-ylmethyl)urea (98).

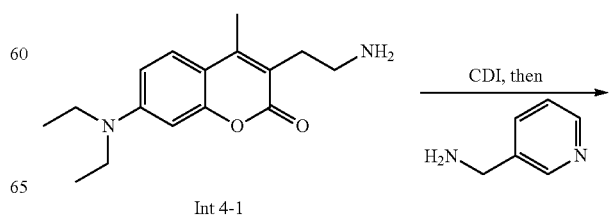

Int 4-1

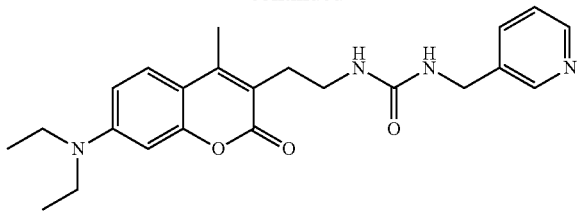

Example 98

To a stirred solution of carbonyldiimidazole (16.5 mg, 1 eq) in 0.5 mL DMF on an ice-water bath was added a solution of Int 4-1 (28 mg, 1 eq) in 0.5 mL DMF dropwise. The yellow solution was stirred for 30 min at 0° C. and an additional 30° min at room temperature. Thereto was added pyridin-3-ylmethanamine (16.2 mg, 1.5 eq) and stirred for 16 hrs at room temperature. The reaction was diluted with 20 mL H$_2$O and extracted with EtOAc (3×10 mL). The combined organics were washed once with brine, dried over MgSO$_4$, filtered, and concentrated under reduced pressure. The residue was purified by flash column chromatography (SiO$_2$, EtOAc/hexanes) to afford the title compound as a yellow solid. ESI-MS [M+1]: 409.1. $^1$H NMR (500 MHz, Chloroform-d) δ 8.54 (d, J=2.0 Hz, 1H), 8.45 (dd, J=4.8, 1.7 Hz, 1H), 7.65 (dt, =7.9, 2.0 Hz, 1H), 7.40 (d, J=9.1 Hz, 1H), 7.19 (dd, J=7.8, 4.8 Hz, 1H), 6.60 (dd, J=9.1, 2.6 Hz, 1H), 6.43 (d, J=2.6 Hz, 1H), 5.77 (s, 1H), 5.51 (s, 1H), 4.39 (d, J=5.9 Hz, 2H), 3.41 (q, J=7.1 Hz, 4H), 3.32 (q, J=6.7 Hz, 2H), 2.81 (t, J=7.2 Hz, 2H), 2.37 (s, 3H), 1.21 (t, J=7.1 Hz, 6H).

1-(2-(7-(diethylamino)-4-methyl-2-oxo-2H-chromen-3-yl)ethyl)-3-(2-(pyridin-3-yl)ethyl)urea (99). The title compound was prepared analogously to 98, using 2-(pyridin-3-yl)ethan-1-amine. ESI-MS [M+1]: 423.2. $^1$H NMR (400 MHz, Chloroform-d) δ 8.43 (dd, J=14.1, 3.4 Hz, 2H), 7.55 (d, J=7.6 Hz, 1H), 7.41 (d, J=9.0 Hz, 1H), 7.20 (dd, J=7.8, 4.9 Hz, 1H), 6.61 (dd, J=9.1, 2.6 Hz, 1H), 6.46 (d, J=2.5 Hz, 1H), 5.27 (d, J=9.1 Hz, 2H), 3.44 (dq, J=21.1, 6.9 Hz, 6H), 3.30 (q, J=6.7 Hz, 2H), 2.82 (q, J=7.4 Hz, 4H), 2.39 (s, 3H), 1.21 (t, J=7.1 Hz, 6H).

Pyridin-3-ylmethyl (2-(7-(diethylamino)-4-methyl-2-oxo-2H-chromen-3-yl)ethyl)carbamate (100). The title compound was prepared analogously to 78, using Int 4-1 and 4-nitrophenyl (pyridin-3-ylmethyl) carbonate. ESI-MS [M+1]: 410.2. $^1$H NMR (500 MHz, Chloroform-d) δ 8.62 (d, J=2.1 Hz, 1H), 8.60-8.54 (m, 1H), 7.70 (dt, J=7.9, 2.0 Hz, 1H), 7.41 (d, J=9.0 Hz, 1H), 7.30 (d, J=4.9 Hz, 1H), 7.28 (s, 1H), 6.61 (dd, J=9.0, 2.6 Hz, 1H), 6.49 (d, J=2.6 Hz, 1H), 5.12 (s, 2H), 3.41 (dq, J=16.2, 6.8 Hz, 6H), 2.88 (t, J=6.9 Hz, 2H), 2.36 (s, 3H), 1.22 (t, J=7.1 Hz, 6H).

2-(7-(diethylamino)-4-methyl-2-oxo-2H-chromen-3-yl) ethyl ((6-(trifluoromethyl)pyridin-3-yl)methyl)carbamate (101). The title compound was prepared analogously to 78, using (6-(trifluoromethyl)pyridin-3-yl)methanamine. ESI-MS [M+1]: 478.2. $^1$H NMR (400 MHz, Chloroform-d) δ 8.66 (s, 1H), 7.83 (d, J=8.1 Hz, 1H), 7.62 (d, J=8.1 Hz, 1H), 7.40 (d, J=9.0 Hz, 1H), 6.61 (dd, J=9.0, 2.5 Hz, 1H), 6.49 (d, J=2.6 Hz, 1H), 5.38 (s, 1H), 4.46 (d, J=6.3 Hz, 2H), 4.29 (t, J=7.0 Hz, 2H), 3.43 (q, J=7.1 Hz, 5H), 2.99 (t, J=6.9 Hz, 2H), 1.22 (t, J=7.1 Hz, 6H).

2-(7-(diethylamino)-4-methyl-2-oxo-2H-chromen-3-yl) ethyl methyl(2-(pyridin-3-yl)ethyl)carbamate (102). The title compound was prepared analogously to 78, using N-methyl-2-(pyridin-3-yl)ethan-1-amine, to afford 102 as a viscous yellow oil (15.1 mg, 84%). ESI-MS [M+1]: 438.2. $^1$H NMR (400 MHz, Chloroform-d) δ 8.57-8.48 (m, 1H), 7.65-7.54 (m, 1H), 7.46-7.35 (m, 1H), 7.18-7.05 (m, 2H), 6.60 (dd, J=9.0, 2.6 Hz, 1H), 6.50 (d, J=2.6 Hz, 1H), 4.19 (ddt, J=20.8, 13.8, 7.0 Hz, 2H), 3.63 (dt, J=14.5, 7.4 Hz, 2H), 3.42 (q, J=7.1 Hz, 4H), 2.96 (q, J=7.3, 5.9 Hz, 5H), 2.87 (s, 2H), 2.80 (s, 2H), 1.21 (t, J=7.1 Hz, 6H).

2-(7-(diethylamino)-4-methyl-2-oxo-2H-chromen-3-yl) ethyl (5-acetamidopyridin-2-yl)carbamate (103). The title compound was prepared analogously to 78, using N-(6-aminopyridin-3-yl)acetamide. ESI-MS [M+1]: 453.2.

1-(2-(7-(diethylamino)-4-methyl-2-oxo-2H-chromen-3-yl)ethyl) 3-methyl azetidine-1,3-dicarboxylate (104). The title compound was prepared analogously to 78, using methyl azetidine-3-carboxylate. ESI-MS [M+1]: 417.2. $^1$H NMR (400 MHz, Chloroform-d) δ 7.43 (d, J=9.0 Hz, 1H), 6.61 (dd, J=9.0, 2.6 Hz, 1H), 6.51 (d, J=2.6 Hz, 1H), 4.23 (t, J=6.9 Hz, 2H), 4.15 (d, J=7.5 Hz, 4H), 3.81-3.68 (m, 5H), 3.49-3.35 (m, 5H), 2.98 (t, J=6.9 Hz, 2H), 2.40 (s, 3H), 1.22 (t, J=7.1 Hz, 6H).

Ethyl 4-(((2-(7-(diethylamino)-4-methyl-2-oxo-2H-chromen-3-yl)ethoxy)carbonyl)amino)piperidine-1-carboxylate (105). The title compound was prepared analogously to 78, using ethyl 4-aminopiperidine-1-carboxylate. ESI-MS [M+1]: 474.2. $^1$H NMR (400 MHz, Chloroform-d) δ 7.42 (d, J=9.0 Hz, 1H), 6.61 (dd, J=9.1, 2.6 Hz, 1H), 6.50 (d, J=2.5 Hz, 1H), 4.65 (d, J=8.0 Hz, 1H), 4.14 (q, J=7.1 Hz, 3H), 3.42 (q, J=7.1 Hz, 6H), 2.39 (s, 4H), 1.24 (dt, J=20.8, 6.9 Hz, 17H).

2-(7-(diethylamino)-4-methyl-2-oxo-2H-chromen-3-yl) ethyl 3-(hydroxymethyl)pyrrolidine-1-carboxylate (106). The title compound was prepared analogously to 78, using pyrrolidin-3-ylmethanol. EST-MS [M+1]: 403.2. $^1$H NMR (400 MHz, Chloroform-d) δ 7.42 (d, J=9.0 Hz, 2H), 6.61 (dd, J=9.0, 2.5 Hz, 2H), 6.50 (d, J=2.6 Hz, 2H), 3.42 (q, J=7.1 Hz, 10H), 1.22 (t, J=7.1 Hz, 13H).

2-(7-(diethylamino)-4-methyl-2-oxo-2H-chromen-3-yl) ethyl 4-(cyclopropylsulfonyl)piperazine-1-carboxylate (107). The title compound was prepared analogously to 78, using 1-(cyclopropylsulfonyl)piperazine. ESI-MS [M+1]: 492.3. $^1$H NMR (500 MHz, Chloroform-d) δ 7.42 (d, J=9.0 Hz, 1H), 6.61 (dd, J=9.0, 2.6 Hz, 1H), 6.50 (d, J=2.6 Hz, 1H), 4.28 (t, J=7.0 Hz, 2H), 3.57 (s, 4H), 3.43 (q, J=7.1 Hz, 4H), 3.27 (d, J=6.5 Hz, 4H), 3.01 (t, J=7.0 Hz, 2H), 2.39 (s, 3H), 2.25 (tt, J=7.9, 4.9 Hz, 1H), 1.26-1.12 (m, 7H), 1.16 (s, 1H), 1.07-0.96 (m, 2H).

2-(7-(diethylamino)-4-methyl-2-oxo-2H-chromen-3-yl) ethyl 3,3-difluoroazetidine-1-carboxylate (108). The title compound was prepared analogously to 78, using 3,3-difluoroazetidine. ESI-MS [M+1]: 395.1. $^1$H NMR (500 MHz, Chloroform-d) δ 7.43 (d, J=9.0 Hz, 1H), 6.62 (dd, J=9.0, 2.6 Hz, 1H), 6.51 (d, J=2.6 Hz, 1H), 4.36-4.23 (m, 6H), 3.43 (q, J=7.1 Hz, 4H), 3.00 (t, J=6.9 Hz, 2H), 2.39 (s, 3H), 1.22 (t, J=7.1 Hz, 6H).

2-(7-(diethylamino)-4-methyl-2-oxo-2H-chromen-3-yl) ethyl 4-(pyrazin-2-yl)piperazine-1-carboxylate (109). The title compound was prepared analogously to 78, using 2-(piperazin-1-yl)pyrazine. ESI-MS [M+1]: 466.3. $^1$H NMR (500 MHz, Chloroform-d) δ 8.15 (d, J=1.6 Hz, 1H), 8.08 (dd, J=2.6, 1.5 Hz, 1H), 7.90 (d, J=2.6 Hz, 1H), 7.41 (d, J=9.0 Hz, 1H), 6.60 (dd, J=9.0, 2.6 Hz, 1H), 6.51 (d, J=2.6 Hz, 1H), 4.30 (t, J=7.0 Hz, 2H), 3.60 (s, 9H), 3.42 (q, J=7.1 Hz, 4H), 3.03 (t, J=7.0 Hz, 2H), 2.41 (s, 3H), 1.22 (t, J=7.1 Hz, 6H).

2-(7-(diethylamino)-4-methyl-2-oxo-2H-chromen-3-yl) ethyl 2-thia-6-azaspiro[3.3]heptane-6-carboxylate 2,2-dioxide (110). The title compound was prepared analogously to 78, using 2-thia-6-azaspiro[3.3]heptane 2,2-dioxide. ESI- MS [M+1]: 449.2. ¹H NMR (500 MHz, Chloroform-d) δ 7.42 (d, J=9.0 Hz, 1H), 6.62 (dd, J=9.0, 2.6 Hz, 1H), 6.50 (d, J=2.6 Hz, 1H), 4.33 (s, 4H), 4.24 (t, J=6.7 Hz, 2H), 4.20 (s, 4H), 3.43 (q, J=7.1 Hz, 4H), 3.02-2.93 (m, 2H), 2.38 (s, 3H), 1.22 (t, J=7.1 Hz, 6H).

2-(7-(diethylamino)-4-methyl-2-oxo-2H-chromen-3-yl) ethyl 3-hydroxy-3-methylpyrrolidine-1-carboxylate (111). The title compound was prepared analogously to 78, using 3-methylpyrrolidin-3-ol. ESI-MS [M+1]: 403.2. ¹H NMR (500 MHz, Chloroform-d) δ 7.42 (d, J=9.0 Hz, 1H), 7.28 (s, 1H), 6.60 (dd, J=9.0, 2.6 Hz, 1H), 6.51 (d, J=2.6 Hz, 1H), 4.35-4.14 (m, 2H), 3.42 (q, J=7.1 Hz, 5H), 3.03 (td, J=13.8, 13.3, 6.7 Hz, 1H), 3.01-2.91 (m, 1H), 2.40 (s, 3H), 1.99-1.89 (m, 1H), 1.94-1.79 (m, 1H), 1.43 (d, J=9.4 Hz, 3H), 1.22 (t, J=7.1 Hz, 6H).

2-(7-(diethylamino)-4-methyl-2-oxo-2H-chromen-3-yl) ethyl thiomorpholine-4-carboxylate 1,1-dioxide (112). The title compound was prepared analogously to 78, using thiomorpholine 1,1-dioxide. ESI-MS [M+1]: 437.2. ¹H NMR (500 MHz, Chloroform-d) δ 7.42 (d, J=9.0 Hz, 1H), 6.62 (dd, J=9.0, 2.6 Hz, 1H), 6.51 (d, J=2.6 Hz, 1H), 4.31 (t, J=6.7 Hz, 2H), 3.97 (s, 4H), 3.43 (q, J=7.1 Hz, 4H), 3.03 (q, J=6.8, 5.3 Hz, 6H), 2.39 (s, 3H), 1.22 (t, J=7.1 Hz, 6H).

2-(7-(diethylamino)-4-methyl-2-oxo-2H-chromen-3-yl) ethyl 4-(3-methylisoxazol-5-yl)piperazine-1-carboxylate (113). The title compound was prepared analogously to 78, using 3-methyl-5-(piperazin-1-yl)isoxazole. ESI-MS [M+1]: 469.3. ¹H NMR (500 MHz, Chloroform-d) δ 7.41 (d, J=9.0 Hz, 1H), 6.61 (dd, J=9.0, 2.6 Hz, 1H), 6.50 (d, J=2.6 Hz, 1H), 4.29 (t, J=6.9 Hz, 2H), 3.58 (s, 9H), 3.43 (q, J=7.1 Hz, 4H), 3.02 (t, J=7.0 Hz, 2H), 2.40 (s, 3H), 2.24 (s, 3H), 1.22 (t, J=7.1 Hz, 6H).

2-(7-(diethylamino)-4-methyl-2-oxo-2H-chromen-3-yl) ethyl 4-(pyridin-2-yl)piperazine-1-carboxylate (114). The title compound was prepared analogously to 78, using 1-(pyridin-2-yl)piperazine. ESI-MS [M+1]: 465.3. ¹H NMR (500 MHz, Chloroform-d) δ 8.55 (dt, J=4.5, 1.5 Hz, 1H), 7.64 (td, J=7.7, 1.9 Hz, 1H), 7.42 (d, J=9.0 Hz, 1H), 7.15 (dd, J=7.5, 5.0 Hz, 2H), 6.60 (dd, J=9.1, 2.6 Hz, 1H), 6.51 (d, J=2.6 Hz, 1H), 4.35 (s, 1H), 3.42 (q, J=7.1 Hz, 4H), 3.02 (t, J=7.1 Hz, 2H), 2.88 (ddt, J=15.7, 8.4, 3.6 Hz, 4H), 2.42 (s, 3H), 1.22 (t, J=7.1 Hz, 6H).

2-(7-(diethylamino)-4-methyl-2-oxo-2H-chromen-3-yl) ethyl 4-(2H-tetrazol-5-yl)piperazine-1-carboxylate (115). The title compound was prepared analogously to 78, using 1-(2H-tetrazol-5-yl)piperazine. ESI-MS [M+1]: 456.2.

2-(7-(diethylamino)-4-methyl-2-oxo-2H-chromen-3-yl) ethyl 4-(pyrimidin-2-yl)piperazine-1-carboxylate (116). The tide compound was prepared analogously to 78, using 2-(piperazin-1-yl)pyrimidine. ESI-MS [M+1]: 466.2. ¹H NMR (500 MHz, Chloroform-d) δ 8.33 (d, J=4.7 Hz, 2H), 7.41 (d, J=9.0 Hz, 1H), 6.60 (dd, J=9.0, 2.6 Hz, 1H), 6.57-6.48 (m, 2H), 4.30 (t, J=7.0 Hz, 2H), 3.82 (s, 4H), 3.54 (s, 4H), 3.42 (q, J=7.1 Hz, 4H), 3.03 (t, J=7.0 Hz, 2H), 2.41 (s, 3H), 1.22 (t, J=7.1 Hz, 6H).

2-(7-(diethylamino)-4-methyl-2-oxo-2H-chromen-3-yl) ethyl (3-acetamidobenzyl)carbamate (117). The title compound was prepared analogously to 78, using N-(3-(aminomethyl)phenyl)acetamide, to afford 117 as a white solid (11.0 mg, 59%). ESI-MS [M+1]: 466.2. ¹H NMR (500 MHz, Chloroform-d) δ 7.91 (s, 1H), 7.66 (d, J=7.6 Hz, 1H), 7.41 (d, J=9.0 Hz, 1H), 7.31 (s, 11H), 7.28 (s, 1H), 7.25 (d, J=7.9 Hz, 11H), 7.04 (s, 1H), 6.97 (d, J=7.6 Hz, 1H), 6.47 (d, J=2.6 Hz, 1H), 4.35 (d, J=6.2 Hz, 2H), 4.31 (s, 2H), 3.42 (q, J=7.1 Hz, 4H), 3.01 (t, J=6.9 Hz, 2H), 2.38 (s, 3H), 2.18 (s, 3H), 1.22 (t, J=7.1 Hz, 6H).

2-(7-(diethylamino)-4-methyl-2-oxo-2H-chromen-3-yl) ethyl 4-(pyridin-3-ylmethyl)piperidine-1-carboxylate (118). The title compound was prepared analogously to 78, using 3-(piperidin-4-ylmethyl)pyridine. ESI-MS [M+1]: 478.3. ¹H NMR (500 MHz, Chloroform-d) δ 8.47 (dd, J=4.8, 1.6 Hz, 1H), 8.41 (d, J=2.2 Hz, 1H), 7.49-7.37 (m, 2H), 7.23 (dd, J=7.8, 4.8 Hz, 1H), 6.60 (dd, J=9.1, 2.6 Hz, 1H), 6.50 (d, J=2.6 Hz, 1H), 4.23 (t, J=7.0 Hz, 2H), 3.42 (q, J=7.1 Hz, 5H), 2.99 (t, J=7.1 Hz, 3H), 2.68 (t, J=12.9 Hz, 3H), 2.54 (d, J=7.1 Hz, 2H), 2.38 (s, 3H), 1.68 (ddp, J=11.0, 7.3, 3.6 Hz, 1H), 1.64 (s, 1H), 1.21 (t, J=7.1 Hz, 6H).

4-((((2-(7-(diethylamino)-4-methyl-2-oxo-2H-chromen-3-yl)ethoxy)carbonyl)amino)methyl)benzoic acid (119). The title compound was prepared analogously to 78, using 4-(aminomethyl)benzoic acid. ESI-MS [M+1]: 453.2.

2-(7-(diethylamino)-4-methyl-2-oxo-2H-chromen-3-yl) ethyl (4-((aminooxy)carbonyl)benzyl)carbamate (120). The title compound was prepared analogously to 55, using 119 and ammonium chloride. ESI-MS [M+1]: 468.2.

2-(7-(diethylamino)-4-methyl-2-oxo-2H-chromen-3-yl) ethyl (4-(((methylamino)oxy)carbonyl)benzyl)carbamate (121). The title compound was prepared analogously to 55, using 119 and methylamine. ESI-MS [M+1]: 482.2.

2-(7-(diethylamino)-4-methyl-2-oxo-2H-chromen-3-yl) ethyl (4-(((dimethylamino)oxy)carbonyl)benzyl)carbamate (122). The title compound was prepared analogously to 55, using 119 and dimethylamine. ESI-MS [M+1]: 496.3.

3-((((2-(7-(diethylamino)-4-methyl-2-oxo-2H-chromen-3-yl)ethoxy)carbonyl)amino)methyl)benzoic acid (123). The title compound was prepared analogously to 78, using 3-(aminomethyl)benzoic acid. ESI-MS [M+1]: 453.2.

2-(7-(diethylamino)-4-methyl-2-oxo-2H-chromen-3-yl) ethyl (3-((aminooxy)carbonyl)benzyl)carbamate (124). The title compound was prepared analogously to 55, using 123 and ammonium chloride. ESI-MS [M+1]: 468.2.

2-(7-(diethylamino)-4-methyl-2-oxo-2H-chromen-3-yl) ethyl (3-(((methylamino)oxy)carbonyl)benzyl)carbamate (125). The title compound was prepared analogously to 55, using 123 and methylamine. ESI-MS [M+1]: 482.2.

2-(7-(diethylamino)-4-methyl-2-oxo-2H-chromen-3-yl) ethyl (3-(((dimethylamino)oxy)carbonyl)benzyl)carbamate (126). The title compound was prepared analogously to 55, using 123 and dimethylamine. ESI-MS [M+1]: 496.3.

2-(7-(diethylamino)-4-methyl-2-oxo-2H-chromen-3-yl) ethyl ((5-acetamidopyridin-2-yl)methyl)carbamate (127). The title compound was prepared analogously to 78, using N-(6-(aminomethyl)pyridin-3-yl)acetamide. ESI-MS [M+1]: 467.2.

2-(7-(diethylamino)-4-methyl-2-oxo-2H-chromen-3-yl) ethyl ((5-acetamidopyridin-3-yl)methyl)carbamate (128). The title compound was prepared analogously to 78, using N-(5-(aminomethyl)pyridin-3-yl)acetamide, to afford 24 as a light yellow solid (10.3 mg, 65%). ESI-MS [M+1]: 467.2.

Scheme 6.

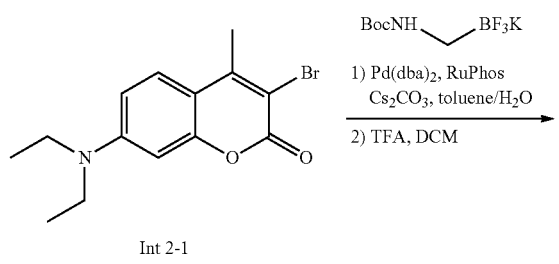

Int 2-1

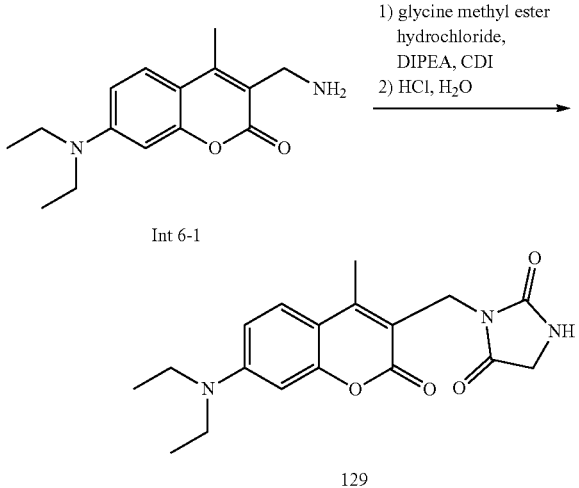

3-(aminomethyl)-7-(diethylamino)-4-methyl-2H-chromen-2-one (Int 6-1). The title intermediate was prepared analogously to Int 4-1, using N-(5-(aminomethyl)pyridin-3-yl)acetamide, to afford Int 6-1 as a yellow solid (683 mg, 15% over 2 steps). ESI-MS [M+1]: 261. 1H NMR (400 MHz, DMSO-d6) δ=8.29 (br s, 3H), 7.66 (d, J=9.2 Hz, 1H), 6.88-6.72 (m, 1H), 6.68-6.53 (m, 1H), 3.91 (q, J=5.6 Hz, 2H), 3.44 (q, J=7.2 Hz, 4H), 2.47 (s, 3H), 1.11 (t, J=7.2 Hz, 6H).

3-((7-(diethylamino)-4-methyl-2-oxo-2H-chromen-3-yl)methyl)imidazolidine-2,4-dione (129). The title compound was prepared in 2 steps from Int 6-1. First, urea formation with glycine methyl ester hydrochloride was performed analogously to preparation of compound 98, and the urea intermediate was purified by flash column chromatography (SiO₂, EtOAc/hexanes). Second, the urea intermediate (25 mg) was refluxed in 5M aqueous HCl for 1 hr. The solution was neutralized with solid Na₂CO₃ and extracted with EtOAc (3×20 mL). The combined organics were washed once with brine, dried over MgSO₄, filtered, and concentrated under reduced pressure. The residue was purified by flash column chromatography (SiO₂, 100% EtOAc) to afford the title compound as a yellow solid. ESI-MS [M+1]: 344.1.

3-(2-(7-(diethylamino)-4-methyl-2-oxo-2H-chromen-3-yl)ethyl)imidazolidine-2,4-dione (130). The title compound was prepared analogously to 129, in two steps starting from Int 4-1. ESI-MS [M+1]: 358.1.

1-(2-(7-(diethylamino)-4-methyl-2-oxo-2H-chromen-3-yl)ethyl)-3-methylurea (131). The title compound was prepared analogously to 98, using methylamine. ESI-MS [M+1]: 332.1.

2-(7-(diethylamino)-4-methyl-2-oxo-2H-chromen-3-yl)ethyl (2-(pyridin-2-ylamino)ethyl)carbamate (132). The title compound was prepared analogously to 78, using $N^1$-(pyridin-2-yl)ethane-1,2-diamine. ESI-MS [M+1]: 439.2.

2-(7-(diethylamino)-4-methyl-2-oxo-2H-chromen-3-yl)ethyl (3-(dimethylamino)propyl)carbamate (133). The title compound was prepared analogously to 78, using $N^1,N^1$-dimethylpropane-1,3-diamine. ESI-MS [M+1]: 404.2.

N,N-diethyl-4-methylquinolin-7-amine (134). A stirred solution of compound 25 (30 mg) in POCl₃ (2 mL) was heated at 100° C. for 1 hr. Afterwards, the solution was poured on ice and basified with solid Na₂CO₃. The suspension was extracted with EtOAc (3×20 mL). The combined organics were washed once with brine, dried over MgSO₄, filtered, and concentrated under reduced pressure. The residue was dissolved in acetic acid (5 mL) and thereto was added 10% palladium on carbon (10 mg). The suspension was hydrogenated using a hydrogen balloon (1 atm) at room temperature for 1 hour, then filtered through Celite and concentrated under reduced pressure. The residue was purified by flash column chromatography (SiO₂, EtOAc/hexanes) to afford the title compound as a viscous, bright yellow oil. ESI-MS [M+1]: 215.0.

2-(7-(diethylamino)-4-methyl-2-oxo-2H-chromen-3-yl)ethyl (3-((dimethylamino)methyl)benzyl)carbamate (135). The title compound was prepared analogously to 78, using 1-(3-(aminomethyl)phenyl)-N,N-dimethylmethanamine. ESI-MS [M+1]: 466.2.

7-(diethylamino)-4-ethyl-2H-chromen-2-one (136). The title compound was prepared analogously to Int 3-1-1, using methyl 3-oxopentanoate. ESI-MS [M+1]: 246.0.

2-(7-(diethylamino)-4-methyl-2-oxo-2H-chromen-3-yl)ethyl ((1H-indol-5-yl)methyl)carbamate (137). The title compound was prepared analogously to 78, using (1H-indol-5-yl)methanamine. ESI-MS [M+1]: 448.2.

2-(7-(diethylamino)-4-methyl-2-oxo-2H-chromen-3-yl)ethyl ((6-oxo-1,6-dihydropyridin-3-yl)methyl)carbamate (138). The title compound was prepared analogously to 78, using 5-(aminomethyl)pyridin-2(1H)-one. ESI-MS [M+1]: 426.2.

2-(7-(diethylamino)-4-methyl-2-oxo-2H-chromen-3-yl)ethyl (isoquinolin-1-ylmethyl)carbamate (139). The title compound was prepared analogously to 78, using isoquinolin-1-ylmethanamine. ESI-MS [M+1]: 460.3.

2-(7-(diethylamino)-4-methyl-2-oxo-2H-chromen-3-yl)ethyl (isoquinolin-4-ylmethyl)carbamate (140). The title compound was prepared analogously to 78, using isoquinolin-4-ylmethanamine. ESI-MS [M+1]: 460.3.

2-(7-(diethylamino)-4-methyl-2-oxo-2H-chromen-3-yl)ethyl (3-(1H-imidazol-4-yl)benzyl)carbamate (141). The title compound was prepared analogously to 78, using (3-(1H-imidazol-4-yl)phenyl)methanamine, to afford 141 as a yellow solid (13.1 mg, 61%). ESI-MS [M+1]: 475.3.

2-(7-(diethylamino)-4-methyl-2-oxo-2H-chromen-3-yl)ethyl ((1H-benzo[d]imidazol-6-yl)methyl)carbamate (142). The title compound was prepared analogously to 78, using (1H-benzo[d]imidazol-6-yl)methanamine. ESI-MS [M+1]: 449.2.

2-(7-(diethylamino)-4-methyl-2-oxo-2H-chromen-3-yl)ethyl ((1-oxo-1,2-dihydroisoquinolin-7-yl)methyl)carbamate (143). The title compound was prepared analogously to 78, using 7-(aminomethyl)isoquinolin-1(2H)-one. ESI-MS [M+1]: 476.3.

2-(7-(diethylamino)-4-methyl-2-oxo-2H-chromen-3-yl)ethyl (3-carbamoyl-4-fluorobenzyl)carbamate (144). The title compound was prepared analogously to 78, using 5-(aminomethyl)-2-fluorobenzamide. ESI-MS [M+1]: 470.2.

2-(7-(diethylamino)-4-methyl-2-oxo-2H-chromen-3-yl)ethyl (3-carbamoyl-5-fluorobenzyl)carbamate (145). The title compound was prepared analogously to 78, using 5-(aminomethyl)-3-fluorobenzamide. ESI-MS [M+1]: 470.2.

2-(7-(diethylamino)-4-methyl-2-oxo-2H-chromen-3-yl)ethyl (piperidin-3-ylmethyl)carbamate (146). The title compound was prepared in two steps. First, the Boc-protected amine was prepared analogously to 78, using tert-butyl 3-(aminomethyl)piperidine-1-carboxylate, and purified by flash column chromatography (SiO₂, EtOAc/hexanes). Second, to a stirred solution of the Boc-protected amine in DCM (2 mL) was added neat TFA (1 mL) and the mixture stirred at room temperature for 16 hrs. The mixture was concentrated under reduced pressure and purified by reverse-phase preparative HPLC to afford 146 as a yellow gum (10.2 mg, 71% over 2 steps). ESI-MS [M+1]: 416.2.

2-(7-(diethylamino)-4-methyl-2-oxo-2H-chromen-3-yl) ethyl (piperidin-4-ylmethyl)carbamate (147). The title compound was prepared analogously to 146, using tert-butyl 4-(aminomethyl)piperidine-1-carboxylate. ESI-MS [M+1]: 416.2.

2-(7-(diethylamino)-4-methyl-2-oxo-2H-chromen-3-yl) ethyl ((1-methylpiperidin-4-yl)methyl)carbamate (148). The title compound was prepared analogously to 78, using (1-methylpiperidin-4-yl)methanamine. ESI-MS [M+1]: 430.3.

2-(7-(diethylamino)-4-methyl-2-oxo-2H-chromen-3-yl) ethyl (3-sulfamoylbenzyl)carbamate (149). The title compound was prepared analogously to 78, using 3-(aminomethyl)benzenesulfonamide. ESI-MS [M+1]: 488.3.

N-(4-(diethylamino)phenyl)-2-(2,5-dioxoimidazolidin-1-yl)acetamide (150). To a stirred solution of 2-(2,5-dioxoimidazolidin-1-yl)acetic acid (20 mg, 1 eq) and DIPEA (50 μL) in DMF (1 mL) was added HATU (53 mg, 1.1 eq) and stirred for 5 min at room temperature. Thereto was added $N^1,N^1$-diethylbenzene-1,4-diamine (32 μL, 1.5 eq) and stirred for 16 hrs at room temperature. The mixture was concentrated under reduced pressure and purified by reverse-phase preparative HPLC. The desired fractions were lyophilized, dissolved in 20 mM aqueous HCl, and lyophilized to afford the tide compound as a hygroscopic white solid ESI-MS [M+1]: 305.2.

2-(2,5-dioxoimidazolidin-1-yl)-N-(4-(trifluoromethyl) phenyl)acetamide (151). The title compound was prepared analogously to 150, using 4-(trifluoromethyl)aniline hydrochloride. ESI-MS [M−1]: 300.2.

Scheme 7.

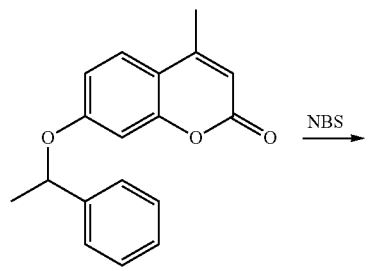

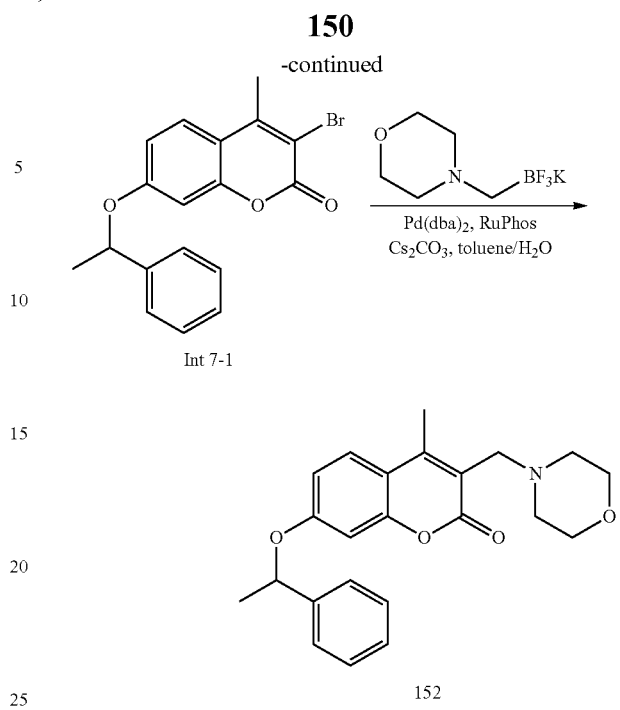

3-bromo-4-methyl-7-(1-phenylethoxy)-2H-chromen-2-one (Int 7-1). To a stirred solution of 4-methyl-7-(1-phenylethoxy)-2H-chromen-2-one (50 mg, 1 eq) in MeCN (2 mL) was added NBS (35.6 mg, 0.2 mmol, 1.1 eq) and the reaction stirred at room temperature for 16 hours. The colorless solution was concentrated under reduced pressure and purified by flash column chromatography (SiO$_2$, 0 to 20% EtOAc in hexanes) to afford Int 7-1 as a white solid (58.2 mg, 90%).

4-methyl-3-(morpholinomethyl)-7-(1-phenylethoxy)-2H-chromen-2-one (152). A mixture of Int 7-1 (20 mg, 0.056 mmol, 1 eq), potassium (morpholin-4-yl)methyltrifluoroborate (18 mg, 0.084 mol, 1.5 eq), RuPhos (5 mg, 0.011 mmol, 0.2 eq) and Cs$_2$CO$_3$ (55 mg, 0.17 mmol, 3 eq) in toluene (0.375 mL) and H$_2$O (0.125 mL) in a microwave vial was sparged with argon for 2 minutes while stirring. To the mixture was added Pd(dba)$_2$ (3.2 mg, 0.056 mmol, 0.1 eq) and further sparged for an additional minute. The vial was sealed and heated at 90° C. for 16 hr. The initially red biphasic mixture turned dark yellow-orange, and a black precipitate appeared. The reaction was then diluted with water (15 mL) and extracted with EtOAc (3×10 mL). The combined organics were washed once with brine, dried over Na$_2$SO$_4$, filtered, and concentrated under reduced pressure. The residue was purified by reverse-phase preparative HPLC to afford 152 as a viscous, colorless oil (3.5 mg, 17%). ESI-MS [M+1]: 380.2.

Scheme 8.

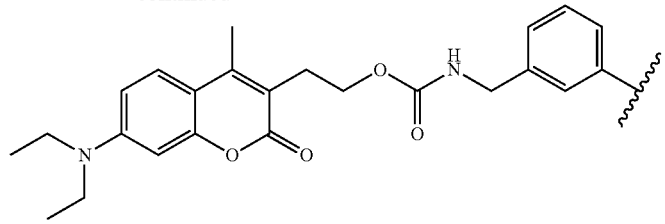

2-(7-(diethylamino)-4-methyl-2-oxo-2H-chromen-3-yl) ethyl (3-(4,4,5-trimethyl-1,3,2-dioxaborolan-2-yl)benzyl) carbamate (Int 8-1). The title intermediate was prepared analogously to 78, using (3-(4,4,5-trimethyl-1,3,2-dioxaborolan-2-yl)phenyl)methanamine, to afford Int 8-1 as a yellow solid (204.4 mg, 86%). LC-MS [ESI, M+1]: 535.2

2-(7-(diethylamino)-4-methyl-2-oxo-2H-chromen-3-yl) ethyl (3-(1H-imidazol-2-yl)benzyl)carbamate (153). A mixture of Int 8-1 (15 mg, 1 eq), tert-butyl 2-iodo-1H-imidazole-1-carboxylate (12 mg, 1.5 eq), and K₂CO₃ (15.5 mg, 4 eq) in 1,4-dioxane (0.9 mL) and H₂O (0.3 mL) in a microwave vial was sparged with argon for 2 minutes while stirring. To the mixture was added Pd(PPh₃)₄ (5 mg, 0.15 eq) and further sparged for an additional minute. The vial was sealed and heated at 90° C. for 8 hr. The reaction was then diluted with water (20 mL) and extracted with EtOAc (3×20 mL). The combined organics were washed once with brine, dried over Na₂SO₄, filtered, and concentrated under reduced pressure. The residue was purified by flash column chromatography (SiO₂, 10 to 100% EtOAc/hexanes) to afford 153 as a yellow solid. LC-MS [ESI, M+1]: 475.3.

2-(7-(diethylamino)-4-methyl-2-oxo-2H-chromen-3-yl) ethyl (3-(pyridin-2-yl)benzyl)carbamate (154). The title compound was prepared analogously to 153, using 2-chloropyridine. LC-MS [ESI, M+1]: 486.3.

2-(7-(diethylamino)-4-methyl-2-oxo-2H-chromen-3-yl) ethyl (3-(pyrimidin-2-yl)benzyl)carbamate (155). The title compound was prepared analogously to 153, using 2-chloropyrimidine. LC-MS [ESI, M+1]: 487.3.

2-(7-(diethylamino)-4-methyl-2-oxo-2H-chromen-3-yl) ethyl (3-(pyrimidin-5-yl)benzyl)carbamate (156). The title compound was prepared analogously to 153, using 5-bromopyrimidine. LC-MS [ESI, M+1]: 487.3.

2-(7-(diethylamino)-4-methyl-2-oxo-2H-chromen-3-yl) ethyl (3-(pyrazin-2-yl)benzyl)carbamate (157). The title compound was prepared analogously to 153, using chloropyrazine. LC-MS [ESI, M+1]: 487.3.

Scheme 9.

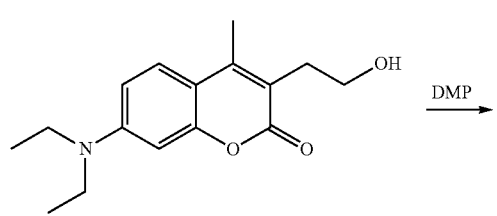

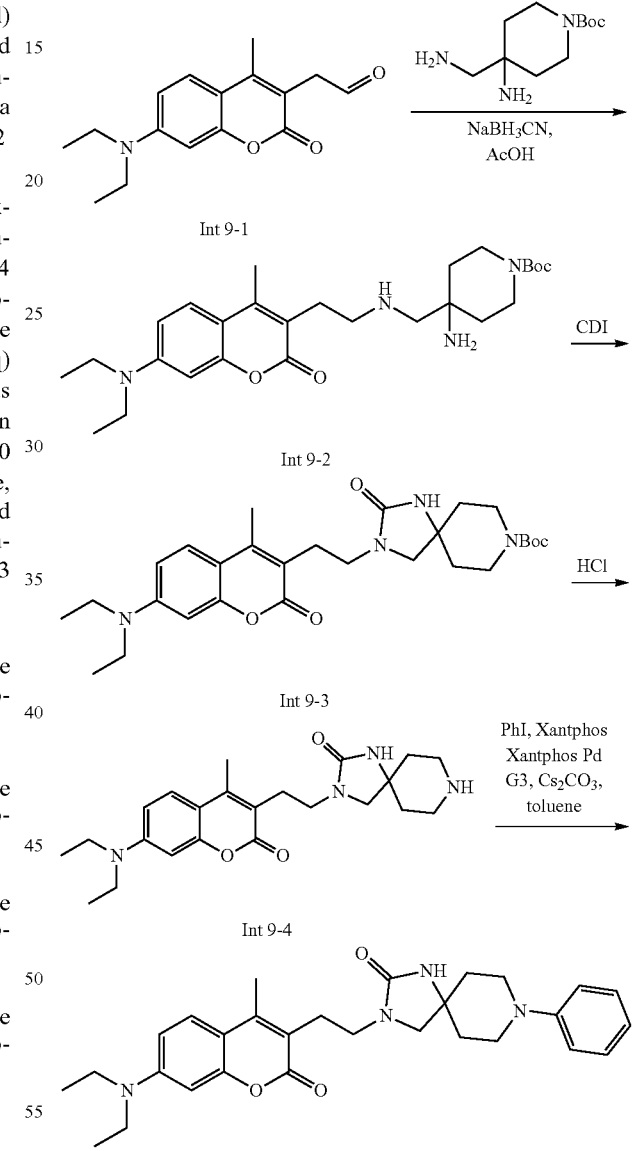

2-(7-(diethylamino)-4-methyl-2-oxo-2H-chromen-3-yl)acetaldehyde (Int 9-1)

To a mixture of 53 (200 mg, 726 μmol, 1 eq.) in DCM (5 mL) was added DMP (462 mg, 1.09 mmol, 1.5 eq.) at 0° C. The mixture was stirred at 20° C. for 12 hours. The reaction mixture was filtered and the filtrate was concentrated under reduced pressure. The residue was purified by reversed phase flash chromatography. The desired fractions were collected and neutralized with saturated NaHCO$_3$ solution, concentrated under vacuum to remove MeCN and extracted with EtOAc (2×50 mL). The organic layers were dried over Na$_2$SO$_4$ and concentrated under vacuum to give Int 9-1 (160 mg, 574 µmol, 79% yield, 98% purity) as a viscous, bright yellow-orange oil, which was used immediately in the next step. LC-MS [ESI, M+1]: 274.2.

Tert-butyl 4-amino-4-(((2-(7-(diethylamino)-4-methyl-2-oxo-2H-chromen-3-yl)ethyl)amino)methyl)piperidine-1-carboxylate (Int 9-2). To a solution of Int 9-1 (380 mg, 1.39 mmol, 1 eq.) in MeOH (5 mL) was added tert-butyl 4-amino-4-(aminomethyl)piperidine-1-carboxylate (351 mg, 1.53 mmol, 1.1 eq.) and AcOH (83.5 mg, 1.39 mmol, 79.5 uL, 1 eq.). The mixture was stirred at 20° C. for 1 hr. Then NaBH$_3$CN (262 mg, 4.17 mmol, 3 eq) was added at 0° C., and the mixture was stirred at 20° C. for 12 hrs. After completion, the reaction mixture was quenched with water (1 mL) at 0° C., and then concentrated under reduced pressure. The residue was purified by reverse-phase preparative HPLC. The desired fractions were collected and neutralized with saturated NaHCO$_3$ solution, concentrated under vacuum to remove MeCN and extracted with EtOAc (6×30 mL). The organic layers were dried over Na$_2$SO$_4$ and concentrated under vacuum to give compound Int 9-2 (275 mg, 554 µmol, 40% yield, 98% purity) as a viscous yellow oil. LC-MS [ESI, M+1]: 487.5.

Tert-butyl 3-(2-(7-(diethylamino)-4-methyl-2-oxo-2H-chromen-3-yl)ethyl)-2-oxo-1,3,8-triazaspiro[4.5]decane-8-carboxylate (Int 9-3). To a mixture of Int 9-2 (260 mg, 534 µmol, 1 eq.) in DCM (10 mL) was added CDI (260 mg, 1.60 mmol, 3 eq.) at 0° C. under N$_2$. The mixture was stirred at 20° C. for 12 hrs. The reaction mixture was quenched with water (1 mL) and then dried over Na$_2$SO$_4$, filtered and concentrated under reduced pressure. The residue was purified by reverse-phase preparative HPLC. The desired fractions were collected and neutralized with saturated NaHCO$_3$ solution, concentrated under vacuum to remove MeCN and extracted with EtOAc (3×30 mL). The organic layers were dried over Na$_2$SO$_4$ and concentrated under vacuum to give Int 9-3 (186 mg, 359 µmol, 67% yield, 99% purity) as a viscous yellow oil which solidified under vacuum. LC-MS [ESI, M+1]: 513.4. $^1$H NMR (400 MHz, CDCl$_3$-d) δ=7.40 (d, J=9.2 Hz, 1H), 6.60 (dd, J=2.4 Hz, 8.8 HZ, 1H), 6.50 (d, J=2.4 Hz, 1H), 4.66 (s, 1H), 3.47-3.35 (m, 12H), 2.92-2.80 (m, 2H), 2.42 (s, 3H), 1.67-1.61 (m, 4H), 1.48 (s, 9H), 1.21 (t, J=7.2 Hz, 6H).

3-(2-(7-(diethylamino)-4-methyl-2-oxo-2H-chromen-3-yl)ethyl)-1,3,8-triazaspiro[4.5]decan-2-one (Int 9-4). To a mixture of Int 9-3 (160 mg, 312 µmol, 1 eq.) in MeCN (1 mL) was added HCl/dioxane (4 M, 5 mL, 64.1 eq.). The mixture was stirred at 15° C. for 30 min. The reaction mixture was concentrated under reduced pressure. Then the residue was dissolved in DCM (15 mL) and adjusted pH to 8 with saturated NaHCO$_3$ solution. The separated water layer was extracted with DCM (10 mL×3). The combined organic layers were washed with brine (5 mL×1), dried over sodium sulfate, filtered and concentrated under reduced pressure to give Int 9-4 (90 mg, 216 µmol, 69% yield, 99% purity) as a yellow solid. LC-MS [ESI, M+1]: 413.3.

3-(2-(7-(diethylamino)-4-methyl-2-oxo-2H-chromen-3-yl)ethyl)-8-phenyl-1,3,8-triazaspiro[4.5]decan-2-one (158). To a mixture of Int 9-4 (70.0 mg, 170 µmol, 1 eq.) and iodobenzene (138 mg, 678 µmol, 75.7 µL, 4 eq.) in toluene (6 mL) was added Xantphos (19.6 mg, 33.9 µmol, 0.2 eq.), Xantphos Pd G3 (16.1 mg, 17.0 µmol, 0.1 eq) and Cs$_2$CO$_3$ (166 mg, 509 µmol, 3 eq.) in one portion in the atmosphere of N$_2$. The mixture was stirred at 110° C. for 12 hours. To the reaction mixture was added water (10 mL) and then extracted with ethyl acetate (20 mL×3). The combined organic layers were washed with brine (10 mL×1), dried over sodium sulfate, filtered and concentrated under reduced pressure. The residue was purified by column chromatography (SiO$_2$, DCM/MeOH=100/1 to 5/1) and triturated with MeOH to give the title compound (46.6 mg, 88.5 µmol, 52% yield, 92.8% purity) as an off-white solid. LCMS [ESI, M+1]: 489.4. $^1$H NMR (400 MHz, CDCl$_3$-d) δ=7.42 (d, J=8.8 Hz, 1H), 7.29 (s, 1H), 7.25 (s, 1H), 6.93 (d, J=7.6 Hz, 2H), 6.87 (t, J=7.2 Hz, 1H), 6.60 (dd, J=2.4, 8.8 Hz, 1H), 6.50 (d, J=2.4 Hz, 1H), 4.54 (s, 1H), 3.41-3.31 (m, 8H), 3.25-3.12 (m, 4H), 2.88 (t, J=7.6 Hz, 2H), 2.43 (s, 3H), 1.86-1.82 (m, 4H), 1.21 (t, J=7.2 Hz, 6H).

2-(7-(diethylamino)-4-methyl-2-oxo-2H-chromen-3-yl)ethyl (3-(1H-pyrazol-5-yl)benzyl)carbamate (159). The title compound was prepared analogously to 153, using tert-butyl 5-bromo-1H-pyrazole-1-carboxylate. LC-MS [ESI, M+1]: 475.3.

2-(7-(diethylamino)-4-methyl-2-oxo-2H-chromen-3-yl) ethyl (3-(5-methyl-1H-imidazol-4-yl)benzyl)carbamate (160). The title compound was prepared analogously to 153, using tert-butyl 4-bromo-5-methyl-1H-imidazole-1-carboxylate. LC-MS [ESI, M+1]: 489.3.

2-(7-(diethylamino)-4-methyl-2-oxo-2H-chromen-3-yl) ethyl (3-(pyridin-3-yl)benzyl)carbamate (161). The title compound was prepared analogously to 153, using 3-bromopyridine. LC-MS [ESI, M+1]: 486.3.

2-(7-(diethylamino)-4-methyl-2-oxo-2H-chromen-3-yl) ethyl (3-(pyridin-4-yl)benzyl)carbamate (162). The title compound was prepared analogously to 153, using 4-bromopyridine hydrochloride. LC-MS [ESI, M+1]: 486.3.

2-(7-(diethylamino)-4-methyl-2-oxo-2H-chromen-3-yl) ethyl (3-(2-oxo-1,2-dihydropyridin-3-yl)benzyl)carbamate (163). The title compound was prepared analogously to 153, using 3-bromopyridin-2(1H)-one, to afford 163 as a white solid (4.4 mg, 40%). LC-MS [ESI, M+1]: 502.3.

2-(7-(diethylamino)-4-methyl-2-oxo-2H-chromen-3-yl) ethyl (3-(1H-pyrazol-4-yl)benzyl)carbamate (164). The title compound was prepared analogously to 153, using tert-butyl 4-bromo-1H-pyrazole-1-carboxylate. LC-MS [ESI, M+1]: 475.3.

2-(7-(diethylamino)-4-methyl-2-oxo-2H-chromen-3-yl) ethyl (3-(1H-1,2,4-triazol-5-yl)benzyl)carbamate (165). The title compound was prepared analogously to 153, using tert-butyl 5-bromo-1H-1,2,4-triazole-1-carboxylate. LC-MS [ESI, M+1]: 476.3.

2-(7-(diethylamino)-4-methyl-2-oxo-2H-chromen-3-yl) ethyl (3-(pyridazin-3-yl)benzyl)carbamate (166). The title compound was prepared analogously to 153, using 3-chloropyridazine. LC-MS [ESI, M+1]: 487.3.

2-(7-(diethylamino)-4-methyl-2-oxo-2H-chromen-3-yl) ethyl (3-(oxazol-2-yl)benzyl)carbamate (167). The title compound was prepared analogously to 153, using 2-chlorooxazole. LC-MS [ESI, M+1]: 476.3.

4-methyl-7-(pentan-3-yl)-2H-chromen-2-one (168). A mixture of 7-iodo-4-methyl-2H-chromen-2-one (40 mg, 1 eq), 1,2-bis(diphenylphosphaneyl)benzene (6.3 mg, 0.1 eq), 4,4'-di-tert-butyl-2,2'-bipyridine (3.8 mg, 0.1 eq), and NiI$_2$ (9.4 mg, 0.214 eq) in DMPU (1 mL) was sparged with argon for 3 min while stirring. Under a flow of argon, pyridine (2.3 µL, 0.2 eq), 3-bromopentane (25.4 mg, 1.2 eq), and manganese metal (15.4 mg, 2 eq) were sequentially added. The vial was sealed and the dark red/gray suspension was heated at 80° C. for 16 hours, turning dark orange/brown and finally dark yellow/brown. The suspension was filtered through Celite and diluted with EtOAc (20 mL). The organic layer was washed with H$_2$O (2×20 mL), once with brine, dried over MgSO$_4$, and concentrated. The residue was purified by reverse-phase preparative HPLC to afford the title compound as a viscous, colorless oil. $^1$H NMR (400 MHz, Chloroform-d) δ 7.54 (d, J=8.0 Hz, 1H), 7.17-7.08 (m, 2H), 6.26 (q, J=1.3 Hz, 1H), 2.51-2.39 (m, 4H), 1.83-1.68 (m, 2H), 1.67-1.51 (m, 2H), 0.80 (t, J=7.4 Hz, 6H).

4-methyl-7-(trifluoromethyl)-2H-chromen-2-one (169). A mixture of 7-iodo-4-methyl-2H-chromen-2-one (30 mg, 1 eq), CuI (4 mg, 0.2 eq), 1,10-phenanthroline (3.8 mg, 0.2 eq), and KF (18.3 mg, 3 eq) was placed under argon in a sealed microwave vial. Afterwards, DMSO (0.5 mL), B(OMe)$_3$ (55 mg, 5 eq), and TMSCF$_3$ (75 mg, 5 eq) were added sequentially. The dark orange solution was stirred at 60° C. for 16 hours and turned dark green. The reaction was then diluted with water (20 mL) and extracted with EtOAc (3×20 mL). The combined organics were washed once with brine, dried over MgSO$_4$, filtered, and concentrated under reduced pressure. The residue was purified by flash column chromatography (SiO$_2$, 0 to 15% EtOAc/hexanes) to afford the title compound as a yellow solid. $^1$H NMR (400 MHz, Chloroform-d) δ 7.75 (d, J=8.3 Hz, 1H), 7.64-7.54 (m, 2H), 6.43 (q, J=1.4 Hz, 1H), 2.51 (d, J=1.3 Hz, 3H). $^{19}$F NMR (376 MHz, Chloroform-d) δ −63.15 ppm.

2-(7-(diethylamino)-4-methyl-2-oxo-2H-chromen-3-yl) ethyl (3-(N-hydroxycarbamimidoyl)benzyl)carbamate (170). The title compound was prepared in two steps. In the first step, Int 5-1 was reacted with 3-(aminomethyl)benzonitrile analogously to the preparation of 78. The intermediate compound was suspended in EtOH (4 mL) and to the stirred suspension was added H$_2$NOH (150 μL, 50% aqueous solution) and stirred for 16 hrs at room temperature. The reaction was then diluted with water (20 mL) and extracted with EtOAc (3×20 mL). The combined organics were washed once with brine, dried over MgSO$_4$, filtered, and concentrated under reduced pressure. The residue was purified by flash column chromatography (SiO$_2$, 0 to 100% EtOAc in hexanes) to afford the title compound as a yellow solid. LC-MS [ESI, M+1]: 467.2.

4-methyl-7-(1-(pyridin-3-yl)ethoxy)-2H-chromen-2-one (171). The title compound was prepared analogously to 32, using 3-(1-bromoethyl)pyridine. LC-MS [ESI, M+1]: 282.0.

4-methyl-7-(1-(pyridin-4-yl)ethoxy)-2H-chromen-2-one (172). The title compound was prepared analogously to 32, using 4-(1-bromoethyl)pyridine. LC-MS [ESI, M+1]: 282.0.

4-methyl-7-(1-(pyrazin-2-yl)ethoxy)-2H-chromen-2-one (173). The title compound was prepared analogously to 32, using 2-(1-bromoethyl)pyrazine. LC-MS [ESI, M+1]: 283.0.

4-methyl-7-(1-(pyridin-2-yl)ethoxy)-2H-chromen-2-one (174). The title compound was prepared analogously to 32, using 2-(1-bromoethyl)pyridine. LC-MS [ESI, M+1]: 282.0.

3-(2-(7-(diethylamino)-4-methyl-2-oxo-2H-chromen-3-yl)ethyl)-1,3,7-triazaspiro[4.4]nonane-2,4-dione (175). A suspension of 53 (200 mg, 0.73 mmol, 1 eq), tert-butyl 2,4-dioxo-1,3,8-triazaspiro[4.5]decane-8-carboxylate (215 mg, 0.80 mmol, 1.1 eq), and PPh$_3$ (382 mg, 1.46 mmol, 2 eq) in anhydrous THF (5 mL) was placed under argon and cooled on an ice bath. To the stirred suspension was added diisopropyl azodicarboxylate (288 μL, 1.46 mmol, 2 eq) dropwise over 2 minutes. The orange suspension was stirred on ice for 10 minutes, followed by at room temperature for an additional 4 hr, during which the hydantoin starting material gradually dissolved. The mixture was concentrated under reduced pressure and purified by flash column chromatography (SiO$_2$, 0 to 50% EtOAc/hexanes) to afford a mixture of the Boc-protected spiro-hydantoin coumarin and Ph$_3$PO as a viscous yellow oil. To a stirred solution of this residue in MeOH (3 mL) was then added concentrated HCl (1 mL) dropwise and stirred overnight at room temperature, during which a white precipitate appeared. The reaction was diluted with water (30 mL) and washed once with EtOAc (15 mL) to remove Ph$_3$PO. Afterwards, the aqueous layer was basified with addition of solid Na$_2$CO$_3$ to give a bright yellow solution, which was extracted with DCM (6×20 mL). The combined organics were washed once with brine, dried over Na$_2$SO$_4$, filtered, and concentrated to afford the title compound as a white solid (257.5 mg, 71% over 2 steps). A sample was further purified by reverse-phase preparative HPLC. LC-MS [ESI, M+1]: 427.4.

3-(2-(7-(diethylamino)-4-methyl-2-oxo-2H-chromen-3-yl)ethyl)-8-(1H-imidazole-4-carbonyl)-1,3,8-triazaspiro [4.5]decane-2,4-dione (176). The title compound was prepared analogously to 150, using 175 and 1H-imidazole-4-carboxylic acid as starting materials, to afford 176 as a yellow solid (6.6 mg, 37%, 2HCl salt). LC-MS [ESI, M+1]: 521.3.

3-(2-(7-(diethylamino)-4-methyl-2-oxo-2H-chromen-3-yl)ethyl)-8-(1H-imidazole-2-carbonyl)-1,3,8-triazaspiro [4.5]decane-2,4-dione (177). The title compound was prepared analogously to 150, using 175 and 1H-imidazole-2-carboxylic acid as starting materials. LC-MS [ESI, M+1]: 521.3.

3-(2-(7-(diethylamino)-4-methyl-2-oxo-2H-chromen-3-yl)ethyl)-8-(2-oxo-1,2-dihydropyridine-3-carbonyl)-1,3,8-triazaspiro[4.5]decane-2,4-dione (178). The title compound was prepared analogously to 150, using 175 and 2-oxo-1,2-dihydropyridine-3-carboxylic acid as starting materials, to afford 176 as a yellow solid (8.1 mg, 46%, HCl salt). LC-MS [ESI, M+1]: 548.3.

3-(2-(7-(diethylamino)-4-methyl-2-oxo-2H-chromen-3-yl)ethyl)-1,3,7-triazaspiro[4.4]nonane-2,4-dione (179). The title compound was prepared analogously to 175, using tert-butyl 2,4-dioxo-1,3,7-triazaspiro[4.4]nonane-7-carboxylate, to afford 179 as a yellow solid (274.3 mg, 91% over 2 steps). LC-MS [ESI, M+1]: 413.2.

3-(2-(7-(diethylamino)-4-methyl-2-oxo-2H-chromen-3-yl)ethyl)-7-(1H-imidazole-4-carbonyl)-1,3,7-triazaspiro [4.4]nonane-2,4-dione (180). The title compound was prepared analogously to 150, using 179 and 1H-imidazole-4-carboxylic acid as starting materials, to afford 180 as a yellow solid (8.6 mg, 50%, 2HCl salt). LC-MS [ESI, M+1]: 507.3.

3-(2-(7-(diethylamino)-4-methyl-2-oxo-2H-chromen-3-yl)ethyl)-7-(1H-imidazole-2-carbonyl)-1,3,7-triazaspiro [4.4]nonane-2,4-dione (181). The title compound was prepared analogously to 150, using 179 and 1H-imidazole-2-carboxylic acid as starting materials. LC-MS [ESI, M+1]: 507.3.

3-(2-(7-(diethylamino)-4-methyl-2-oxo-2H-chromen-3-yl)ethyl)-7-(2-oxo-1,2-dihydropyridine-3-carbonyl)-1,3,7-triazaspiro[4.4]nonane-2,4-dione (182). The title compound was prepared analogously to 150, using 179 and 2-oxo-1,2-dihydropyridine-3-carboxylic acid as starting materials, to afford 182 as a yellow solid (10.6 mg, 62%, HCl salt). LC-MS [ESI, M+1]: 534.3.

4-methyl-3-(morpholinomethyl)-7-(2-phenylpropoxy)-2H-chromen-2-one (183). The title compound was prepared in two steps, analogously to 152, using 43 as starting material. LC-MS [ESI, M+1]: 394.2.

4-methyl-3-(morpholinomethyl)-7-((1-phenylpropan-2-yl)oxy)-2H-chromen-2-one (184). The title compound was prepared in two steps, analogously to 152, using 47 as starting material. LC-MS [ESI, M+1]: 394.2.

3-(2-(7-(diethylamino)-4-methyl-2-oxo-2H-chromen-3-yl)ethyl)-8-(pyrimidin-2-yl)-1,3,8-triazaspiro[4.5]decane-2,4-dione (185). A stirred solution of 175 (10 mg, 1 eq), 2-chloropyrimidine (5.3 mg, 2 eq), DIPEA (12 µL, 3 eq) in DMF (1 mL) was heated at 80° C. for 16 hrs. The mixture was concentrated under reduced pressure and purified by flash column chromatography to afford the title compound as a yellow solid (8.7 mg, 75%). In other examples, purification was achieved through reverse-phase preparative HPLC. LC-MS [ESI, M+1]: 505.3.

3-(2-(7-(diethylamino)-4-methyl-2-oxo-2H-chromen-3-yl)ethyl)-8-(5-(trifluoromethyl)pyrimidin-2-yl)-1,3,8-triazaspiro[4.5]decane-2,4-dione (186). The title compound was prepared analogously to 185, using 2-chloro-5-(trifluoromethyl)pyrimidine. LC-MS [ESI, M+1]: 573.3.

3-(2-(7-(diethylamino)-4-methyl-2-oxo-2H-chromen-3-yl)ethyl)-8-(5-(trifluoromethyl)pyridin-2-yl)-1,3,8-triazaspiro[4.5]decane-2,4-dione (187). The title compound was prepared analogously to 185, using 2-chloro-5-(trifluoromethyl)pyridine. LC-MS [ESI, M+1]: 572.3.

3-(2-(7-(diethylamino)-4-methyl-2-oxo-2H-chromen-3-yl)ethyl)-8-(9H-purin-6-yl)-1,3,8-triazaspiro[4.5]decane-2,4-dione (188). The title compound was prepared analogously to 185, using 6-chloropurine, to afford 188 as a yellow solid (9.2 mg, 69%, HCl salt). LC-MS [ESI, M+1]: 545.3.

2-(3-(2-(7-(diethylamino)-4-methyl-2-oxo-2H-chromen-3-yl)ethyl)-2,4-dioxo-1,3,8-triazaspiro[4.5]decan-8-yl)pyrimidine-5-carbonitrile (189). The title compound was prepared analogously to 185, using 2-chloropyrimidine-5-carbonitrile. LC-MS [ESI, M+1]: 530.3.

2-(3-(2-(7-(diethylamino)-4-methyl-2-oxo-2H-chromen-3-yl)ethyl)-2,4-dioxo-1,3,8-triazaspiro[4.5]decan-8-yl)pyrimidine-4-carbonitrile (190). The title compound was prepared analogously to 185, using 2-chloropyrimidine-4-carbonitrile. LC-MS [ESI, M+1]: 530.3.

6-(3-(2-(7-(diethylamino)-4-methyl-2-oxo-2H-chromen-3-yl)ethyl)-2,4-dioxo-1,3,8-triazaspiro[4.5]decan-8-yl)nicotinonitrile (191). The title compound was prepared analogously to 185, using 6-chloronicotinonitrile. LC-MS [ESI, M+1]: 529.3.

3-(2-(7-(diethylamino)-4-methyl-2-oxo-2H-chromen-3-yl)ethyl)-8-(1H-pyrazolo[3,4-d]pyrimidin-4-yl)-1,3,8-triazaspiro[4.5]decane-2,4-dione (192). The title compound was prepared analogously to 185, using 4-chloro-1H-pyrazolo[3,4-d]pyrimidine, to afford 192 as a yellow solid (8.1 mg, 61%, HCl salt). LC-MS [ESI, M+1]: 545.6.

3-(2-(7-(diethylamino)-4-methyl-2-oxo-2H-chromen-3-yl)ethyl)-8-(9H-purin-2-yl)-1,3,8-triazaspiro[4.5]decane-2,4-dione (193). The title compound was prepared analogously to 185, using 2-chloro-9H-purine. LC-MS [ESI, M+1]: 545.6.

3-(2-(7-(diethylamino)-4-methyl-2-oxo-2H-chromen-3-yl)ethyl)-7-(pyrimidin-2-yl)-1,3,7-triazaspiro[4.4]nonane-2,4-dione (194). The title compound was prepared analogously to 185, using 179, to afford 194 as a yellow solid (8.6 mg, 68%). LC-MS [ESI, M+1]: 491.3.

3-(2-(7-(diethylamino)-4-methyl-2-oxo-2H-chromen-3-yl)ethyl)-7-(5-(trifluoromethyl)pyrimidin-2-yl)-1,3,7-triazaspiro[4.4]nonane-2,4-dione (195). The title compound was prepared analogously to 185, using 179 and 2-chloro-5-(trifluoromethyl)pyrimidine as starting materials. LC-MS [ESI, M+1]: 559.3.

3-(2-(7-(diethylamino)-4-methyl-2-oxo-2H-chromen-3-yl)ethyl)-7-(5-(trifluoromethyl)pyridin-2-yl)-1,3,7-triazaspiro[4.4]nonane-2,4-dione (196). The title compound was prepared analogously to 185, using 179 and 2-chloro-5-(trifluoromethyl)pyridine as starting materials. LC-MS [ESI, M+1]: 558.3.

3-(2-(7-(diethylamino)-4-methyl-2-oxo-2H-chromen-3-yl)ethyl)-7-(9H-purin-6-yl)-1,3,7-triazaspiro[4.4]nonane-2,4-dione (197). The title compound was prepared analogously to 185, using 179 and 6-chloropurine as starting materials, to afford 197 as a yellow solid (10.1 mg, 74%, HCl salt). LC-MS [ESI, M+1]: 531.3.

4-(3-(2-(7-(diethylamino)-4-methyl-2-oxo-2H-chromen-3-yl)ethyl)-2,4-dioxo-1,3,8-triazaspiro[4.5]decane-8-carbonyl)benzamide (198). The title compound was prepared analogously to 150, using 175 and 4-carbamoylbenzoic acid as starting materials. LC-MS [ESI, M+1]: 574.4.

4-(3-(2-(7-(diethylamino)-4-methyl-2-oxo-2H-chromen-3-yl)ethyl)-2,4-dioxo-1,3,7-triazaspiro[4.4]nonane-7-carbonyl)benzamide (199). The title compound was prepared analogously to 150, using 179 and 4-carbamoylbenzoic acid as starting materials. LC-MS [ESI, M+1]: 560.3.

3-(2-(7-(diethylamino)-4-methyl-2-oxo-2H-chromen-3-yl)ethyl)-8-(phenylsulfonyl)-1,3,8-triazaspiro[4.5]decane-2,4-dione (200). To a stirred solution of 175 (10 mg, 1 eq) and DIPEA (12 µL) in DMF (1 mL) was added benzenesulfonyl chloride (3.8 µL, 1.3 eq) on an ice-water bath. The reaction was stirred at 0° C. for 3 hr, then concentrated under reduced pressure. The residue was purified by flash column chromatography (SiO₂, EtOAc/hexanes) to afford the title compound as a yellow solid. LC-MS [ESI, M+1]: 567.4.

3-(2-(7-(diethylamino)-4-methyl-2-oxo-2H-chromen-3-yl)ethyl)-7-(phenylsulfonyl)-1,3,7-triazaspiro[4.4]nonane-2,4-dione (201). The title compound was prepared analogously to 200, using 179, to afford 201 as a yellow solid (12.7 mg, quant). LC-MS [ESI, M+1]: 553.4.

3-(2-(7-(diethylamino)-4-methyl-2-oxo-2H-chromen-3-yl)ethyl)-7-(pyridin-3-ylsulfonyl)-1,3,7-triazaspiro[4.4]nonane-2,4-dione (202). The title compound was prepared analogously to 200, using 179 and pyridine-3-sulfonyl chloride as starting materials, to afford 202 as a yellow solid (11.8 mg, 93%). LC-MS [ESI, M+1]: 554.3.

3-(2-(7-(diethylamino)-4-methyl-2-oxo-2H-chromen-3-yl)ethyl)-7-(ethylsulfonyl)-1,3,7-triazaspiro[4.4]nonane-2,4-dione (203). The title compound was prepared analogously to 200, using 179 and ethanesulfonyl chloride as starting materials. LC-MS [ESI, M+1]: 505.3.

3-(2-(7-(diethylamino)-4-methyl-2-oxo-2H-chromen-3-yl)ethyl)-N-methyl-2,4-dioxo-1,3,7-triazaspiro[4.4]nonane-7-sulfonamide (204). The title compound was prepared analogously to 200, using 179 and methylsulfamoyl chloride as starting materials. LC-MS [ESI, M+1]: 506.3.

3-(2-(7-(diethylamino)-4-methyl-2-oxo-2H-chromen-3-yl)ethyl)-7-(pyrimidine-2-carbonyl)-1,3,7-triazaspiro[4.4]nonane-2,4-dione (205). The title compound was prepared analogously to 150, using 179 and pyrimidine-2-carboxylic acid as starting materials. LC-MS [ESI, M+1]: 519.3.

3-(2-(7-(diethylamino)-4-methyl-2-oxo-2H-chromen-3-yl)ethyl)-8-(pyrimidine-2-carbonyl)-1,3,8-triazaspiro[4.5]decane-2,4-dione (206). The title compound was prepared analogously to 150, using 175 and pyrimidine-2-carboxylic acid as starting materials. LC-MS [ESI, M+1]: 533.3.

3-(2-(7-(diethylamino)-4-methyl-2-oxo-2H-chromen-3-yl)ethyl)-7-(pyrimidine-4-carbonyl)-1,3,7-triazaspiro[4.4]nonane-2,4-dione (207). The title compound was prepared analogously to 150, using 179 and pyrimidine-4-carboxylic acid as starting materials. LC-MS [ESI, M+1]: 519.3.

3-(2-(7-(diethylamino)-4-methyl-2-oxo-2H-chromen-3-yl)ethyl)-8-(pyrimidine-4-carbonyl)-1,3,8-triazaspiro[4.5]

decane-2,4-dione (208). The title compound was prepared analogously to 150, using 175 and pyrimidine-4-carboxylic acid as starting materials. LC-MS [ESI, M+1]: 533.3.

3-(2-(7-(diethylamino)-4-methyl-2-oxo-2H-chromen-3-yl)ethyl)-7-(pyrimidine-5-carbonyl)-1,3,7-triazaspiro[4.4]nonane-2,4-dione (209). The title compound was prepared analogously to 150, using 179 and pyrimidine-5-carboxylic acid as starting materials. LC-MS [ESI, M+1]: 519.3.

3-(2-(7-(diethylamino)-4-methyl-2-oxo-2H-chromen-3-yl)ethyl)-8-(pyrimidine-5-carbonyl)-1,3,8-triazaspiro[4.5]decane-2,4-dione (210). The title compound was prepared analogously to 150, using 175 and pyrimidine-5-carboxylic acid as starting materials. LC-MS [ESI, M+1]: 533.3.

3-(2-(7-(diethylamino)-4-methyl-2-oxo-2H-chromen-3-yl)ethyl)-7-(pyrazine-2-carbonyl)-1,3,7-triazaspiro[4.4]nonane-2,4-dione (211). The title compound was prepared analogously to 150, using 179 and pyrazine-2-carboxylic acid as starting materials. LC-MS [ESI, M+1]: 519.3.

3-(2-(7-(diethylamino)-4-methyl-2-oxo-2H-chromen-3-yl)ethyl)-8-(pyrazine-2-carbonyl)-1,3,8-triazaspiro[4.5]decane-2,4-dione (212). The title compound was prepared analogously to 150, using 175 and pyrazine-2-carboxylic acid as starting materials. LC-MS [ESI, M+1]: 533.3.

3-((7-(diethylamino)-4-methyl-2-oxo-2H-chromen-3-yl)methyl)-5-isobutylimidazolidine-2,4-dione (213). The title compound was prepared analogously to the first step for preparation of 175, using Int 2-3 and 5-isobutylimidazolidine-2,4-dione as starting materials. LC-MS [ESI, M+1]: 400.2.

3-(2-(7-(diethylamino)-4-methyl-2-oxo-2H-chromen-3-yl)ethyl)-5-isobutylimidazolidine-2,4-dione (214). The title compound was prepared analogously to the first step for preparation of 175, using 5-isobutylimidazolidine-2,4-dione. LC-MS [ESI, M+1]: 414.2.

3-(2-(7-(diethylamino)-4-methyl-2-oxo-2H-chromen-3-yl)ethyl)-8-(imidazo[1,2-a]pyrazin-8-yl)-1,3,8-triazaspiro[4.5]decane-2,4-dione (215). The title compound was prepared analogously to 185, using 8-chloroimidazo[1,2-a]pyrazine, to afford 215 as a yellow solid (6.4 mg, 48%, HCl salt). LC-MS [ESI, M+1]: 544.3.

3-(2-(7-(diethylamino)-4-methyl-2-oxo-2H-chromen-3-yl)ethyl)-8-(1-methyl-1H-pyrazolo[3,4-d]pyrimidin-4-yl)-1,3,8-triazaspiro[4.5]decane-2,4-dione (216). The title compound was prepared analogously to 185, using 8-chloroimidazo[1,2-a]pyrazine. LC-MS [ESI, M+1]: 559.3.

8-([1,2,4]triazolo[4,3-a]pyrazin-8-yl)-3-(2-(7-(diethylamino)-4-methyl-2-oxo-2H-chromen-3-yl)ethyl)-1,3,8-triazaspiro[4.5]decane-2,4-dione (217). The title compound was prepared analogously to 185, using 8-chloro-[1,2,4]triazolo[1,5-a]pyrazine, to afford 217 as a light yellow solid (10.9 mg, 76%, HCl salt). LC-MS [ESI, M+1]: 545.3.

2-(7-(diethylamino)-4-methyl-2-oxo-2H-chromen-3-yl) ethyl ((2'-hydroxy-[1,1'-biphenyl]-3-yl)methyl)carbamate (218). The title compound was prepared in two steps. The first step was analogous to preparation of 153, using 1-iodo-2-(methoxymethoxy)benzene. Next, a solution of the MOM-protected intermediate (~15 mg) in 0.5M HCl in MeOH (3 mL) was stirred at room temperature for 16 hrs. The reaction was quenched by addition of saturated NaHCO₃ and extracted with EtOAc (3×10 mL). The combined organics were washed once with brine, dried over MgSO₄, filtered, and concentrated under reduced pressure to afford the title compound as a brown solid. LC-MS [ESI, M+1]: 501.3.

3'-((((2-(7-(diethylamino)-4-methyl-2-oxo-2H-chromen-3-yl)ethoxy)carbonyl)amino)methyl)-[1,1'-biphenyl]-2-yl sulfurofluoridate (219). The atmosphere above a solution of 218 (12.2 mg, 1 eq) and DIPEA (3 eq) in MeCN (2 mL) was evacuated and refilled with $SO_2F_2$ gas (1 atm) using a balloon. The solution was stirred for 2 hr at room temperature and concentrated under reduced pressure. The residue was purified by flash column chromatography ($SiO_2$, EtOAc/hexanes) to afford the title compound as a yellow gum. LC-MS [ESI, M+1]: 583.3.

2-(7-(diethylamino)-4-methyl-2-oxo-2H-chromen-3-yl) ethyl ((2'-oxo-1',2'-dihydro-[3,3'-bipyridin]-5-yl)methyl) carbamate (220). The title compound was prepared analogously to 78, using 5'-(aminomethyl)-[3,3'-bipyridin]-2 (1H)-one. LC-MS [ESI, M+1]: 503.3.

3-(2-(7-(diethylamino)-4-methyl-2-oxo-2H-chromen-3-yl)ethyl)-8-(pyrimidin-2-yl)-1,3,8-triazaspiro[4.5]decan-2-one (221). The title compound was prepared analogously to 185, using Int 9-4, to afford 221 as a yellow solid (8.1 mg, 40%, HCl salt). LC-MS [ESI, M+1]: 491.3.

3-(2-(7-(diethylamino)-4-methyl-2-oxo-2H-chromen-3-yl)ethyl)-8-(1H-pyrazolo[3,4-d]pyrimidin-4-yl)-1,3,8-triazaspiro[4.5]decan-2-one (222). The title compound was prepared analogously to 185, using Int 9-4 and 4-chloro-1H-pyrazolo[3,4-d]pyrimidine as starting materials, to afford 222 as a light yellow solid (8.4 mg, 38%, HCl salt). LC-MS [ESI, M+1]: 531.3.

3-(2-(7-(diethylamino)-4-methyl-2-oxo-2H-chromen-3-yl)ethyl)-8-(imidazo[1,2-a]pyrazin-8-yl)-1,3,8-triazaspiro [4.5]decan-2-one (223). The title compound was prepared analogously to 185, using Int 9-4 and 8-chloroimidazo[1,2-a]pyrazine as starting materials, to afford 223 as a brown solid (4.3 mg, 20%, HCl salt). LC-MS [ESI, M+1]: 530.4.

4-methyl-2-oxo-2H-chromene-7-carbonitrile (224). The title compound was prepared using literature procedures. Characterization data matched the literature.

4-methyl-2-oxo-2H-chromene-7-carboxylic acid (225). The title compound was prepared using literature procedures. Characterization data matched the literature.

4-methyl-2-oxo-N-(pyridin-2-ylmethyl)-2H-chromene-7-carboxamide (226). The title compound was prepared analogously to 150, using 225 and pyridin-2-ylmethanamine as starting materials. LC-MS [ESI, M+1]: 295.0. ¹H NMR (600 MHz, DMSO-d6) δ 9.38 (t, J=5.9 Hz, 1H), 8.56 (ddd, J=4.9, 1.8, 0.9 Hz, 1H), 7.93-7.88 (m, 2H), 7.83 (td, J=7.7, 1.8 Hz, 1H), 7.41 (d, J=7.9 Hz, 1H), 7.36-7.31 (m, 1H), 5.76 (s, 1H), 4.63 (d, J=5.9 Hz, 1H), 2.48 (d, J=1.3 Hz, 2H).

4-methyl-N-(naphthalen-2-yl)-2-oxo-2H-chromene-7-carboxamide (227). The title compound was prepared analogously to 150, using 225 and naphthalen-2-amine as starting materials. LC-MS [ESI, M−1]: 328.0.

4-methyl-2-oxo-N-(pyridin-4-ylmethyl)-2H-chromene-7-carboxamide (228). The title compound was prepared analogously to 150, using 225 and pyridin-4-ylmethanamine as starting materials. LC-MS [ESI, M+1]: 295.0.

N-(3,5-dichloro-4-hydroxyphenyl)-4-methyl-2-oxo-2H-chromene-7-carboxamide (229). The title compound was prepared analogously to 150, using 225 and 4-amino-2,6-dichlorophenol as starting materials. LC-MS [ESI, M+1]: 365.0.

N-(4-hydroxybenzyl)-4-methyl-2-oxo-2H-chromene-7-carboxamide (230). The title compound was prepared analogously to 150, using 225 and 4-(aminomethyl)phenol as starting materials. LC-MS [ESI, M+1]: 310.0.

7-(diallylamino)-4-methyl-2H-chromen-2-one (231). The title compound was prepared analogously to 36, using 225 and allyl bromide as starting materials, to afford 231 and 240 as a mixture of products. LC-MS [ESI, M+1]: 256.0.

N-(4-hydroxyphenethyl)-4-methyl-2-oxo-2H-chromene-7-carboxamide (232). The title compound was prepared analogously to 150, using 225 and 4-(2-aminoethyl)phenol as starting materials. LC-MS [ESI, M+1]: 324.0.

4-methyl-2-oxo-N-(quinolin-2-yl)-2H-chromene-7-carboxamide (233). The title compound was prepared analogously to 150, using 225 and quinolin-2-amine as starting materials. LC-MS [ESI, M+1]: 331.0.

4-methyl-2-oxo-N-(quinolin-4-yl)-2H-chromene-7-carboxamide (234). The title compound was prepared analogously to 150, using 225 and quinolin-4-amine as starting materials. LC-MS [ESI, M+1]: 331.0.

4-methyl-2-oxo-N-(quinolin-6-yl)-2H-chromene-7-carboxamide (235). The title compound was prepared analogously to 150, using 225 and quinolin-6-amine as starting materials. LC-MS [ESI, M+1]: 331.0.

N-((1H-indol-3-yl)methyl)-4-methyl-2-oxo-2H-chromene-7-carboxamide (236). The title compound was prepared analogously to 150, using 225 and (1H-indol-3-yl)methanamine as starting materials. LC-MS [ESI, M+1]: 333.1.

N-((1H-indol-5-yl)methyl)-4-methyl-2-oxo-2H-chromene-7-carboxamide (237). The title compound was prepared analogously to 150, using 225 and (1H-indol-5-yl)methanamine as starting materials. LC-MS [ESI, M+1]: 333.1.

N-(1H-benzo[d]imidazol-6-yl)-4-methyl-2-oxo-2H-chromene-7-carboxamide (238). The title compound was prepared analogously to 150, using 225 and 1H-benzo[d]imidazol-6-amine as starting materials. LC-MS [ESI, M+1]: 320.0.

N-(benzo[d]thiazol-5-yl)-4-methyl-2-oxo-2H-chromene-7-carboxamide (239). The title compound was prepared analogously to 150, using 225 and benzo[d]thiazol-5-amine as starting materials. LC-MS [ESI, M+1]: 337.1.

7-(allylamino)-4-methyl-2H-chromen-2-one (240). The title compound was prepared analogously to 36, using 225 and allyl bromide as starting materials, to afford 231 and 240 as a mixture of products that was separated by flash column chromatography (SiO$_2$, EtOAc/hexanes). LC-MS [ESI, M+1]: 216.0.

7-(dipropylamino)-4-methyl-2H-chromen-2-one (241). The title compound was prepared analogously to 36, using 225 and 1-iodopropane as starting materials, to afford 241 and 242 as a mixture of products that was separated by flash column chromatography (SiO$_2$, EtOAc/hexanes). LC-MS [ESI, M+1]: 260.0. $^1$H NMR (600 MHz, Chloroform-d) δ 7.39 (d, J=9.0 Hz, 1H), 6.59 (dd, J=9.0, 2.6 Hz, 1H), 6.50 (d, J=2.6 Hz, 1H), 5.97 (q, J=1.2 Hz, 1H), 3.34-3.28 (m, 4H), 2.36 (d, J=1.2 Hz, 3H), 1.72-1.61 (m, 3H), 0.97 (t, J=7.4 Hz, 5H).

4-methyl-7-(propylamino)-2H-chromen-2-one (242). The title compound was prepared analogously to 36, using 225 and 1-iodopropane as starting materials, to afford 241 and 242 as a mixture of products that was separated by flash column chromatography (SiO$_2$, EtOAc/hexanes). LC-MS [ESI, M+1]: 218.0. $^1$H NMR (600 MHz, Chloroform-d) δ 7.37 (d, J=8.7 Hz, 1H), 6.54 (dd, J=8.6, 2.3 Hz, 1H), 6.48 (d, J=2.3 Hz, 1H), 6.01 (d, J=1.3 Hz, 1H), 3.83 (s, 3H), 3.17 (t, J=7.1 Hz, 2H), 2.37 (d, J=1.2 Hz, 3H), 1.70 (h, J=7.3 Hz, 2H), 1.04 (t, J=7.4 Hz, 3H).

7-(bis(2-methylallyl)amino)-4-methyl-2H-chromen-2-one (243). The title compound was prepared analogously to 36, using 225 and 3-bromo-2-methylprop-1-ene as starting materials, to afford 243 and 244 as a mixture of products that was separated by flash column chromatography (SiO$_2$, EtOAc/hexanes). LC-MS [ESI, M+1]: 284.1. $^1$H NMR (600 MHz, Chloroform-d) δ 7.38 (d, J=8.9 Hz, 1H), 6.56 (dd, J=8.9, 2.6 Hz, 1H), 6.49 (d, J=2.6 Hz, 1H), 5.97 (t, J=1.3 Hz, 1H), 4.75 (t, J=1.5 Hz, 2H), 3.88 (s, 4H), 2.34 (d, J=1.2 Hz, 3H), 1.77 (s, 6H).

4-methyl-7-((2-methylallyl)amino)-2H-chromen-2-one (244). The title compound was prepared analogously to 36, using 225 and 3-bromo-2-methylprop-1-ene as starting materials, to afford 243 and 244 as a mixture of products that was separated by flash column chromatography (SiO$_2$, EtOAc/hexanes). LC-MS [ESI, M+1]: 230.0. $^1$H NMR (600 MHz, Chloroform-d) δ 7.36 (d, J=8.7 Hz, 11H), 6.54 (dd, J=8.7, 2.4 Hz, 11H), 6.46 (d, J=2.4 Hz, 11H), 5.98 (q, J=1.2 Hz, 11H), 4.96 (tt, J=1.6, 0.9 Hz, 11H), 4.92 (p, J=1.4 Hz, 1H), 3.75 (d, J=1.5 Hz, 2H), 2.34 (d, J=1.2 Hz, 3H), 1.79 (dd, J=1.6, 0.8 Hz, 3H).

7-(bis(cyclopropylmethyl)amino)-4-methyl-2H-chromen-2-one (245). The title compound was prepared analogously to 36, using 225 and (bromomethyl)cyclopropane as starting materials, to afford 245 and 246 as a mixture of products that was separated by flash column chromatography (SiO$_2$, EtOAc/hexanes). LC-MS [ESI, M+1]: 284.1. $^1$H NMR (600 MHz, Chloroform-d) δ 7.46 (d, J=8.9 Hz, 11H), 6.88 (dd, J=8.9, 2.6 Hz, 11H), 6.77 (d, J=2.6 Hz, 11H), 6.04 (d, J=1.3 Hz, 1H), 2.76 (s, 3H), 2.39 (d, J=1.2 Hz, 2H), 1.14-1.02 (m, 2H), 0.66-0.54 (m, 3H), 0.29 (h, J=4.8, 4.1 Hz, 3H).

7-((cyclopropylmethyl)amino)-4-methyl-2H-chromen-2-one (246). The title compound was prepared analogously to 36, using 225 and (bromomethyl)cyclopropane as starting materials, to afford 245 and 246 as a mixture of products that was separated by flash column chromatography (SiO$_2$, EtOAc/hexanes). LC-MS [ESI, M+1]: 230.0. $^1$H NMR (600 MHz, Chloroform-d) δ 7.37 (d, J=8.7 Hz, 1H), 6.54 (dd, J=8.7, 2.3 Hz, 1H), 6.45 (d, J=2.3 Hz, 1H), 6.00 (t, J=1.2 Hz, 1H), 3.61 (s, 2H), 3.03 (d, J=7.0 Hz, 2H), 2.36 (d, J=1.2 Hz, 3H), 1.18-1.07 (m, 1H), 0.63-0.53 (m, 1H), 0.30 (dt, J=6.1, 4.6 Hz, 2H).

7-(but-3-en-1-ylamino)-4-methyl-2H-chromen-2-one (247). The title compound was prepared analogously to 36, using 225 and 4-iodobut-1-ene as starting materials. LC-MS [ESI, M+1]: 230.0. $^1$H NMR (600 MHz, Chloroform-d) δ 7.36 (d, J=8.7 Hz, 1H), 6.52 (dd, J=8.6, 2.3 Hz, 1H), 6.46 (d, J=2.4 Hz, 1H), 5.99 (q, J=1.1 Hz, 1H), 5.84 (ddt, J=17.0, 10.2, 6.8 Hz, 1H), 5.22-5.15 (m, 1H), 5.19-5.13 (m, 1H), 3.26 (t, J=6.7 Hz, 2H), 2.43 (qt, J=6.8, 1.3 Hz, 2H), 2.35 (d, J=1.2 Hz, 4H).

7-(di(prop-2-yn-1-yl)amino)-4-methyl-2H-chromen-2-one (248). The title compound was prepared analogously to 36, using 225 and propargyl bromide as starting materials, to afford 248 and 249 as a mixture of products that was separated by flash column chromatography (SiO$_2$, EtOAc/hexanes). LC-MS [ESI, M+1]: 252.0. $^1$H NMR (600 MHz, Chloroform-d) δ 7.51 (d, J=8.8 Hz, 1H), 6.87 (dd, J=8.8, 2.6 Hz, 1H), 6.84 (d, J=2.5 Hz, 1H), 6.10 (q, J=1.2 Hz, 1H), 4.21 (d, J=2.4 Hz, 4H), 2.40 (d, J=1.2 Hz, 3H), 2.32 (t, J=2.4 Hz, 2H).

4-methyl-7-(prop-2-yn-1-ylamino)-2H-chromen-2-one (249). The title compound was prepared analogously to 36, using 225 and propargyl bromide as starting materials, to afford 248 and 249 as a mixture of products that was separated by flash column chromatography (SiO$_2$, EtOAc/hexanes). Characterization data matched that of the literature.

7-(bis(3-fluoropropyl)amino)-4-methyl-2H-chromen-2-one (250). The title compound was prepared analogously to 36, using 225 and 1-fluoro-3-iodopropane as starting materials, to afford 250 and 251 as a mixture of products that was separated by flash column chromatography (SiO$_2$, EtOAc/hexanes). LC-MS [ESI, M+1]: 296.0.

7-((3-fluoropropyl)amino)-4-methyl-2H-chromen-2-one (251). The title compound was prepared analogously to 36, using 225 and 1-fluoro-3-iodopropane as starting materials, to afford 250 and 251 as a mixture of products that was separated by flash column chromatography (SiO$_2$, EtOAc/hexanes). LC-MS [ESI, M+1]: 236.0.

7-(allyl(methyl)amino)-4-methyl-2H-chromen-2-one (252). The title compound was prepared analogously to 36, using 240 and methyl iodide as starting materials. LC-MS [ESI, M+1]: 230.0. $^1$H NMR (600 MHz, DMSO-d$_6$) δ 7.52 (d, J=8.9 Hz, 1H), 6.73 (dd, J=8.9, 2.6 Hz, 1H), 6.55 (d, J=2.6 Hz, 1H), 5.97 (q, J=1.2 Hz, 1H), 5.84 (ddt, J=17.3, 10.1, 4.8 Hz, 1H), 5.15 (dq, J=10.3, 1.7 Hz, 1H), 4.07 (dt, J=4.9, 1.8 Hz, 2H), 3.02 (s, 3H), 2.34 (d, J=1.2 Hz, 2H).

4-methyl-7-(methyl(propyl)amino)-2H-chromen-2-one (253). The title compound was prepared analogously to 36, using 242 and methyl iodide as starting materials. LC-MS [ESI, M+1]: 232.0. $^1$H NMR (600 MHz, DMSO-d$_6$) δ 7.50 (d, J=8.9 Hz, 1H), 6.73 (dd, J=9.0, 2.6 Hz, 1H), 6.52 (d, J=2.6 Hz, 1H), 5.95 (d, J=1.3 Hz, 1H), 3.41-3.36 (m, 2H), 2.99 (s, 3H), 2.33 (d, J=1.2 Hz, 3H), 1.56 (hept, J=7.4, 7.0 Hz, 2H), 0.89 (t, J=7.4 Hz, 3H).

4-methyl-7-(methyl(2-methylallyl)amino)-2H-chromen-2-one (254). The title compound was prepared analogously to 36, using 244 and methyl iodide as starting materials. LC-MS [ESI, M+1]: 244.0. $^1$H NMR (600 MHz, DMSO-d$_6$) δ 7.51 (d, J=9.0 Hz, 1H), 6.70 (dd, J=9.0, 2.6 Hz, 1H), 6.52 (d, J=2.6 Hz, 1H), 5.96 (t, J=1.2 Hz, 1H), 4.83 (p, J=1.5 Hz, 1H), 3.98 (s, 2H), 3.04 (s, 3H), 2.34 (d, J=1.2 Hz, 3H), 1.69 (t, J=1.1 Hz, 3H).

7-((cyclopropylmethyl)(methyl)amino)-4-methyl-2H-chromen-2-one (255). The title compound was prepared analogously to 36, using 246 and methyl iodide as starting materials. LC-MS [ESI, M+1]: 244.0. $^1$H NMR (600 MHz, DMSO-d$_6$) δ 7.52 (d, J=9.0 Hz, 1H), 6.79 (dd, J=9.0, 2.6 Hz, 1H), 6.58 (d, J=2.6 Hz, 1H), 5.96 (t, J=1.2 Hz, 1H), 3.36 (s, 1H), 3.03 (s, 3H), 2.34 (d, J=1.2 Hz, 4H), 1.08-0.97 (m, 1H), 0.52-0.42 (m, 2H), 0.34-0.24 (m, 2H).

7-(but-3-en-1-yl(methyl)amino)-4-methyl-2H-chromen-2-one (256). The title compound was prepared analogously to 36, using 247 and methyl iodide as starting materials. LC-MS [ESI, M+1]: 244.0. $^1$H NMR (600 MHz, DMSO-d$_6$) δ 7.52 (d, J=9.0 Hz, 1H), 6.74 (dd, J=8.9, 2.6 Hz, 1H), 6.54 (d, J=2.6 Hz, 1H), 5.96 (q, J=1.1 Hz, 1H), 5.86 (ddt, J=17.2, 10.2, 6.9 Hz, 1H), 5.03 (ddd, J=10.2, 2.1, 1.1 Hz, 1H), 3.54-3.48 (m, 2H), 3.00 (s, 3H), 2.36-2.26 (m, 5H).

4-methyl-7-(methyl(prop-2-yn-1-yl)amino)-2H-chromen-2-one (257). The title compound was prepared analogously to 36, using 249 and methyl iodide as starting materials. LC-MS [ESI, M+1]: 228.0. $^1$H NMR (600 MHz, DMSO-d$_6$) δ 7.58 (d, J=8.9 Hz, 1H), 6.86 (dd, J=8.9, 2.5 Hz, 1H), 6.76-6.69 (m, 1H), 6.04 (q, J=1.1 Hz, 1H), 4.27 (d, J=2.4 Hz, 1H), 3.16 (t, J=2.4 Hz, 1H), 3.05-3.00 (m, 4H), 2.35 (dt, J=11.3, 0.9 Hz, 3H).

7-((3-fluoropropyl)(methyl)amino)-4-methyl-2H-chromen-2-one (258). The title compound was prepared analogously to 36, using 251 and methyl iodide as starting materials. LC-MS [ESI, M+1]: 250.0. $^1$H NMR (600 MHz, DMSO-d$_6$) δ 7.52 (d, J=8.9 Hz, 1H), 6.74 (dd, J=9.0, 2.6 Hz, 1H), 6.56 (d, J=2.5 Hz, 1H), 5.97 (t, J=1.2 Hz, 1H), 4.51 (dt, J=47.4, 5.8 Hz, 2H), 3.62-3.43 (m, 2H), 3.00 (s, 3H), 2.34 (d, J=1.2 Hz, 3H), 2.03-1.81 (m, 2H).

7-(allyl(prop-2-yn-1-yl)amino)-4-methyl-2H-chromen-2-one (259). The title compound was prepared analogously to 36, using 249 and allyl bromide as starting materials.

LC-MS [ESI, M+1]: 254.0. $^1$H NMR (600 MHz, DMSO-d$_6$) δ 7.57 (d, J=9.0 Hz, 1H), 6.81 (dd, J=8.9, 2.6 Hz, 1H), 6.66 (d, J=2.5 Hz, 1H), 6.03 (t, J=1.3 Hz, 1H), 5.88 (ddt, J=17.2, 10.2, 5.0 Hz, 1H), 5.22 (dq, J=17.2, 1.8 Hz, 1H), 5.18 (dq, J=10.4, 1.6 Hz, 1H), 4.25 (d, J=2.4 Hz, 2H), 4.11 (dt, J=5.1, 1.8 Hz, 2H), 3.23 (t, J=2.4 Hz, 1H), 2.36 (d, J=1.2 Hz, 3H).

4-methyl-7-(prop-2-yn-1-yl(propyl)amino)-2H-chromen-2-one (260). The title compound was prepared analogously to 36, using 249 and 1-iodopropane as starting materials. LC-MS [ESI, M+1]: 256.0. $^1$H NMR (600 MHz, DMSO-d$_6$) δ 7.55 (d, J=8.9 Hz, 1H), 6.81 (dd, J=9.0, 2.6 Hz, 1H), 6.65 (d, J=2.6 Hz, 1H), 6.01 (d, J=1.3 Hz, 1H), 4.23 (d, J=2.5 Hz, 2H), 3.42 (s, 1H), 3.20 (t, J=2.4 Hz, 1H), 2.35 (d, J=1.2 Hz, 4H), 1.62 (h, J=7.4 Hz, 2H), 0.91 (t, J=7.4 Hz, 4H).

4-methyl-7-((2-methylallyl)(prop-2-yn-1-yl)amino)-2H-chromen-2-one (261). The title compound was prepared analogously to 36, using 249 and 3-bromo-2-methylprop-1-ene as starting materials. LC-MS [ESI, M+1]: 268.0. $^1$H NMR (600 MHz, DMSO-d$_6$) δ 7.56 (d, J=8.9 Hz, 1H), 6.78 (dd, J=8.9, 2.6 Hz, 1H), 6.62 (d, J=2.5 Hz, 1H), 6.02 (t, J=1.2 Hz, 1H), 4.81-4.77 (m, 1H), 4.23 (d, J=2.4 Hz, 2H), 3.99 (s, 2H), 3.24 (t, J=2.4 Hz, 1H), 2.35 (d, J=1.2 Hz, 3H), 1.72 (s, 3H).

7-((cyclopropylmethyl)(prop-2-yn-1-yl)amino)-4-methyl-2H-chromen-2-one (262). The title compound was prepared analogously to 36, using 249 and (bromomethyl)cyclopropane as starting materials. LC-MS [ESI, M+1]: 268.0. $^1$H NMR (600 MHz, DMSO-d$_6$) δ 7.57 (d, J=8.9 Hz, 1H), 6.88 (dd, J=9.0, 2.6 Hz, 1H), 6.71 (d, J=2.6 Hz, 1H), 6.03 (d, J=1.3 Hz, 1H), 4.29 (d, J=2.4 Hz, 2H), 3.36 (d, J=6.6 Hz, 2H), 3.18 (t, J=2.3 Hz, 1H), 2.36 (d, J=1.2 Hz, 3H), 1.08 (dtdd, J=11.4, 7.8, 6.4, 4.9 Hz, 1H), 0.53-0.45 (m, 2H), 0.43-0.30 (m, 2H).

7-(but-3-en-1-yl(prop-2-yn-1-yl)amino)-4-methyl-2H-chromen-2-one (263). The title compound was prepared analogously to 36, using 249 and 4-iodobut-1-ene as starting materials. LC-MS [ESI, M+1]: 268.0. $^1$H NMR (600 MHz, DMSO-d$_6$) δ 7.57 (d, J=8.9 Hz, 1H), 6.83 (dd, J=9.0, 2.6 Hz, 1H), 6.67 (d, J=2.6 Hz, 1H), 6.02 (d, J=1.4 Hz, 1H), 5.88 (ddt, J=17.1, 10.2, 6.8 Hz, 1H), 5.14 (dt, J=17.2, 1.8 Hz, 1H), 5.05 (dd, J=10.2, 2.0 Hz, 1H), 4.25 (d, J=2.4 Hz, 2H), 3.53 (dd, J=8.6, 6.4 Hz, 2H), 3.21 (t, J=2.3 Hz, 1H), 2.43-2.32 (m, 5H).

7-((3-fluoropropyl)(prop-2-yn-1-yl)amino)-4-methyl-2H-chromen-2-one (264). The title compound was prepared analogously to 36, using 249 and 1-fluoro-3-iodopropane as starting materials. LC-MS [ESI, M+1]: 274.0. $^1$H NMR (600 MHz, DMSO-d$_6$) δ 7.58 (d, J=8.9 Hz, 1H), 6.83 (dd, J=8.9, 2.6 Hz, 1H), 6.69 (d, J=2.6 Hz, 1H), 6.03 (d, J=1.4 Hz, 1H), 4.55 (dt, J=47.3, 5.8 Hz, 2H), 4.25 (d, J=2.4 Hz, 2H), 3.69-3.48 (m, 2H), 3.22 (t, J=2.4 Hz, 1H), 2.36 (d, J=1.2 Hz, 3H), 2.14-1.84 (m, 2H).

4-methyl-7-((3,3,3-trifluoropropyl)amino)-2H-chromen-2-one (265). The title compound was prepared analogously to 36, using 1,1,1-trifluoro-3-iodopropane. LC-MS [ESI, M+1]: 271.9.

7-(dimethylamino)-4-methyl-2H-chromen-2-one (266). The title compound was prepared analogously to 36, using methyl iodide. Characterization data matched that of the literature.

4-methyl-2-oxo-N-(prop-2-yn-1-yl)-2H-chromene-7-carboxamide (267). The title compound was prepared analogously to 150, using 225 and propargylamine as starting materials. LC-MS [ESI, M+1]: 242.0.

7-(ethyl(methyl)amino)-4-methyl-2H-chromen-2-one (268). The title compound was prepared analogously to 36, using 270 and methyl iodide as starting materials. LC-MS [ESI, M+1]: 218.0.

2-((4-methyl-2-oxo-2H-chromen-7-yl)amino)acetonitrile (269). The title compound was prepared analogously to 36, using bromoacetonitrile. LC-MS [ESI, M+1]: 214.9. $^1$H NMR (600 MHz, Acetone-d$_6$) δ 7.60 (d, J=8.7 Hz, 1H), 6.83 (ddd, J=8.6, 2.3, 0.8 Hz, 1H), 6.70 (dd, J=2.4, 1.4 Hz, 1H), 6.42 (s, 1H), 6.03 (s, 1H), 4.47 (d, J=6.4 Hz, 1H), 2.41 (d, J=1.2 Hz, 2H).

7-(ethylamino)-4-methyl-2H-chromen-2-one (270). The title compound was prepared analogously to 36, using iodoethane. LC-MS [ESI, M+1]: 203.9. $^1$H NMR (600 MHz, Acetone-d$_6$) δ 7.45 (d, J=8.7 Hz, 1H), 6.64 (dd, J=8.7, 2.3 Hz, 1H), 6.42 (d, J=2.3 Hz, 1H), 5.89 (q, J=1.2 Hz, 1H), 5.83 (s, 1H), 3.25 (qd, J=7.1, 5.1 Hz, 2H), 2.36 (d, J=1.2 Hz, 2H), 1.27 (td, J=7.2, 1.2 Hz, 4H).

7-(ethyl(prop-2-yn-1-yl)amino)-4-methyl-2H-chromen-2-one (271). The title compound was prepared analogously to 36, using 270 and propargyl bromide as starting materials. LC-MS [ESI, M+1]: 242.0.

2-(ethyl(4-methyl-2-oxo-2H-chromen-7-yl)amino)acetonitrile (272). The title compound was prepared analogously to 36, using 270 and bromoacetonitrile as starting materials. LC-MS [ESI, M+1]: 243.0.

7-(ethyl(2-fluoroethyl)amino)-4-methyl-2H-chromen-2-one (273). The title compound was prepared analogously to 36, using 270 and 1-fluoro-3-iodopropane as starting materials. LC-MS [ESI, M+1]: 250.0.

7-(ethyl(isopropyl)amino)-4-methyl-2H-chromen-2-one (274). The title compound was prepared analogously to 36, using 270 and 2-iodopropane as starting materials. LC-MS [ESI, M+1]: 246.0. $^1$H NMR (600 MHz, Acetone-d$_6$) δ 7.52 (d, J=9.0 Hz, 1H), 6.82 (dd, J=9.0, 2.6 Hz, 1H), 6.58 (d, J=2.7 Hz, 1H), 5.90 (q, J=1.2 Hz, 1H), 4.27 (hept, J=6.6 Hz, 1H), 3.44 (q, J=7.1 Hz, 2H), 2.38 (d, J=1.2 Hz, 2H), 1.28 (d, J=6.6 Hz, 5H), 1.23 (t, J=7.1 Hz, 3H).

7-(ethyl(propyl)amino)-4-methyl-2H-chromen-2-one (275). The title compound was prepared analogously to 36, using 270 and 1-iodopropane as starting materials. LC-MS [ESI, M+1]: 246.0. $^1$H NMR (600 MHz, Acetone-d$_6$) δ 7.50 (d, J=9.0 Hz, 1H), 6.72 (dd, J=9.0, 2.6 Hz, 1H), 6.49 (d, J=2.6 Hz, 1H), 5.89 (q, J=1.2 Hz, 1H), 3.53 (q, J=7.1 Hz, 2H), 3.43-3.37 (m, 2H), 2.37 (d, J=1.2 Hz, 3H), 1.74-1.64 (m, 2H), 1.21 (t, J=7.1 Hz, 3H), 0.99 (t, J=7.4 Hz, 3H).

1-(2-(7-(diethylamino)-4-methyl-2-oxo-2H-chromen-3-yl)ethyl)-3-(pyridin-2-ylmethyl)urea (276). The title compound was prepared analogously to 98, using pyridin-2-ylmethanamine. LC-MS [ESI, M+1]: 409.2.

1-(2-(7-(diethylamino)-4-methyl-2-oxo-2H-chromen-3-yl)ethyl)-3-(pyridin-4-ylmethyl)urea (277). The title compound was prepared analogously to 98, using pyridin-4-ylmethanamine. LC-MS [ESI, M+1]: 409.2.

1-benzyl-3-(2-(7-(diethylamino)-4-methyl-2-oxo-2H-chromen-3-yl)ethyl)urea (278). The title compound was prepared analogously to 98, using benzylamine. LC-MS [ESI, M+1]: 408.2.

1-((1H-indol-5-yl)methyl)-3-(2-(7-(diethylamino)-4-methyl-2-oxo-2H-chromen-3-yl)ethyl)urea (279). The title compound was prepared analogously to 98, using (1H-indol-5-yl)methanamine. LC-MS [ESI, M+1]: 447.3.

1-(2-(7-(diethylamino)-4-methyl-2-oxo-2H-chromen-3-yl)ethyl)-3-(4-hydroxyphenethyl)urea (280). The title compound was prepared analogously to 98, using 4-(2-aminoethyl)phenol. LC-MS [ESI, M+1]: 438.2. $^1$H NMR (600 MHz, DMSO-d$_6$) δ 9.15 (s, 1H), 7.51 (d, J=9.0 Hz, 1H), 6.99-6.91 (m, 2H), 6.72-6.63 (m, 3H), 6.49 (d, J=2.6 Hz, 1H), 5.94 (s, 1H), 5.76 (s, 1H), 3.42 (q, J=7.0 Hz, 4H), 3.15-3.07 (m, 4H), 2.62 (t, J=6.9 Hz, 2H), 2.49 (d, J=7.2 Hz, 1H), 2.31 (s, 3H), 1.12 (t, J=7.0 Hz, 6H).

1-(2-(1H-imidazol-5-yl)ethyl)-3-(2-(7-(diethylamino)-4-methyl-2-oxo-2H-chromen-3-yl)ethyl)urea (281). The title compound was prepared analogously to 98, using 2-(1H-imidazol-5-yl)ethan-1-amine. LC-MS [ESI, M+1]: 412.2.

1-((6-chloropyridin-2-yl)methyl)-3-(2-(7-(diethylamino)-4-methyl-2-oxo-2H-chromen-3-yl)ethyl)urea (282). The title compound was prepared analogously to 98, using (6-chloropyridin-2-yl)methanamine. LC-MS [ESI, M+1]: 443.6. $^1$H NMR (600 MHz, DMSO-d$_6$) δ 7.75 (t, J=7.7 Hz, 1H), 7.52 (d, J=9.1 Hz, 1H), 7.37-7.31 (m, 1H), 7.22 (dd, J=7.6, 0.8 Hz, 1H), 6.70 (dd, J=9.1, 2.6 Hz, 1H), 6.50 (d, J=2.6 Hz, 1H), 6.49 (s, 1H), 6.23 (s, 2H), 4.24 (s, 2H), 3.42 (q, J=7.0 Hz, 4H), 3.15 (t, J=6.9 Hz, 2H), 2.64 (t, J=6.9 Hz, 2H), 2.32 (s, 3H), 1.12 (t, J=7.0 Hz, 6H).

1-([1,1'-biphenyl]-4-ylmethyl)-3-(2-(7-(diethylamino)-4-methyl-2-oxo-2H-chromen-3-yl)ethyl)urea (283). The title compound was prepared analogously to 98, using [1,1'-biphenyl]-4-ylmethanamine. LC-MS [ESI, M+1]: 484.3. $^1$H NMR (600 MHz, DMSO-d$_6$) δ 7.66-7.60 (m, 2H), 7.58-7.50 (m, 3H), 7.50-7.42 (m, 2H), 7.39-7.32 (m, 1H), 7.31-7.24 (m, 2H), 6.69 (dd, J=9.1, 2.6 Hz, 1H), 6.49 (d, J=2.6 Hz, 1H), 6.42 (s, 1H), 6.05 (s, 1H), 4.22 (s, 2H), 3.41 (q, J=7.0 Hz, 4H), 3.18 (t, J=6.9 Hz, 2H), 2.66 (t, J=6.8 Hz, 2H), 2.34 (s, 3H), 1.10 (t, J=7.0 Hz, 6H).

1-([1,1'-biphenyl]-3-ylmethyl)-3-(2-(7-(diethylamino)-4-methyl-2-oxo-2H-chromen-3-yl)ethyl)urea (284). The title compound was prepared analogously to 98, using [1,1'-biphenyl]-3-ylmethanamine. LC-MS [ESI, M+1]: 484.3. $^1$H NMR (600 MHz, DMSO-d$_6$) δ 7.67-7.60 (m, 2H), 7.57-7.42 (m, 5H), 7.42-7.34 (m, 2H), 7.22 (dt, J=7.6, 1.4 Hz, 1H), 6.48 (d, J=2.5 Hz, 1H), 6.40 (s, 1H), 6.06 (s, 1H), 4.26 (s, 2H), 3.42 (q, J=7.0 Hz, 4H), 3.16 (t, J=6.9 Hz, 2H), 2.65 (t, J=6.9 Hz, 2H), 2.54 (s, 1H), 2.28 (s, 3H), 1.12 (t, J=7.0 Hz, 6H).

1-(2-(7-(diethylamino)-4-methyl-2-oxo-2H-chromen-3-yl)ethyl)-3-(naphthalen-1-ylmethyl)urea (285). The title compound was prepared analogously to 98, using naphthalen-1-ylmethanamine. LC-MS [ESI, M+1]: 458.3. $^1$H NMR (600 MHz, DMSO-d$_6$) δ 8.12-8.04 (m, 1H), 7.98-7.90 (m, 1H), 7.82 (d, J=8.1 Hz, 1H), 7.57-7.50 (m, 2H), 7.54-7.47 (m, 1H), 7.47-7.36 (m, 2H), 6.49 (d, J=2.6 Hz, 1H), 6.35 (s, 1H), 6.01 (s, 1H), 4.65 (s, 2H), 3.42 (q, J=7.0 Hz, 4H), 3.18 (t, J=6.9 Hz, 2H), 2.66 (t, J=6.9 Hz, 2H), 2.53 (s, 1H), 2.31 (s, 3H), 1.12 (t, J=7.0 Hz, 6H).

1-(2-(7-(diethylamino)-4-methyl-2-oxo-2H-chromen-3-yl)ethyl)-3-((6-oxo-1,6-dihydropyridin-3-yl)methyl)urea (286). The title compound was prepared analogously to 98, using 5-(aminomethyl)pyridin-2(1H)-one. LC-MS [ESI, M+1]: 425.2. $^1$H NMR (600 MHz, DMSO-d$_6$) δ 7.51 (d, J=9.0 Hz, 1H), 7.36 (dd, J=9.4, 2.6 Hz, 1H), 7.21 (d, J=2.6 Hz, 1H), 6.69 (dd, J=9.1, 2.6 Hz, 1H), 6.49 (d, J=2.6 Hz, 1H), 6.31 (d, J=9.4 Hz, 1H), 6.21 (s, 1H), 6.02 (s, 1H), 3.90 (s, 2H), 3.42 (q, J=7.0 Hz, 4H), 3.13 (dt, J=13.8, 5.0 Hz, 2H), 2.63 (t, J=6.9 Hz, 2H), 2.30 (s, 3H), 1.27 (dd, J=9.2, 6.7 Hz, 2H), 1.12 (t, J=7.0 Hz, 6H).

1-(2-(7-(diethylamino)-4-methyl-2-oxo-2H-chromen-3-yl)ethyl)-3-(quinolin-4-ylmethyl)urea (287). The title compound was prepared analogously to 98, using quinolin-4-ylmethanamine. LC-MS [ESI, M+1]: 459.3. $^1$H NMR (600 MHz, DMSO-d$_6$) δ 11.07 (s, 1H), 8.50 (s, 1H), 8.32 (s, 1H), 8.12 (dd, J=10.3, 4.8 Hz, 1H), 8.01 (d, J=8.7 Hz, 1H), 7.85 (tt, J=16.9, 7.3 Hz, 1H), 7.76-7.69 (m, 1H), 7.60-7.49 (m, 1H), 6.69 (s, 1H), 6.54-6.47 (m, 1H), 3.62 (ddt, J=11.1, 7.4, 4.2 Hz, 1H), 3.49-3.38 (m, 4H), 3.15 (qd, J=7.5, 4.3 Hz, 1H), 2.83 (d, J=6.7 Hz, 1H), 2.44-2.37 (m, 2H), 1.12 (p, J=6.3, 5.7 Hz, 5H).

1-(2-(7-(diethylamino)-4-methyl-2-oxo-2H-chromen-3-yl)ethyl)-3-(quinolin-3-ylmethyl)urea (288). The title compound was prepared analogously to 98, using quinolin-3-ylmethanamine. LC-MS [ESI, M+1]: 459.3.

1-(2-(7-(diethylamino)-4-methyl-2-oxo-2H-chromen-3-yl)ethyl)-3-(isoquinolin-4-ylmethyl)urea (289). The title compound was prepared analogously to 98, using isoquinolin-4-ylmethanamine. LC-MS [ESI, M+1]: 459.3. $^1$H NMR (600 MHz, DMSO-$d_6$) δ 8.48 (d, J=8.2 Hz, 1H), 8.45 (s, 1H), 8.40 (d, J=8.5 Hz, 1H), 8.15 (ddd, J=8.4, 6.9, 1.3 Hz, 1H), 7.98 (ddd, J=8.1, 6.9, 1.0 Hz, 1H), 7.46 (d, J=9.1 Hz, 1H), 6.68 (dd, J=9.1, 2.6 Hz, 1H), 6.64 (s, 1H), 6.47 (d, J=2.6 Hz, 1H), 6.25 (s, 1H), 4.76 (d, J=5.3 Hz, 2H), 3.42 (q, J=7.0 Hz, 4H), 2.65 (t, J=6.9 Hz, 2H), 2.27 (s, 3H), 1.12 (t, J=7.0 Hz, 6H).

1-(2-(7-(diethylamino)-4-methyl-2-oxo-2H-chromen-3-yl)ethyl)-3-(isoquinolin-1-ylmethyl)urea (290). The title compound was prepared analogously to 98, using isoquinolin-1-ylmethanamine. LC-MS [ESI, M+1]: 459.3.

1-(3-(1H-imidazol-4-yl)benzyl)-3-(2-(7-(diethylamino)-4-methyl-2-oxo-2H-chromen-3-yl)ethyl)urea (291). The title compound was prepared analogously to 98, using (3-(1H-imidazol-4-yl)phenyl)methanamine. LC-MS [ESI, M+1]: 474.3. $^1$H NMR (600 MHz, DMSO-$d_6$) δ 7.90-7.80 (m, 3H), 7.70 (d, J=1.0 Hz, 1H), 7.53-7.43 (m, 3H), 7.38 (dd, J=8.5, 1.8 Hz, 1H), 6.69 (dd, J=9.1, 2.6 Hz, 1H), 6.49 (d, J=2.6 Hz, 1H), 6.44 (s, 1H), 6.08 (s, 1H), 5.76 (s, 2H), 4.36 (s, 2H), 3.42 (q, J=7.0 Hz, 4H), 3.18 (t, J=6.8 Hz, 2H), 2.67 (t, J=6.9 Hz, 2H), 2.33 (s, 3H), 1.12 (t, J=7.0 Hz, 6H).

1-(2-(7-(diethylamino)-4-methyl-2-oxo-2H-chromen-3-yl)ethyl)-3-(naphthalen-2-ylmethyl)urea (292). The title compound was prepared analogously to 98, using naphthalen-2-ylmethanamine. LC-MS [ESI, M+1]: 474.3. $^1$H NMR (600 MHz, DMSO-$d_6$) δ 7.90-7.80 (m, 3H), 7.70 (s, 1H), 7.53-7.43 (m, 3H), 7.38 (dd, J=8.4, 1.8 Hz, 1H), 6.69 (dd, J=9.1, 2.6 Hz, 1H), 6.49 (d, J=2.6 Hz, 1H), 6.44 (s, 1H), 6.08 (s, 1H), 4.36 (s, 2H), 3.42 (q, J=7.0 Hz, 4H), 3.18 (t, J=6.9 Hz, 2H), 2.67 (t, J=6.9 Hz, 2H), 2.33 (s, 3H), 1.12 (t, J=7.0 Hz, 6H).

1-(2-(7-(diethylamino)-4-methyl-2-oxo-2H-chromen-3-yl)ethyl)-3-(quinolin-2-ylmethyl)urea (293). The title compound was prepared analogously to 98, using quinolin-2-ylmethanamine. LC-MS [ESI, M+1]: 459.3.

1-(2-(7-(diethylamino)-4-methyl-2-oxo-2H-chromen-3-yl)ethyl)-3-(pyrimidin-4-ylmethyl)urea (294). The title compound was prepared analogously to 98, using pyrimidin-4-ylmethanamine. LC-MS [ESI, M+1]: 410.2.

1-(2-(7-(diethylamino)-4-methyl-2-oxo-2H-chromen-3-yl)ethyl)-3-(isoquinolin-3-ylmethyl)urea (295). The title compound was prepared analogously to 98, using isoquinolin-3-ylmethanamine. LC-MS [ESI, M+1]: 459.3.

1-(2-(7-(diethylamino)-4-methyl-2-oxo-2H-chromen-3-yl)ethyl)-3-((1-oxo-1,2-dihydroisoquinolin-6-yl)methyl)urea (296). The title compound was prepared analogously to 98, using 6-(aminomethyl)isoquinolin-1(2H)-one. LC-MS [ESI, M+1]: 475.3.

3-((3-(2-(7-(diethylamino)-4-methyl-2-oxo-2H-chromen-3-yl)ethyl)ureido)methyl)-5-fluorobenzoic acid (297). The title compound was prepared analogously to 98, using 3-(aminomethyl)-5-fluorobenzoic acid. LC-MS [ESI, M+1]: 470.2.

3-((3-(2-(7-(diethylamino)-4-methyl-2-oxo-2H-chromen-3-yl)ethyl)ureido)methyl)benzamide (298). The title compound was prepared analogously to 98, using 3-(aminomethyl)benzamide. LC-MS [ESI, M+1]: 451.2.

3-((3-(2-(7-(diethylamino)-4-methyl-2-oxo-2H-chromen-3-yl)ethyl)ureido)methyl)benzenesulfonamide (299). The title compound was prepared analogously to 98, using 3-(aminomethyl)benzenesulfonamide. LC-MS [ESI, M+1]: 487.3.

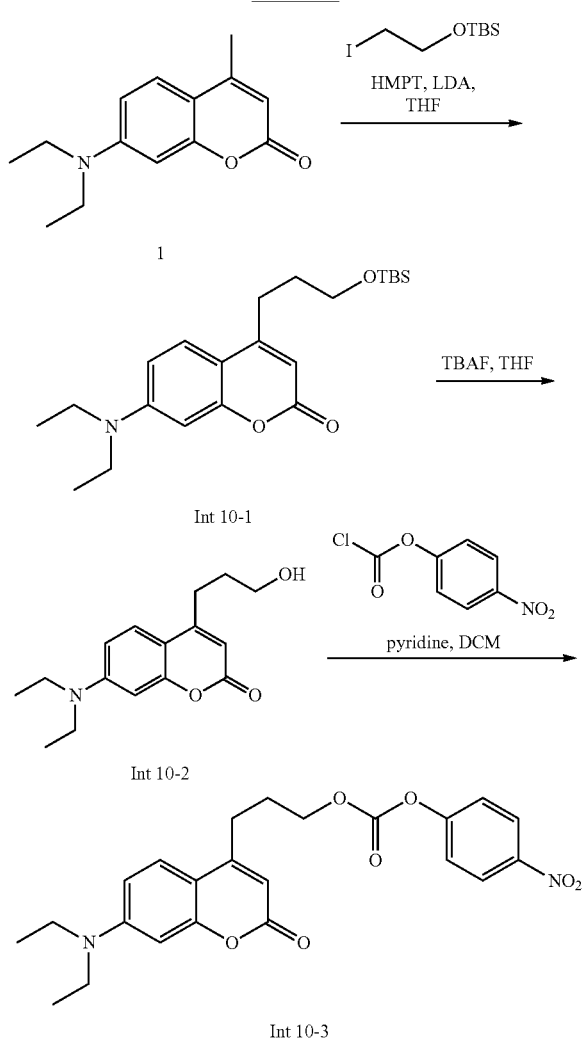

Scheme 10.

4-(3-((tert-butyldimethylsilyl)oxy)propyl)-7-(diethylamino)-2H-chromen-2-one (Int 10-1). To solution of LDA (2 M in hexanes, 32.4 mL, 1.50 eq.) in THF (50 mL) was added N-[bis(dimethylamino)phosphoryl]-N-methyl-methanamine (11.6 g, 64.9 mmol, 11.4 mL, 1.50 eq.) at 0° C. After stirring at 0° C. for 5 mins, a solution of 7-(diethylamino)-4-methyl-chromen-2-one (10.0 g, 43.2 mmol, 1.00 eq.) in THF (50 mL) was added slowly over 10 mins at 0° C. The resultant mixture was allowed to stir at 0° C. for 45 mins, and thereto was added a solution of tert-butyl-(2-iodoethoxy)-dimethyl-silane (12.4 g, 43.3 mmol, 1.00 eq.) in THF (50 mL) slowly at 0° C. The temperature was maintained for another 30 mins, then the mixture was warmed up to 30° C. slowly. After completion the mixture was quenched with saturated sodium bicarbonate (20 mL) and diluted with ethyl acetate (50 mL). The separated organic layer was dried over sodium sulfate, filtered and concentrated under reduced pressure to give a residue. The mixture was purified by column chromatography over silica gel (petroleum ether/ethyl acetate=50/1 to 3/1). The title intermediate Int 10-1 (5.00 g, 12.8 mmol, 30% yield) was obtained as a yellow gum. $^1$H NMR (400 MHz, chloroform-d) δ=7.46 (d, J=8.8 Hz, 1H), 6.58 (dd, J=2.4, 8.8 Hz, 1H), 6.50 (d, J=2.4 Hz, 1H), 5.94 (s, 1H), 3.71 (br t, J=5.6 Hz, 2H), 3.43 (q, J=7.2 Hz, 4H), 2.80-2.70 (m, 2H), 1.90-1.82 (m, 2H), 1.20 (t, J=7.2 Hz, 6H), 0.92 (s, 9H), 0.07 (s, 6H).

7-(diethylamino)-4-(3-hydroxypropyl)-2H-chromen-2-one (Int 10-2). To a solution of 4-[3-[tert-butyl(dimethyl)silyl]oxypropyl]-7-(diethylamino)chromen-2-one (5.00 g, 12.8 mmol, 4.00 eq.) in THF (100 mL) was added TBAF (1 M, 19.3 mL, 6.00 eq.). The reaction mixture was stirred at 30° C. for 2 hrs. The reaction mixture was diluted with water (200 mL) and extracted with ethyl acetate (200 mL×3). The combined organic layers were washed with brine (100 mL 2), dried over anhydrous sodium sulfate, filtered and concentrated under reduced pressure to give a residue. The residue was purified by column chromatography over silica gel (petroleum ether/ethyl acetate=10/1 to 1/1). Compound 7-(diethylamino)-4-(3-hydroxypropyl)chromen-2-one (0.27 g, 976 µmol, 30% yield, 99%/c purity) was obtained as a yellow oil. LC-MS [ESI, M+1]: 276.1. $^1$H NMR (400 MHz, chloroform-d) δ=7.46 (d, J=9.2 Hz, 1H), 6.60 (dd, J=2.4, 9.2 Hz, 1H), 6.50 (d, J=2.8 Hz, 1H), 6.0 (s, 1H), 3.78 (br t, J=5.6 Hz, 2H), 3.40 (q, J=7.2 Hz, 4H), 2.84-2.78 (m, 2H), 1.98-1.88 (m, 2H), 1.63-1.57 (m, 1H), 1.22 (t, J=7.2 Hz, 6H).

3-(7-(diethylamino)-2-oxo-2H-chromen-4-yl)propyl (4-nitrophenyl) carbonate (Int 10-3). The title intermediate was prepared analogously to Int 5-1, using Int 10-2, to afford an orange solid. LC-MS [ESI, M+1]: 441.2. $^1$H NMR (600 MHz, DMSO-d$_6$) δ 8.36-8.29 (m, 2H), 7.60-7.52 (m, 3H), 6.69 (dd, J=9.0, 2.6 Hz, 1H), 6.52 (d, J=2.6 Hz, 1H), 5.97 (d, J=0.9 Hz, 1H), 4.35 (t, J=6.4 Hz, 2H), 3.43 (q, J=7.0 Hz, 4H), 2.86-2.79 (m, 2H), 2.11-2.00 (m, 2H), 1.12 (t, J=7.0 Hz, 6H).

3-(7-(diethylamino)-2-oxo-2H-chromen-4-yl)propyl benzylcarbamate (300). The title compound was prepared analogously to 78, using Int 10-3 and benzylamine as starting materials. LC-MS [ESI, M+1]: 409.3. $^1$H NMR (600 MHz, DMSO-d$_6$) δ 7.74 (t, J=6.2 Hz, 1H), 7.53 (d, J=9.0 Hz, 1H), 7.32 (t, J=7.6 Hz, 2H), 7.29-7.20 (m, 3H), 6.67 (dd, J=9.1, 2.6 Hz, 1H), 6.52 (d, J=2.5 Hz, 1H), 5.92 (s, 1H), 4.20 (d, J=6.2 Hz, 2H), 4.05 (t, J=6.4 Hz, 2H), 3.43 (q, J=7.0 Hz, 4H), 2.76 (t, J=7.7 Hz, 2H), 1.90 (t, J=7.6 Hz, 2H), 1.13 (t, J=7.0 Hz, 6H).

3-(7-(diethylamino)-2-oxo-2H-chromen-4-yl)propyl (pyridin-4-ylmethyl)carbamate (301). The title compound was prepared analogously to 78, using Int 10-3 and pyridin-4-ylmethanamine as starting materials. LC-MS [ESI, M+1]: 410.2. $^1$H NMR (600 MHz, DMSO-d$_6$) δ 8.76 (s, 2H), 8.27 (d, J=8.1 Hz, 1H), 7.92 (t, J=6.0 Hz, 1H), 7.53 (d, J=9.0 Hz, 1H), 6.68 (dd, J=9.0, 2.6 Hz, 1H), 6.52 (d, J=2.5 Hz, 1H), 5.91 (s, 1H), 4.37 (d, J=6.1 Hz, 2H), 4.06 (t, J=6.5 Hz, 2H), 3.43 (q, J=7.0 Hz, 4H), 2.75 (dd, J=14.1, 6.5 Hz, 2H), 1.91 (p, J=6.7 Hz, 2H), 1.13 (t, J=7.0 Hz, 6H).

3-(7-(diethylamino)-2-oxo-2H-chromen-4-yl)propyl (3-carbamoylbenzyl)carbamate (302). The title compound was prepared analogously to 78, using Int 10-3 and 3-(aminomethyl)benzamide as starting materials. LC-MS [ESI, M+1]: 452.2. $^1$H NMR (600 MHz, DMSO-d$_6$) δ 7.95 (s, 1H), 7.82-7.71 (m, 3H), 7.53 (d, J=9.0 Hz, 1H), 7.46-7.36 (m, 2H), 7.34 (s, 1H), 6.67 (dd, J=9.1, 2.6 Hz, 1H), 6.52 (d, J=2.6 Hz, 1H), 5.92 (s, 1H), 4.24 (d, J=6.2 Hz, 2H), 4.06 (t, J=6.4 Hz, 2H), 3.43 (q, J=7.0 Hz, 4H), 2.75 (q, J=6.9, 6.1 Hz, 2H), 1.90 (p, J=6.7 Hz, 2H), 1.12 (t, J=7.0 Hz, 6H).

3-(7-(diethylamino)-2-oxo-2H-chromen-4-yl)propyl (3-sulfamoylbenzyl)carbamate (303). The title compound was prepared analogously to 78, using Int 10-3 and 3-(aminomethyl)benzenesulfonamide as starting materials. LC-MS [ESI, M+1]: 488.3. $^1$H NMR (600 MHz, DMSO-d$_6$) δ 7.86 (t, J=6.2 Hz, 1H), 7.77-7.68 (m, 2H), 7.58-7.47 (m, 2H), 7.48 (dd, J=7.8, 1.5 Hz, 1H), 7.36 (s, 2H), 6.69 (dd, J=9.0, 2.5 Hz, 1H), 6.52 (d, J=2.5 Hz, 1H), 5.92 (s, 1H), 4.27 (d, J=6.2 Hz, 2H), 4.06 (t, J=6.5 Hz, 2H), 3.43 (q, J=7.0 Hz, 4H), 2.76 (q, J=7.5 Hz, 2H), 1.91 (p, J=6.7 Hz, 2H), 1.13 (t, J=7.0 Hz, 6H).

3-(7-(diethylamino)-2-oxo-2H-chromen-4-yl)propyl (3-(1H-imidazol-4-yl)benzyl)carbamate (304). The title compound was prepared analogously to 78, using Int 10-3 and (3-(1H-imidazol-4-yl)phenyl)methanamine as starting materials. LC-MS [ESI, M+1]: 475.3. $^1$H NMR (600 MHz, DMSO-d$_6$) δ 9.20 (s, 1H), 8.14 (s, 1H), 7.80 (t, J=6.1 Hz, 1H), 7.74-7.66 (m, 2H), 7.57-7.44 (m, 2H), 7.39-7.32 (m, 1H), 6.66 (dd, J=9.1, 2.6 Hz, 1H), 6.52 (d, J=2.6 Hz, 1H), 5.92 (s, 1H), 4.76 (s, 1H), 4.27 (d, J=6.1 Hz, 2H), 4.06 (t, J=6.5 Hz, 2H), 3.42 (q, J=7.1 Hz, 4H), 2.76 (dd, J=16.2, 8.5 Hz, 2H), 1.91 (p, J=6.6 Hz, 2H), 1.12 (t, J=7.0 Hz, 6H).

3-(3-((((3-(7-(diethylamino)-2-oxo-2H-chromen-4-yl)propoxy)carbonyl)amino)methyl)phenyl)propanoic acid (305). The title compound was prepared analogously to 78, using Int 10-3 and 3-(3-(aminomethyl)phenyl)propanoic acid as starting materials. LC-MS [ESI, M+1]: 481.3. $^1$H NMR (600 MHz, DMSO-d$_6$) δ 7.70 (t, J=5.8 Hz, 1H), 7.54 (d, J=9.0 Hz, 1H), 7.23 (t, J=7.6 Hz, 1H), 7.15-7.06 (m, 3H), 6.67 (dd, J=9.0, 2.6 Hz, 1H), 6.52 (d, J=2.5 Hz, 1H), 5.92 (s, 1H), 4.17 (d, J=6.2 Hz, 2H), 4.05 (t, J=6.4 Hz, 2H), 3.43 (q, J=7.0 Hz, 5H), 2.78 (dt, J=24.4, 7.8 Hz, 4H), 1.90 (p, J=6.7 Hz, 2H), 1.33-1.22 (m, 1H), 1.13 (t, J=7.0 Hz, 6H).

Methyl 3-(3-(((((3-(7-(diethylamino)-2-oxo-2H-chromen-4yl)propoxy)carbonyl)amino)methyl)phenyl)propanoate (306). The title compound was prepared analogously to 78, using Int 10-3 and methyl 3-(3-(aminomethyl)phenyl)propanoate as starting materials. LC-MS [ESI, M+1]: 495.3.

3-(3-((3-(2-(7-(diethylamino)-4-methyl-2-oxo-2H-chromen-3-yl)ethyl)ureido)methyl)phenyl)propanoic acid (307). The tide compound was prepared analogously to 98, using 3-(3-(aminomethyl)phenyl)propanoic acid. LC-MS [ESI, M+1]: 480.3.

Methyl 3-(3-((3-(2-(7-(diethylamino)-4-methyl-2-oxo-2H-chromen-3-yl)ethyl)ureido)methyl)phenyl)propanoate (308). The title compound was prepared analogously to 98, using methyl 3-(3-(aminomethyl)phenyl)propanoate. LC-MS [ESI, M+1]: 494.3.

3-(3-((((2-(7-(diethylamino)-4-methyl-2-oxo-2H-chromen-3-yl)ethoxy)carbonyl)amino)methyl)phenyl)propanoic acid (309). The title compound was prepared analogously to 78, using 3-(3-(aminomethyl)phenyl)propanoic acid. LC-MS [ESI, M+1]: 481.3. $^1$H NMR (600 MHz, DMSO-d$_6$) δ 7.73 (t, J=6.2 Hz, 1H), 7.54 (d, J=9.1 Hz, 1H), 7.23 (t, J=7.9 Hz, 1H), 6.82 (t, J=2.0 Hz, 1H), 6.77 (dd, J=8.2, 2.6 Hz, 1H), 6.68 (dd, J=9.1, 2.6 Hz, 1H), 6.52 (d, J=2.6 Hz, 1H), 4.64 (s, 2H), 4.17 (d, J=6.2 Hz, 2H), 3.43 (q, J=7.0 Hz, 5H), 2.80-2.71 (m, 2H), 1.13 (t, J=7.0 Hz, 6H).

Methyl 3-(3-((((2-(7-(diethylamino)-4-methyl-2-oxo-2H-chromen-3-yl)ethoxy)carbonyl)amino)methyl)phenyl)propanoate (310). The title compound was prepared analogously to 78, using methyl 3-(3-(aminomethyl)phenyl)propanoate. LC-MS [ESI, M+1]: 495.3.

2-(3-((3-(2-(7-(diethylamino)-4-methyl-2-oxo-2H-chromen-3-yl)ethyl)ureido)methyl)phenoxy)acetic acid (311). The title compound was prepared analogously to 98, using 2-(3-(aminomethyl)phenoxy)acetic acid. LC-MS [ESI, M+1]: 482.3. $^1$H NMR (600 MHz, DMSO-$d_6$) δ 7.52 (d, J=9.1 Hz, 1H), 7.19 (t, J=7.8 Hz, 1H), 6.84-6.72 (m, 3H), 6.69 (dd, J=9.1, 2.6 Hz, 1H), 6.49 (d, J=2.6 Hz, 1H), 6.32 (s, 1H), 6.04 (s, 1H), 4.64 (s, 2H), 3.42 (q, J=7.0 Hz, 4H), 3.15 (t, J=6.8 Hz, 2H), 2.65 (t, J=6.9 Hz, 2H), 2.32 (s, 3H), 1.12 (t, J=7.0 Hz, 6H).

Methyl 2-(3-((3-(2-(7-(diethylamino)-4-methyl-2-oxo-2H-chromen-3-yl)ethyl)ureido)methyl)phenoxy)acetate (312). The title compound was prepared analogously to 98, using methyl 2-(3-(aminomethyl)phenoxy)acetate. LC-MS [ESI, M+1]: 496.3.

General Biological Methods and Materials

Recombinant proteins were expressed in E. coli and purified as previously described (4). WIL-FL K83C and JTO-FL K83C were conjugated with fluorescein maleimide (Vector Laboratories) and the labeled proteins, WIL-FL* and JTO-FL*, respectively, purified by ion exchange chromatography. From 400 mL of bacterial culture, we obtained approximately 40 mg (1.7 μmol monomer equivalent) of pure, natively folded WIL-FL K79C. 500 nmol of this LC was reacted with 2 equivalents of fluorescein maleimide, yielding 420 nmol of WIL-FL* after repurification. 75 nmol of JTO-FL* was produced at similar overall yield. The screening campaign required 223 nmol of WIL-FL* and 40 nmol of JTO-FL*. Proteolysis assays were generally carried out by incubating LC (10 μM for unlabeled LCs, 20 nM for fluorescein-labeled LCs) with proteinase K (Thermo Fisher, 200 nM), in PBS at 37° C. or ambient temperature (22° C.) for screening. FP was measured using either a Jasco 8600 fluorimeter ($\lambda_{ex}$=488 nm, $\lambda_{em}$=520 nm) or Perkin Elmer EnVision plate reader equipped with polarizing excitation and emission filters ($\lambda_{ex}$=485±20 nm, $\lambda_{em}$=535±20 nm) and a 505 nm dichroic mirror. FP values were calculated using the formula:

$$P = G\frac{FS - FP}{FS + FP}$$

P is the polarization, and FP are the emission intensities of parallel and perpendicular-polarized light, respectively, and G is a dye- and instrument-specific correction factor. Values are reported as mP. For the high-throughput screen, 653,085 small molecules from the Scripps Florida screening library were assayed in 1536-well plates. Final LC concentration was 10 nM in 5 μl. Small molecules were added by pintool from DMSO stock plates to a final concentration of 6.8 μM compound and 0.68% DMSO. Fluorogenic binding of 1 to LCs was measured using a Molecular Devices Gemini platereader ($\lambda_{ex}$=373 nm, $\lambda_{em}$=480 nm). Crystals of JTO-FL were grown via sitting-drop vapor diffusion using a crystallization buffer consisting of 20% PEG 3350 and 0.2 M $NH_4H_2PO_4$ at 23° C. To generate JTO-FL•1 complexes, crystals of apo JTO-FL were soaked with a tenfold molar excess of 1 for 10 days. Diffraction data were collected at 80 K and a wavelength of 1.0332 Å at beamline 23-ID-D (for apo JTO-FL) or 23-ID-B (for JTO-FL•1) at the Advanced Photon Source (Argonne, IL). The refined models were deposited in the Protein Data Bank under accession codes 6MG4 for apo JTO-FL and 6MG5 for JTO-FL•1. All samples for NMR were buffered in 50 mM Bis Tris, pH 6.4, 1 mM EDTA, 10% $D_2O$. $^1$H, $^{15}$N experiments were recorded at 37° C. on a 14.1 T Bruker AVANCE III HD spectrometer equipped with a cryogenically cooled x,y,z gradient probe. SV-AUC, unfolding and aggregation experiments were performed as previously described (4).

Protein expression and purification. Full-length LCs were expressed as inclusion bodies in E. coli as previously described (1). Briefly, inclusion bodies were isolated from cells by five rounds of sonication and centrifugation; dissolved in 4 M GuHCl containing 5 mM DTT; refolded by dropwise dilution into Tris-Cl at pH 8.5 containing 5 mM reduced glutathione and 0.5 mM oxidized glutathione; and purified by ammonium sulfate precipitation followed by ion exchange and size exclusion chromatography. LC V-domains were expressed in the periplasm of E. coli using a pelB leader sequence; isolated by periplasmic shock; and purified by ammonium sulfate precipitation followed by ion exchange and size exclusion chromatography.

ALMC2 LC was purified after secretion from the ALMC2 plasma cell line (2). ALMC2 cells were grown in Iscove's modified Dulbecco's media (IMDM) containing 5% fetal bovine serum (FBS), 292 μg/ml glutamine, 100 U/ml penicillin, 100 μg/ml streptomycin and 2 ng/ml nM interleukin-6 (Thermo). Approximately 450,000,000 cells (300 ml of culture) were pelleted and resuspended in 300 ml of IMDM lacking FBS and phenol red indicator, but containing glutamine, penicillin, streptomycin and interleukin-6. Cells were allowed to secrete protein for 24 h, after which cells were removed by centrifugation and filtration. Media containing ALMC2 LC was dialyzed overnight against 25 mM Tris-Cl, pH 8. LC was concentrated by ion exchange chromatography using a FastflowQ column (GE). ALMC IgG was removed by passing the eluate through a protein A column (GE), and the LC was dialyzed and then purified by ion exchange chromatography using a MonoQ column (GE).

5J8 Fab was expressed in HEK293F suspension cells and purified by Ni-NTA and ion exchange chromatography as previously described (3).

Protein labeling. Surface-exposed cysteine residues were incorporated into LCs by mutation using the Novagen QuikChange or NEB SDM mutagenesis protocols according to the manufacturers' instructions. LCs (20-50 μM) were expressed as described above and conjugated with fluorescein by reaction with equimolar fluorescein maleimide (Vector Laboratories) for 1 h at room temperature (22° C.). Unreacted fluorescein was removed by ion exchange chromatography. Labeling efficiency was determined to be 50% by absorbance spectroscopy, corresponding to a single fluorescein molecule per LC dimer. LC misfolding (4) or modification of K83C LCs by glutathione upon refolding may account for some of the heterogeneity in the conjugated protein product. Experiments (FIG. 1) showed that proteolysis of the LCs resulted in a sufficiently large change in fluorescence polarization, so we did not attempt to optimize the labeling and purification further.

Proteolysis assays. Unless otherwise described, LCs were incubated with proteinase K (100 nM; Thermo) in phosphate buffered saline (PBS, 10 mM $Na_2HPO_4$, 1.8 mM $KH_2PO_4$, 137 mM NaCl, and 2.7 mM KCl, pH 7.4), after which the reaction was quenched with phenylmethyl sulfonyl fluoride (100 μM) and remaining LC quantified by SDS-PAGE or fluorescence polarization. The experiment in FIG. 1b measured simultaneous proteolysis of labeled and unlabeled LC by adding 20 nM WIL-FL* or JTO-FL* to 5 μM WIL-FL or JTO-FL, respectively. Fluorescein fluorescence images of the SDS-PAGE gels were recorded, after which the gels were Coomassie stained and imaged. Gel images shown have had their contrast increased after quantification for clarity.

Fluorescence polarization measurements. FP in cuvettes was measured in a Jasco 8600 fluorimeter fitted with polarizing filters and excitation and emission monochromators, using an excitation wavelength of 488 nm and emission wavelength of 520 nm. FP on plates was measured using a Perkin Elmer EnVision plate reader equipped with polarizing excitation and emission filters ($\lambda_{ex}$=485±20 nm, $\lambda_{em}$=535±20 nm) and a 505 nm dichroic mirror. Fluorescein-labeled LC (20 nM) in PBS containing 0.02% (v/v) Pluronic F-127 detergent (Thermo) was used for all measurements. Fluorescence polarization was calculated using the formula:

$$P = G\frac{FS - FP}{FS + FP}$$

P is the polarization, FS and FP are the emission intensities of parallel and perpendicular-polarized light, respectively, and G is a dye- and instrument-specific correction factor. Total fluorescence was calculated using the formula:

$$TF = FS + 2FP$$

Addition of detergent appears to prevent denaturation of the LC upon binding to the polystyrene surface of the plate, since it did not affect the kinetics of proteolysis in quartz cuvettes.

Pilot screen. For screening in a plate format, each compound's effect on the PK proteolysis of WIL-FL* was measured by FP after 24 h incubation at room temperature (typically 22° C.). The measured FP was normalized platewise by comparing the compound wells to high and low control wells on each plate (n=32). The high FP control wells contained JTO-FL* and DMSO vehicle without proteinase K. Low FP control wells contained WIL-FL*, DMSO vehicle and proteinase K, to determine the rate of proteolysis of unliganded WIL-FL*. Percent activity was calculated for each plate using the formula:

$$\text{Percent actitvity} = 100 \times \frac{\text{Test well} - \text{median(data wells)}}{\text{Median (high control)} - \text{median(data wells)}}$$

To screen the commercial library, WIL-FL* and JTO-FL* in PBS, pH 7.4, containing 0.02% Pluronic F-127 detergent were dispensed into black polystyrene microplates (Greiner catalog #788076) using a Beckman Coulter BioRAPTR Final LC concentration was 20 nM in 10 µl, equivalent to 10 nM fluorescein. Compounds (n=1) were added by 50 nl pintool from 10 mM DMSO stock solutions using a Beckman Coulter BioMek robot for a final concentration of 10 µM compound and 0.5% DMSO. Plates were incubated at room temperature (22° C.) for 10 min to allow compounds to dissolve, after which proteinase K was dispensed to a final concentration of 500 nM. Plates were centrifuged at 1000 rpm for 1 minute, stacked, wrapped to minimize evaporation, and incubated for 24 h at 22° C. FP was measured as described above. We used hits from the commercial library screen (compounds 17 and 18,) to validate the assay for use on 1,536-well plates.

Primary screen. 653,085 small molecules from the Scripps Florida screening library were screened using the PCFP assay in 1,536-well plates. Final LC concentration was 10 nM in 5 µl. Small molecules were added by pintool from DMSO stock plates to a final concentration of 6.75 µM compound and 0.675% DMSO. Activity relative to the high control (JTO-FL* with no protease) and low control (WIL-FL* with DMSO vehicle) was calculated using equation 3, above. 2,779 small molecules were selected as hits based on an activity greater than three standard deviations above the mean activity of the plate. This result corresponds to an initial hit rate of 0.4%. Assay performance was consistent with a platewise average Z' of 0.75 t 0.03 and an average signal-to-background ratio of 1.36±0.02 (mean±sd, n=526 plates). Two compounds were unavailable for further study, so 2,777 small molecules were replated at 10 mM in DMSO to create a stock plate for secondary screens.

Secondary screens. We used three rounds of secondary screening to remove false positive hits from the primary screen. The 2,777 small molecules identified in the primary screen were used for each secondary screen.

Firstly, the PCFP assay was repeated in triplicate with each of the 2,777 primary screening hits, with an average Z' of 0.71±0.03. We identified 1,422 molecules with >20.6% activity (the mean plus three standard deviations of this dataset). Note that many compounds show apparent protection greater than the JTO-FL* positive control, which we attribute to autofluorescence of the small molecule affecting the FP measurement.

Figure 1B:
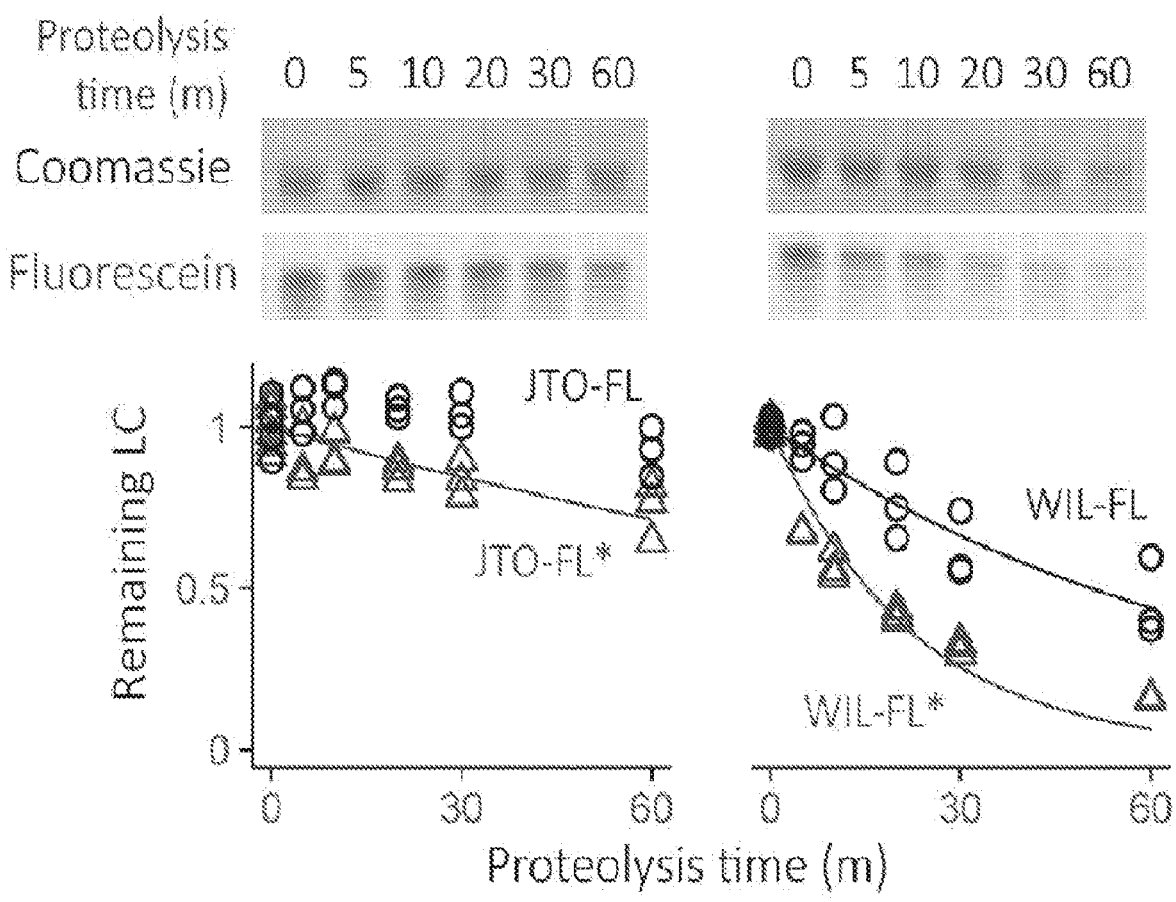
Figure 1C:
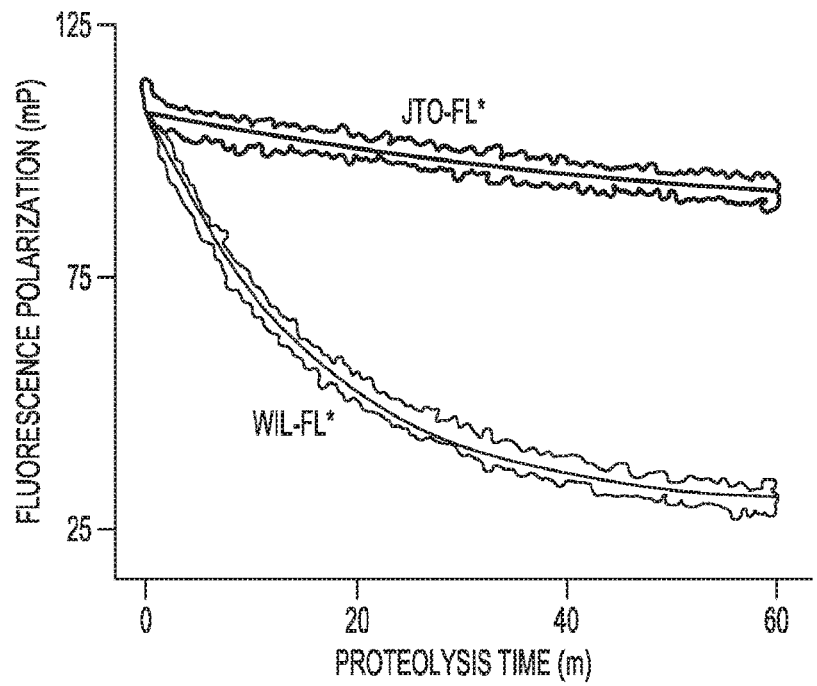
Figure 1D:
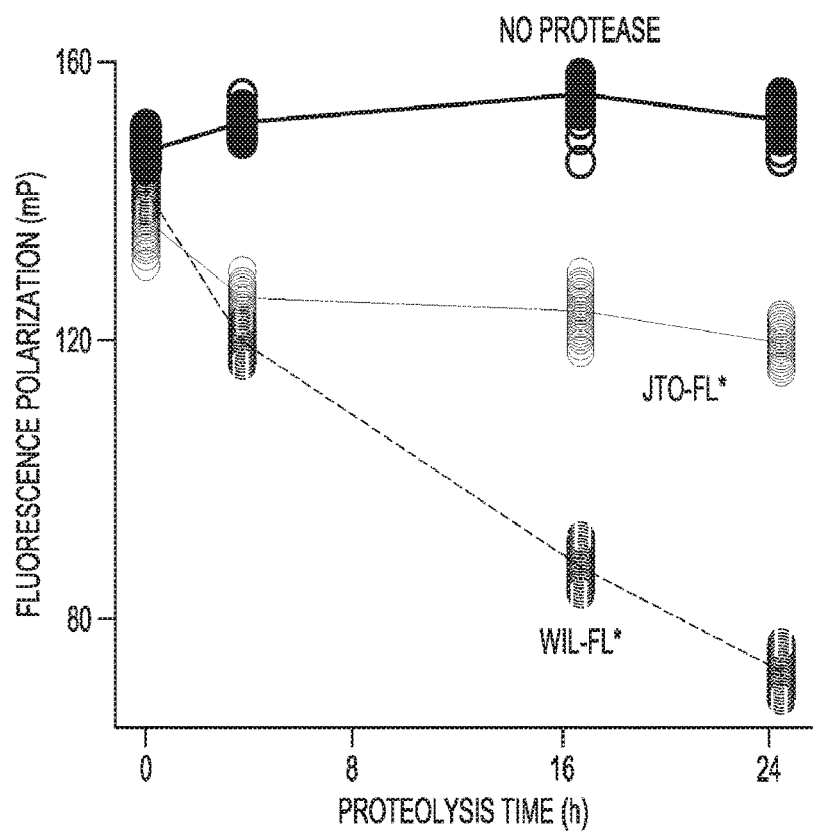
Figure 1E:
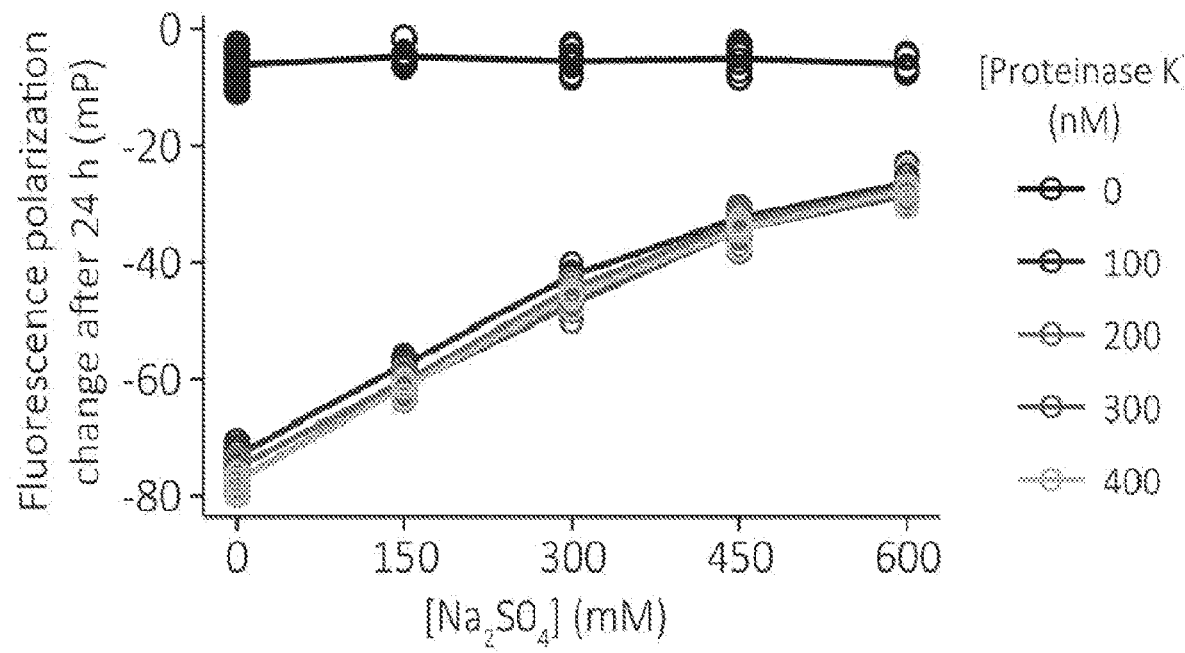
Figure 1F:
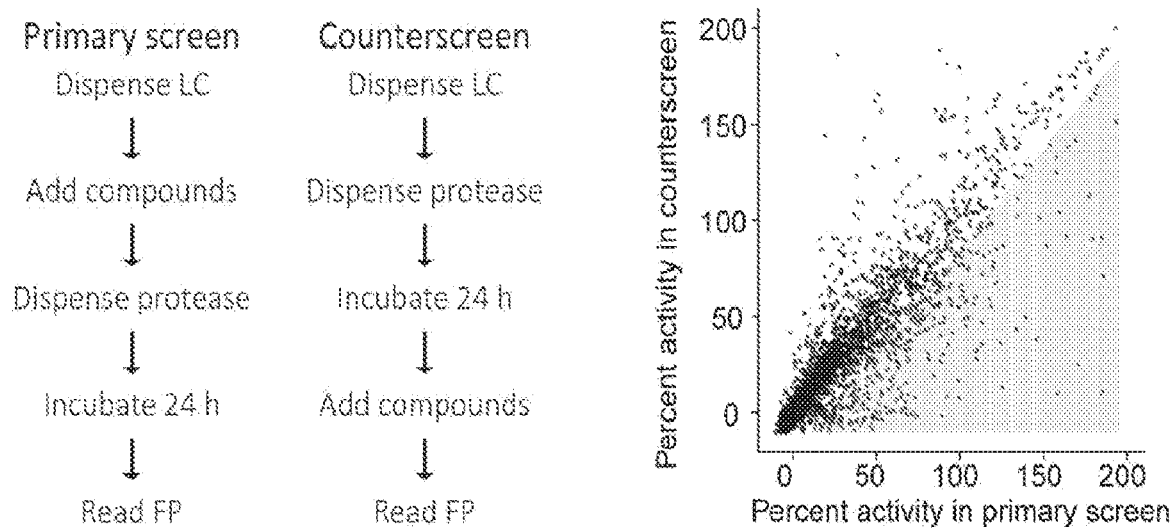

Secondly, to remove compounds that interfere with the FP measurement, the primary screen was repeated in triplicate but compounds were added after 24 h of proteinase K treatment (FIG. 1f). This assay had an average Z' of 0.73±0.01. Bona fide hits should retain no FP beyond the low control. Six hundred sixty two small molecules that showed 1.25-fold lower mean activity in this assay compared to the secondary screen described in the previous paragraph were retained.

Thirdly, to remove molecules that inhibit proteinase K, the assay was repeated in triplicate using 100 nM thermolysin (Thermo). The assay was carried out in 50 mM Tris-Cl, pH 7.5, containing 150 mM NaCl, 100 µM ZnCl$_2$, 100 µM CaCl$_2$ and 0.02% v/v Pluronic F-127 detergent. The additional metal ions were added to bind to ion-chelating small molecules and prevent them from inhibiting the metalloproteinase. This assay yielded an average Z' of 0.64±0.02. We identified 1,578 compounds that were active in this assay, which we define as >20% activity (mean plus three standard deviations of this dataset). Of these, 1,243 molecules showed similar activity against PK and thermolysin.

Two hundred sixty nine molecules that passed all three secondary screens were retained for further analysis. We also retained 147 additional molecules that passed the FP artefact secondary screen but failed one of the two other secondary screens assessing protease inhibition (PCFP with PK or with thermolysin).

The concentration-dependence assay employed the same reagents, protocols, and detection systems as the secondary assays, but tested each of the selected compounds as 10-point dose-response titrations (3-fold dilutions) in triplicate, in each of the three formats described above. A four-parameter equation describing a sigmoidal dose-response curve was then fitted with adjustable baseline using Assay Explorer software (Symyx Technologies Inc.). The reported EC$_{50}$ values were generated from fitted curves by solving for the X-intercept value at the 50% activation level of the Y-intercept value. Small molecules which showed similar concentration dependent FP retention in the PK and thermolysin screens and contrasting activity in the FP artefact counterscreen were retained.

All compounds used for titration assays were analyzed by LC-MS to confirm purity and identify mass. Of the 416 samples submitted for LC-MS analysis, 386 samples confirmed mass, i.e., the molecular weight of the structure in Scripps' database matched that identified by LC-MS analysis of the screening sample. As determined by nominal methods (UV-vis spectroscopy, MS and ELSD), 379 samples demonstrated purity of >80%.

Protease inhibition assay. PK (5 µl of 200 nM), or buffer without protease, were dispensed into wells of a microplate. Compounds were added by pintool (n=2) and incubated for 5 min at room temperature (22° C.). Five µl of EnzCheck Red fluorogenic protease substrate (Thermo) were dispensed into the wells. Fluorescence ($\lambda$ex=580 nm, $\lambda$em=620 nm) was read at 30 sec intervals for 5 min. An increase in fluorescence indicated protease activity. Some compounds exhibit an apparently higher protease activity than vehicle, which we attribute to autofluorescence.

Equilibrium dialysis. Eight compounds were dialyzed against 20 µM WIL-FL in PBS containing 0.02% Pluronic F-127 detergent in 8 kDa-cutoff Rapid Equilibrium Dialysis cartridges (Thermo) for 4 h according to the manufacturers' instructions. Small molecule concentrations inside and outside the dialysis cartridge were measured by reverse phase HPLC and dissociation constants calculated using the equation:

$$K_D = \frac{[LC] \times [Ligand_{out}]}{[Ligand_{in}] - [Ligand_{out}]}$$

[LC] is the LC concentration inside the dialysis cartridge, [$Ligand_{in}$] and [$Ligand_{out}$] are the measured small molecule concentrations inside and outside the dialysis cartridge, respectively.

Isothermal Titration Calorimetry (ITC). WIL-FL was dialyzed into PBS, and the dialysate was filtered and used to dilute the LC and small molecules for ITC analysis. DMSO and Pluronic F-127 concentrations were matched as closely as possible between the protein and ligand solutions. Small molecule (100 µM) was titrated into 20 µM LC (monomer equivalent) with a Microcal Auto ITC 200. Heats were analyzed using Origin software (OriginLab Corporation).

Fluorogenic coumarin titration. LCs were concentrated to 200 µM in centrifugal concentrators with a 10 kDa membrane, unless the available material was limiting. 1.5-fold serial dilutions of LCs in PBS containing 1 µM 1 and 0.02% (v/v) Pluronic F-127 were prepared in 384-well plates. Fluorescence of 1 was measured on a Gemini plate reader (Molecular Devices) using an excitation wavelength of 373 nm and emission wavelength of 445 nm. Data were normalized platewise to the plateau fluorescence value for WIL-FL to calculate the fraction of 1 bound. These data were initially fit to a 2-state, 1-site binding equation:

$$\text{fraction bound} = \frac{[LC]}{K_{D\ ligand} \times [LC]}$$

Figure 2A:
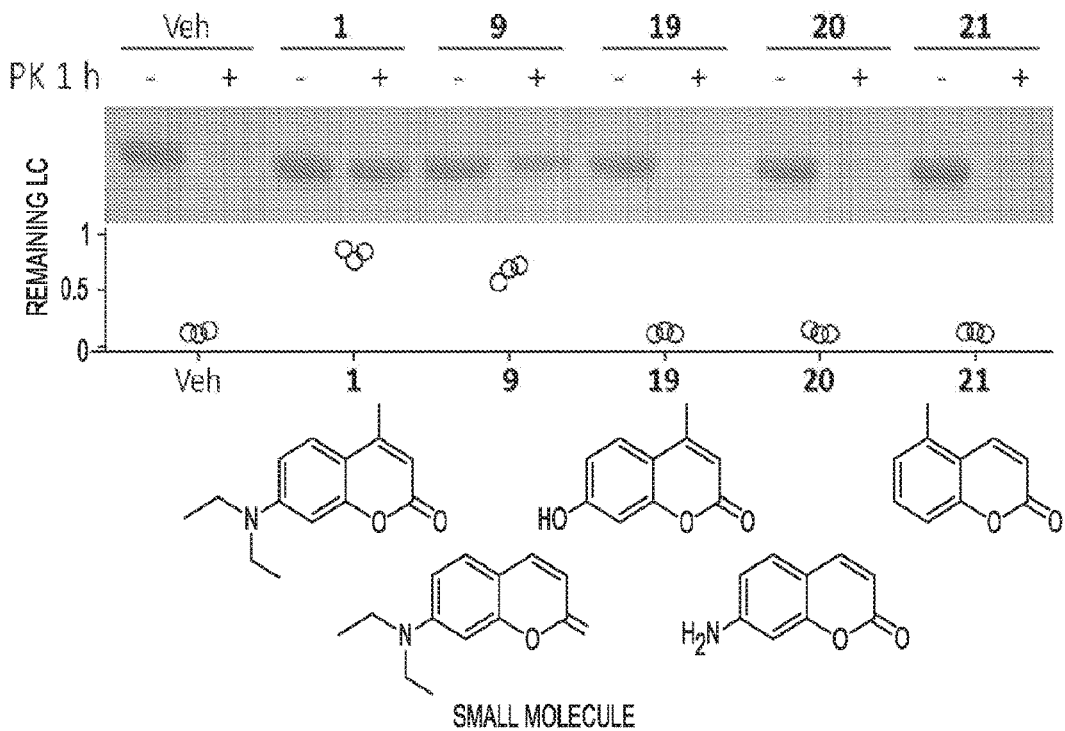
FIG. 2: 7-Diethylamino-4-methylcoumarin (1) is an environment-sensitive fluorophore that stabilizes LCs. a) SDS-PAGE gel showing proteolysis of unlabeled WIL-FL (10 µM) in the presence of 1% DMSO vehicle and 100 µM small molecule; t=2 h. Modifications to the core coumarin structure (21) are shown in red for each small molecule. b) Fluorescence emission (A, =373 nm) of 1 (1 µM), but not 19 (1 µM), increases in the presence of unlabeled WIL-FL (20
Figure 2B:
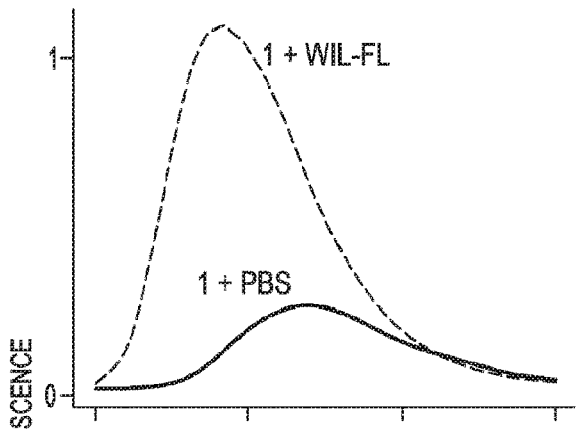
Figure 2B:
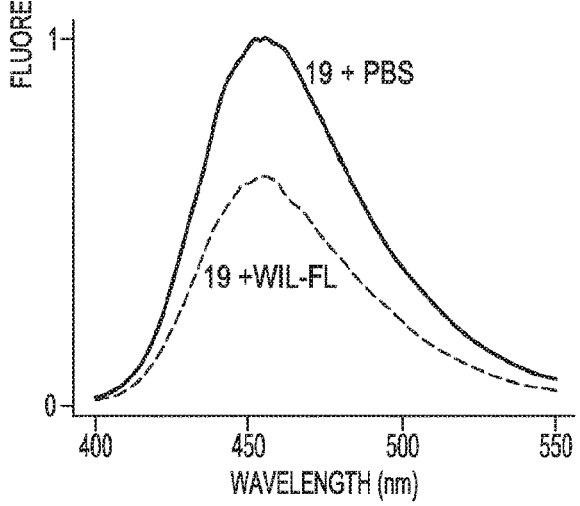
Figure 2C:
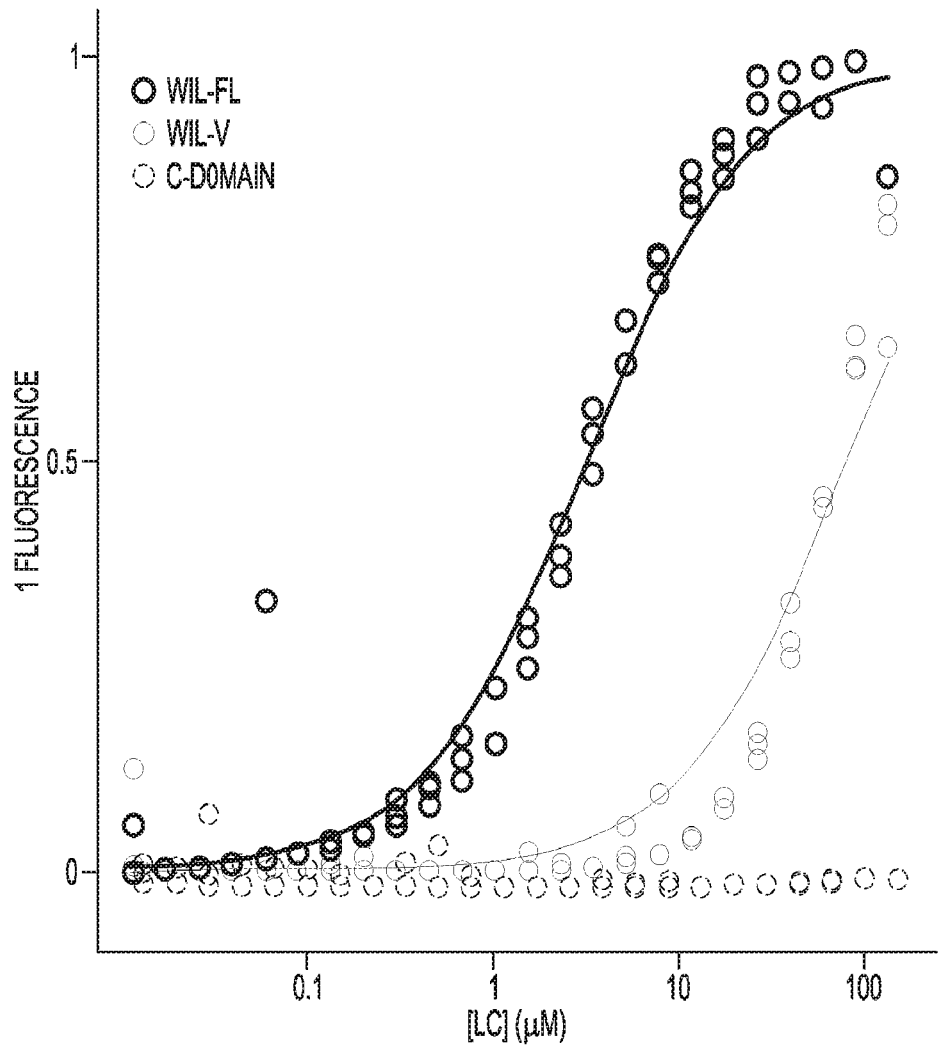
Figure 2D:
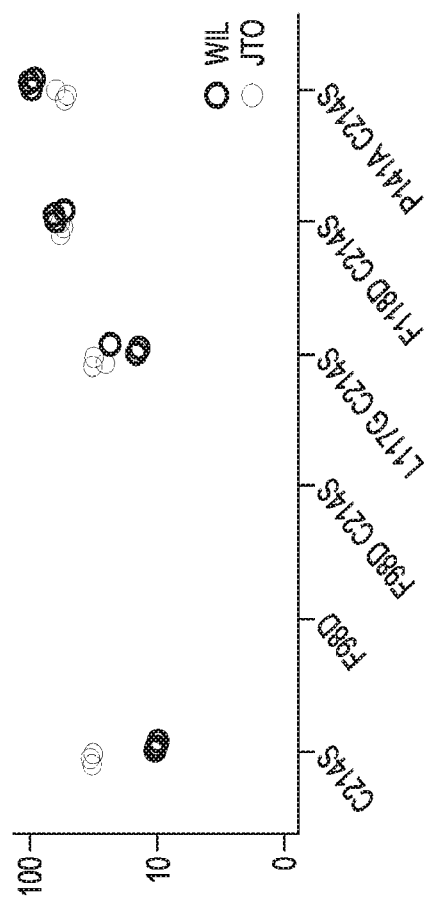
Figure 2D:
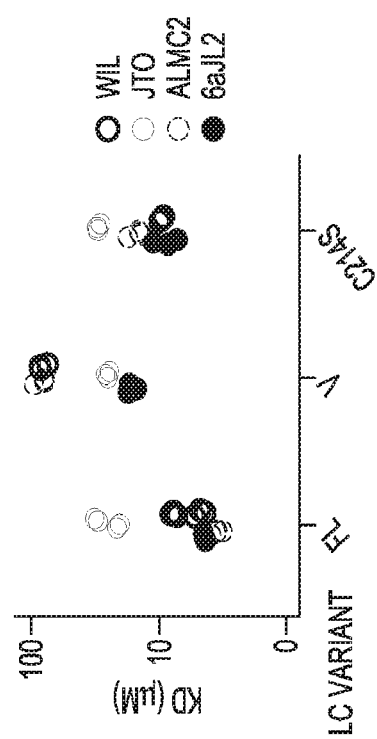
Figure 2E:
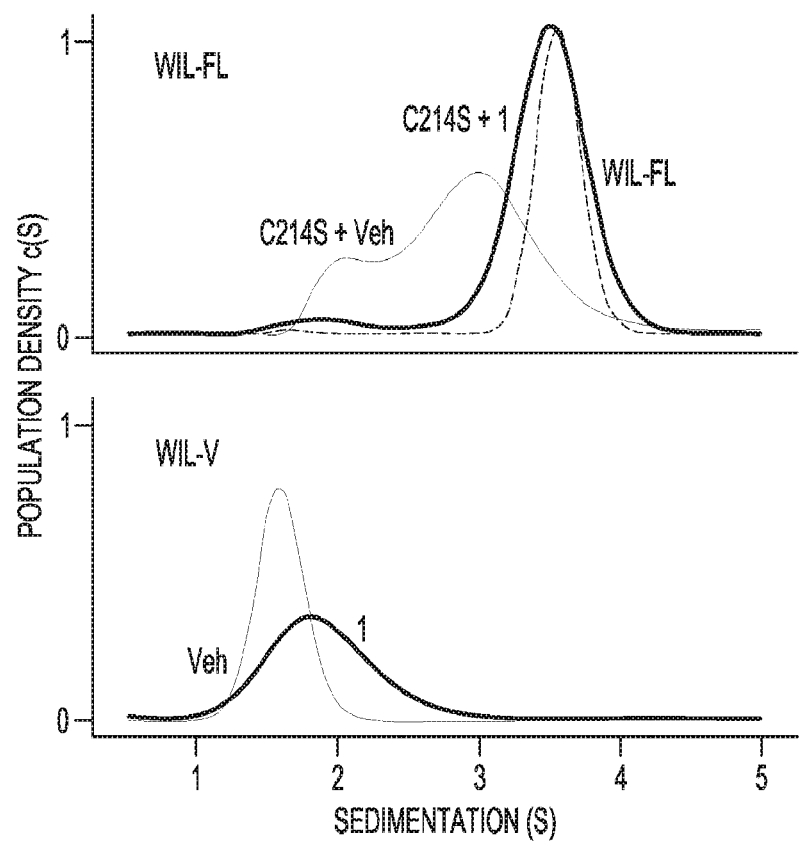

$K_{D\ ligand}$ is the LC•1 dissociation constant. For LCs lacking an inter-chain disulfide bond, 1 binds to the dimer and shifts the monomer-dimer equilibrium towards dimer (FIG. 2e). To estimate the affinity of the e fit the fluorescence data to a 3-state, 1-site binding equation:

$$\text{fraction bound} = \frac{[LC]^2 / K_{D\ dimerization}}{K_{D\ ligand} \times [LC]^2 / K_{D\ dimerization}}$$

The dimerization dissociation constant, $K_{D\ ligand}$, is constrained to 1-10 µM based on NMR affinity measurements (5).

Analytical Ultracentrifugation (AUC). WIL-FL and WIL-V (20 µM) in PBS containing either 0.5% DMSO vehicle or 100 µM 1 were run in a Beckman XL-1 analytical ultracentrifuge at 50,000 rpm at 20° C. Sedimentation was measured by absorbance at 280 nm. Data were processed using SedFit (6).

Crystal structure determination. Purified JTO-FL was concentrated to 200 µM and subjected to crystallization trials using the high-throughput robotic Rigaku CrystalMation platform at The Scripps Research Institute. Crystals of JTO-FL were grown via sitting-drop vapor diffusion using a crystallization buffer consisting of 20% PEG 3350 and 0.2 M $NH_4H_2PO_4$ at 23° C. Both diamond-shaped and plate-shaped crystals were generated in the same drop using these conditions, but only the plate-shaped crystals produced usable diffraction data. To generate JTO-FL•1 complexes, crystals of apo JTO-FL were soaked with a tenfold molar excess of 1 for 10 days. Crystals were harvested and immediately flash cooled in liquid nitrogen.

Diffraction data were collected from crystals at 80 K and a wavelength of 1.0332 Å at beamline 23-ID-D (for apo JTO-FL) or 23-ID-B (for JTO-FL•1) at the Advanced Photon Source (Argonne, IL). Frames were indexed and integrated using HKL-2000 (7) (for apo JTO-FL) or XDS (8) (for JTO-FL•1), the space group was assigned as $P2_12_12_1$ using Pointless, and data were scaled in Scala (9). Five percent of reflections (randomly distributed) were flagged for model cross-validation using $R_{free}$ (10).

The apo JTO-FL structure was solved to 1.75 Å resolution by molecular replacement (MR) with Phaser (11), using the existing full-length CLE light chain structure (12) (PDB: 1LIL) as the search model. The JTO-FL•1 structure was similarly solved to 1.8 Å resolution with MR using apo JTO-FL as the search model. Both models were refined with iterative cycles of manual adjustment in Coot (13), and refinement in Refmac5 (14) using isotropic thermal parameters and hydrogen atoms at calculated positions. Final adjustments were made after analysis with MolProbity (15). The refined models were deposited in the Protein Data Bank under accession codes 6MG4 for apo JTO-FL and 6MG5 for JTO-FL•1.

NMR. A stock solution of 1 (40 mM) was made by dissolving the ligand into ethanol. All samples were buffered in 50 mM Bis Tris, pH 6.4, 1 mM EDTA, 10% $D_2O$. All in-phase (for $^{15}N$ WIL-V and $^{15}N$ JTO-V) and TROSY (for $^{15}N$ WIL-FL) based $^1H$, $^{15}N$ experiments were recorded at 37° C. on a 14.1 T Bruker AVANCE III HD spectrometer equipped with a cryogenically cooled x,y,z gradient probe.

For the titrations, samples with different protein:1 ratios were generated starting from two mother solutions, the first without the ligand, the second with a ratio of 1:2.2 between concentration of monomeric protein and ligand. The concentration of ethanol was identical in the two mother solutions. The concentration of monomeric protein was 0.05, 0.4 and 0.14 mM respectively for WIL-FL, WIL-V and JTO-V. Intensities for 8 $LC_2$ peaks (Asn 30, Tyr 32, Trp 35, Gln 38, Gly 41, Phe 50, Gly 101) and 4 $LC_2$•L peaks (Asn 30, Gln 38, Gly 41, Asp 52) were fitted to get an estimate of the $K_D$ for WIL-FL.

$^{15}N$ transverse relaxation rates were calculated from $R_1$ and $R_{1\rho}$ experiments acquired for JTO-V and WIL-V at 0.4 mM protein concentration with or without 1 mM 1. A $^{15}N$ $\gamma B_1$ field of 1.7 kHz was applied during the relaxation delay for $R_{1\rho}$ experiments.

Chemical exchange saturation transfer (CEST) experiments were acquired on WIL-V samples at 0.4 mM in the presence of 0.2 or 0.3 mM 1 using a multi-site excitation scheme (16). 4.25 ρs DANTE pulses with $\gamma B_1$=6.4 kHz were applied every 9.1 ms during a saturation delay of 0.35 s, giving an effective $^{15}$N $B_1$ field of 3 Hz and a spacing on 110 Hz between consecutive excitation frequencies. Longitudinal two-spin order ZZ-exchange experiments were acquired on JTO-V samples at 0.14 mM in the presence of 0.06 mM 1, with the 1-50 ms ZZ-mixing delay occurring after $t_1$ evolution (17). Further details of the analysis of these experiments are given in the Supplemental NMR Analysis described below.

Native-state hydrogen exchange experiments were measured for WIL-V at 0.2 mM and JTO-V at 0.1 mM with or without 0.5 mM 1. The proteins, previously desalted and lyophilized, were dissolved in a $D_2O$ based sodium citrate buffer, pD 5.0, containing 1.25% v/v of either pure ethanol or 40 mM 1 stock solution. Per-residue exchange rates $k_i$ were converted to free energies using the equation where krc are the residue-specific exchange rates of unprotected amides (18):

$$\Delta G = -RT\ln\left(\frac{k_{ex}}{k_{rc}}\right)$$

Kinetic unfolding. WIL-FL (5 μM) in 50 mM sodium phosphate buffer, pH 7.0, containing 50 μM 5 was rapidly diluted into urea in 50 mM sodium phosphate buffer and 50 μM 5 using an APP SX-20 stopped flow fluorimeter at 37° C. The change in fluorescence emission >335 nm was measured as a function of time ($\lambda_{ex}$=280 nm). Measurement of unfolding rates in the presence of 1 was not possible on this filter-based fluorimeter due to fluorescence of 1. Kinetic transients were fitted to single exponential curves and rates extracted.

Equilibrium unfolding. WIL-FL (5 μM) was titrated against urea in 50 mM sodium phosphate buffer, pH 7.0, containing 50 μM 5 or 100 μM 1. After incubation overnight at 25° C., intrinsic tryptophan fluorescence emission spectra were measured using a Jasco 8600 fluorimeter ($\mu_{ex}$=280 nm, $\mu_{em}$=300-420 nm). Average wavelength (also known as center of spectral mass) values were calculated using the equation:

$$\text{Average wavelength} = \frac{\sum_i \lambda_i \times I_i}{\sum_i I_i}$$

$\lambda_i$ and $I_i$ are the are the wavelength and intensity at i, respectively. Average wavelength data were normalized for comparison. LCs do not refold fully reversibly from urea (1), so we cannot report free energies of unfolding. Midpoint urea concentrations were calculated by fitting the titration data to a 2-state unfolding equation:

$$\text{Fraction folded} = \frac{(a+bx)e^{\frac{G-mx}{RT}} + (c+dx)}{1 + e^{\frac{G-mx}{RT}}}$$

x is the urea concentration (M), G is the free energy of unfolding (kJ mol$^{-1}$), m is the denaturant dependence of the unfolding reaction (kJ mol$^{-1}$ M$^{-1}$), R is the ideal gas constant, T is the temperature in K, a and c are the fluorescence of the folded and unfolded states, and b and d are the denaturant dependence of the fluorescence of the folded and unfolded states, respectively. $C_m$, the midpoint concentration, is:

$$C_m = \frac{G}{m}$$

Aggregation. WIL C214S was dialyzed into ddH$_2$O and filtered. Each 1 ml reaction contained 10 μM LC, ddH$_2$O, 1% DMSO or 200 μM 1 in 1% DMSO, 150 mM NaCl, and ABC buffer (20 mM sodium acetate, 20 mM boric acid, 20 mM sodium citrate, pH 5 with HCl). Components are listed in the order they were added.

For analysis by SEC, reactions were set up in 2 ml tubes (Axygen #SCT-200-B-S) equipped with 4 mm stir bars. For each experiment, four reactions (two replicates each of vehicle and 1) were placed in a microfuge tube rack on top of the center of a stir plate. Reactions were stirred at approximately 2,000 rpm at 37° C., and 60 μl aliquots were removed at the indicated timepoints. Aliquots were centrifuged at 16,000 g at 4° C. for 5 min. 10 μl of the supernatant was injected into a Waters Acquity H-Class Bio-UPLC (ultra performance liquid chromatography) instrument equipped with a BEH200 SEC column (Waters, Milford, MA) equilibrated with PBS with 1 mM EDTA. At the end of an experiment, stir bars were washed for at least 3 h with 1 M NaOH, followed by at least 3 h with 6 M GuHCl at room temperature to remove residual aggregates.

Thioflavin T (ThT)-containing aggregation reactions were set up in 96-well plates with similar conditions used for the reactions described above, except each 100 μl reaction also contained 2 μM ThT. Aggregation was induced with shaking as previously described (4). In total, 21 replicates for both vehicle and 1, over four independent experiments (plates) were performed.

Electron micrographs were recorded by the Scripps Research microscopy core facility.

A protease-coupled fluorescence polarization assay of LC stability. To identify FL LC kinetic stabilizers, a protease-coupled fluorescence polarization (PCFP) assay was developed (FIG. 1a). This assay measures the protease resistance of FL LCs—a reflection of the kinetic stability imparted by small molecule binding (4, 5). Cleavage of the AL patient-derived λ6-57 FL LC known as WIL (23) to smaller fragments requires conformational excursions (4) and leads to reduced fluorescence polarization (FP) of the LC-conjugated fluorescein fluorophore (FIG. 1a) (24). A surface-exposed K79C V-domain mutation (numbered according to the Kabat scheme (25)) was introduced into FL WIL and into the non-AL FL LC JTO (23), to which we conjugated fluorescein via an attached maleimide. The resulting conjugates, referred to as WIL-FL* and JTO-FL*, were purified by ion-exchange chromatography. Both WIL-FL* and JTO-FL* are obligate dimers because of the disulfide bond between monomers. Proteinase K (PK), a broad-spectrum serine protease that efficiently cleaves transiently unfolded LCs under physiological conditions (4) was used for the PCFP assay in order to minimize any sequence-specific cleavage site differences between LCs.

We measured PK proteolysis of WIL-FL* and JTO-FL* (20 nM) spiked into unlabeled WIL-FL and JTO-FL (10 μM), respectively, at 37° C. in phosphate buffered saline (PBS; pH 7.4). Both labeled LCs are degraded at increased rates compared to the parent sequences based on the disappearance of the LC band by SDS-PAGE (FIG. 1b; $k_{obs}$=7.6±0.3*$10^{-4}$ $s^{-1}$ for WIL-FL* versus 2.4±0.9*$10^{-4}$ $s^{-1}$ for WIL-FL; 9.5±3.5*$10^{-5}$ $s^{-1}$ for JTO-FL* versus no measurable decrease for JTO-FL, mean±sd, n=3). The K to C mutation and subsequent fluorescein conjugation reduces the kinetic stability of both LCs, possibly by decreasing the solvent entropy change upon folding in the region displaying the solvated dye, i.e., by attenuating the hydrophobic effect. Importantly, endoproteolysis of AL-associated WIL-FL* is significantly faster than that of the more kinetically stable JTO-FL* (FIG. 1b). Treatment of WIL-FL* (20 nM) with PK (500 nM) at 37° C. in PBS leads to reduction of FP ($\lambda_{ex}$=488 nm, $\lambda_{em}$=520 nm) at a rate ($k_{obs}$=9.9*$10^{-4}$ $s^{-1}$) comparable to that measured by SDS-PAGE, whereas the FP of JTO-FL* is reduced more slowly ($k_{obs}$=1.8*$10^{-4}$ $s^{-1}$), as expected (FIG. 1c).

The PCFP assay was miniaturized to a 384-well microplate format and verified that we observed similar patterns of proteolysis under conditions suitable for high-throughput screening. In PBS at 22° C., WIL-FL* (20 nM) is cleaved by PK (500 nM) over 24 h, whereas JTO-FL* is cleaved more slowly (FIG. 1d). We previously observed correlations between rates of denaturant-induced unfolding and rates of endoproteolysis (4). Initial experiments showed that the FP of both WIL-FL* and JTO-FL* decreased at a similar rate in the presence of PK, and increased in the absence of PK This appears to be due to denaturation of the LCs on the plate surface. Addition of Pluronic F-127 detergent to untreated plates (Greiner #655076) prevented the increase in FP in the absence of PK and yielded proteolysis kinetics similar to those in cuvettes with PK. Employing low-binding plates with or without Pluronic F-127 detergent (0.02%) does not alter the rate of WIL-FL* endoproteolysis. Thus, we added Pluronic F-127 detergent to untreated plates for the high-throughput screen and subsequent experiments due to the increased cost of low-binding plates. This detergent may have the additional benefit of reducing colloidal aggregation of small molecules (26). Addition of the kosmotropic salt sodium sulfate reduces the extent of WIL-FL* proteolysis after 24 h, consistent with its stabilizing effect (FIG. 1e). The extent of WIL-FL* endoproteolysis is not influenced by the concentration of PK, consistent with FL LC conformational excursions from the native state being rate limiting for proteolysis (4), a condition referred to as EX1 kinetics (FIG. 1e). The assay exhibited a robust Z' score of 0.8 (27).

Identification of small molecules that protect LCs from proteolysis. We screened a commercial library of 16,000 small molecules, employing the 384-well PCFP assay with WIL-FL*. The results guided further miniaturization of the assay to 1,536-well plates, optimizing the concentrations of WIL-FL* (10 nM), PK (250 nM) and kinetic stabilizer candidate (6.75 µM). We screened an additional library of 653,085 small molecules, identifying 2,777 primary hits exhibiting >20.6% (mean+3 standard deviations) retention of WIL-FL* FP (relative to 0.68% vehicle (DMSO) control assigned 0%, with 100% corresponding to the FP of JTO-FL* without PK). The PCFP assay was repeated in triplicate on the 2,777 primary screening hits, of which 1,422 molecules had >20.6% mean retention of WIL-FL* FP.

Figure 1G:
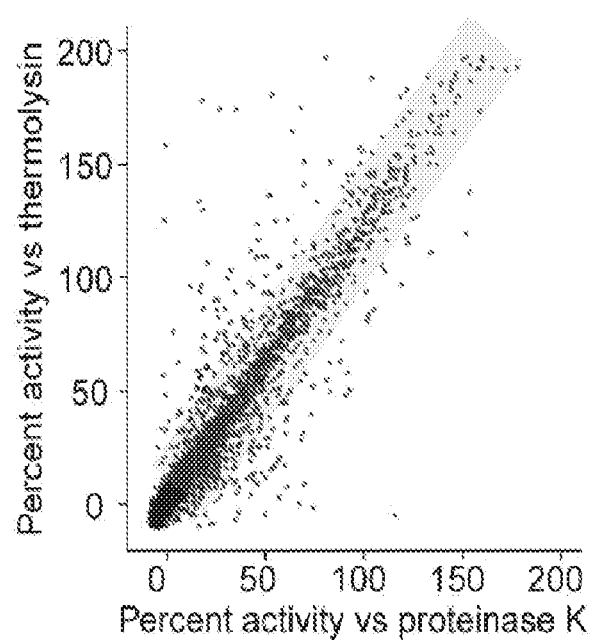

To identify and exclude molecules that interfered with FP measurements, the assay was repeated, but candidate stabilizers were not added until after 24 h of PK treatment (FIG. 1f). Compounds that artefactually increase FP would result in similar apparent retention of FP in both assay configurations. Six hundred sixty-two molecules had >1.25-fold greater mean activity (n=3) in the primary screen than in this counterscreen (2,115 molecules artefactually increased FP). To eliminate PK inhibitors, the PCFP screen was rerun in triplicate on the 2,777 hits using the protease thermolysin (200 nM; candidate stabilizer concentration 6.75 µM; FIG. 1g). Thermolysin is a broad-spectrum metalloprotease that is likely not inhibited by compounds that inhibit PK, a serine protease. Plotting the thermolysin versus PK data identified 1,243 compounds on the diagonal that were not protease inhibitors (FIG. 1g). The 269 small molecules that fulfilled all three assessment criteria (exhibited PCFP activity in triplicate, passed the FP artefact counterscreen (FIG. 1f), and exhibited >20% efficacy in the PCFP thermolysin counterscreen) were retained.

The potency of these surviving 269 LC kinetic stabilizers was measured by recording concentration-dependence data in the three PCFP configurations covered in the preceding paragraph, along with 147 candidates that appeared to inhibit one or both proteases. One hundred twenty-eight compounds exhibiting a dose-response curve were chosen for further evaluation. We further verified that these 128 compounds do not inhibit PK by measuring their ability to inhibit proteolysis of a fluorogenic peptide substrate. To exclude the possibility that differences in the initial FP amplitude could lead to misinterpretation of the endpoint FP measurement, we measured FP kinetics upon PK treatment. Ninety of the 128 compounds reduced the rate and amplitude of FP change relative to vehicle, consistent with LC kinetic stabilization. Finally, to verify that the FP measurements were reporting on FL LC proteolysis sensitivity, we measured protection of WIL-FL* from PK proteolysis imparted by the 128 compounds mentioned above using SDS-PAGE. Twenty-six molecules stabilize FL LCs by this assay. Sixteen molecules showed clear activity in both the kinetic FP and SDS-PAGE assays (Table 1).

The sixteen hit molecules fall into four classes (Table 1-compounds 1-16): coumarins (1-3, 9-15), an aryl cyanoacrylamide (4), biaryl hydrazones (5-6), and hydantoins (7-8). Two sulfones (17-18) derived from the commercial library were also validated as hits.

Small molecules 1 to 16 were identified as hits from the Scripps Florida screen and showed clear activity in both the PCFP and SDS-PAGE assays. Small molecules 17 to 18 were identified as hits from the commercial library. Data for the related but inactive coumarins 19, 20 and 21 are included for reference. Activity is normalized to the activity of the high and low controls from either the pilot screen (n=1), primary screen (n=1), or counterscreen (mean+sd, n=3). $EC_{50}$ values are calculated from dose response curves measured during the screening process. LC-MS validation was obtained for compounds 1-15, multiple peaks were observed for compound 16, not determined for compounds 17-21. ND=not determined.

We purchased eight representative small molecules and determined their midpoint effective concentration ($EC_{50}$) values in the PCFP assay by titration. Dissociation constants ($K_{D\ ligand}$) measured for each compound using equilibrium dialysis are similar to the $EC_{50}$ values, indicating that the small molecule-bound FL LC is highly resistant to proteolysis.

TABLE 1

Screening data for selected small molecules that stabilize LCs and selected inactive analogs.

| ID | Structure | PK activity (%) | Thermolysin activity (%) | Counterscreen activity (%) | EC$_{50}$ (μM) |
|---|---|---|---|---|---|
| 1 | 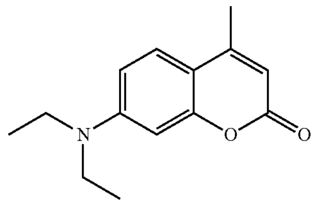 [SMILES: CCN(CC)c1ccc2c(C)cc(=O)oc2c1] | 47.8 ± 0.7 | 36.4 ± 2.0 | −8.07 ± 3.3 | 12.5 |
| 2 | 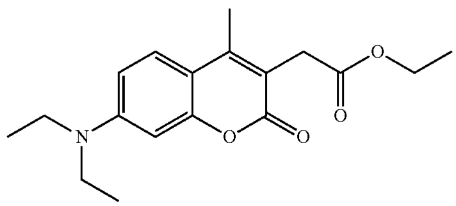 [SMILES: CCOC(=O)Cc1c(C)c2ccc(N(CC)CC)cc2oc1=O] | 37.8 ± 1.4 | 33.8 ± 3.1 | −4.13 ± 5.2 | 6.92 |
| 3 | 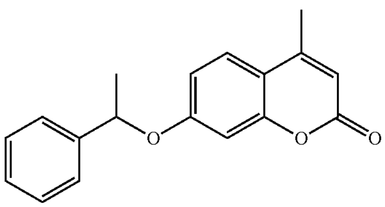 [SMILES: Cc1cc(=O)oc2cc(OC(C)c3ccccc3)ccc12] | 43.3 ± 1.5 | 38.7 ± 3.7 | −2.52 ± 5.8 | 7.1 |
| 4 | 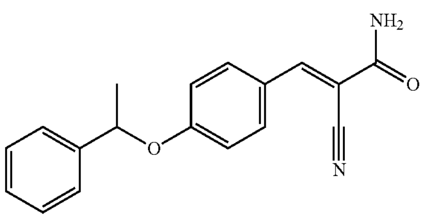 [SMILES: CC(Oc1ccc(/C=C(\C#N)C(N)=O)cc1)c1ccccc1] | 48.9 ± 2.6 | 40.4 ± 1.2 | −7.4 ± 4.0 | 6.33 |
| 5 | 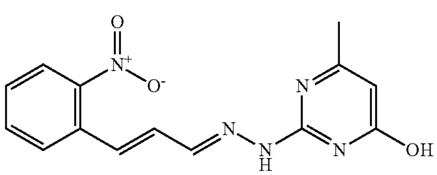 [SMILES: Cc1cc(O)nc(N/N=C/C=C/c2ccccc2[N+](=O)[O-])n1] | 65.2 ± 2.8 | 61.1 ± 5.0 | 8.04 ± 2.6 | 5.51 |
| 6 | 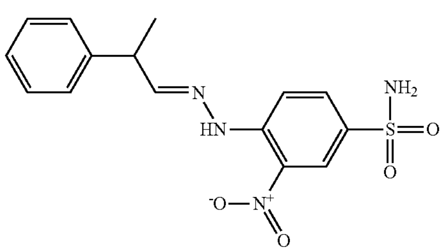 | 60.8 ± 2.7 | 45.1 ± 6.6 | 1.00 ± 2.6 | 4.92 |
| 7 | 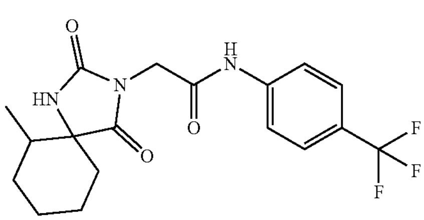 [SMILES: CC1CCCCC12NC(=O)N(CC(=O)Nc1ccc(C(F)(F)F)cc1)C2=O] | 29.3 ± 2.5 | 26.3 ± 1.7 | 2.51 ± 4.7 | 5.87 |

TABLE 1-continued

Screening data for selected small molecules that stabilize LCs and selected inactive analogs.

| ID | Structure | PK activity (%) | Thermolysin activity (%) | Counterscreen activity (%) | $EC_{50}$ (μM) |
|---|---|---|---|---|---|
| 8 | 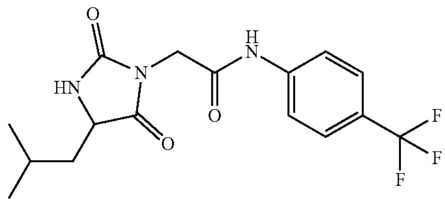 [SMILES: CC(C)CC1NC(=O)N(CC(=O)Nc2ccc(C(F)(F)F)cc2)C1=O] | 48.0 ± 2.4 | 50.8 ± 1.7 | −2.05 ± 2.9 | 7.36 |
| 9 | 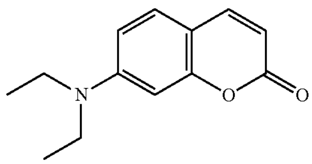 [SMILES: CCN(CC)c1ccc2ccc(=O)oc2c1] | 37.9 ± 1.1 | 27.1 ± 1.3 | −3.45 ± 3.89 | 7.9 |
| 10 | 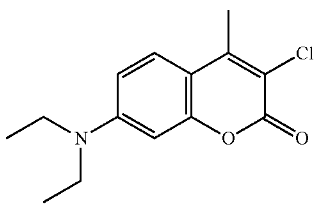 [SMILES: CCN(CC)c1ccc2c(C)c(Cl)c(=O)oc2c1] | 48.0 ± 3.8 | 55.5 ± 3.3 | −1.54 ± 2.4 | 4.0 |
| 11 | 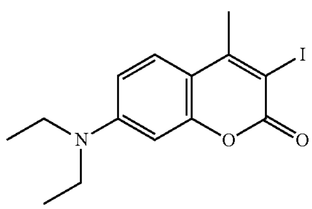 [SMILES: CCN(CC)c1ccc2c(C)c(I)c(=O)oc2c1] | 58.7 ± 2.0 | 45.7 ± 7.0 | 0.94 ± 3.9 | 4.18 |
| 12 | 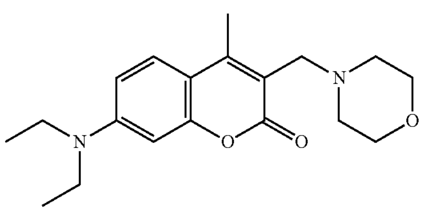 [SMILES: CCN(CC)c1ccc2c(C)c(CN3CCOCC3)c(=O)oc2c1] | 37.2 ± 7.3 | 30.2 ± 4.2 | 0.41 ± 2.5 | 11.3 |
| 13 | 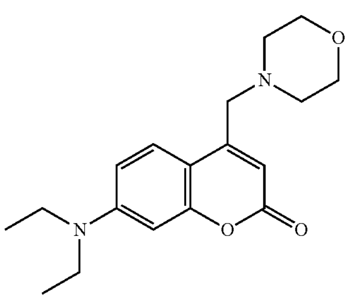 [SMILES: CCN(CC)c1ccc2c(CN3CCOCC3)cc(=O)oc2c1] | 4.21 ± 4.4 | 23.3 ± 8.5 | −4.10 ± 1.5 | 9.15 |
| 14 | 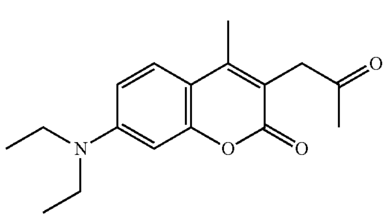 [SMILES: CCN(CC)c1ccc2c(C)c(CC(C)=O)c(=O)oc2c1] | 41.9 ± 3.0 | 34.8 ± 3.1 | 1.67 ± 4.7 | 9.04 |

TABLE 1-continued

Screening data for selected small molecules that stabilize LCs and selected inactive analogs.

| ID | Structure | PK activity (%) | Thermolysin activity (%) | Counterscreen activity (%) | EC$_{50}$ (μM) |
|---|---|---|---|---|---|
| 15 | 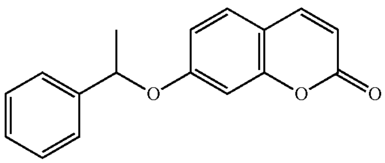 [SMILES: CC(Oc1ccc2ccc(=O)oc2c1)c1ccccc1] | 34.2 ± 3.0 | 18.3 ± 4.9 | −4.35 ± 5.6 | 9.28 |
| 16 | 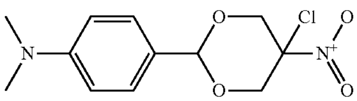 | 50.5 ± 5.3 | 29.1 ± 0.3 | −3.09 ± 3.0 | 6.73 |
| 17 | 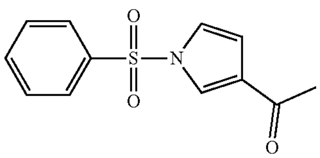 [SMILES: CC(=O)c1ccn(S(=O)(=O)c2ccccc2)c1] | 58.1 (10 μM in pilot screen) | ND | ND | 18.5 |
| 18 | 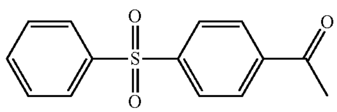 [SMILES: CC(=O)c1ccc(S(=O)(=O)c2ccccc2)cc1] | 46.5 (10 μM in pilot screen) | ND | ND | 18.0 |
| 19 | 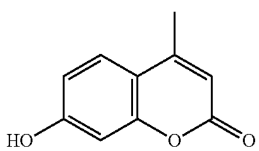 | 2.27 (Primary screen) | ND | ND | ND |
| 20 | 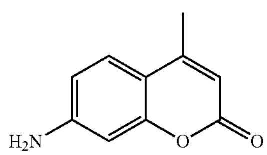 | −3.02 (Primary screen) | ND | ND | ND |
| 21 | 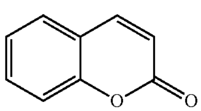 [SMILES: O=c1ccc2ccccc2o1] | 2.58 (Primary screen) | ND | ND | ND |

7-amino-coumarins are fluorogenic kinetic stabilizers of λ6a LCs. Twenty four of 128 screening hits surviving the counterscreens are coumarins modified at the 7-position by either a diethylamino group (21 molecules, e.g., 1 and 2; Table 1) or a 1-phenylethoxy group (3 molecules, e.g. 3; Table 1). Coumarins are often regarded as promiscuous binders; however, 7,839 other coumarin-containing molecules in the library, of which 432 are modified at the 7 position, were not identified as hits after counterscreening. We initially focused on compound 1, 7-diethylamino-4-methylcoumarin, a commercially available dye known as "Coumarin 1".

To verify the activity of 1 and investigate the structural requirements at the 7 position of coumarins, we measured protection from PK proteolysis of unlabeled WIL-FL. Incubation of WIL-FL (10 μM) with 1 (100 μM; Table 1 and FIG. 2a), but not the related compounds 19, 20 and 21 (100 μM, FIG. 2a and Table 1), protects this FL LC against PK proteolysis (t=2 h). Compound 9, which lacks a methyl group at the 4-position, also stabilizes WIL-FL, but is less efficacious than 1 (FIG. 2a and Table 1). Incubation of WIL-FL (20 μM) with 1 (1 μM) results in a large fluorescence emission increase of 1 relative to the weaker, red-shifted fluorescence of 1 in PBS (FIG. 2b, $\lambda_{ex}$=373 nm), suggesting that the altered environment of 1 associated with binding and the restricted mobility of the 7-diethylamino group contribute to its fluorogenicity (28). In contrast, 19 (1 μM) is fluorescent in PBS, but its emission intensity is reduced in the presence of WIL-FL (20 μM; FIG. 2b). The FP of 1 increases from 0.05 in buffer to 0.35 in the WIL-FL•1 complex, consistent with an increase in rotational correlation time.

The fluorogenicity of 1 makes it a convenient probe to investigate whether LCs other than WIL-FL can be kinetically stabilized and whether other non-fluorescent candidate kinetic stabilizers bind LCs at the same site. Isothermal titration calorimetry measurements indicate that 1 binds to WIL-FL with a $K_{D\ ligand}$ of 3.08±0.52 μM (mean±sd, n=3). To measure binding we titrated different WIL constructs into 1 in PBS containing 0.02% Pluronic F-127 and measured the fluorescence emission of the LC•1 complex in a 384-well plate format (FIG. 2c, $\lambda_{ex}$=373 nm, $\lambda_{em}$=445 nm). We used a low concentration of 1 (1 µM) and varied LC concentration (serial dilution from 133 µM to 18 nM in 1.5-fold decrements) to minimize background fluorescence and simplify the analysis. Binding of compound 1 to WIL-FL is fit well by a 1-site model with an apparent $K_{D\ ligand}$ of 3.14±0.3 µM (mean±sd, n=5), whereas binding to the WIL V-domain has a steeper dependence on LC concentration and is fit less well by a 1:1 binding model (apparent $K_{D\ ligand}$ of 79.3±5.2 µM). No binding of 1 (1 µM) was detected to the isolated λ3 C-domain (FIG. 2c). Recombinant FL λ6-57 LCs form disulfide-linked dimers (4), but their isolated V-domains populate an equilibrium between monomers and dimers (4, 22, 29). The apparent positive cooperativity in the binding of 1 to WIL-V is consistent with induced dimerization of the LC V-domain.

Concentration-dependent NMR chemical shift data indicate that WIL-V has a dimerization equilibrium constant ($K_{D\ dimer}$) of approximately 5 mM (22). Fitting the fluorescence data to a model of binding-induced dimerization constrained by the NMR-derived $K_{D\ dimer}$ yields an apparent $K_{D\ ligand}$ and of 3.0±1.2 µM for WIL-$V_2$•1 indicating that the apparent low affinity for WIL-V compared to WIL-FL is due to a low concentration of WIL-V dimer at equilibrium. Since the affinities for WIL-FL and dimeric WIL-V are indistinguishable, we can assume that 1 binds only to dimeric WIL-V and, hence, estimate the apparent $K_{D\ dimer}$ from the fluorogenic binding data in the presence of 1 (1 µM) to be 1.45 mM, compared to 5 mM in the absence of 1.

A successful kinetic stabilizer should, but is not required to, bind to and stabilize patient LCs with a vast range of sequences (30, 31). To ask whether 1 can stabilize other FL LC sequences, we measured binding of 1 to three more recombinant λ6-57 FL LC disulfide-linked dimers: JTO-FL; ALMC2-FL, an AL-associated LC sequence derived from the ALMC2 cell line (32); and the germline sequence 6aJL2-FL. Serial dilution of these LCs from 133 µM to 18 nM in 1.5-fold decrements into 1 (1 µM) in PBS yields $K_{D\ ligand}$ values of between 1 and 20 µM (FIG. 2d, left panel). The isolated V-domains from WIL, ALMC2 and 6aJL2 bind to 1 (1 µM) with reduced affinity (FIG. 2d, left panel), while JTO-V has $K_{D\ ligand}$ of 16.5±0.4 µM (mean±sd, n=3), similar to that of JTO-FL (20.3±1 µM), consistent with JTO-V being mainly dimeric at this concentration (22). Eliminating the inter-chain disulfide bond between the C-domains by the C214S mutation reduces the affinity of LCs for 1 (1 µM) (FIG. 2d), consistent with this mutation's destabilization of the dimeric interface (4).

To further test the hypothesis that 1 binds at the interface between the V-domains, we measured binding of 1 to WIL-FL and JTO-FL variants with mutations designed to disrupt the dimer (22). The F98D mutation, which disrupts the V-domain-V-domain interface, rendered binding of 1 (1 µM) undetectable in the presence or absence of the C214 inter-chain disulfide bond (FIG. 2d, right panel). The F118D mutation, which destabilizes the C-domain-C-domain interface, or the L117G or P141A mutations, which destabilize the hydrophobic core of the C-domain, resulted in reduced binding affinity of 1 (1 µM) to WIL-FL C214S and, to a lesser extent, JTO-FL C214S (FIG. 2d, right panel), with $K_D$ values similar to those exhibited by the isolated V-domains (≈20-50 µM).

To further investigate the ability of small molecules to induce dimerization of LCs, we performed sedimentation velocity analytical ultracentrifugation (SV-AUC) analysis of WIL-V and WIL-FL C214S (20 µM) in the presence or absence of 1 (100 µM). Continuous sedimentation distributions (FIG. 2e) show the apparent size of the sedimenting species. Deviations from the expected size indicate exchange between species, in this case monomer and dimer. The size distributions of both LCs (20 µM) increase upon binding 1 (100 µM). WIL-FL C214S has a $K_{D\ dimer}$ of approximately 16 µM, estimated by concentration-dependent SV-AUC experiments.

Figure 2F:
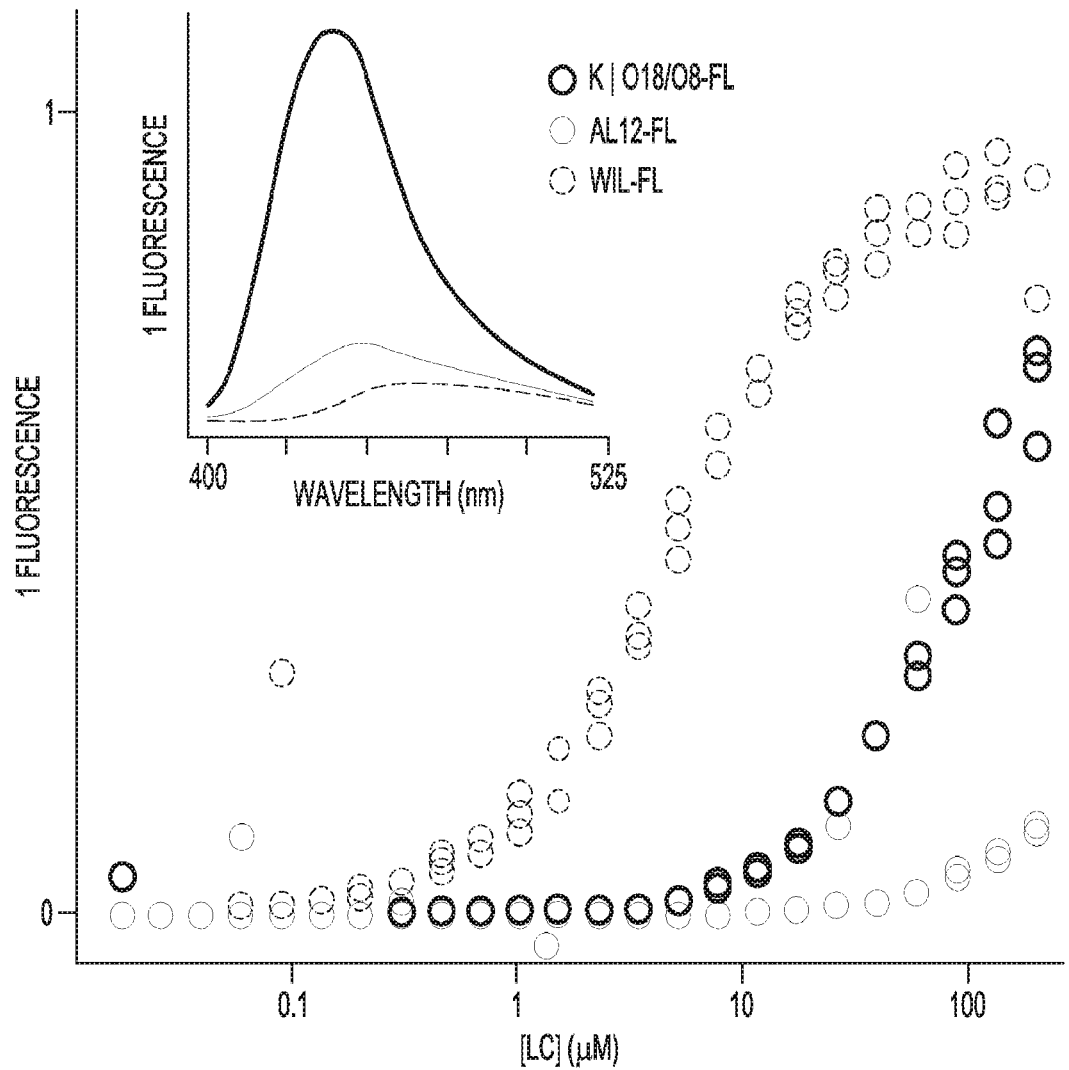

Of the two classes of human LCs, λ and κ, λ LCs are more commonly observed in AL, but a fraction of patients secrete κ1-33 LCs (12, 33). To ask whether K LCs possess a similar small molecule binding site as λ LCs, we incubated 1 (1 µM) with two κ1-33 LCs (serial dilution from 133 µM to 18 nM in 1.5-fold decrements), which represent the patient-derived sequence AL12-FL (34) and its germline precursor K I 018/08-FL (7). Recombinant expression of these κ1-33 LCs using a similar protocol to that used for λ6-57 LCs yielded both monomeric and dimeric LCs, as shown by SV-AUC (SI Appendix FIG. S7). Consistent with this reduced propensity to dimerize, binding of 1 to κ1-33 LCs is weaker than binding to λ6-57 LCs (FIG. 2f). Binding of an excess of κ1-33 LCs (20 µM) to 1 (1 µM) afforded FL LC•1 fluorescence (FIG. 2f, inset). This result indicates that a binding site for 1 is present in dimers of both λ6-57 and κ1-33 LCs.

Figure 2G:
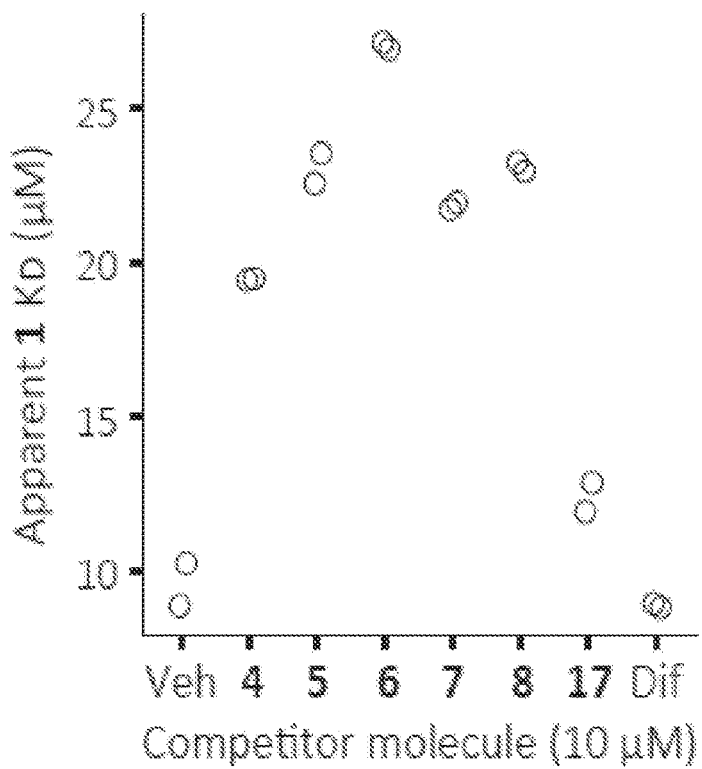

To ask whether the non-coumarin small molecules in Table 1 bind to FL LCs at the same or an overlapping site, we measured binding of 1 (1 µM) to WIL-FL (serial dilution from 150 µM to 20 nM in 1.5-fold decrements) in the presence of the other screening hits (10 µM). The apparent binding affinity of LCs for 1 was reduced by six non-fluorescent molecules identified in the screen, but not by the negative control diflunisal, an anti-inflammatory drug that stabilizes transthyretin (15, 35) (FIG. 2g). These data suggest that the hits have binding sites that overlap with that of 1, or exhibit negatively cooperative binding with 1 to WIL-FL.

Figure 2H:
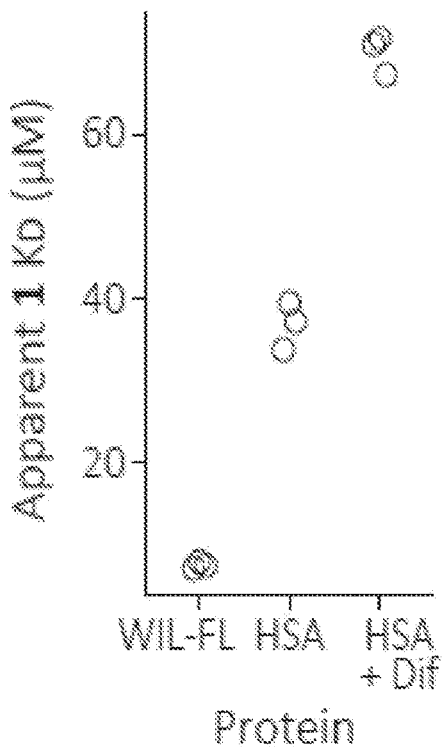

The free monoclonal LC concentration in the plasma of AL patients is typically in the range of 1-20 µM (10-100 mg/dl) (36), whereas the concentration of antibodies and albumin is much higher. Therefore, kinetic stabilizer binding selectivity to FL LCs in preference to other plasma proteins is important to minimize the proportion of free FL LC. Albumin binds many small molecules in blood, typically with µM $K_D$ values. Titration of albumin (serial dilution from 400 µM to 53 nM in 1.5-fold decrements) with 1 (1 µM) results in increased coumarin fluorescence, with an apparent $K_D$ of 37±3 µM (FIG. 2h). Affinity of 1 for albumin is reduced in the presence of 100 µM diflunisal (FIG. 2h), consistent with diflunisal binding competitively to albumin.

Figure 2I:
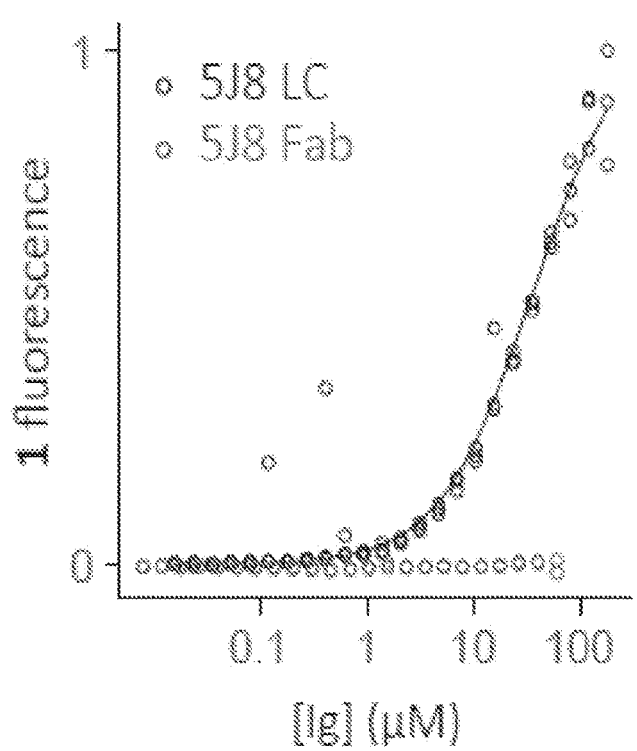

The heterodimeric interface between LCs and heavy chains (HCs) in an antibody is structurally distinct from that of the LC homodimer interface. To verify that our kinetic stabilizers bind FL LC dimers selectively over antibodies, we compared the binding of 1 (1 µM) to the LC and antigen binding fragment (Fab, the LC:HC dimer) of 5J8, a human anti-influenza hemagglutinin antibody (serial dilution from 120 µM to 16 nM in 1.5-fold decrements) (37). The 5J8 FL LC from the 3 class (not associated with AL) binds to 1 with an apparent $K_D$ of ≈50 µM (FIG. 2i), an event that protects the 5J8 LC from proteolysis by PK In contrast, the 5J8 Fab shows no apparent binding to 1 as measured by fluorescence (FIG. 2i), and 1 does not protect the 5J8 Fab from PK proteolysis.

Wildtype (WT) full-length λ6-57 LC constructs are obligate, disulfide-crosslinked dimers. Other species are in equilibrium between monomer and dimer. See Table 2. NMR measurements show that full-length, C214S LC constructs are dimeric at 200 μM The percentage of residues at the domain interfaces between protomers which have dimer-like chemical shifts is reported. NMR data are described further in Rennella et al. (5).

TABLE 2

Summary of monomer-dimer equilibria for different LC species.

| LC | NMR (200 μM) | AUC (20 μM) |
|---|---|---|
| WT JTO-FL | Obligate dimer | Single peak 3.5 S |
| WT WIL-FL | Obligate dimer | Single peak 3.5 S |
| JTO-V | $K_D$ = 12.5 μM | Single peak 2 S |
| WIL-V | $K_D$ = 5000 μM | Single peak 1.5 S |
| JTO-FL C214S | 100% dimer-like (V-domain interface) 93% dimer-like (C-domain interface) | Single peak 3.5 S |
| WIL-FL C214S | 95% dimer-like (V-domain interface) 93% dimer-like (C-domain interface) | Two peaks, 2 S and 3.2 S; $K_D$ = 16 μM |
| κ I O18/O8-FL | Not measured | Two peaks, 2.4 S and 3.2 S |
| AL12-FL | Not measured | Major peak at 2.4 S with shoulder at 2.9 S |

Figure 3A:
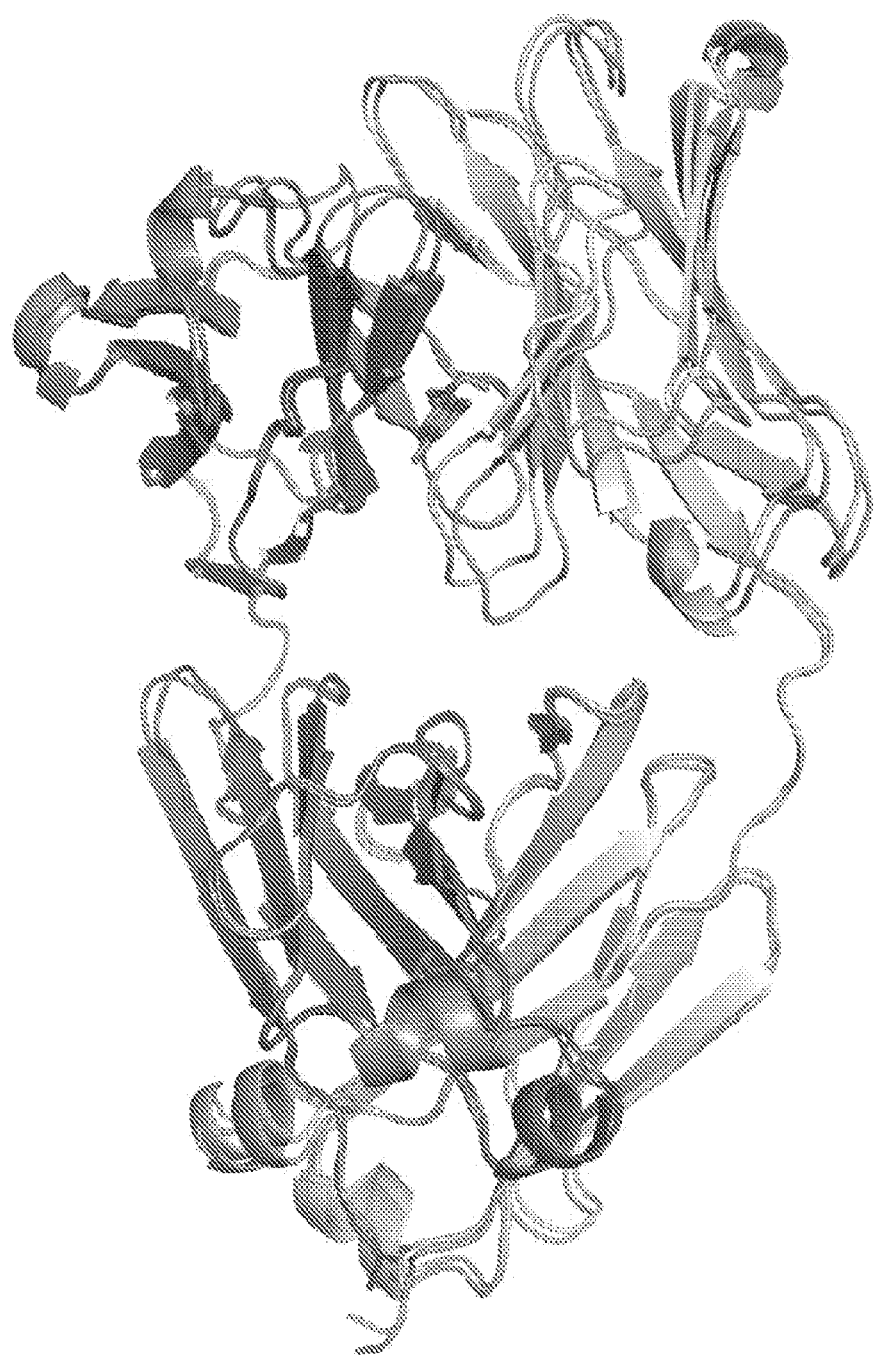
Figure 3B:
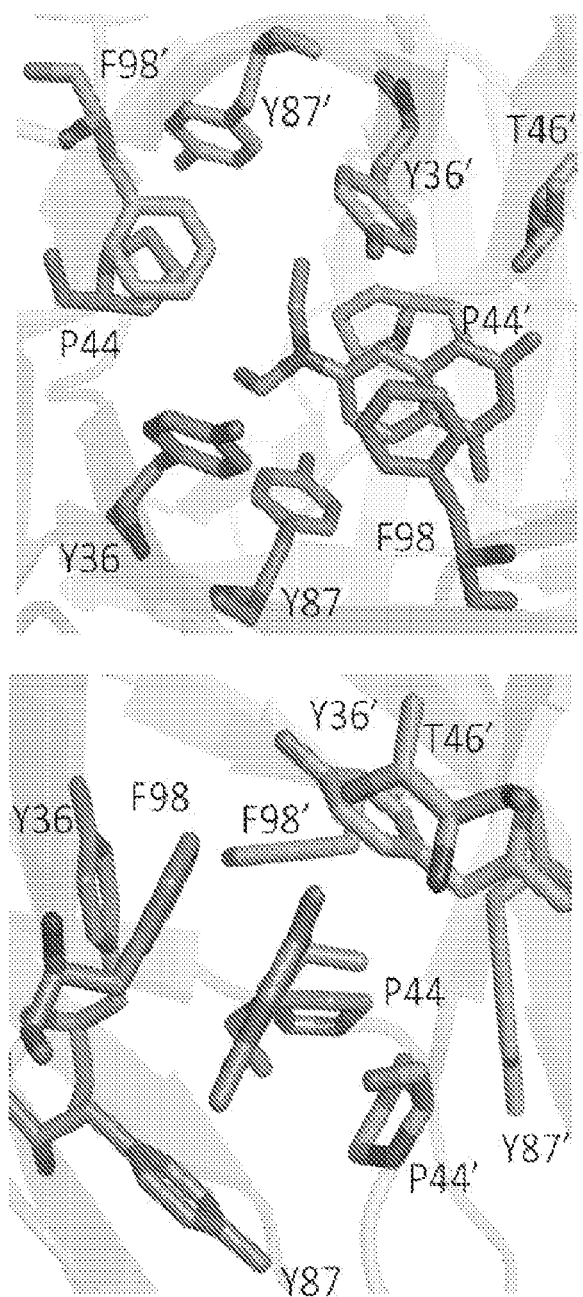

Structural insight into LC kinetic stabilizer binding. We determined the crystal structures of JTO-FL with and without bound 1. Our attempts to crystallize other LC•kinetic stabilizer complexes (e.g., the WIL-FL•1 complex) have so far been unsuccessful. The unbound JTO-FL LC structure is very similar to previously published FL LC structures (3, 5, 38) (FIG. 3a). LC homodimers are covalently linked by an inter-chain disulfide bond between C214 residues in the C-domains of the monomers. In the apo JTO-FL structure, refined at 1.75 Å resolution, the conformation of the V-domains is the same as that in the published JTO-V dimer structure (39).

Figure 3C:
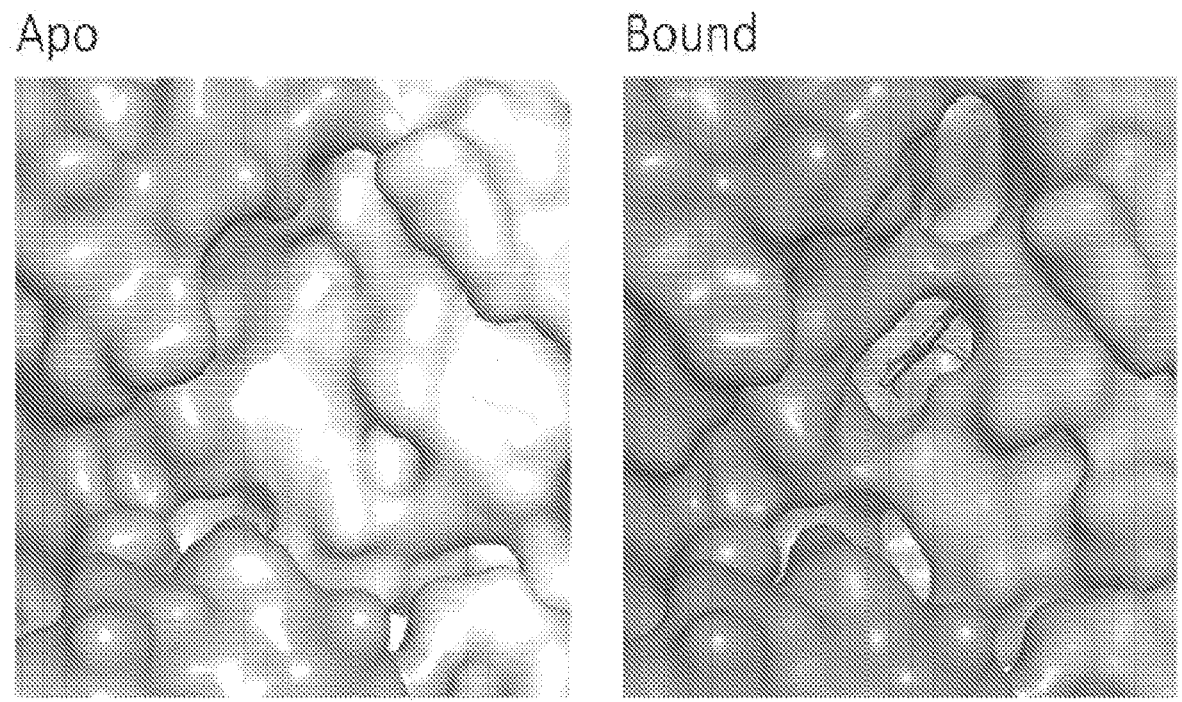

The structure of the JTO-FL•1 complex, refined at 1.8 Å resolution, unambiguously shows density for 1 at the interface formed by the two V-domains. This binding site is consistent with previous reports that the interface between V-domains in the dimer can accommodate various aromatic ligands (21, 40), although the exact binding site that we identify below has not been previously observed. The binding site for 1 comprises residues P44, Y87 and F98 from one protomer and Y36', P44' and T46' from the other protomer (FIG. 3b), which together form a cavity that is not present in the unbound structure (FIG. 3c; cf. right to left panels). The JTO-FL F98D variant (22) has no measurable affinity for 1 (FIG. 2d), consistent with disruption of the π-π stacking interaction observed in the structure. The 7-diethylamino substructure projects through the V-domain-V-domain interface, interacting with both P44 residues. These interactions may explain the apparent requirement for modification at the 7 position of the coumarin scaffold. The carbonyl oxygen of 1 hydrogen bonds with the sidechain hydroxyl and/or backbone amide of T46'. A CH-π interaction between 1 and Y87 may also contribute to the binding free energy. Binding of 1 causes a rotation of the V domains relative to each other, which creates the interface cavity (FIG. 3c). The distance between the Cα residues of F98 and P44' increases from 7.2 Å to 9.7 Å to accommodate 1. The LC dimer has two pairs of F98 and P44 residues, creating two potential binding sites, but only one molecule of 1 is observed per dimer. Aligning a second molecule of 1 utilizing the same intermolecular interactions results in a steric clash between the diethylamino substructures.

Figure 3D:
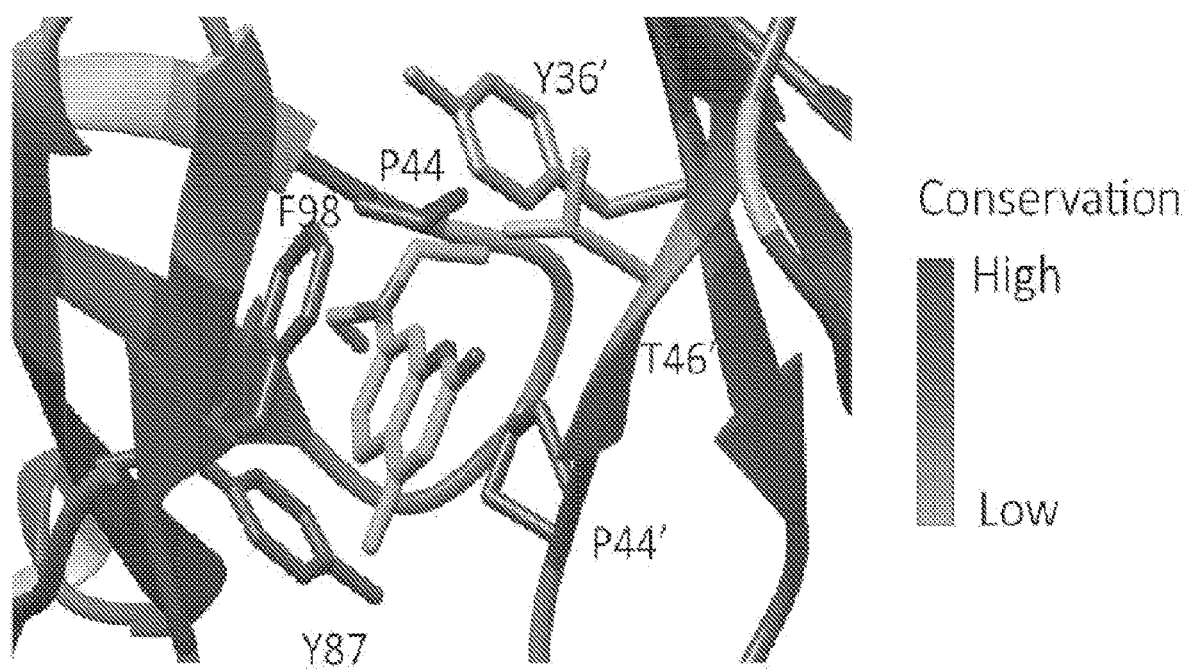

The residues used by JTO to bind 1 are highly conserved (FIG. 3d). Residues Y36, P44, Y87 and F98 are present in 88, 99, 95 and 100% of all human germline LC genes, respectively, whereas T46 is only present in two functional germline genes. Mutation of residue 46 in WIL-FL and JTO-FL to leucine, which is the residue present in 75% of LC germline genes, slightly enhances the binding affinity of 1 for these FL LCs, indicating that the sidechain hydroxyl group of T46' is not necessary for binding of 1.

Figure 4A:
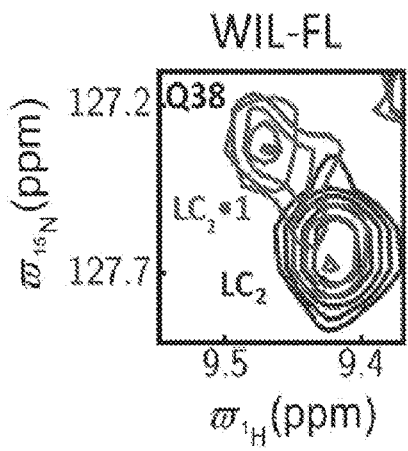
Figure 4B:
Figure 4C:
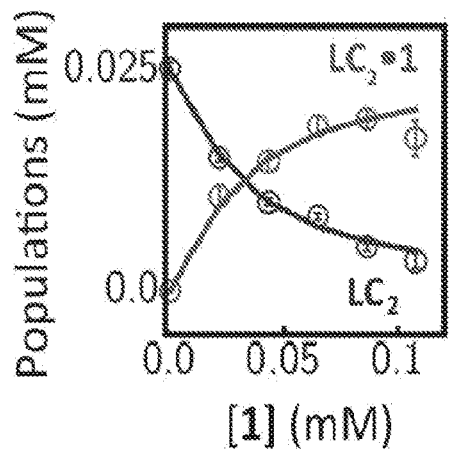
Figure 4D:
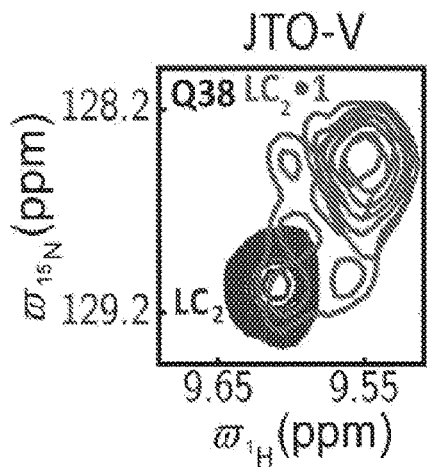

To verify that 1 binds to different LCs in solution at the same site identified in the crystal structure, we recorded the NMR spectra of WIL-FL, WIL-V and JTO-V in the absence and presence of 1. We used high concentrations of LC (100-500 μM) and solubility-limited concentrations of 1 (up to 500 μM) to maximize the NMR signal from the bound state. 2-dimensional $^1$H—$^{15}$N heteronuclear single-quantum coherence (HSQC) experiments, wherein each amide in a protein is represented as a peak in the spectrum, allowed identification of residues perturbed by binding of 1. Chemical shift and intensity perturbations of similar residues in each spectrum occur upon addition of 1 (FIG. 4a). In each case, the perturbed residues are concentrated in the interface between the two V-domains, close to the site at which 1 binds according to the crystal structure (FIG. 4b). Upon titration of 1 into WIL-FL, which is an obligate dimer (4), new peaks of the bound state $LC_2$•1 appear for the amides close to the binding site (FIG. 4a, b). The changes in intensity for $LC_2$ and $LC_2$•1 peaks can be fit by a two-state binding model with an apparent $K_D$ of 19±2 μM (FIG. 4c).

Concentration-dependent chemical shift measurements (22) indicate that JTO-V is dimeric at concentrations used for NMR (generally greater than 100 μM) with a dimerization $K_D$ of approximately 12.5 μM. Binding of 1 to JTO-V (140 μM) at approximately equimolar stoichiometry results in the appearance of exchange cross-peaks between peaks originating from $LC_2$ and $LC_2$•1 (FIG. 4d, red contours) in a regular HSQC experiment that is not designed to measure exchange rates. A ZZ-exchange experiment (41) measured on- and off-rates of 1:00±0.10 μM$^{-1}$ s$^{-1}$ and 57±2 s$^{-1}$, respectively, for the JTO-$V_2$•1 complex, yielding a $K_D$ of 57±4 μM for a two-state model, in agreement with the value measured by fluorescence (FIG. 2d).

Figure 4E:
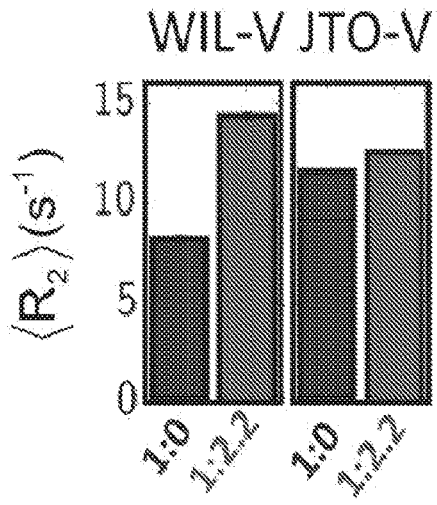
Figure 4F:
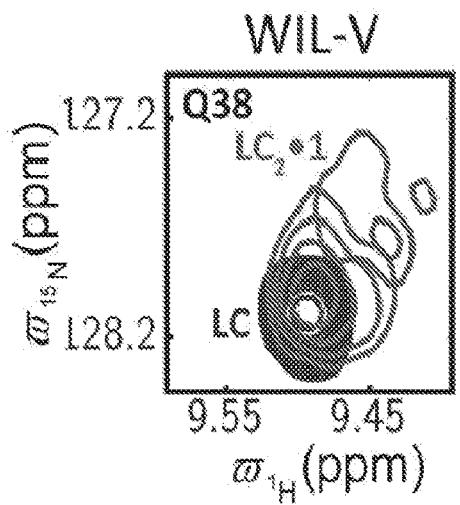

Binding of 1 to isolated WIL-V (400 μM) is more complex, since this V-domain is monomeric in the absence of ligand ($K_D$≈5 mM) (22) and becomes dimeric upon addition of 1. $^{15}$N transverse relaxation ($R_2$) rates, which report on overall protein tumbling and hence on molecular size, double for WIL-V upon addition of excess 1 (500 μM), whereas they do not change for JTO-V (140 μM), which is dimeric without and with 1 bound (FIG. 4e). Notably, WIL-V bound to 1 exhibits multiple HSQC peaks for most interfacial residues and may represent alternative conformations of the dimer or of the bound ligand (FIG. 4f). The presence of multiple conformations for the LC$_2$•1 complex of WIL-V prevents accurate quantification of K$_D$. Chemical exchange saturation transfer (CEST) experiments (42) indicate that the K$_D$ for WIL-V$_2$•1 is <50 µM, in agreement with the effective K$_D$ of 3±1.6 µM determined from fluorogenic binding titrations (FIG. 2c). Removal of 1 from WIL-V by dialysis yielded an HSQC spectrum indistinguishable from that of the starting material, indicating that binding is reversible and non-covalent. Thus, that the heterogeneity observed in the bound state spectra (FIG. 4f) is likely due to alternate binding modes.

Figure 5A:
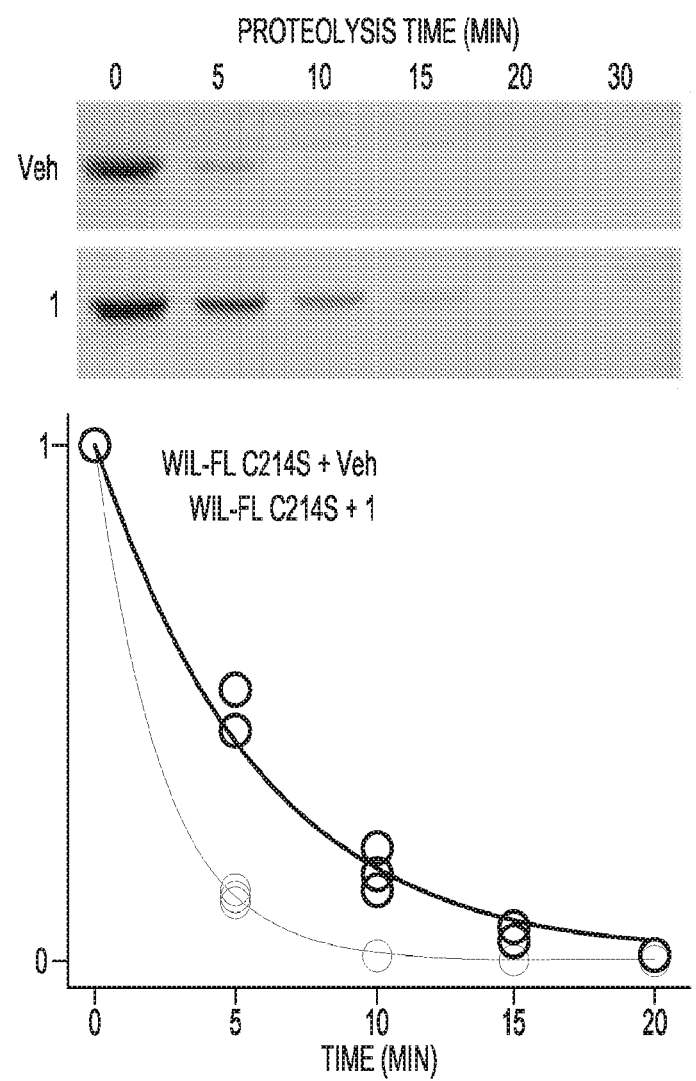

We next asked how binding of kinetic stabilizers would affect the stability of different LCs. In these experiments, we generally used an excess of kinetic stabilizer (limited by small molecule solubility) to saturate LC binding and thus investigate the properties of ligand-stabilized LCs, as a proxy for the behavior of small molecules that bind to LCs with nanomolar affinity. Ablation of the inter-chain disulfide bond by the C214S mutation results in reduced LC kinetic stability (4) and reduced small molecule binding affinity (FIG. 2d). Nonetheless, binding of 1 (100 µM) reduces the rate constant of PK proteolysis of WIL-FL C214S (10 µM) from $6.9×10^{-3}$ to $2.8×10^{-3}$ s$^{-1}$ (FIG. 5a).

Figure 5B:
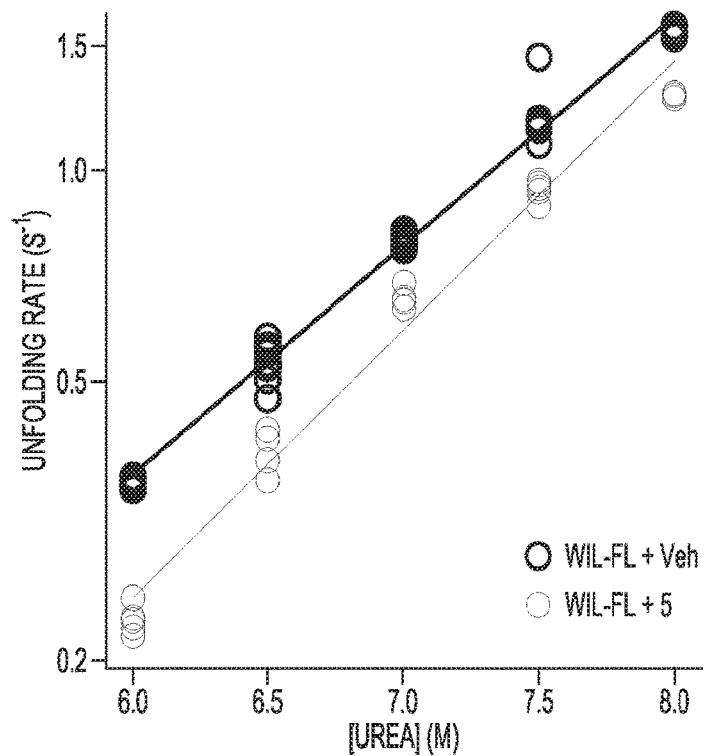
Figure 5C:
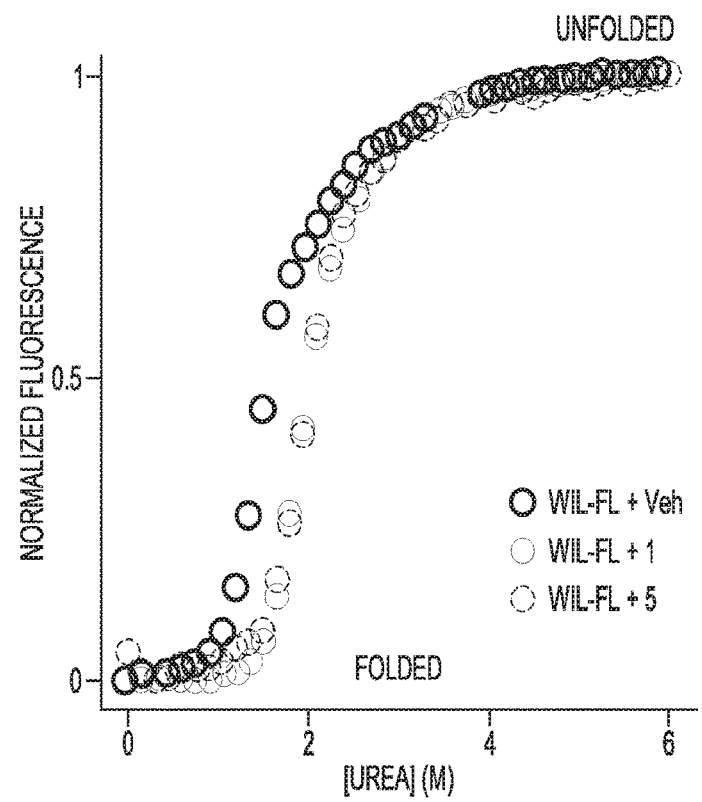
Figure 5D:
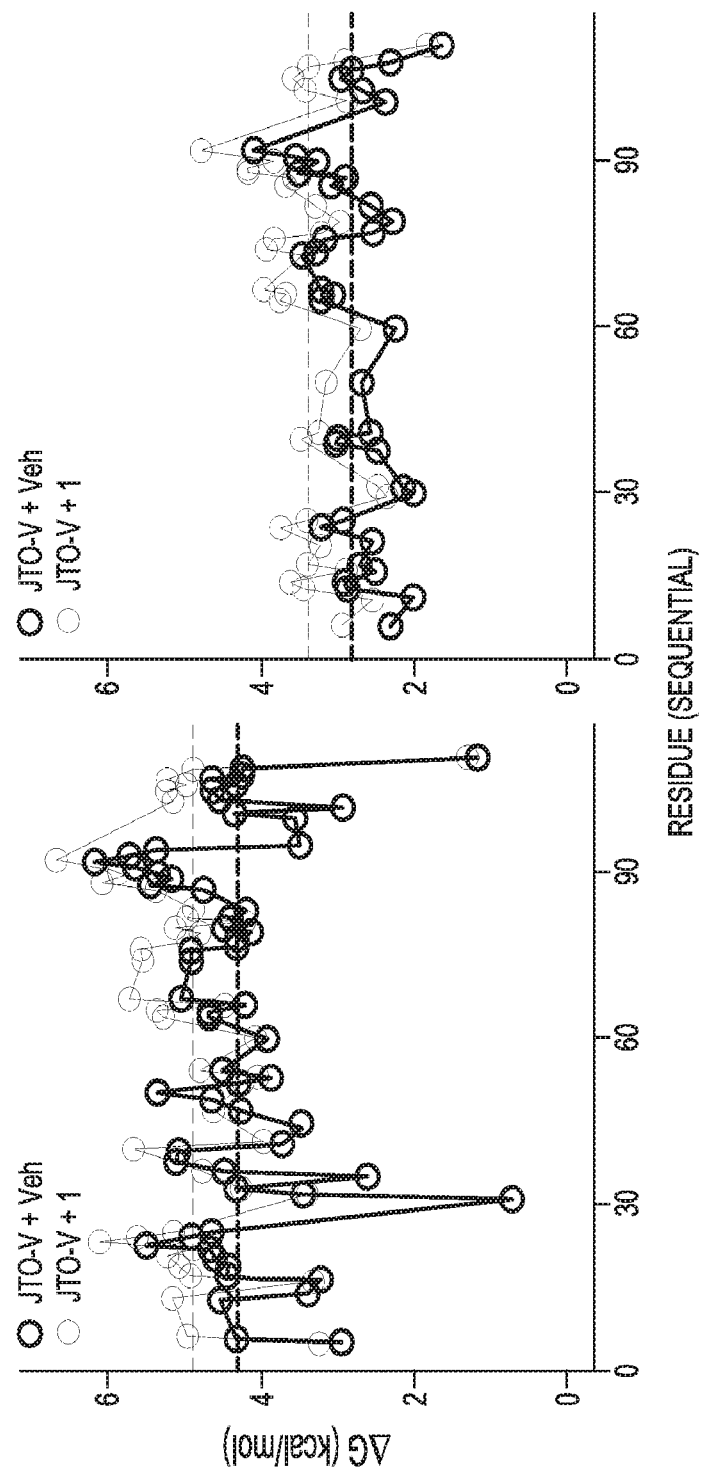

To confirm that protease resistance is driven by stabilization of the LC native state ensemble by small molecule binding, we measured urea-mediated unfolding rates of LCs in solution by tryptophan emission fluorescence (4). The intrinsic fluorescence of 1 precluded its use in these experiments. WIL-FL (5 µM) in the presence of 5 (a non-fluorescent kinetic stabilizer used at a solubility-limited concentration of 50 µM, Table 1) unfolds with a rate constant (extrapolated to the absence of denaturant) of 2.43 s$^{-1}$ compared to 3.57 s$^{-1}$ for WIL-FL alone (FIG. 5b). Binding of 5 increases the kinetic stability of the FL LC, even though the >5 M urea concentrations used in this experiment will lower the affinity of 5 for the FL LC. Titration of urea into WIL-FL (5 µM) in the absence or presence of 1 (100 µM) or 5 (50 µM) revealed an increase in the midpoint concentration of urea required to unfold the FL LC (FIG. 5c) from 1.4 to 2.0 M. The magnitude of this stabilization imparted by 1 and 5 was indistinguishable (FIG. 5c), indicating that the ligand-bound states are similarly stable.

To verify that binding of 1 reduces LC unfolding under non-denaturing conditions, we measured residue-specific hydrogen-deuterium exchange rates by NMR of WIL-V and JTO-V (100 µM) in the absence of or with 1 (500 µM). These rates (the decrease in intensity of the HSQC peak associated with each amide) are converted to free energies that report on each amide's folding equilibrium by normalizing for the published exchange rates of amides in unstructured peptides. Both V-domains are stabilized by an average of 0.6 kcal/mol in the presence of 1 (500 µM, FIG. 5d), indicating that transient unfolding is reduced by binding of 1.

Figure 5E:
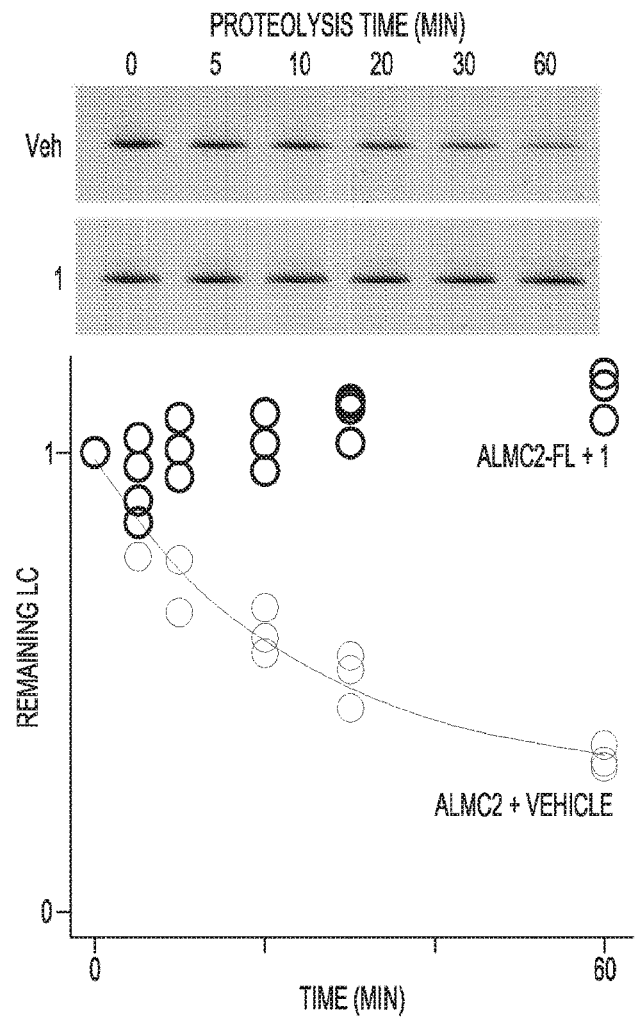

To verify that the kinetic stabilizers bind LCs secreted from cells analogously to recombinant FL LCs, we measured proteolysis of LCs secreted by ALMC2 cells, an AL patient-derived cell line (32). Purified ALMC2-derived LC (5 µM) is cleaved by PK (100 nM) with a rate constant of $3.83×10^{-4}$ s$^{-1}$, whereas no proteolysis was detected after 1 h of incubation by PK in the presence of 1 (100 µM; FIG. 5e).

Inhibition of LC aggregation. Full-length LCs aggregate much less readily than their isolated V-domains in vitro (4, 7). Although aggregation can be measured in vitro, it is not clear to what extent these experiments recapitulate processes that occur in patients, where the mechanism of aggregation is unknown. Assessment of the effect of kinetic stabilizers on FL LC aggregation at the hit stage of drug discovery is complicated by the denaturing acidic pH used to destabilize the FL LCs to promote aggregation in vitro, which can also reduce the binding affinity of the kinetic stabilizers, sometimes dramatically.

To assess the influence of 1 on FL LC aggregation, we used WIL-FL C214S, which forms weak dimers (K$_D$=16 µM), increasing its propensity to aggregate compared to WIL-FL, while retaining affinity for 1 (FIG. 2d). WIL-FL C214S aggregates upon vigorous stirring at or below pH 5 to form heterogenous aggregate structures. WIL-FL C214S aggregation kinetics assessed by fluorescence of the amyloid-binding dye thioflavin T demonstrate that 1 decreases the rate of aggregation significantly versus vehicle control, but the variability in these experiments is greater than desired. This may be because a given LC can stochastically form different aggregate structures with different kinetics.

Figure 5F:
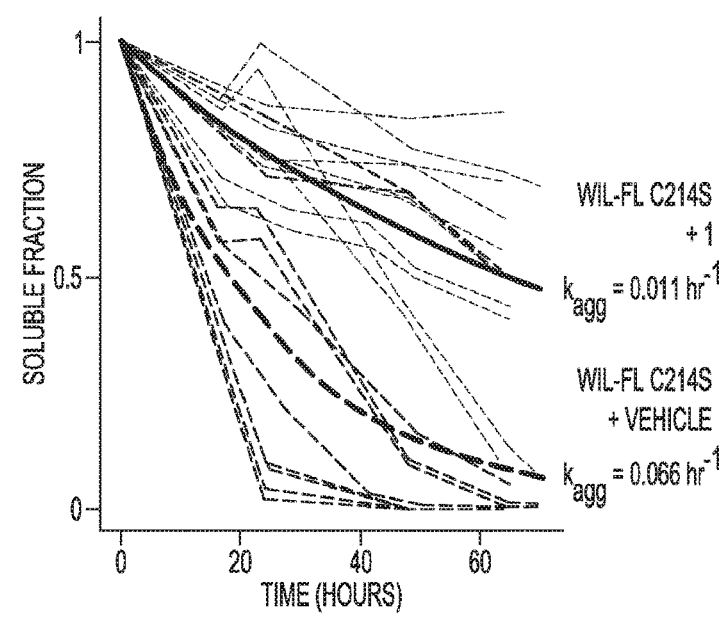

Thus, we also quantified aggregation by measuring the rate of disappearance of soluble dimeric LC using size exclusion chromatography (SEC) (4). Binding of 1 (200 µM) to WIL-FL C214S (10 µM), which stabilizes the dimer and enhances kinetic stability (FIG. 5a), results in a larger proportion of soluble, dimeric LC eluting from the SEC column after 64 h of shaking at pH 5, which promotes aggregation. While individual WIL-FL C214S aggregation reactions exhibit variation in kinetics from run-to-run, aggregation in the presence of 1 (200 µM; dashed blue lines, FIG. 5f, n=10) is generally slower than in the absence of 1 (FIG. 5f, red dashed lines, n=10). Fitting all the aggregation data in FIG. 5f to a single exponential decay model reveals that WIL-FL C214S aggregates significantly more slowly in the presence of 1 ($k_{agg}$=0.011 hr$^{-1}$, FIG. 5f, bold blue curve) than in the absence of 1 ($k_{agg}$=0.066 hr$^{-1}$, FIG. 5f, bold red curve, P<0.001, t-test on log-transformed rates).

Unlabeled LC Protease Sensitivity Assay. WIL-FL (5 µM) in phosphate-buffered saline (PBS, pH 7.4)+0.02% Pluronic F-127 was incubated with proteinase K (50 nM) with small molecule (10 µM) in 1% DMSO vehicle, or vehicle alone. After 2 hours at 37° C., reactions were quenched with 2 mM phenylmethyl sulfonyl fluoride in methanol and centrifuged at 14,000 rpm for 2 minutes. Remaining WIL-FL was quantified by injecting 10 µL of the supernatant into a Waters Acquity H-Class Bio-UPLC (ultra performance liquid chromatography) instrument equipped with a BEH200 analytical size-exclusion column (1.7 µm, 4.6×150 mm) under isocratic conditions (0.2 mL/min, PBS+1 mM EDTA, 2400 psi backpressure, 15 min), monitoring absorbance at 280 nm. Activity of each compound is given as fold protection from protease=(A_compound−A_vehicle)/(A_no_protease−A_vehicle), where each "A" corresponds to peak integration of the respective treatment. Results from the LC Protease Sensitivity Assay are shown in Table 3.

TABLE 3

Fold protection of LC from protease in the proteinase K sensitivity assay for WIL-FL at 10 µM. Protection: A < 0.3); 3 ≤ B < 0.6; and C ≥ 0.6.

| Compound | Protection |
| --- | --- |
| 22 | A |
| 23 | A |
| 24 | A |
| 25 | A |
| 26 | A |

TABLE 3-continued

Fold protection of LC from protease in the proteinase K sensitivity assay for WIL-FL at 10 μM. Protection: A < 0.3; 3 ≤ B < 0.6; and C ≥ 0.6.

| Compound | Protection |
|---|---|
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | B |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | C |
| 76 | A |
| 77 | A |
| 78 | A |
| 79 | A |
| 80 | A |
| 81 | A |
| 82 | A |
| 83 | A |
| 84 | A |
| 85 | B |
| 86 | B |
| 87 | B |
| 88 | B |
| 89 | C |
| 90 | A |
| 91 | B |
| 92 | B |
| 93 | B |
| 94 | A |
| 95 | B |
| 96 | A |
| 97 | A |
| 98 | C |
| 99 | B |
| 100 | A |
| 101 | A |
| 102 | A |
| 103 | B |
| 104 | A |
| 105 | B |
| 106 | A |
| 107 | A |
| 108 | A |
| 109 | A |
| 110 | B |
| 111 | A |
| 112 | A |
| 113 | A |
| 114 | A |
| 115 | A |
| 116 | A |
| 117 | C |
| 118 | B |
| 119 | B |
| 120 | B |
| 121 | B |
| 122 | B |
| 123 | B |
| 124 | C |
| 125 | C |
| 126 | C |
| 127 | B |
| 128 | B |
| 129 | B |
| 130 | B |
| 131 | B |
| 132 | C |
| 133 | B |
| 134 | A |
| 135 | C |
| 136 | A |
| 137 | B |
| 138 | A |
| 139 | A |
| 140 | A |
| 141 | C |
| 142 | C |
| 143 | B |
| 144 | C |
| 145 | C |
| 146 | B |
| 147 | B |
| 148 | B |
| 149 | C |
| 150 | A |
| 151 | A |
| 152 | B |
| 153 | C |
| 154 | C |
| 155 | C |
| 156 | B |
| 157 | C |
| 158 | B |
| 159 | C |
| 160 | C |
| 161 | C |
| 162 | C |
| 163 | C |
| 164 | C |
| 165 | C |
| 166 | C |
| 167 | C |
| 168 | A |

TABLE 3-continued

Fold protection of LC from protease in the proteinase K sensitivity assay for WIL-FL at 10 µM. Protection: A < 0.3); 3 ≤ B < 0.6; and C ≥ 0.6.

| Compound | Protection |
| --- | --- |
| 169 | A |
| 170 | C |
| 171 | A |
| 172 | A |
| 173 | A |
| 174 | A |
| 175 | C |
| 176 | B |
| 177 | C |
| 178 | A |
| 179 | B |
| 180 | C |
| 181 | C |
| 182 | B |
| 183 | B |
| 184 | A |
| 185 | C |
| 186 | A |
| 187 | A |
| 188 | C |
| 189 | A |
| 190 | C |
| 191 | A |
| 192 | C |
| 193 | C |
| 194 | C |
| 195 | A |
| 196 | A |
| 197 | C |
| 198 | B |
| 199 | B |
| 200 | A |
| 201 | B |
| 202 | C |
| 203 | C |
| 204 | B |
| 205 | B |
| 206 | A |
| 207 | B |
| 208 | B |
| 209 | B |
| 210 | B |
| 211 | B |
| 212 | B |
| 213 | C |
| 214 | C |
| 215 | C |
| 216 | C |
| 217 | C |
| 218 | C |
| 219 | A |
| 220 | A |
| 221 | C |
| 222 | C |
| 223 | C |
| 224 | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | B |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 270 | A |
| 271 | A |
| 272 | A |
| 273 | A |
| 274 | A |
| 275 | A |
| 276 | A |
| 277 | B |
| 278 | C |
| 279 | A |
| 280 | B |
| 281 | B |
| 282 | B |
| 283 | A |
| 284 | B |
| 285 | A |
| 286 | A |
| 287 | A |
| 288 | B |
| 289 | C |
| 290 | C |
| 291 | C |
| 292 | C |
| 293 | B |
| 294 | A |
| 295 | B |
| 296 | B |
| 297 | A |
| 298 | B |
| 299 | B |
| 300 | A |
| 301 | A |
| 302 | A |
| 303 | A |
| 304 | A |
| 305 | A |
| 306 | A |
| 307 | B |
| 308 | B |
| 309 | A |
| 310 | A |

TABLE 3-continued

Fold protection of LC from protease in the proteinase K sensitivity assay for WIL-FL at 10 µM. Protection: A < 0.3); 3 ≤ B < 0.6; and C ≥ 0.6.

| Compound | Protection |
| --- | --- |
| 311 | B |
| 312 | C |

NUMBERED REFERENCES CITED IN THIS DISCLOSURE

1. Sipe J D, et al. (2016) Amyloid fibril proteins and amiyloidosis: chemical identification and clinical classification International Society of Amyloidosis 2016 Nomenclature Guidelines. Amyloid: the international journal of experimental and clinical investigation: the official journal of the International Society of Amyloidosis 23(4):209-213.
2. Merlini G, et al. (2018) Systemic immunoglobulin light chain amyloidosis. Nat Rev Dis Primers 4(1):38.
3. Schiffer M, Girling R L, Ely K R, & Edmundson A B (1973) Structure of a λ-type Bence-Jones protein at 3.5-Å resolution. Biochemistry 12(23):4620-4631.
4. Morgan G J & Kelly J W (2016) The Kinetic Stability of a Full-Length Antibody Light Chain Dimer Determines whether Endoproteolysis Can Release Amyloidogenic Variable Domains. J Mol Biol 428(21):4280-4297.
5. Oberti L, et al. (2017) Concurrent structural and biophysical traits link with immunoglobulin light chains amyloid propensity. Sci Rep 7(1):16809.
6. Ramirez-Alvarado M (2012) Amyloid formation in light chain amyloidosis. Curr Top Med Chem 12(22):2523-2533.
7. Blancas-Mejia L M, et al. (2015) Thermodynamic and fibril formation studies of full length immunoglobulin light chain AL-09 and its germline protein using scan rate dependent thermal unfolding. Biophys Chem 207:13-20.
8. Hurle M R, Helms L R, Li L, Chan W, & Wetzel R (1994) A role for destabilizing amino acid replacements in light-chain amyloidosis. Proc Natl Acad Sci USA 91(12):5446-5450.
9. Morgan G J, Usher G A, & Kelly J W (2017) Incomplete Refolding of Antibody Light Chains to Non-Native, Protease-Sensitive Conformations Leads to Aggregation: A Mechanism of Amyloidogenesis in Patients? Biochemistry 56(50):6597-6614.
10. Glenner G G, et al. (1971) Creation of "amyloid" fibrils from Bence Jones proteins in vitro. Science 174(4010): 712-714.
11. Glenner G G, Harbaugh J, Ohma J I, Harada M, & Cuatrecasas P (1970) An amyloid protein: the amino-terminal variable fragment of an immunoglobulin light chain. Biochem Biophys Res Commun 41(5):1287-1289.
12. Lavatelli F, et al. (2008) Amyloidogenic and associated proteins in systemic amyloidosis proteome of adipose tissue. Mol Cell Proteomics 7(8):1570-1583.
13. Olsen K E, Sletten K, & Westermark P (1998) Fragments of the constant region of immunoglobulin light chains are constituents of A L-amyloid proteins. Biochem Biophys Res Commun 251(2):642-647.
14. Bulawa C E, et al. (2012) Tafamidis, a potent and selective transthyretin kinetic stabilizer that inhibits the amyloid cascade. Proc Natl Acad Sci USA 109(24):9629-9634.
15. Berk J L, et al. (2013) Repurposing diflunisal for familial amyloid polyneuropathy: a randomized clinical trial. JAMA 310(24):2658-2667.
16. Coelho T, et al. (2012) Tafamidis for transthyretin familial amyloid polyneuropathy: a randomized, controlled trial. Neurology 79(8):785-792.
17. Rosenblum H, et al. (2018) TTR (Transthyretin) Stabilizers Are Associated With Improved Survival in Patients With TTR Cardiac Amyloidosis. Circ Heart Fail 11(4): e004769.
18. Coelho T, et al. (2013) Long-term effects of tafamidis for the treatment of transthyretin familial amyloid polyneuropathy. Journal of neurology 260(11):2802-2814.
19. Maurer M S, et al. (2018) Tafamidis Treatment for Patients with Transthyretin Amyloid Cardiomyopathy. N Engl J Med 379(11):1007-1016.
20. Hammarstrom P, Wiseman R L, Powers E T, & Kelly J W (2003) Prevention of transthyretin amyloid disease by changing protein misfolding energetics. Science 299 (5607):713-716.
21. Brumshtein B, et al. (2015) Inhibition by small-molecule ligands of formation of amyloid fibrils of an immunoglobulin light chain variable domain. Elife 4:e10935.
22. Rennella E, Morgan G J, Kelly J W, & Kay L E (2018) The role of domain interactions in the aggregation of full-length immunoglobulin light chains. Proc. Natl. Acad. Sci. USA 116:854-863.
23. Wall J, et al. (1999) Thermodynamic instability of human 16 light chains: correlation with fibrillogenicity. Biochemistry 38(42):14101-14108.
24. Bolger R & Checovich W (1994) A new protease activity assay using fluorescence polarization. Biotechniques 17(3):585-589.
25. Kabat E A (1991) Sequences of proteins of immunological interest (National Institutes of Health; Bethesda, MD: Department of Health and Human Services) 5th ed Ed.
26. McGovern S L, Caselli E, Grigorieff N, & Shoichet B K (2002) A common mechanism underlying promiscuous inhibitors from virtual and high-throughput screening. J Med Chem 45(8):1712-1722.
27. Zhang J H, Chung T D, & Oldenburg K R (1999) A Simple Statistical Parameter for Use in Evaluation and Validation of High Throughput Screening Assays. J Biomol Screen 4(2):67-73.
28. Barik A, Kumbhakar M, Nath S, & Pal H (2005) Evidence for the TICT mediated nonradiative deexcitation process for the excited coumarin-1 dye in high polarity protic solvents. Chemical Physics 315(3):277-285.
29. Wolwertz M L, Nguyen P T, Quittot N, & Bourgault S (2016) Probing the role of lambda6 immunoglobulin light chain dimerization in amyloid formation. Biochim Biophys Acta 1864(4):409-418.
30. Perfetti V, et al. (1998) Evidence that amyloidogenic light chains undergo antigen-driven selection. Blood 91(8):2948-2954.
31. Bodi K, et al. (2009) AL-Base: a visual platform analysis tool for the study of amyloidogenic immunoglobulin light chain sequences. Amyloid 16(1):1-8.

32. Arendt B K, et al. (2008) Biologic and genetic characterization of the novel amyloidogenic lambda light chain-secreting human cell lines, ALMC-1 and ALMC-2. Blood 112(5):1931-1941.
33. Kourelis T V, et al. (2017) Clarifying immunoglobulin gene usage in systemic and localized immunoglobulin light-chain amyloidosis by mass spectrometry. Blood 129(3):299-306.
34. Sikkink L A & Ramirez-Alvarado M (2008) Salts enhance both protein stability and amyloid formation of an immunoglobulin light chain. Biophys Chem 135(1-3): 25-31.
35. Sekijima Y, Dendle M A, & Kelly J W (2006) Orally administered diflunisal stabilizes transthyretin against dissociation required for amyloidogenesis. Amyloid 13(4): 236-249.
36. Palladini G, et al. (2012) New criteria for response to treatment in immunoglobulin light chain amyloidosis based on free light chain measurement and cardiac biomarkers: impact on survival outcomes. J Clin Oncol 30(36):4541-4549.
37. Hong M, et al. (2013) Antibody recognition of the pandemic H1N1 Influenza virus hemagglutinin receptor binding site. J Virol 87(22):12471-12480.
38. Huang D B, Ainsworth C, Solomon A, & Schiffer M (1996) Pitfalls of molecular replacement: the structure determination of an immunoglobulin light-chain dimer. Acta crystallographica. Section D, Biological crystallography 52(Pt 6):1058-1066.
39. Pokkuluri P R, Solomon A, Weiss D T, Stevens F J, & Schiffer M (1999) Tertiary structure of human lambda 6 light chains. Amyloid: the international journal of experimental and clinical investigation: the official journal of the International Society of Amyloidosis 6(3):165-171.
40. Edmundson A B, et al. (1974) Binding of 2,4-dinitrophenyl compounds and other small molecules to a crystalline lambda-type Bence-Jones dimer. Biochemistry 13(18):3816-3827.
41. Kloiber K, Spitzer R, Grutsch S, Kreutz C, & Tollinger M (2011) Longitudinal exchange: an alternative strategy towards quantification of dynamics parameters in ZZ exchange spectroscopy. J Biomol NMR 51(1-2):123-129.
42. Yuwen T, Kay L E, & Bouvignies G (2018) Dramatic Decrease in CEST Measurement Times Using Multi-Site Excitation. Chemphyschem 19(14):1707-1710.
43. Liao R, et al. (2001) Infusion of light chains from patients with cardiac amyloidosis causes diastolic dysfunction in isolated mouse hearts. Circulation 104(14): 1594-1597.
44. Pantoliano M W, et al. (2001) High-density miniaturized thermal shift assays as a general strategy for drug discovery. J Biomol Screen 6(6):429-440.
45. Makley L N, et al. (2015) Pharmacological chaperone for alpha-crystallin partially restores transparency in cataract models. Science 350(6261):674-677.
46. Milani P, Merlini G, & Palladini G (2018) Novel Therapies in Light Chain Amyloidosis. Kidney Int Rep 3(3):530-541.
47. Palladini G, et al. (2018) Presentation and outcome with second-line treatment in AL amyloidosis previously sensitive to nontransplant therapies. Blood 131(5):525-532.

All patents and publications referred to herein, including numbered references appearing throughout the present disclosure, are incorporated by reference herein to the same extent as if each individual publication was specifically and individually indicated to be incorporated by reference in its entirety.

We claim:
1. A method of stabilizing an immunoglobulin light chain dimer in a native conformation thereof, comprising contacting the dimer and an effective amount of a compound of Formula Ia, or a pharmaceutically acceptable salt thereof:

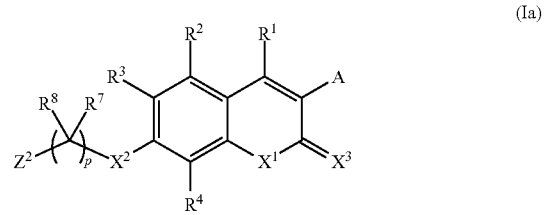

(Ia)

wherein
A is

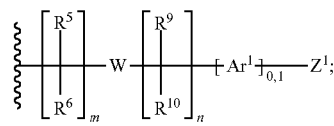

$X^1$ is O or $NR^0$;
$X^2$ is selected from the group consisting of a bond, $NR^{12}$, O, C(O), C(O)$NR^{11}$, and $CR^{12}R^{11}$;
$X^3$ is O or $NR^{13}$;
W is

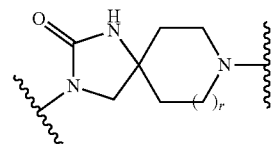

m is an integer selected from 1, 2, 3, 4, 5, and 6;
n is an integer selected from 0, 1, 2, 3, 4, 5, and 6;
p is an integer selected from 0, 1, 2, 3, 4, 5, and 6;
r is an integer selected from 0, 1, 2, and 3;
$Z^1$ is selected from the group consisting of
H,
$C_1$-$C_6$-alkyl,
$C_3$-$C_8$-cycloalkyl,
3- to 6-membered heterocycloalkyl wherein 1-4 ring members are independently selected from N, O, and S,
$C_2$-$C_6$-alkenyl,
$C_3$-$C_8$-cycloalkenyl,
3- to 6-membered heterocycloalkenyl wherein 1-4 ring members are independently selected from N, O, and S,
$C_6$-$C_{10}$-aryl,
5- to 10-membered heteroaryl wherein 1-4 heteroaryl members are independently selected from N, O, and S,
—($C_1$-$C_6$-alkyl)($C_6$-$C_{10}$-aryl),
—($C_1$-$C_6$-alkyl)(5- to 10-membered heteroaryl) wherein 1-4 heteroaryl members are independently selected from N, O, and S,
halogen,
$NR^{16}NR^{17}$, COOR$^{18}$;
OR$^{18}$,
NR$^{16}$SO$_2$R$^{18}$,
NR$^{16}$COR$^{18}$,
X$^4$(CR$^{21}$R$^{22}$)$_a$CONR$^{16}$R$^{17}$,
X$^4$(CR$^{21}$R$^{22}$)$_a$COOR$^{18}$,
X$^4$(CR$^{21}$R$^{22}$)$_a$COR$^{18}$,
X$^4$(CR$^{21}$R$^{22}$)$_a$NR$^{16}$R$^{17}$,
X$^4$(CR$^{21}$R$^{22}$)$_a$OR$^{18}$,
SO$_2$NR$^{16}$R$^{17}$,
X$^4$(CR$^{21}$R$^{22}$)$_a$NR$^{16}$COR$^{18}$,
C(N=R$^{23}$)NR$^{24}$OH, and

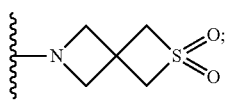

wherein
X$^4$ is a bond, O, or NR$^0$; and
a is an integer selected from 0, 1, 2, 3, 4, 5, and 6;
Z$^2$ is selected from the group consisting of
H,
C$_1$-C$_6$-alkyl,
C$_3$-C$_8$-cycloalkyl,
3- to 6-membered heterocycloalkyl wherein 1-4 ring members are independently selected from N, O, and S,
C$_2$-C$_6$-alkenyl,
C$_2$-C$_6$-alkynyl,
C$_3$-C$_8$-cycloalkenyl,
3- to 6-membered heterocycloalkenyl wherein 1-4 ring members are independently selected from N, O, and S,
C$_6$-C$_{10}$-aryl,
5- to 10-membered heteroaryl wherein 1-4 heteroaryl members are independently selected from N, O, and S,
—(C$_1$-C$_6$-alkyl)(C$_6$-C$_{10}$-aryl),
—(C$_1$-C$_6$-alkyl)(5- to 10-membered heteroaryl) wherein 1-4 heteroaryl members are independently selected from N, O, and S,
CN,
OR$^{18}$ and
NR$^{19}$R$^{20}$;
Ar$^1$ is a divalent moiety selected from
C$_6$-C$_{10}$-arylene and
5- to 10-membered heteroarylene wherein 1-4 heteroaryl members are independently selected from N, O, and S;
R$^1$ is selected from the group consisting of
H,
C$_1$-C$_6$-alkyl,
C$_3$-C$_8$-cycloalkyl,
3- to 6-membered heterocycloalkyl wherein 1-4 ring members are independently selected from N, O, and S,
C$_2$-C$_6$-alkenyl,
C$_3$-C$_8$-cycloalkenyl,
3- to 6-membered heterocycloalkenyl wherein 1-4 ring members are independently selected from N, O, and S,
C$_6$-C$_{10}$-aryl,
5- to 10-membered heteroaryl wherein 1-4 heteroaryl members are independently selected from N, O, and S,
—(C$_1$-C$_6$-alkyl)(C$_6$-C$_{10}$-aryl),
—(C$_1$-C$_6$-alkyl)(5- to 10-membered heteroaryl) wherein 1-4 heteroaryl members are independently selected from N, O, and S,
OH,
(CR$^{21}$R$^{22}$)$_b$OR$^{18}$ where b is an integer selected from 0, 1, 2, 3, 4, 5, and 6,
halogen, and
(C$_1$-C$_6$)haloalkyl;
R$^2$, R$^3$, and R$^4$ are independently selected from the group consisting of
H,
C$_1$-C$_6$-alkyl,
—(C$_1$-C$_6$-alkyl)(C$_6$-C$_{10}$-aryl),
OH,
(CR$^{21}$R$^{22}$)$_b$OR$^{18}$,
halogen,
C$_3$-C$_8$-cycloalkyl,
3- to 6-membered heterocycloalkyl wherein 1-4 ring members are independently selected from N, O, and S,
C$_2$-C$_6$-alkenyl,
C$_3$-C$_8$-cycloalkenyl,
3- to 6-membered heterocycloalkenyl wherein 1-4 ring members are independently selected from N, O, and S,
C$_6$-C$_{10}$-aryl,
5- to 10-membered heteroaryl wherein 1-4 heteroaryl members are independently selected from N, O, and S,
—(C$_1$-C$_6$-alkyl)(C$_6$-C$_{10}$-aryl), and
—(C$_1$-C$_6$-alkyl)(5- to 10-membered heteroaryl) wherein 1-4 heteroaryl members are independently selected from N, O, and S;
R$^0$, R$^5$-R$^{13}$ and R$^{18}$-R$^{22}$ are independently selected from the group consisting of H,
C$_1$-C$_6$-alkyl,
C$_1$-C$_6$-haloalkyl,
C$_3$-C$_8$-cycloalkyl,
3- to 6-membered heterocycloalkyl wherein 1-4 ring members are independently selected from N, O, and S,
C$_2$-C$_6$-alkenyl,
C$_2$-C$_6$-alkynyl,
C$_3$-C$_8$-cycloalkenyl,
3- to 6-membered heterocycloalkenyl wherein 1-4 ring members are independently selected from N, O, and S,
C$_6$-C$_{10}$-aryl,
5- to 10-membered heteroaryl wherein 1-4 heteroaryl members are independently selected from N, O, and S,
—(C$_1$-C$_6$-alkyl)(C$_6$-C$_{10}$-aryl), and
—(C$_1$-C$_6$-alkyl)(5- to 10-membered heteroaryl) wherein 1-4 heteroaryl members are independently selected from N, O, and S;
R$^{16}$ and R$^{17}$ are independently selected from the group consisting of H,
C$_1$-C$_6$-alkyl,
C$_3$-C$_8$-cycloalkyl,
3- to 6-membered heterocycloalkyl wherein 1-4 ring members are independently selected from N, O, and S,
C$_2$-C$_6$-alkenyl,
C$_3$-C$_8$-cycloalkenyl, 3- to 6-membered heterocycloalkenyl wherein 1-4 ring members are independently selected from N, O, and S, $C_6$-$C_{10}$-aryl, 5- to 10-membered heteroaryl 4 wherein 1-4 heteroaryl members are independently selected from N, O, and S, —($C_1$-$C_6$-alkyl)($C_6$-$C_{10}$-aryl), —($C_1$-$C_6$-alkyl)(5- to 10-membered heteroaryl) wherein 1-4 heteroaryl members are independently selected from N, O, and S, $C(O)OR^{18}$, $C(O)R^{18}$, and $SO_2R^{18}$;

$R^{16}$ and $R^{17}$, together with the atoms to which they are bound, optionally are a 3- to 8-membered ring wherein ring members are selected from C, O and N;

$R^{19}$ and $R^{20}$, together with the atoms to which they are bound, optionally are a 3- to 8-membered ring;

$R^{21}$ and $R^{22}$, together with the atoms to which they are bound, optionally are a 3- to 8-membered ring.

2. A method of treatment of light chain amyloidosis in a patient, comprising administering to the patient an effective amount of a compound of Formula Ia, or a pharmaceutically acceptable salt thereof:

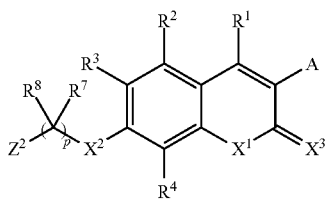

(Ia)

wherein

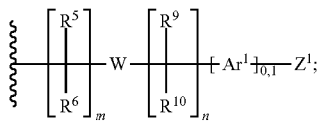

A is $X^1$ is O or $NR^0$;

$X^2$ is selected from the group consisting of a bond, $NR^{12}$, O, C(O), C(O)$NR^{11}$, and $CR^{12}R^{11}$;

$X^3$ is O or $NR^{13}$

W is

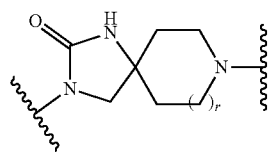

m is an integer selected from 1, 2, 3, 4, 5, and 6;
n is an integer selected from 0, 1, 2, 3, 4, 5, and 6;
p is an integer selected from 0, 1, 2, 3, 4, 5, and 6;
r is an integer selected from 0, 1, 2, and 3;

$Z^1$ is selected from the group consisting of

H, $C_1$-$C_6$-alkyl, $C_3$-$C_8$-cycloalkyl, 3- to 6-membered heterocycloalkyl wherein 1-4 ring members are independently selected from N, O, and S, $C_2$-$C_6$-alkenyl, $C_3$-$C_8$-cycloalkenyl, 3- to 6-membered heterocycloalkenyl wherein 1-4 ring members are independently selected from N, O, and S, $C_6$-$C_{10}$-aryl, 5- to 10-membered heteroaryl wherein 1-4 heteroaryl members are independently selected from N, O, and S, —($C_1$-$C_6$-alkyl)($C_6$-$C_{10}$-aryl), —($C_1$-$C_6$-alkyl)(5- to 10-membered heteroaryl) wherein 1-4 heteroaryl members are independently selected from N, O, and S, halogen, $NR^{16}R^{17}$, $COOR^{18}$;

$OR^{18}$, $NR^{16}SO_2R^{18}$, $NR^{16}COR^{18}$, $X^4(CR^{21}R^{22})_aCONR^{16}R^{17}$, $X^4(CR^{21}R^{22})_aCOOR^{18}$, $X^4(CR^{21}R^{22})_aCOR^{18}$, $X^4(CR^{21}R^{22})_aNR^{16}R^{17}$, $X^4(CR^{21}R^{22})_aOR^{18}$, $SO_2NR^{16}R^{17}$, $X^4(CR^{21}R^{22})_aNR^{16}COR^{18}$, $C(N=R^{23})NR^{24}OH$, and

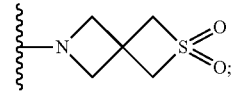

wherein $X^4$ is a bond, O, or $NR^0$; and a is an integer selected from 0, 1, 2, 3, 4, 5, and 6;

$Z^2$ is selected from the group consisting of

H, $C_1$-$C_6$-alkyl, $C_3$-$C_8$-cycloalkyl, 3- to 6-membered heterocycloalkyl wherein 1-4 ring members are independently selected from N, O, and S, $C_2$-$C_6$-alkenyl, $C_2$-$C_6$-alkynyl, $C_3$-$C_8$-cycloalkenyl, 3- to 6-membered heterocycloalkenyl wherein 1-4 ring members are independently selected from N, O, and S, $C_6$-$C_{10}$-aryl, 5- to 10-membered heteroaryl wherein 1-4 heteroaryl members are independently selected from N, O, and S, —($C_1$-$C_6$-alkyl)($C_6$-$C_{10}$-aryl), —($C_1$-$C_6$-alkyl)(5- to 10-membered heteroaryl) wherein 1-4 heteroaryl members are independently selected from N, O, and S,

CN, $OR^{18}$ and $NR^{19}R^{20}$;

Ar¹ is a divalent moiety selected from
C₆-C₁₀-arylene and
5- to 10-membered heteroarylene wherein 1-4 heteroaryl members are independently selected from N, O, and S;

R¹ is selected from the group consisting of
H,
$C_1$-$C_6$-alkyl,
$C_3$-$C_8$-cycloalkyl,
3- to 6-membered heterocycloalkyl wherein 1-4 ring members are independently selected from N, O, and S,
$C_2$-$C_6$-alkenyl,
$C_3$-$C_8$-cycloalkenyl,
3- to 6-membered heterocycloalkenyl wherein 1-4 ring members are independently selected from N, O, and S,
$C_6$-$C_{10}$-aryl,
5- to 10-membered heteroaryl wherein 1-4 heteroaryl members are independently selected from N, O, and S,
—($C_1$-$C_6$-alkyl)($C_6$-$C_{10}$-aryl),
—($C_1$-$C_6$-alkyl)(5- to 10-membered heteroaryl) wherein 1-4 heteroaryl members are independently selected from N, O, and S,
OH,
$(CR^{21}R^{22})_bOR^{18}$ wherein b is an integer selected from 0, 1, 2, 3, 4, 5, and 6,
halogen, and
$(C_1$-$C_6)$haloalkyl;

R², R³, and R⁴ are independently selected from the group consisting of
H,
$C_1$-$C_6$-alkyl,
—($C_1$-$C_6$-alkyl)($C_6$-$C_{10}$-aryl),
OH,
$(CR^{21}R^{22})_bOR^{18}$,
halogen,
$C_3$-$C_8$-cycloalkyl,
3- to 6-membered heterocycloalkyl wherein 1-4 ring members are independently selected from N, O, and S,
$C_2$-$C_6$-alkenyl,
$C_3$-$C_8$-cycloalkenyl,
3- to 6-membered heterocycloalkenyl wherein 1-4 ring members are independently selected from N, O, and S,
$C_6$-$C_{10}$-aryl,
5- to 10-membered heteroaryl wherein 1-4 heteroaryl members are independently selected from N, O, and S,
—($C_1$-$C_6$-alkyl)($C_6$-$C_{10}$-aryl), and
—($C_1$-$C_6$-alkyl)(5- to 10-membered heteroaryl) wherein 1-4 heteroaryl members are independently selected from N, O, and S;

R⁰, and R⁵-R¹³ and R¹⁸-R²² are independently selected from the group consisting of
H,
$C_1$-$C_6$-alkyl,
$C_1$-$C_6$-haloalkyl,
$C_3$-$C_8$-cycloalkyl,
3- to 6-membered heterocycloalkyl wherein 1-4 ring members are independently selected from N, O, and S,
$C_2$-$C_6$-alkenyl,
$C_2$-$C_6$-alkynyl,
$C_3$-$C_8$-cycloalkenyl,
3- to 6-membered heterocycloalkenyl wherein 1-4 ring members are independently selected from N, O, and S,
$C_6$-$C_{10}$-aryl,
5- to 10-membered heteroaryl wherein 1-4 heteroaryl members are independently selected from N, O, and S,
—($C_1$-$C_6$-alkyl)($C_6$-$C_{10}$-aryl), and
—($C_1$-$C_6$-alkyl)(5- to 10-membered heteroaryl) wherein 1-4 heteroaryl members are independently selected from N, O, and S;

R¹⁶ and R¹⁷ are independently selected from the group consisting of
H,
$C_1$-$C_6$-alkyl,
$C_3$-$C_8$-cycloalkyl,
3- to 6-membered heterocycloalkyl wherein 1-4 ring members are independently selected from N, O, and S,
$C_2$-$C_6$-alkenyl,
$C_3$-$C_8$-cycloalkenyl,
3- to 6-membered heterocycloalkenyl wherein 1-4 ring members are independently selected from N, O, and S,
$C_6$-$C_{10}$-aryl,
5- to 10-membered heteroaryl wherein 1-4 heteroaryl members are independently selected from N, O, and S,
—($C_1$-$C_6$-alkyl)($C_6$-$C_{10}$-aryl),
—($C_1$-$C_6$-alkyl)(5- to 10-membered heteroaryl) wherein 1-4 heteroaryl members are
independently selected from N, O, and S,
$C(O)OR^{18}$,
$C(O)R^{18}$, and
$SO_2R^{18}$;

R¹⁶ and R⁹, together with the atoms to which they are bound, optionally are a 3- to 8-membered ring;

R¹⁶ and R¹⁷, together with the atoms to which they are bound, optionally are a 3- to 8-membered ring wherein ring members are selected from C, O and N;

R¹⁹ and R²⁰, together with the atoms to which they are bound, optionally are a 3- to 8-membered ring;

R²¹ and R²², together with the atoms to which they are bound, optionally are a 3- to 8-membered ring.

3. The method according to claim 2, wherein the compound of Formula Ia, or a pharmaceutically acceptable thereof, is selected from the following table:

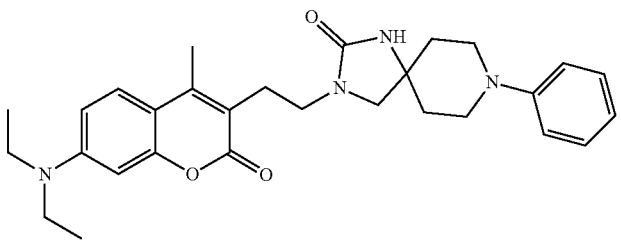 [SMILES: CCN(CC)c1ccc2c(C)c(CCN3CC4(CCN(c5ccccc5)CC4)NC3=O)c(=O)oc2c1]

-continued
| 221 | 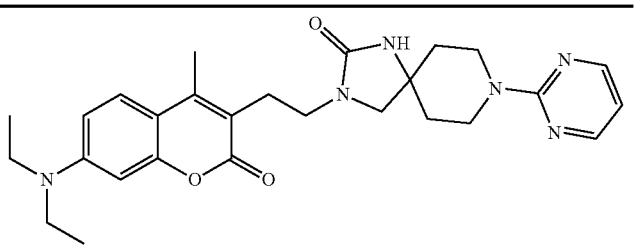 |
| 222 | 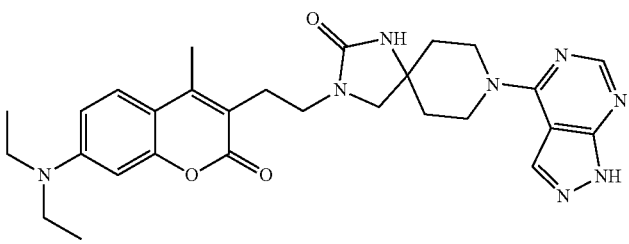 |
| 223 | 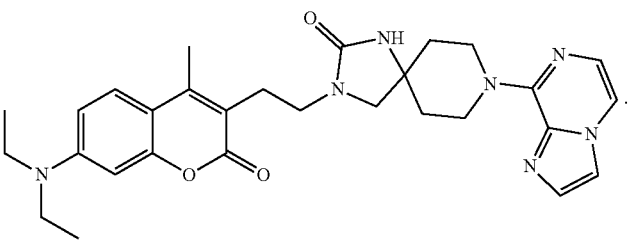 |
* * * * *